US008106169B2

(12) United States Patent
Briggs et al.

(10) Patent No.: US 8,106,169 B2
(45) Date of Patent: Jan. 31, 2012

(54) PLANT PRODUCTION OF IMMUNOGLOBULINS WITH REDUCED FUCOSYLATION

(75) Inventors: Kristen Briggs, Del Mar, CA (US); Todd Glancy, Fairmont, IN (US); Mich B. Hein, Chicago, IL (US); Andrew C. Hiatt, San Diego, CA (US); Anton S. Karnoup, Midland, MI (US); W. H. Kerr Anderson, Midland, MI (US); Dayakar Pareddy, Carmel, IN (US); Joseph Petolino, Zionsville, IN (US); Beth Rubin-Wilson, Indianapolis, IN (US); Doug Taylor, San Diego, CA (US); Jean L. Roberts, Arcadia, IN (US)

(73) Assignee: Phyton Holdings, LLC, San Antonio, TX (US)

( * ) Notice: Subject to any disclaimer, the term of this patent is extended or adjusted under 35 U.S.C. 154(b) by 935 days.

(21) Appl. No.: 10/536,875

(22) PCT Filed: Nov. 28, 2003

(86) PCT No.: PCT/US03/37905
§ 371 (c)(1), (2), (4) Date: Dec. 1, 2006

(87) PCT Pub. No.: WO2004/050838
PCT Pub. Date: Jun. 17, 2004

(65) Prior Publication Data
US 2007/0089201 A1    Apr. 19, 2007

Related U.S. Application Data

(60) Provisional application No. 60/429,385, filed on Nov. 27, 2002.

(51) Int. Cl.
*C07K 16/08* (2006.01)
*C07K 16/00* (2006.01)
*C12N 15/82* (2006.01)

(52) U.S. Cl. ............... 530/388.3; 530/388.1; 530/387.1; 435/69.6

(58) Field of Classification Search ........................ None
See application file for complete search history.

(56) References Cited

U.S. PATENT DOCUMENTS

| | | |
|---|---|---|
| 4,956,282 A | 9/1990 | Goodman et al. |
| 5,202,422 A | 4/1993 | Hiatt et al. |
| 5,639,947 A | 6/1997 | Hiatt et al. |
| 5,874,271 A | 2/1999 | Nishikawa et al. |
| 5,879,912 A | 3/1999 | Roth |
| 5,939,288 A | 8/1999 | Thornburg |
| 5,959,177 A | 9/1999 | Hein et al. |
| 6,046,040 A | 4/2000 | Nishiguchi et al. |
| 6,054,304 A | 4/2000 | Taniguchi et al. |
| 6,331,418 B1 | 12/2001 | Roth |
| 6,344,600 B1 | 2/2002 | Merot et al. |
| 6,388,068 B1 | 5/2002 | Satoh et al. |
| 6,602,684 B1 | 8/2003 | Umana et al. |
| 6,653,459 B1 | 11/2003 | Von Schaewen et al. |
| 6,998,267 B1 | 2/2006 | Seki et al. |
| 7,001,998 B2 | 2/2006 | McKenzie et al. |
| 2002/0174453 A1 | 11/2002 | Daniell et al. |
| 2004/0014174 A1* | 1/2004 | Mayfield et al. ............ 435/69.1 |
| 2004/0072290 A1 | 4/2004 | Umana et al. |
| 2004/0181827 A1 | 9/2004 | Schaewen et al. |
| 2004/0214273 A1 | 10/2004 | Fujiyama et al. |
| 2005/0143564 A1 | 6/2005 | Seki et al. |
| 2005/0144670 A1 | 6/2005 | Fujiyama et al. |
| 2005/0223430 A1 | 10/2005 | Bakker et al. |
| 2006/0253928 A1 | 11/2006 | Bakker et al. |
| 2007/0214519 A1 | 9/2007 | Fujiyama et al. |

FOREIGN PATENT DOCUMENTS

| | | |
|---|---|---|
| AU | 1681300 | 6/2000 |
| DE | 19754622 | 6/1999 |
| EP | 0 351 313 A2 | 1/1990 |
| EP | 0 550 756 A1 | 7/1993 |
| EP | 0 737 745 A1 | 10/1996 |
| EP | 0 816 503 A1 | 7/1998 |
| EP | 1243647 | 9/2002 |
| JP | 2000-245470 | 9/2000 |
| JP | 2000287692 | 10/2000 |
| WO | WO 87/00865 | 2/1987 |
| WO | WO 92/18537 | 10/1992 |
| WO | WO 94/12646 | 6/1994 |
| WO | WO 95/02683 | 1/1995 |
| WO | WO 95/21248 | 8/1995 |

(Continued)

OTHER PUBLICATIONS

Sakai et al., "Expression of Human β1,4-Galactosyltransferase in Tobacco BY2 Cells Modifies Glycosylation Patterns of Intracellular and Extracellular Glycoproteins," Translation of Abstract from the Ann. Meeting of Japan Society for Bioscience, Biotechnology, and Agrochemistry, Published Mar. 1998.
Yosida et al., "Challenge for production of human-compatible glycoprotein therapeutics in yeast", Bioscience and Industry, vol. 54, pp. 420-422 (1996).
Bailey et al. Metabolic engineering of N-linked glycoform synthesis systems in Chinese hamster ovary (CHO) cells (1997) Animal Cell Technology, pp. 489-494.
Fischer et al. Molecular farming of recombinant antibodies in plants. (1999) Biol. Chem. 380: 825-839.
Kitagawa et al. Molecular cloning and expression of glucuronyltransferase I involved in the biosynthesis of the glycosaminoglycan-protein linkage region of proteoglycans. (1998) JBC 273:6615-6618.

(Continued)

*Primary Examiner* — Sharon Wen
(74) *Attorney, Agent, or Firm* — Wolf, Greenfield & Sacks, P.C.

(57) ABSTRACT

This invention provides for the plant production of immunoglobulins, wherein at least a portion of the glycans attached to the immunoglobulins lack fucose. The invention also provides the constructs; plasmids; vectors; transformed plant cells, transformed plant calli; transformed plant tissues (e.g., leaves, seeds, tubers, etc.); transformed whole plants used to produce such immunoglobulins; methods of producing the immunoglobulins; the immunoglobulins produced by the disclosed methods; and the use of such immunoglobulins.

22 Claims, 38 Drawing Sheets

FOREIGN PATENT DOCUMENTS

| | | |
|---|---|---|
| WO | WO 97/04122 | 2/1997 |
| WO | WO 98/31826 | 7/1998 |
| WO | WO 98/31828 | 7/1998 |
| WO | WO 99/09187 | 2/1999 |
| WO | WO 99/24584 | 5/1999 |
| WO | WO 99/29879 | 6/1999 |
| WO | WO 99/38987 | 8/1999 |
| WO | WO 99/38990 | 8/1999 |
| WO | WO 99/51185 | 10/1999 |
| WO | WO 00/28792 | 5/2000 |
| WO | WO 00/29603 | 5/2000 |
| WO | WO 00/34490 | 6/2000 |
| WO | WO 00/49153 | 8/2000 |
| WO | WO 00/52136 | 9/2000 |
| WO | WO 01/29241 | 4/2001 |
| WO | WO 01/29242 | 4/2001 |
| WO | WO 01/31044 | 5/2001 |
| WO | WO 01/31045 * | 5/2001 |
| WO | WO 01/49821 | 7/2001 |
| WO | WO 01/49831 | 7/2001 |
| WO | WO 01/62912 | 8/2001 |
| WO | WO 01/64901 | 9/2001 |
| WO | WO 01/81591 | 11/2001 |
| WO | WO 01/82912 | 11/2001 |
| WO | WO 02/00879 | 1/2002 |
| WO | WO 02/057468 | 7/2002 |
| WO | WO 02/070672 | 9/2002 |
| WO | WO 03/011878 | 2/2003 |
| WO | WO 03/076614 | 9/2003 |
| WO | WO 03/078614 | 9/2003 |
| WO | WO 03/078637 | 9/2003 |
| WO | WO 2004/050838 | 6/2004 |

OTHER PUBLICATIONS

Umana et al. Engineered glycoforms of an antineuroblastoma IgG1 with optimize antibody-dependent cellular cytotoxic activity. (1999) Nature Biotech. 17: 176-180.

Whitelam GC., The production of recombinant proteins in plants. (1995) J. Sci. Food Agric., 68:1-9.

Wiebauer et al., Nuclear pre-mRNA processing in plants: distinct modes of 3' splice-site selection in plants and animals (1988) MCB: vol. 8 pp. 2042-2051.

GENBANK Submission; NIH/NCBI, Accession No. AJ277603. Bakker et al. Apr. 28, 2000.

Asano et al., Growth retardation and early death of beta-1,4-galactosyltransferase knockout mice with augmented proliferation and abnormal differentiation of epithelial cells. EMBO J. Apr. 15, 1997;16(8):1850-7.

Bakker et al., Galactose-extended glycans of antibodies produced by transgenic plants. Proc Natl Acad Sci U S A. Feb. 27, 2001;98(5):2899-904.

Bakker et al., An *Arabidopsis thaliana* Cdna complements the N-acetylglucosaminyltransferase I deficiency of CHO Lec1 cells. Biochem Biophys Res Commun. Aug. 11, 1999;261(3):829-32.

Cabanes-Macheteau et al., N-Glycosylation of a mouse IgG expressed in transgenic tobacco plants. Glycobiology. Apr. 1999;9(4):365-72.

Choi et al., Use of combinatorial genetic libraries to humanize N-linked glycosylation in the yeast *Pichia pastoris*. Proc Natl Acad Sci U S A. Apr. 29, 2003;100(9):5022-7. Epub Apr. 17, 2003.

Chrispeels and Faye, The production of recombinant glycoproteins with defined non-immunogenic glycans. In: Transgenic plants: a production system for industrial and pharmaceutical proteins. John Wiley Pub, UK. 1996:99-113.

Dinter and Berger, The regulation of cell- and tissue-specific expression of glycans by glycosyltransferases. Adv Exp Med Biol. 1995;376:53-82.

Elbers et al., Influence of growth conditions and developmental stage on N-glycan heterogeneity of transgenic immunoglobulin G and endogenous proteins in tobacco leaves. Plant Physiol. Jul. 2001;126(3):1314-22.

Essl et al., The N-terminal 77 amino acids from tobacco N-acetylglucosaminyltransferase I are sufficient to retain a reporter protein in the Golgi apparatus of Nicotiana benthamiana cells. FEBS Lett. Jun. 18, 1999;453(1-2):169-73.

Fischer and Evans, Molecular farming of pharmaceutical proteins. Transgenic Research. 2000;9:279-299.

Fuchs et al., Purification and characterization of microbially expressed neomycin phosphotransferase II (NPTII) protein and its equivalence to the plant expressed protein. Biotechnology (N Y). Dec. 1993;11(13):1537-42.

Fujiyama et al., In vivo conversion of a glycan to human compatible type by transformed tobacco cells. Biochem Biophys Res Commun. Nov. 30, 2001;289(2):553-7.

Gasser and Fraley, Genetically Engineering Plants for Crop Improvement. Science. Jun. 16, 1989;244(4910):1293-1299.

Gomez and Chrispeels, Complementation of an *Arabidopsis thaliana* mutant that lacks complex asparagine-linked glycans with the human cDNA encoding N-acetylglucosaminyltransferase I. Proc Natl Acad Sci U S A. Mar. 1, 1994;91(5):1829-33.

Grabenhorst and Conradt, The cytoplasmic, transmembrane, and stem regions of glycosyltransferases specify their in vivo functional sublocalization and stability in the Golgi. J Biol Chem. Dec. 17, 1999;274(51):36107-16.

Hamilton et al., Production of complex human glycoproteins in yeast. Science. Aug. 29, 2003;301(5637):1244-6.

Handa et al., The alpha 1→3 fucosylation at the penultimate GlcNAc catalyzed by fucosyltransferase VII is blocked by internally fucosylated residue in sialosyl long-chain poly-LacNAc: enzymatic basis for expression of physiological E-selectin epitope. Biochem Biophys Res Commun. Feb. 4, 1998;243(1):199-204.

Herman and Horvitz, Three proteins involved in *Caenorhabditis elegans* vulval invagination are similar to components of a glycosylation pathway. Proc Natl Acad Sci U S A. Feb. 2, 1999;96(3):974-9.

Hein et al., Evaluation of immunoglobulins from plant cells. Biotechnol Prog. Sep.-Oct. 1991;7(5):455-61.

Hess et al., Transformation experiments by pipetting *Agrobacterium* into the spikelets of wheat (*Triticum aestivum* L.). Plant Science 1990;72:233-44.

Hiei et al., Efficient transformation of rice (*Oryza sativa* L.) mediated by *Agrobacterium* and sequence analysis of the boundaries of the T-DNA. Plant J. Aug. 1994;6(2):271-82.

Hiei et al., Transformation of rice mediated by *Agrobacterium tumefaciens*. Plant Mol Biol. Sep. 1997;35(1-2):205-18.

Hollister et al., Engineering the protein N-glycosylation pathway in insect cells for production of biantennary, complex N-glycans. Biochemistry. Dec. 17, 2002;41(50):15093-104.

Ihara et al., cDNA cloning, expression, and chromosomal localization of human N-acetylglucosaminyltransferase III (GnT-III). J Biochem (Tokyo). Jun. 1993;113(6):692-8.

Ioffe and Stanley, Mice lacking N-acetylglucosaminyltransferase I activity die at mid-gestation, revealing an essential role for complex or hybrid N-linked carbohydrates. Proc Natl Acad Sci U S A. Jan. 18, 1994;91(2):728-32.

Ishida et al., High efficiency transformation of maize (*Zea mays* L.) mediated by *Agrobacterium tumefaciens*. Nat Biotechnol. Jun. 1996;14(6):745-50.

Jähne et al., Genetic engineering of ceral crop plants: a review. Euphyica. Kluwer Academic Publishers. 1995:85:35-44.

James et al., Production and characterization of biologically active human GM-CSF secreted by genetically modified plant cells. Protein Expr Purif. Jun. 2000;19(1):131-8.

Jenkins et al., Getting the glycosylation right: implications for the biotechnology industry. Nat Biotechnol. Aug. 1996; 14(8):975-81.

Kawar et al., Insect cells encode a class II alpha-mannosidase with unique properties. J Biol Chem. May 11, 2001;276(19):16335-40. Epub Feb. 9, 2001.

Kieliszewski et al., Tandem mass spectrometry and structural elucidation of glycopeptides from a hydroxyproline-rich plant cell wall glycoprotein indicate that contiguous hydroxyproline residues are the major sites of hydroxyproline O-arabinosylation. J Biol Chem. Feb. 10, 1995;270(6):2541-9.

Kleene et al., Expression of soluble active human beta 1,4 galactosyltransferase in *Saccharomyces cerevisiae*. Biochem Biophys Res Commun. May 30, 1994;201(1):160-7.

Ku et al., High-level expression of maize phosphoenolpyruvate carboxylase in transgenic rice plants. Nat Biotechnol. Jan. 1999;17(1):76-80.

Leiter et al., Purification, cDNA cloning, and expression of GDP-L-Fuc:Asn-linked GlcNAc alpha1,3-fucosyltransferase from mung beans. J Biol Chem. Jul. 30, 1999;274(31):21830-9.

Lerouge et al., Control of the N-Glycosylation of therapeutic glycoproteins produced in transgenic plants: a new challenge for glycobiologists. Molecular Farming of Plants and Animals for Human and Veterinary Medicine. Chapter 4, 2002;73-109.

Lerouge et al., N-glycoprotein biosynthesis in plants: recent developments and future trends. Plant Mol Biol. Sep. 1998;38(1-2):31-48.

Lerouge et al., N-glycosylation of recombinant pharmaceutical glycoproteins produced in transgenic plants: towards an humanisation of plant N-glycans. Curr Pharm Biotechnol. Dec. 2000;1(4):347-54.

Li et al., Cloning, expression and characterization of a cDNA (6A8) encoding a novel human alpha-mannosidase. Eur J Biochem. Dec. 2000;267(24):7176-83. Erratum in: Eur J Biochem Nov. 2001;268(21):5653.

Madson et al., Altered xyloglucans of *Arabidopsis thalianamutants* bind normally to cellulose in vivo and in vitro. Poster from Plant Biology(Rockville) Jul. 27, 2001 Abstract #527.

Magnuson et al., Secretion of biologically active human interleukin-2 and interleukin-4 from genetically modified tobacco cells in suspension culture. Protein Expr Purif. Jun. 1998;13(1):45-52.

Magnuson et al., Enhanced recovery of a secreted mammalian protein from suspension culture of genetically modified tobacco cells. Protein Expr Purif. Mar. 1996;7(2):220-8.

Maras et al., In vitro conversion of the carbohydrate moiety of fungal glycoproteins to mammalian-type oligosaccharides—evidence for N-acetylglucosaminyltransferase-I-accepting glycans from *Trichoderma reesei*. Eur J Biochem. Nov. 1, 1997;249(3):701-7.

Masri et al., Identification of the full-length coding sequence for human galactosyltransferase (beta-N-acetylglucosaminide: beta 1,4-galactosyltransferase). Biochem Biophys Res Commun. Dec. 15, 1988;157(2):657-63.

Miyake et al., Purification of human erythropoietin. J Biol Chem. Aug. 10, 1977;252(15):5558-64.

Miyoshi et al., The alpha1-6-fucosyltransferase gene and its biological significance. Biochim Biophys Acta. Dec. 6, 1999;1473(1):9-20.

Mokrzycki-Issartel et al., A transient tobacco expression system coupled to MALDI-TOF-MS allows validation of the impact of differential targeting on structure and activity of a recombinant therapeutic glycoprotein produced in plants. FEBS Lett. Sep. 25, 2003;552(2-3):170-6.

Palacpac et al., Stable expression of human beta 1,4-galactosyltransferase in plant cells modifies N-linked glycosylation patterns. Proc Natl Acad Sci U S A. Apr. 13, 1999;96(8):4692-7.

Palacpac et al., Structures of N-linked oligosaccharides of glycoproteins from tobacco BY2 suspension cultured cells. Biosci Biotechnol Biochem. Jan. 1999;63(1):35-9.

Rayon et al., N-Glycosylation of phytohemagglutinin expressed in bean cotyledons or in transgenic tobacco plants. Plant Physiol Biochem. 1996;34:273-81.

Rothman, Protein sorting by selective retention in the endoplasmic reticulum and Golgi stack. Cell. Aug. 14, 1987;50(4):521-2.

Sakai et al., Fatty Acid acylation of apoE by human monocyte/marophages and helptocytes. Apr. 1998; 417. Abstract.

Sakai et al., Human glycosyltransferase expression and intracellular/intercellular glycoprotein sugar chain structure in cultured tobacco BY2 cells. Corrected title: Expression of human β 1,4-galactosyltransferase in tobacco BY2 cells modifies glycosylation patterns of intracellular and extracellular glycoproteins. IC Biotech. Osaska, Nara Institute. Mar. 1998. Abstract.

Schachter, The 'yellow brick road' to branched complex N-glycans. Glycobiology. Nov. 1991;1(5):453-61.

Seveno et al., Glycoprotein Sialylation in plants? Nat Biotechnol. Nov. 2004;22(11):1351-2.

Shah et al., Sialylated endogenous glycoconjugates in plant cells. Nat Biotechnol. Dec. 2003;21(12):1470-1. Epub Nov. 9, 2003.

Strasser et al., Molecular cloning of cDNA encoding N-acetylglucosaminyltransferase II from *Arabidopsis thaliana*. Glycoconj J. Dec. 1999;16(12):787-91.

Takahashi et al., Xylose-containing common structural unit in N-linked oligosaccharides of laccase from sycamore cells. Biochemistry. 1986;25(2):388-95.

Tang et al., The transmembrane domain of N-glucosaminyltransferase I contains a Golgi retention signal. J Biol Chem. May 15, 1992;267(14):10122-6.

Taniguchi et al., A glycomic approach to the identification and characterization of glycoprotein function in cells transfected with glycosyltransferase genes. Proteomics. Feb. 2001;1(2):239-47.

Terayama et al., Cloning and functional expression of a novel glucuronyltransferase involved in the biosynthesis of the carbohydrate epitope HNK-1. Proc Natl Acad Sci U S A. Jun. 10, 1997;94(12):6093-8.

Van Engelen et al., Coordinate expression of antibody subunit genes yields high levels of functional antibodies in roots of transgenic tobacco. Plant Mol Biol. Dec. 1994;26(6):1701-10.

Van Ree et al., Beta(1,2)-xylose and alpha(1,3)-fucose residues have a strong contribution in IgE binding to plant glycoallergens. J Biol Chem. Apr. 14, 2000;275(15):11451-8.

Vitale and Chrispeels, Transient N-acetylglucosamine in the biosynthesis of phytohemagglutinin: attachment in the Golgi apparatus and removal in protein bodies. J Cell Biol. Jul. 1984;99(1 Pt 1):133-40.

Voelker et al., In vitro mutated phytohemagglutinin genes expressed in tobacco seeds: role of glycans in protein targeting and stability. Plant Cell. Jan. 1989;1(1):95-104.

Warner, T.G., Metabolic engineering glycosylation: biotechnology's challenge to the glycobiologist in the next millenium; Carbohydrates in chemistry and biology, part II vol. 4. editors Earnst et al. (2000) Wiley-VCH. 1042-64.

Wee et al., Targeting of active sialyltransferase to the plant Golgi apparatus. Plant Cell. Oct. 1998;10(10):1759-68.

Wilson et al., Core alpha1,3-fucose is a key part of the epitope recognized by antibodies reacting against plant N-linked oligosaccharides and is present in a wide variety of plant extracts. Glycobiology. Jul. 1998;8(7):651-61.

Wilson et al., Cloning and expression of cDNAs encoding alpha1,3-fucosyltransferase homologues from *Arabidopsis thaliana*. Biochim Biophys Acta. Jul. 2, 2001;1527(1-2):88-96.

Wright and Morrison, Effect of glycosylation on antibody function: implications for genetic engineering. Trends Biotechnol. Jan. 1997;15(1):26-32.

Yamaguchi et al., Genomic structure and promoter analysis of the human alpha1,6-fucosyltransferase gene (FUT8). Glycobiology. Jun. 2000;10(6):637-43.

Yin et al., [Obtaining transgenic rice plants and their progenies using *Agrobacterium tumefaciens*] Yi Chuan Xue Bao. Dec. 1998;25(6):517-24. Chinese.

Yoshida et al., Molecular biology and application of plant peroxidase genes. Appl Microbiol Biotechnol. Feb. 2003;60(6):665-70. Epub Dec. 18, 2002.

Yoshida et al., Expression of β1 4 galactosyltransferase in tobacco culture cell. Program for Congress of the Society for Bioscience and Bioengineering of Japan. Sep. 15, 1995;1-5.

Zhang et al., Transformation of tobacco using human β-1 , 4 galactosyltransferase gene and regeneration of transgenic plants. Annual reports of IC Biotech. 1995;18:241-7.

Zhang et al., Agrobacterium-mediated transformation of elite indica and japonica rice cultivars. Mol Biotechnol. Dec. 1997;8(3):223-31.

Zhang and Wang, Quantitative analysis and process monitoring of site-specific glycosylation microheterogeneity in recombinant human interferon-gamma from Chinese hamster ovary cell culture by hydrophilic interaction chromatography. J Chromatogr B Biomed Sci Appl. Aug. 7, 1998;712(1-2):73-82.

Zhu et al., Beta 1,4 N-acetylgalactosaminyltransferase (GM2/GD2/GA2 synthase) forms homodimers in the endoplasmic reticulum: a strategy to test for dimerization of Golgi membrane proteins. Glycobiology. Oct. 1997;7(7):987-96.

Aoki et al. Golgi retention of a trans-Golgi membrane protein, galactosyl-transferase, requires cysteine and histidine residues within the membrane-anchoring domain. (1992) Cell Biology 89, 4319-4323.

Boyd et al. The effect of the removal of sialic acid, galactose and total carbohydrate on the functional activity of Campath-1H (1995) Mol Imm. 32, 1311-8.

Colley "Golgi localization of glycosyltransferases: more questions than answers" (1997) Glycobiology 7(1):1-13.

De Vries et al. Isolation of total and polysomal RNA from plant tissues. (1991) Plant Mol. Biology B6/1-13.

Dieryck et al. Human Haemoglobin from transgenic tobacco (1997) Nature 386, 29-30.

Faye et al Affinity purification of antibodies specific for Asn-linked glycans containing alpha 1—> 3 fucose or beta—> 2 xylose. (1993) Anal Biochem 209, 104-8.

Fitchette Laine et al. N-glycans harboring the Lewis a epitope are expressed at the surface of plant cells. (1997) Plan J 12, 1411-7.

Florack et al. Expression of giant silkmoth cecropin B genes in tobacco. (1995) Transgenic Research 4, 132-141.

Gleeson "Targeting of proteins to the Golgi apparatus" (1998) Histochem Cell Biol. 109: 517-532.

Hollister et al. Stable expression of mammalian β1,4-galactosyltransferase extends the N-glycosylation pathway in insect cells. (1998) Glycobiology 8(5): 473-480.

Horsch et al. A simple and general method for transferring genes into plants. (1985) Science 227, 1229-1231.

Jarvis and Finn Modifying the insect cell N-glycosylation pathway with immediate early baculovirus expression vectors. (1996) Nat Biotechnol 14, 1288-92.

Johnson and Chrispeels Substrate specificities of N-acetylglucosaminyl-, fucosyl-, and xylosyltransferases that modify glycoproteins in the Golgi apparatus of bean cotyledons. (1987) Plant Physiology 84, 1301-1308.

Ma et al. Generation and assembly of secretory antibodies in plants (1995) Science 268, 716-9.

Matsumoto et al. Characterization of a human glycoprotein (erythropoietin) produced in cultured tobacco cells. Mol. Biol. 27, 1163-1172, 1995.

Melo et al. Identification of the human Lewis(a) carbohydrate motif in a secretory peroxidase from a plant cell suspension culture (*Vaccinium myrtillus* L.) FEBS Lett 415, 186-91, 1997.

Milland et al. "The cytoplasmic tail of α1,2-fucosyltransferase contains a sequence for golgi localization" (2001) J. Biol. Chem. 276(15):12012-12018.

Munro "Localization of proteins to the Golgi apparatus" (1998) Trends Cell Biol. 8(1): 11-15.

Rayon et al. Characterization of N-Glycans from *Arabidopsis*. Application to a Fucose-Deficient Mutant (1999) Plant Physiology 119, 725-733.

Saito et al. Integration and expression of a rabbit liver cytochrome P-450 gene in transgenic *Nicotiana tabacum* (1991) Proc. Natl. Acad. Sci. 88, 7041-7045.

Schindler et al. Arabinogalactan proteins in maize coleoptiles: developmental relationship to cell death during xylem differentiation but not to extention growth. (1995) Plant JU 7, 25-36.

Shaper et al. Bovine galactosyltransferase: identification of a clone by direct immunological screening of a cDNA expression library. (1986) Proc Natl Acad Sci USA 83, 1573-7.

Smant et al. Potato root diffusate- induced secretion of soluble, basic proteins originating from the subventral esophageal glands of potato cyst nematodes (1997) Phytopathology 87, 839-845.

Stanley and Ioffe Glycosyltransferase mutants: key to new insights in glycobiology (1995) Faseb j 9, 1436-44.

Stanley et al. CHO cells provide access to novel N-glycans and developmentally regulated glycosyltransferases. (1996) Glycobiology 6, 695-9.

Sturm et al. "Subcellular localization of glycosidases and glycosyltransferases involved in the processing of N-linked oligosaccharides" (1987) Plant Physiol. 85(3):741-745.

Thanavala et al. Immunogenicity of transgenetic plant derived hepatitis B surface antigen. (1995) Proc Natl Acad Sci USA 92, 3358-3361.

Van Engelen et al. pBINPLUS: an improved plant transformation vector based on pBIN19. (1995) Transgenetic Res 4, 288-90.

Von Schaewen et al. Isolation of a mutant *Arabidopsis* plant that lacks N-acetyl glucosaminyl transferase I and is unable to synthesize Golgi-modified complex N-linked glycans. (1993) Plant Physiol 102, 1109-18.

Yamaguchi and Fukuda Golgi retention mechanism of β-1,4-Galactosyltransferase (1995) J of Biol Chemistry 270(20): 12170-12176.

GENBANK Submission; Accession No. Q92074. Shaper J.H. Nov. 1, 1996.

GENBANK Submission; Accession No. ADL27179. Hillman J. L. et al. May 20, 2004.

GENBANK Submission; Accession No. U19890. Shaper J. H. Aug. 3, 1996.

GENBANK Submission; Accession No. BC124813. Aug. 5, 2006.

GENBANK Submission; Accession No. Q08B99. Strausberg et al. Oct. 31, 2006.

Borisjuk et al., Production of Recombinant Proteins in Plant Root Exudates. Nat. Biotechnology 17(5): 466-469 (1999).

Chrispeels, M., *Glycobiology of Plant Cells*, Essentials of Glycobiology, Ch. 20; Varki et al., 1st ed. (1999) Cold Spring Harbor Laboratory Press, NY.

Cousin et al. "Human variant sex hormone-binding globulin (SHBG) with an additional carbohydrate chain has a reduced clearance rate in rabbit." (1998) J of Clin. Endocrin. And Metab. 83: 245-240.

Ihara et al "Ectopic Expression of N-acetylglucosaminyltransferase III in transgenic hepatocytes disrupts apolipoprotein B secretion and induces aberrant cellular morphology with lipid storage." Proc Natl Acad Sci USA 1998 95:2526-2530.

Kang et al. "Salt tolerance of *Arabidopsis thaliana* requires maturation of N-glycosylated proteins in the Golgi apparatus." PNAS 2008 105(15):5933-5938.

Kihlberg et al. "Glysocylated peptide hormones: pharmacological properties and conformation studies of analogues of [1-Desamino,8-D-arginine]vasopressin." J. Med. Chem.; 38:161-169, 1995.

Krezdorn et al "Human beta 1,4 galactosyltransferase and alpha 2,6 sialyltransferase expressed in *Saccharomyces cerevisiae* are retained as active enzymes in the endoplasmic reticulum" Eur J Biochem. Mar. 15, 1994;220(3):809-17.

Naigai et al., "N-Glycosylation is Requisite for the Enzyme Activity and Golgi Retention of N-AcetylglucosaminyltransferaseIII." Glycobiology 7(6):769-776 (1997).

Philipp et al., "Characterization of nuclear membranes and endoplasmic reticulum isolated from plant tissue" JCB 1976 68:11-29.

Rishi et al. "Molecular Farming in Plants: A Current Perspective." (2001) J. Plant Biochem. & Biotech 10: 1-12.

Saint-Jore-Dupas et al. "Plant N-Glycan Processing Enzymes Employ Different Targeting Mechanisms for Their Spatial Arrangement along the Secretory Pathway." The Plant Cell 2006 18:3182-3200.

Scherer et al., "Action and Inhibition of Endogenous Phospholipases during Isolation of Plant Membranes" Plant Physiol 1978 62:933-37.

Staudacher E, "Functional purification and characterization of a GDP-fucose: beta-N-acetylglucosamine (Fuc to Asn linked GlcNAc) alpha 1,3-fucosyltransferase from mung beans." Glycoconj J. Dec. 1995;12(6):780-6.

Staudacher E, "Strict order of (Fuc to Asn-linked GlcNAc) fucosyltransferases forming core-difucosylated structures." Glycoconj J. Apr. 1998;15(4):355-60.

Strasser et al., "Molecular cloning and functional expression of beta 1,2-sylosyltransferase cDNA from *Arabidopsis thaliana*[1]" Febs Letters, Elsevier, Amsterdam, NL, Apr. 2000 472(1): 105-108.

Strasser et al. "Molecular basis of N-acetylglucosaminyltransferase I deficiency in *Arabidopsis thaliana* plants lacking complex N-glycans." Biochem J. 2005 387:385-391.

Terayama et al., "Purification and Characterization of a Glucuronyltransferase Involved in the Biosynthesis of the HNK-1 Epitope on Glycoproteins from Rat Brain." The Journal of Biological Chemistry 273(46):30295-30300 (1998).

* cited by examiner

Native Western Blot (A)

Western blot condition: 4-12% GEL nonreducing sample buffer
62 ng total protein each well
1:5000 Goat anti-Human Kappa-HRP one hour RT
5 minute expose Neutralization of HSV-2 Using Endosperm Derived HX8

Monomeric IgA

Dimeric IgA

Secretory IgA

Figure 16A

| Event | Glycans | | | | Method of glycan release |
|---|---|---|---|---|---|
| | observed m/z, [M+Na] | Theor. m/z, [M+Na] | % by MALDI (based on peak heights) | Proposed structure | |
| 81 (5XH751/ 280-081.005.006) | 903.28 | 903.32 | 40.6 | H2N2X | whole affinity purified IgA-HX8 was digested with pepsin, then PNGase A |
| | 1013.27 | 1013.29 | 12.9 | H3N2P | |
| | 1065.31 | 1065.38 | 25.7 | H3N2X | |
| | 1157.29 | ? | 3.3 | ? | |
| | 1175.29 | 1179.34 | 6.5 | H4N2P | |
| | 1211.31 | 1211.44 | 3.0 | H3N2XF | |
| | ND | 1257.46 | ND | H5N2 | |
| | 1268.37 | 1268.46 | 2.1 | H3N3X | |
| | 1337.34 | 1337.40 | 3.7 | H5N2P | |
| | 1499.33 | 1499.45 | 1.0 | H6N2P | |
| | 1661.36 | 1661.50 | 1.1 | H7N2P | |
| 81 (5XH751/ 280-081.005.006) | 903.5 | 903.32 | 20.7 | H2N2X | affinity purified IgA-HX8 was separated by SDS-PAGE, band at ~50 kDa was digested in-gel with trypsin, peptides were extracted, purified (C18), then digested with PNGase A |
| | 933.52 | 933.34 | 15.3 | H3N2 | |
| | 1013.52 | 1013.29 | 9.9 | H3N2P | |
| | 1065.59 | 1065.38 | 35.6 | H3N2X | |
| | 1157.61 | ? | 12.0 | ? | |
| | ND | 1211.44 | ND | H3N2XF | |
| | 1257.65 | 1257.46 | 2.9 | H5N2 | |
| | 1268.69 | 1268.46 | 3.5 | H3N3X | |

Figure 16B

| Event | Glycans | | | | Method of glycan release |
|---|---|---|---|---|---|
| | observed m/z, [M+Na] | Theor. m/z, [M+Na] | % by MALDI (based on peak heights) | Proposed structure | |
| 81 (6RC172/ 280-081.005.006) | 903.2 | 903.32 | 36.9 | H2N2X | whole affinity purified IgA-HX8 was digested with pepsin, then PNGase A |
| | 1013.19 | 1013.29 | 10.4 | H3N2P | |
| | 1065.23 | 1065.38 | 28.3 | H3N2X | |
| | 1175.24 | 1175.34 | 7.3 | H4N2P | |
| | 1211.38 | 1211.44 | 2.8 | H3N2XF | |
| | 1257.27 | 1257.46 | 2.8 | H5N2 | |
| | ND | 1268.46 | ND | H3N3X | |
| | 1337.26 | 1337.40 | 4.6 | H5N2P | |
| | 1499.27 | 1499.45 | 3.4 | H6N2P | |
| | 1661.36 | 1661.50 | 2.0 | H7N2P | |
| | 1823.42 | 1823.55 | 1.7 | H8N2P | |
| 81 (6RC172/ 280-081.005.006) | 903.51 | 903.32 | 21.9 | H2N2X | affinity purified IgA-HX8 was separated by SDS-PAGE, band at ~50 kDa was digested in-gel with trypsin, peptides were extracted, purified (C18), then digested with PNGase A |
| | 933.51 | 933.34 | 17.5 | H3N2 | |
| | 1013.54 | 1013.29 | 11.8 | H3N2P | |
| | 1065.6 | 1065.38 | 32.0 | H3N2X | |
| | 1157.61 | ? | 11.1 | ? | |
| | 1211.66 | 1211.44 | 2.5 | H3N2XF | |
| | 1257.69 | 1257.46 | 3.4 | H5N2 | |
| | ND | 1268.46 | ND | H3N3X | |

Figure 16C

| Event | Glycans | | | | Method of glycan release |
|---|---|---|---|---|---|
| | observed m/z, [M+Na] | Theor. m/z, [M+Na] | % by MALDI (based on peak heights) | Proposed structure | |
| 21 self | 903.26 | 903.32 | 57.4 | H2N2X | whole affinity purified IgA-HX8 was digested with pepsin, then PNGase A |
| | 1013.24 | 1013.29 | 10.6 | H3N2P | |
| | 1065.3 | 1065.38 | 16.2 | H3N2X | |
| | 1175.3 | | 4.0 | H4N2P | |
| | 1211.36 | 1211.44 | 3.8 | H3N2XF | |
| | 1257.34 | 1257.46 | 1.3 | H5N2 | |
| | ND | 1268.46 | ND | H3N3X | |
| | 1337.37 | 1337.40 | 2.7 | H5N2P | |
| | 1499.43 | 1499.45 | 1.5 | H6N2P | |
| | 1661.49 | 1661.50 | 1.3 | H7N2P | |
| | 1823.54 | 1823.55 | 1.0 | H8N2P | |
| 21 (5HX751/ 280-021.002.007) | 903.17 | 903.32 | 36.2 | H2N2X | whole affinity purified IgA-HX8 was reduced/ alkylated, digested with trypsin, then digested with PNGase A and released glycans were analyzed by MALDI |
| | 933.16 | 933.34 | 5.3 | H3N2 | |
| | 1049.2 | 1049.38 | 2.7 | H2N2XF | |
| | 1065.2 | 1065.38 | 42.8 | H3N2X | |
| | 1095.18 | 1095.40 | 1.8 | H4N2 | |
| | ND | 1136.42 | ND | H3N3 | |
| | 1211.25 | 1211.44 | 3.5 | H3N2XF | |
| | 1257.25 | 1257.46 | 3.2 | H5N2 | |
| | 1268.26 | 1268.46 | 3.6 | H3N3X | |
| | 1419.29 | 1419.52 | 1.0 | H6N2 | |
| | detected on H-T13 glycopeptide | | | N (single GlcNAc) | |
| | trace detected on H-T13 glycopeptide | | | N2 (double GlcNAc) | |

Figure 16D

| Event | Glycans | | | | Method of glycan release |
|---|---|---|---|---|---|
| | observed m/z, [M+Na] | Theor. m/z, [M+Na] | % by MALDI (based on peak heights) | Proposed structure | |
| 21 (6RC172/ 280-021.002.007) | 903.12 | 903.32 | 42.8 | H2N2X | whole affinity purified IgA-HX8 was reduced/ alkylated, digested with trypsin, then digested with PNGase A and released glycans were analyzed by MALDI |
| | 933.12 | 933.34 | 9.3 | H3N2 | |
| | 1049.14 | 1049.38 | 2.8 | H2N2XF | |
| | 1065.13 | 1065.38 | 35.2 | H3N2X | |
| | 1095.13 | 1095.40 | 2.2 | H4N2 | |
| | 1136.16 | 1136.42 | trace | H3N3 | |
| | 1211.16 | 1211.44 | 2.7 | H3N2XF | |
| | 1257.16 | 1257.46 | 3.6 | H5N2 | |
| | 1268.16 | 1268.46 | 1.4 | H3N3X | |
| | 1419.17 | 1419.52 | trace | H6N2 | |
| | detected on H-T13 glycopeptide | | | N (single GlcNAc) | |
| | trace detected on H-T13 glycopeptide | | | N2 (double GlcNAc) | |

Figure 16E

| Event | Glycans | | | | Method of glycan release |
|---|---|---|---|---|---|
| | observed m/z, [M+Na] | Theor. m/z, [M+Na] | % by MALDI (based on peak heights) | Proposed structure | |
| 193 self | 903.35 | 903.32 | 42.7 | H2N2X | whole affinity purified IgA-HX8 was reduced/ alkylated, digested with trypsin, peptides separated by C18-HPLC, HPLC fractions analyzed by MALDI, then fractions containing glyco- peptides were digested with PNGase A and released glycans were analyzed by MALDI |
| | 933.35 | 933.34 | 6.2 | H3N2 | |
| | 1049.39 | 1049.38 | 1.3 | H2N2XF | |
| | 1065.41 | 1065.38 | 38.0 | H3N2X | |
| | 1095.4 | 1095.40 | 1.4 | H4N2 | |
| | 1136.44 | 1136.42 | 1.0 | H3N3 | |
| | 1211.45 | 1211.44 | 0.9 | H3N2XF | |
| | 1257.47 | 1257.46 | 4.5 | H5N2 | |
| | 1268.49 | 1268.46 | 1.7 | H3N3X | |
| | 1419.55 | 1419.52 | trace | H6N2 | |
| | detected on H-T13 glycopeptide | | | N (single GlcNAc) | |
| | detected on H-T13 glycopeptide | | | N2 (double GlcNAc) | |

Figure 16F

| Event | Glycans | | | | Method of glycan release |
|---|---|---|---|---|---|
| | observed m/z, [M+Na] | Theor. m/z, [M+Na] | % by MALDI (based on peak heights) | Proposed structure | |
| 223 self | 903.51 | 903.32 | 34.6 | H2N2X | whole affinity purified IgA-HX8 was reduced/ alkylated, digested with trypsin, then digested with PNGase A and released glycans were analyzed by MALDI |
| | ND | 933.34 | ND | H3N2 | |
| | 1065.61 | 1065.38 | 55.8 | H3N2X | |
| | 1211.68 | 1211.44 | 3.9 | H3N2XF | |
| | 1257.71 | 1257.46 | 5.7 | H5N2 | |
| | ND | 1268.46 | ND | H3N3X | |
| 223 self | 903.18 | 903.32 | 42.6 | H2N2X | whole affinity purified IgA-HX8 was reduced/ alkylated, digested with trypsin, peptides separated by C18-HPLC, HPLC fractions analyzed by MALDI, then fractions containing glyco-peptides were digested with PNGase A and released glycans were analyzed by MALDI |
| | ND | 933.34 | ND | H3N2 | |
| | ND | 1049.38 | ND | H2N2XF | |
| | 1065.21 | 1065.38 | 49.9 | H3N2X | |
| | 1095.23 | 1095.40 | trace | H4N2 | |
| | ND | 1136.42 | ND | H3N3 | |
| | 1211.24 | 1211.44 | trace | H3N2XF | |
| | 1257.26 | 1257.46 | 7.5 | H5N2 | |
| | ND | 1268.46 | ND | H3N3X | |
| | ND | 1419.52 | ND | H6N2 | |
| | detected on H-T13 glycopeptide | | | N (single GlcNAc) | |
| | detected on H-T13 glycopeptide | | | N2 (double GlcNAc) | |

Figure 16G

| Event | Glycans | | | | Method of glycan release |
|---|---|---|---|---|---|
| | observed m/z, [M+Na] | Theor. m/z, [M+Na] | % by MALDI (based on peak heights) | Proposed structure | |
| 223 (5HX751/ 280-223.005.006) | 903.28 | 903.32 | 40.8 | H2N2X | whole affinity purified IgA-HX8 was reduced/ alkylated, digested with trypsin, then digested with PNGase A and released glycans were analyzed by MALDI |
| | 933.29 | 933.34 | 6.1 | H3N2 | |
| | 1049.33 | 1049.38 | 2.0 | H2N2XF | |
| | 1065.33 | 1065.38 | 40.6 | H3N2X | |
| | 1095.33 | 1095.40 | 1.3 | H4N2 | |
| | 1136.4 | 1136.42 | 1.2 | H3N3 | |
| | 1211.37 | 1211.44 | 2.8 | H3N2XF | |
| | 1257.39 | 1257.46 | 2.7 | H5N2 | |
| | 1268.39 | 1268.46 | 2.5 | H3N3X | |
| | 1419.12 | 1419.52 | trace | H6N2 | |
| | detected on H-T13 glycopeptide | | | N (single GlcNAc) | |
| | detected on H-T13 glycopeptide | | | N2 (double GlcNAc) | |

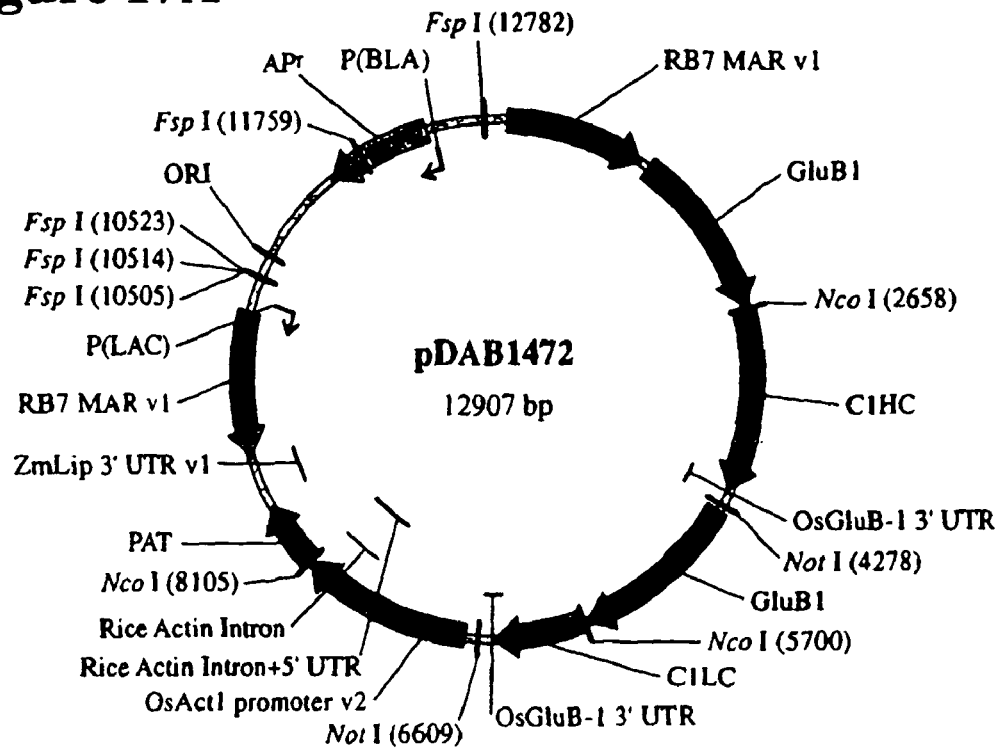
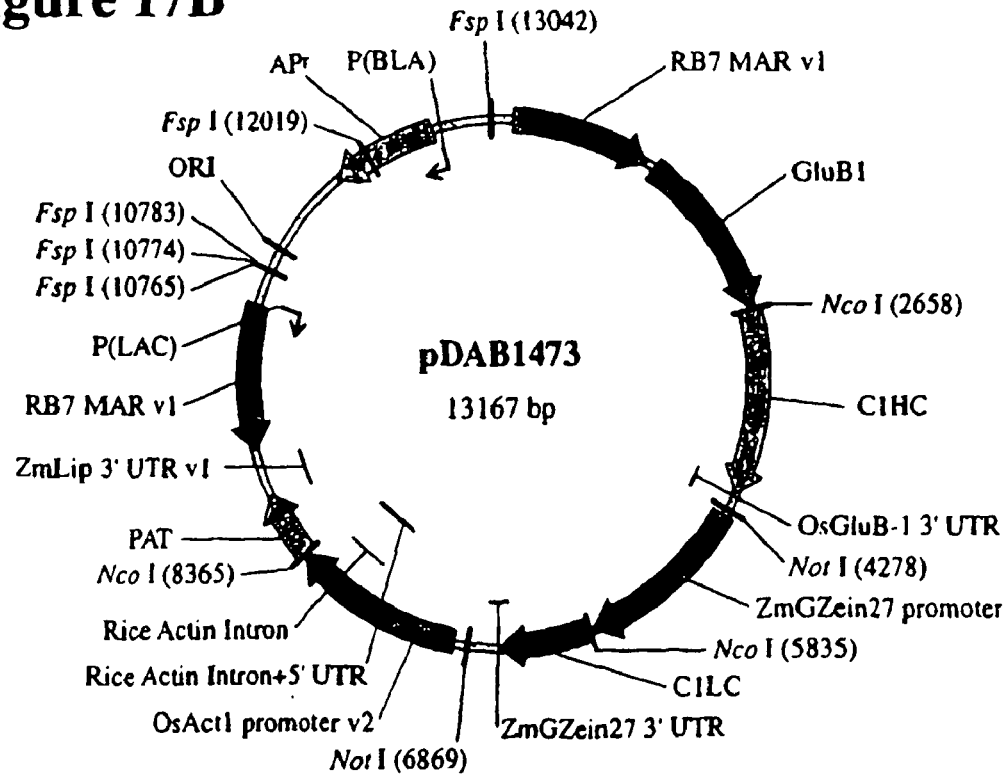

Figure 19

C1-660 IgG

| m/z theor. | m/z /obs. | Glycan (glycopeptide) | Comment |
|---|---|---|---|
| 1189.51 | 1189.47 | no glycans | Asn converts to Asp with mass-shift of +1 Da after PNGase-A treatment; obs. M/z = 1190.65 strong signal |
| 1392.59 | 1392.54 | N | major signal |
| 1595.67 | 1595.61 | N2 | ** |
| 1757.72 | 1757.83 | N2H | minor |
| 1889.76 | ND | N2HX | ND |
| 1903.78 | 1903.90 | N2HXF | trace |
| 1919.77 | 1919.90 | N2H2 | trace |
| 2035.82 | 2035.95 | N2HXF | * |
| 2051.81 | 2051.95 | N2H2X | * |
| 2065.83 | 2065.96 | N2H2F | * |
| 2081.82 | 2081.95 | N2H3 | minor |
| 2197.87 | 2197.99 | N2H2XF | major signal |
| 2213.86 | 2214.00 | N2H3X | ** |
| 2227.88 | 2228.01 | N2H3F | * |
| 2243.87 | 2244.02 | N2H4 | * |
| 2284.90 | 2285.03 | N3H3 | trace |
| 2359.92 | 2360.06 | N2H3XF | major signal |
| 2375.91 | 2376.07 | N2H4X | ** |
| 2389.93 | ND | N2H4F | ND |
| 2405.92 | 2406.07 | N2H5 | significant signal |
| 2521.97 | 2522.16 | N2H4XF | * |
| 2537.96 | 2538.34 | N2H5X | trace |
| 2551.98 | ND | N2H5F | ND |
| 2563.00 | 2563.16 | N3H3XF | significant signal |
| 2567.97 | 2568.18 | N2H6 | ** |
| 2684.02 | 2684.22 | N2H5XF | * |
| 2700.01 | ND | N2H6X | ND |
| 2714.03 | ND | N2H6F | ND |
| 2725.05 | 2725.24 | N3H4XF | ** |
| 2730.02 | 2730.22 | N2H7 | ** |
| 2766.08 | 2766.26 | N4H3XF | significant signal |
| 2892.07 | 2892.25 | N2H8 | *** |
| 2846.07 | ND | N2H6XF | ND |
| 2862.06 | ND | N2H7X | ND |
| 2876.08 | ND | N2H7F | ND |
| 2928.13 | 2928.32 | N4H4F | trace |
| 3008.12 | ND | N2H7XF | ND |
| 3054.12 | 3054.39 | N2H9 | trace |

NOTE: all these glycans are removed from glycopeptides by PNGase-A treatment; for single N removal is incomplete Signal intensity:  * -- S/N > 3-5, but <10
 ** -- S/N >10
 *** -- intense signal, but less intense than "minor"
 "significant signal" -- intensity between "minor" and "major"

Figure 21

C1-661 IgG

| m/z theor. | m/z /obs. | Glycan (tryptic glycopeptide) | Comment | Corresponding observed free glycan after enzymatic release (see Fig 4) | % of total intensity in MALDI of free glycans |
|---|---|---|---|---|---|
| 1189.51 | 1189.61 | no glycans | strong signal | n/a | |
| 1392.59 | 1392.59 | N | major signal | n/a | |
| 1595.67 | 1595.77 | N2 | * | n/a | |
| 1757.72 | 1757.89 | N2H | trace | ND | |
| 1889.76 | ND | N2HX | ND | ND | |
| 1903.78 | 1903.93 | N2HXF | trace | ND | |
| 1919.77 | 1919.96 | N2H2 | * | ND | |
| 2035.82 | 2036.01 | N2HXF | * | ND | |
| 2051.81 | 2052.01 | N2H2X | * | ND | |
| 2065.83 | 2066.03 | N2H2F | ** | ND | |
| 2081.82 | 2082.02 | N2H3 | * | ND | |
| 2197.87 | 2198.07 | N2H2XF | major signal | 1049.32 (trace) (1049.38 theor) | trace |
| 2213.86 | 2214.07 | N2H3X | ** | 1065.34 (1065.38 theor) | 24.3 |
| 2227.88 | 2228.09 | N2H3F | * | ND | |
| 2243.87 | 2244.08 | N2H4 | * | 1095.35 (1095.40 theor) | 10.5 |
| 2284.90 | 2285.13 | N3H3 | trace | ND | |
| 2359.92 | 2360.14 | N2H3XF | major signal | 1211.40 (1211.44 theor) | 31.0 |
| 2375.91 | 2376.14 | N2H4X | * | ND | |
| 2389.93 | ND | N2H4F | ND | ND | |
| 2405.92 | 2406.15 | N2H5 | significant signal | 1257.40 (1257.46 theor) | 24.6 |
| 2521.97 | 2522.23 | N2H4XF | * | ND | |
| 2537.96 | ND | N2H5X | ND | ND | |
| 2551.98 | ND | N2H5F | ND | ND | |
| 2563.00 | 2563.25 | N3H3XF | significant signal | 1414.46 (1414.52 theor) | 9.6 |
| 2567.97 | 2568.26 | N2H6 | ** | ND | |
| 2684.02 | ND | N2H5XF | ND | ND | |
| 2700.01 | ND | N2H6X | ND | ND | |
| 2714.03 | ND | N2H6F | ND | ND | |
| 2725.05 | 2725.32 | N3H4XF | * | ND | |
| 2730.02 | 2730.30 | N2H7 | ** | ND | |
| 2766.08 | 2766.34 | N4H3XF | significant signal | ND | |
| 2892.07 | 2892.37 | N2H8 | ** | ND | |
| 2846.07 | ND | N2H6XF | ND. | ND | |
| 2862.06 | ND | N2H7X | ND | ND | |
| 2876.08 | ND | N2H7F | ND | ND | |
| 2928.13 | 2928.40 | N4H4XF | trace | ND | |
| 3008.12 | ND | N2H7XF | ND | ND | |
| 3054.12 | ND | N2H9 | ND | ND | |

Signal intensity:
* -- S/N > 3-5, but <10
** -- S/N >10
*** -- intense signal, but less intense than "minor"
"significant signal" -- intensity between "minor" and "major"

Figure 23

C1-663 IgG

| m/z theor. | m/z /obs. | Glycan (glycopeptide) | Comment |
|---|---|---|---|
| 1189.51 | 1189.38 | no glycans | Asn converts to Asp with mass-shift of +1 Da after PNGase-A treatment; obs. M/z = 1190.59  strong signal |
| 1392.59 | 1392.45 | N | major signal |
| 1595.67 | 1594.72 | N2 | * |
| 1757.72 | 1757.84 | N2H | trace |
| 1889.76 | ND | N2HX | ND |
| 1903.78 | ND | N2HXF | ND |
| 1919.77 | 1919.90 | N2H2 | trace |
| 2035.82 | 2035.95 | N2HXF | * |
| 2051.81 | 2051.95 | N2H2X | * |
| 2065.83 | 2065.97 | N2H2F | * |
| 2081.82 | 2081.97 | N2H3 | * |
| 2197.87 | 2198.01 | N2H2XF | major signal |
| 2213.86 | 2214.01 | N2H3X | ** |
| 2227.88 | 2228.02 | N2H3F | * |
| 2243.87 | 2244.02 | N2H4 | * |
| 2284.90 | ND | N3H3 | ND |
| 2359.92 | 2360.07 | N2H3XF | major signal |
| 2375.91 | 2376.09 | N2H4X | * |
| 2389.93 | ND | N2H4F | ND |
| 2405.92 | 2406.08 | N2H5 | *** |
| 2521.97 | 2522.16 | N2H4XF | * |
| 2537.96 | ND | N2H5X | ND |
| 2551.98 | ND | N2H5F | ND |
| 2563.00 | 2563.18 | N3H3XF | significant signal |
| 2567.97 | 2568.18 | N2H6 | ** |
| 2684.02 | ND | N2H5XF | ND |
| 2700.01 | ND | N2H6X | ND |
| 2714.03 | ND | N2H6F | ND |
| 2725.05 | 2725.28 | N3H4XF | * |
| 2730.02 | 2730.24 | N2H7 | * |
| 2766.08 | 2766.27 | N4H3XF | significant signal |
| 2846.07 | ND | N2H6XF | ND |
| 2862.06 | ND | N2H7X | ND |
| 2876.08 | ND | N2H7F | ND |
| 2892.07 | 2892.29 | N2H8 | *** |
| 2928.13 | ND | N4H4XF | ND |
| 3008.12 | ND | N2H7XF | ND |
| 3054.12 | ND | N2H9 | ND |

NOTE: all these glycans are removed from glycopeptides by PNGase-A treatment; for single N removal is incomplete Signal intensity:   * -- S/N > 3-5, but <10
                  ** -- S/N >10
                  *** -- intense signal, but less intense than "minor"
                  "significant signal" -- intensity between "minor" and "major"

Figure 25

(CHO-expressed)

| m/z theor. | m/z /obs. | Glycan (glycopeptide) | Comment | |
|---|---|---|---|---|
| 1189.51 | 1189.63 | no glycans | Asn converts to Asp with mass shift of +1 Da after PNGase-A treatment; obs. M/z = 1190.49 | |
| 1392.59 | 1392.74 | N | ** | |
| 1595.67 | 1595.38 | N2 | * | |
| 1757.72 | 1757.41 | N2H | * | |
| 1919.77 | 1919.44 | N2H2 | * | |
| 2065.83 | 2065.48 | N2H2F | * | |
| 2081.82 | 2081.48 | N2H3 | * | |
| 2227.88 | 2227.51 | N2H3F | * | |
| 2243.87 | 2243.51 | N2H4 | * | |
| 2268.91 | 2268.52 | N3H2F | significant signal | |
| 2284.90 | 2284.52 | N3H3 | ** | |
| 2389.93 | 2389.54 | N2H4F | * | |
| 2405.92 | 2405.52 | N2H5 | significant signal | |
| 2430.96 | 2430.55 | N3H3F | significant signal | |
| 2446.95 | 2446.55 | N3H4 | * | |
| 2487.98 | 2487.56 | N4H3 | significant signal | |
| 2551.98 | 2552.57 | N2H5F | trace | |
| 2567.97 | 2567.57 | N2H6 | * | |
| 2593.01 | 2592.60 | N3H4F | minor | |
| 2609.00 | 2608.60 | N3H5 | ** | |
| 2634.04 | 2633.61 | N4H3F | major signal | free glycan also observed after release (M/Na+ = 1485.87) |
| 2650.03 | 2649.58 | N4H4 | minor | |
| 2714.03 | ND | N2H6F | ND | |
| 2730.02 | 2730.61 | N2H7 | trace | |
| 2755.06 | 2754.64 | N3H5F | ** | |
| 2771.05 | 2770.64 | N3H6 | ** | |
| 2796.09 | 2795.64 | N4H4F | major signal | free glycan also observed after release (M/Na+ = 1647.96) |
| 2812.08 | 2811.63 | N4H5 | trace | |
| 2876.08 | ND | N2H7F | ND | |
| 2892.07 | ND | N2H8 | ND | |
| 2933.10 | 2932.67 | N3H7 | * | |
| 2958.14 | 2957.68 | N4H5F | significant signal | |
| 3054.12 | ND | N2H9 | ND | |
| 3120.19 | 3119.73 | N4H6F | minor | |
| 3282.24 | 3281.76 | N4H7F | *** | |

NOTE: glycans are removed from glycopeptides by PNGase-A treatment; for single N removal is incomplete Signal intensity:  * -- S/N > 3-5, but <10
                ** -- S/N >10
                *** -- intense signal, but less intense than "minor"
                "significant signal" -- intensity between "minor" and "major"

PLANT PRODUCTION OF IMMUNOGLOBULINS WITH REDUCED FUCOSYLATION

CROSS REFERENCE TO RELATED APPLICATIONS

This application is a 371 filing of PCT/US2003/037905 filed Nov. 28, 2003, which claims priority to U.S. Provisional Application No. 60/429,385 filed Nov. 27, 2002, each of which are herein incorporated by reference in their entireties.

FIELD OF THE INVENTION

This invention relates generally to the production of immunoglobulin compositions in plants, wherein at least a portion of the glycans attached to the plant-produced immunoglobulins lack fucose. This invention also relates generally to the production of monomeric antibody compositions in plants, wherein at least a portion of the glycans attached to the plant-produced monomeric antibodies lack fucose. An immunoglobulin produced by the methods of the present invention can be of any class (IgG, IgA, IgM, IgE, IgD, etc.) or isotype. In addition, this invention also relates to the production of monomeric immunoglobulin A (monomeric IgA) antibody compositions in plants, wherein the monomeric IgA antibodies lack fucose by virtue of missing the antibody tailpiece which has the only glycosylation site typically fucosylated. This invention also relates to the production of anti-herpes simplex virus (HSV) monomeric immunoglobulin A (anti-HSV monomeric IgA) antibody compositions in plants, wherein at least a portion of the glycans attached to the anti-HSV monomeric IgA antibodies lack fucose by virtue of missing the antibody tailpiece which has the only glycosylation site typically fucosylated. In addition, this invention also relates to the production of monomeric immunoglobulin G (monomeric IgG) antibody compositions in plants. This invention also relates to the production of anti-alpha-v-beta3, alpha-v-beta5 (i.e., αVβ3 and αVβ5) dual integrin IgG antibody compositions in plants, wherein at least a portion of the glycans attached to the plant-produced antibody compositions lack fucose. The invention also provides the constructs; plasmids; vectors; transformed plant cells, plant calli, plant tissues, plantlets, seeds and whole plants used to produce all such immunoglobulins and antibodies; the methods of producing such immunoglobulins and antibodies; the immunoglobulins and antibodies produced by the disclosed methods; and the use of such immunoglobulins and antibodies.

BACKGROUND OF THE INVENTION

All referenced publications and patent applications herein are incorporated by reference to the same extent as if each individual publication or patent application was specifically and individually indicated to be incorporated by reference.

The following description includes information that may be useful in understanding the present invention. It is not an admission that any of the information provided herein is prior art or relevant to the presently claimed inventions, or that any publication specifically or implicitly referenced is prior alt.

Increasingly, greater attention is being focused on the production and use of larger and more complex protein molecules as therapeutic agents. Examples of such therapeutic proteins include antigens used in vaccinations to induce immune responses and antibodies.

Plants have great potential as hosts for the production of mammalian therapeutic proteins including multimeric proteins such as antibodies. See, for example, Hiatt, A. et al., Nature 342(6245):76-78 (1989); Hein et al., Biotechnol. Prog. 7(5):455-461 (1991); Hiatt, A., and Ma, J. K., FEBS Lett 307(1):71-5 (1992); Ma et al., Eur. J. Immunol. 24:131-138 (1994); Ma et al., TIBTECH 13:522-527 (1995); Zeitlin et al., Nature Biotechnology 16(1361-1364 (1998); Ma, H. K.-C et al. Nature Medicine 4(5):601-606 (1998); Miele, L., Trends Biotechnol. 15: 45-50 (1997); Khoudi et al., Biotechnology and Bioengineering 64(2):135-143 (1999); and, Hood, E. E. & Jilka, J. M., Curr. Opin. Biotechnol. 10: 382-386 (1999). The benefits of using plants for antibody production include large scale production, reduced costs for production, maintenance and delivery as well as eliminating the risk of the resultant product containing possibly harmful contaminants such as viruses or prions that are pathogenic to humans and other mammals. Plants, like other heterologous expression systems including mammalian cells, bacteria, yeast, and insects, exhibit differences in glycosylation. See, for example, Ma et al., Science 268:716-719 (1995); Jenkins et al., Nat. Biotechnol. 14: 975-981 (1996); and Lerouge et al., Plant Mol. Biol. 38: 31-48 (1998).

In plants, as in other eukaryotes, most of the soluble and membrane bound proteins that are synthesized on polyribosomes associated with the endoplasmic reticulum (ER) are glycoproteins, including those proteins which will later be exported to the Golgi apparatus, lysosomes, plasma membrane or extracellular matrix. The glycans attached to glycoproteins contain a variety of sugar residues linked in linear or branched structures that can assume many different conformations. These glycans can play a fundamental role in promoting correct protein folding and assembly and, as a consequence, enhance protein stability. They may also contain targeting information, or may be directly involved in protein recognition (Maia et al., Genetics and Molecular Biology 24: 231-234 (2001)). The three main posttranslational modifications of proteins that involve carbohydrates are N- and O-linked glycosylation and the insertion of glycosyl phosphatidyl inositol anchors.

The N-linked glycosylation mechanisms in mammalian and plant systems have been conserved during evolution. However, differences are observed in the final steps of oligosaccharide trimming and glycan modification in the Golgi apparatus. In contrast to bacteria, having no N-linked glycans, and yeast, having polymannose glycans, plants produce glycoprotein multimers with complex N-linked glycans having a core substituted by two N-acetylglucosamine (GlcNAc) residues. These glycoprotein multimers are also observed in mammals. See, for example, Kornfeld and Kornfeld, Ann. Rev. Biochem. 54:631 (1985). Plant and animal glycopolypeptide multimers contain different terminal carbohydrates that are directly linked to the outer branches of the oligosaccharides present. Animal glycopolypeptide multimers, including mammalian glycopolypeptide multimers, have sialic acid present as a terminal carbohydrate residue, while plant glycopolypeptide multimers do not. The terminal core is substituted by β1,2-linked xylose (Xyl) and α1,3-linked core fucose (Fuc) instead of α1,6-linked core fucose as occur in mammals. Furthermore, plant glycoprotein multimers lack the characteristic galactose (Gal)- and sialic acid-containing complex N-glycans (N-acetylneuraminic-α2-6/3Galβ1-4) found in mammals. See, for example, Sturm et al., J. Biol. Chem: 262:13392 (1987). A murine monoclonal antibody produced in transgenic plants with plant-specific glycans was found not to be immunogenic in mice (Chargelegue et al., Transgenic Research 9:187-194 (2000)).

Antibodies have conserved N-linked glycosylation of the Fc region of each of the two heavy chains. Human IgA antibodies have O-linked oligosaccharides in their hinge portion and two N-linked carbohydrate chains; one occurring on an asparagine (Asn) residue in the CH2 region of the heavy chain and the other on an Asn residue in the tailpiece region. See, for example, Baenzinger, J. and Kornfield, S. J., Biol. Chem. 249:7260-7269 (1974); and Torano et al., PNAS 74:2301-2305 (1997). Fucosylation of the IgA isolated from human serum occurs only on the Asn in the tailpiece region (Tanaka et al., Glycoconj. J. 10: 995-1000 (1998)).

Hiatt et al. have produced transgenic plants expressing nucleotide sequences encoding individual or assembled immunoglobulin heavy- and light-chain immunoglobulin polypeptides. Each immunoglobulin product was expressed as a proprotein containing a leader sequence forming a sequence which directs the protein into the endosecretory pathway allowing correct assembly and glycosylation of the antibody molecule. The leader sequence is cleaved from the mature protein. See, for example, U.S. Pat. Nos. 5,202,422; 5,639,947 and 6,417,429. Methods for the coordinated expression and production of secretory immunoglobulins containing heavy chain, light chain, J chain and secretory component polypeptides which are assembled into functional antibodies have been disclosed. See, for example, U.S. Pat. Nos. 5,959,177; 6,046,037 and 6,303,341. Each of the U.S. patents cited herein is incorporated by reference in its entirety. A murine immunoglobulin transmembrane sequence was used for plasma membrane targeting of recombinant immunoglobulin chains in plants (Vine et al., Plant Molecular Biology 45:159-167 (2001)).

SUMMARY OF THE INVENTION

The importance of this invention centers around simplifying the immunoglobulin profile for the manufacturing of immunoglobulin compositions in plants. In one aspect, this invention provides the materials and methods to produce immunoglobulins in plants, wherein at least some of the glycans attached to the immunoglobulins are not fucosylated (i.e., at least one of the glycans lack fucose and/or the immunoglobulins are at least partly afucosylated). In another aspect, this invention provides the materials and methods to produce monomeric immunoglobulins in plants, wherein at least some of the immunoglobulins comprise glycans which are afucosylated. Thus, in one aspect, this invention provides the materials and methods to produce IgA, IgD, IgE, IgG and IgM compositions in plants, wherein the compositions comprise at least one glycan structure that lacks fucose. In yet another aspect, this invention provides the materials and methods to produce immunoglobulins in plants, wherein the heavy chain of the immunoglobulins lack a tailpiece.

In one aspect, the mixture of immunoglobulins produced by the materials and methods of the present invention can be said to be pauci-fucosylated or deminimus fucosylated, indicating that some, most or all of the immunoglobulins so produced lack fucosylation. In another aspect, the mixture of immunoglobulins produced by the materials and methods of the instant invention can be used as such or, alternatively, the afucosylated immunoglobulins can be separated from the mixture of immunoglobulins and used separately.

In another aspect, the invention also produces the materials and methods for treating herpes simplex virus ("HSV") or tumor angiogenesis by administration of the immunoglobulins produced by the plants, wherein at least one of the glycan structures of the immunoglobulins lack fucose.

In another aspect of the invention, expression of the immunoglobulins is accomplished using a single vector comprising nucleic acids encoding both the light chain and heavy chain.

In one aspect, this invention provides plant-produced immunoglobulins, wherein the immunoglobulins have glycopeptide profiles comprising a least one glycopeptide which lacks fucose. In another aspect, this invention provides such immunoglobulins wherein the at least one glycopeptide comprises an asparagine (Asn) residue.

In one aspect, this invention provides a plant-produced heavy chain (HC) or light chain (LC) of an immunoglobulin, wherein the HC or LC has a glycopeptide profile comprising at least one glycopeptide which lacks fucose. In yet another aspect, the HC has at least one glycopeptide comprising an asparagine (Asn) residue in the CH2 region.

In one aspect, this invention provides a plant-produced immunoglobulin, wherein the immunoglobulin has a free glycan profile comprising a least one glycan which lacks fucose. In another aspect, this invention provides such immunoglobulins which comprise an asparagine (Asn) residue.

In yet another aspect, the glycan profile is the same as or substantially the same as that provided in FIG. 12. In one aspect, the glycan is selected from the group consisting of 3Man, 2GlcNAc, 1Xyl; 2 Man, 2GlcNAc, 1Xyl; 3Man, 3GlcNAc, 1Xyl; 3Man, 2GlcNAc; 3Man, 3GlcNAc; 4Man, 2GlcNAc; 5 Man, 2GlcNAc; and 6Man, 2GlcNAc, wherein Man=Mannose, GlcNAc=N-acetylglucosamine and Xyl=xylose. In still another aspect, the glycan selected is selected 3Man, 2GlcNAc, 1Xyl or 2 Man, 2GlcNAc, 1Xyl, wherein Man=Mannose, GlcNAc=N-acetylglucosamine and Xyl=xylose.

In yet another aspect, the glycan profile is the same as or substantially the same as one of the glycan profiles provided in FIG. 16. In still another aspect, the glycan is selected from the group consisting of H2N2X; H3N2; and H3N2X, wherein H=hexose, N=HexNAc=N-acetylhexose and X=xylose. In yet another aspect, the glycan is selected from the group consisting of N2H8; N2H3X; N2H3X; N2H4X; N2H5; N2H6; N2H7; N2H8; N3H3X; N2H4; and N2H5, wherein H=hexose, N=HexNAc=N-acetylhexose and X=xylose. In one aspect of this invention, for each of these immunoglobulins the hexose is mannose and the N-acetylhexose is N-acetylglucosamine.

In one aspect of this invention, the immunoglobulins detailed herein can be any immunoglobulin selected from the group consisting of IgG, IgA, IgM, IgE and IgD. In one aspect, the immunoglobulin of interest is IgA or IgG. For example, in one aspect of the invention, the immunoglobulin is an IgA antibody with a heavy chain and a light chain. A specific example of such an IgA is an anti-herpes simplex virus antibody. In another example, the immunoglobulin is an IgG antibody with a heavy chain and a light chain. A specific example of such an IgG is an anti-dual integrin antibody, such as an anti-αVβ3, αVβ5 dual integrin antibody.

In one aspect, the glycan profile of the immunoglobulins of the present invention is the same as or substantially the same as the glycan profile provided in FIG. 19, or FIG. 21, or FIG. 23.

In one aspect, this inventions provides plant-produced immunoglobulins comprising at least one attached glycan without a terminal fucose. In yet another aspect, such immunoglobulins comprise an asparagine (Asn) residue in the CH2 region.

In one aspect, this invention provides a plant-produced immunoglobulin having a glycan profile which comprises at least one glycan lacking fucose, wherein the glycan profile is determined using matrix-assisted laser desorption/ionization time-of-flight mass spectrometry (MALDI-Tof MS) analysis of free N-linked glycans enzymatically-released from the immunoglobulin. An example of such an immunoglobulin is IgA, such as an anti-herpes simplex virus antibody. In another aspect, an example of such an immunoglobulin is IgG, such as an anti-dual integrin antibody. An example of such an anti-dual integrin antibody is an anti-αVβ3, αVβ5 dual integrin antibody.

In one aspect, this invention provides a plant cell, plant tissue, plant callus, plantlet, whole plant or seed comprising the immunoglobulins described and disclosed herein. In one aspect, the plant cell, plant tissue, plant callus, or seed are those of a monocotyledonous plant. In another aspect, this invention provides the plant cell, plant tissue, plant callus, or seed wherein the monocotyledonous plant is a maize plant. In yet another aspect, this invention provides the plantlet or whole plant wherein the plantlet or whole plant are monocotyledonous. For example, the plant cell, plant tissue, plant callus, or seed of the present invention can be those of a maize plant.

In one aspect, the immunoglobulins of the present invention can be located in the endosperm of the seed.

In one aspect, the immunoglobulins of the present invention can be human immunoglobulins.

In one aspect, the immunoglobulins of the present invention have a heavy chain lacking a tailpiece. In one aspect, such immunoglobulins are IgA antibodies, such as an anti-herpes simplex virus antibody.

In one aspect, the immunoglobulin provided by the present invention are isolated from the plant used to produce the immunoglobulin.

In one aspect, this invention provides a monomeric antibody composition comprising at least one glycan having structure number 1 (3Man, 2GlcNAc, 1Xyl) as provided in FIG. 12, wherein Man=mannose, GlcNAc—acetylglucosamine and Xyl=xylose.

In another aspect, this invention provides a monomeric antibody composition comprising at least one glycan having structure number 2 (2Man, 2GlcNAc, 1Xyl) as provided in FIG. 12, wherein Man=mannose, GlcNAc—acetylglucosamine and Xyl=xylose.

In one aspect, this invention provides a plant-produced immunoglobulin comprising an amino acid fragment lacking an attached glycan with fucose, wherein the immunoglobulin has an attached glycan with fucose on the same amino acid fragment or on substantially the same amino acid fragment when the immunoglobulin is mammalian-produced.

In one aspect, this invention provides a plant-produced immunoglobulin comprising a glycan profile for a specified amino acid fragment, wherein the immunoglobulin has the same or substantially the same glycan profile for the same amino acid sequence or for substantially the same amino acid fragment when the immunoglobulin is mammalian-produced.

In one aspect, this invention provides a plant-produced immunoglobulin comprising an amino acid fragment having an attached glycan lacking fucose, wherein the immunoglobulin also lacks an attached glycan with fucose on the same amino acid fragment or on substantially the same amino acid fragment when the immunoglobulin is mammalian-produced.

In one aspect, this invention provides a plant-produced immunoglobulin, wherein the immunoglobulin has a free glycan profile comprising a glycan lacking fucose, wherein the immunoglobulin has a free glycan profile comprising the same glycan also lacking fucose when the immunoglobulin is mammalian-produced.

In one aspect, this invention provides such immunoglobulins wherein the mammalian-produced immunoglobulin is produced in a CHO cell.

In one aspect, the invention provides such immunoglobulins wherein the plant-produced immunoglobulin is produced in a maize cell and the mammalian-produced immunoglobulin is produced in a CHO cell.

In one aspect, this invention provides a method of producing a transformed plant cell expressing an immunoglobulin having at least one attached glycan without fucose, said method comprising transforming a plant cell by introducing into the plant cell a single vector comprising a nucleic acid sequence encoding a heavy chain and a light chain of the immunoglobulin, each nucleic acid being operably-linked to a promoter, and culturing the transformed plant cell to produce a plant cell expressing the immunoglobulin having at least one attached glycan without fucose. In yet another aspect, this invention further provides methods of isolating the immunoglobulin from the transformed plant cell. In another aspect, this invention provides methods of regenerating transformed plant calli or a transformed whole plant from the transformed plant cell. In yet another aspect, this invention provides methods for isolating the immunoglobulin from the transformed plant calli or transformed whole plant. In still another aspect, this invention provides such methods wherein the sequences for the heavy chain and the light chain are operably-linked to the same promoter. In still another aspect, this invention provides such methods wherein the sequences for the heavy chain and the light chain are operably-linked to a different promoter. In one aspect, this invention provides such methods wherein the promoter is a constitutive promoter. For example, the 35S CaMV promoter or the maize ubiquitin-1 promoter can be used in the methods of the present invention. In yet another aspect, the methods of the present invention utilize seed-specific promoters. In still another aspect, the invention utilizes endosperm-specific promoters.

In one aspect, this invention provides such methods wherein the vector is selected from the group consisting of pDAB8505; pDAB1472; pDAB1473; pDAB1474; and pDAB1475.

In one aspect, this invention provides the vectors pDAB8505; pDAB1472; pDAB1473; pDAB1474; and pDAB1475.

In one aspect, this invention provides such methods wherein the plant cell is transformed using an *agrobacterium*-mediated transformation method or a WHISKERS™ transformation method.

In one aspect, this invention provides a method of producing an isolated a monomeric anti-herpes simplex virus antibody comprising: (i) introducing into a plant cell nucleic acids having either SEQ ID NO: 1 or either SEQ ID NO: 5 and SEQ ID NO: 9 or SEQ ID NO: 13, each of which is operably-linked to a promoter, to produce a transformed plant cell; (ii) culturing the transformed plant cell to express the introduced nucleic acids; and (iii) isolating the monomeric anti-herpes simplex virus antibody produced by the plant cell. In one aspect, this invention further provides such methods including regenerating a transformed plant from the transformed plant cell.

In one aspect, this invention provides a nucleic acid molecule comprising a nucleic acid sequence selected from the group consisting of SEQ ID NO: 15 (pDAB635); SEQ ID NO: 16 (pDAB16); SEQ ID NO: 17 (pDAB637); SEQ ID NO: 84 (pDAB3014); and SEQ ID NO: 85 (pDAB8505).

In one aspect, this invention provides an isolated nucleic acid molecule comprising a nucleic acid sequence encoding the amino acid encoded by SEQ ID NO: 10 or SEQ ID NO: 14.

In one aspect, this invention provides an isolated nucleic acid molecule comprising SEQ ID NO: 1 or SEQ ID NO: 5.

In one aspect, this invention provides an isolated nucleic acid molecule comprising SEQ ID NO: 9 or SEQ ID NO: 13.

In one aspect, this invention provides an isolated vector or plasmid comprising SEQ ID NO: 1 or SEQ ID NO: 5.

In one aspect, this invention provides an isolated nucleic acid molecule comprising a nucleic acid sequence encoding the amino acid encoded by SEQ ID NO: 2 or SEQ ID NO: 6.

In another aspect, the immunoglobulins of the present invention having heavy chain comprising the amino acid sequence of SEQ ID NO: 6. In yet another aspect, the immunoglobulins of the present invention have a light chain comprising the amino acid sequence of SEQ ID NO: 14.

In one aspect, this invention provides an isolated vector or plasmid comprising SEQ ID NO: 9 or SEQ ID NO: 13.

It will be appreciated from the above that the tools and methods of the present invention have application to all plants that produce gametes. Such plants include, but are not limited to, dicots and monocots including herbs, forage grasses, turf grasses, forage legumes (e.g., alfalfa), vegetables, agronomic crop plants (e.g., maize and soybean), trees and ornamental flowers.

Other objects, advantages and features of the present invention become apparent to one skilled in the art upon reviewing the specification and the drawings provided herein.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown.

In the Drawings

FIG. 16A to 16G. Summary of glycan profiling of IgA-HX8 expressed in transgenic maize (different events). Pictorial representations of suggested glycan structures are also included, wherein 'H' or a circle=hexose (Man, Gal, Glc); 'N' or a rectangle=HexNAc (GlcNAc or GalNAc); 'X' or a cross=xylose; 'F' or a triangle=fucose; and 'P'=phosphate (PO3). Note: the percentage (%) of glycans based on peak heights in MALDI mass-spectra are provided only for reference and cannot be used for accurate quantitation.

FIG. 17A. Plasmid pDAB1472 (FIG. 17A) and pDAB1473 (FIG. 17B).

FIG. 19. Glycoforms observed for event 660 for IgG. All glycans were removed from glycopeptides by PNGase-A treatment. For single N, removal is incomplete. Codes: 'H'=hexose (Man, Gal, Glc); 'N'=HexNAc (GlcNAc or GalNac); 'X'=xylose; and 'F'=fucose.
Signal intensity:
*=S/N>3–5, but <10;
**=S/N>10;
=intense signal, but less than "minor"; and
"significant signal"=intensity between "minor" and "major".

FIG. 21. Glycoforms observed for event 661 for IgG. All glycans were removed from glycopeptides by PNGase-A treatment. For single N, removal is incomplete. Codes: 'H' or circle=hexose (Man, Gal, Glc); 'N' or rectangle=HexNAc (GlcNAc or GalNac); 'X' or cross=xylose; and 'F' or triangle=fucose.
Signal intensity:
*=S/N>3–5, but <10;
**=S/N>10;
***=intense signal, but less than "minor"; and
"significant signal"=intensity between "minor" and "major".

FIG. 22D. N-glycans released from H-T27 glycopeptide. MALDI MS of free glycans. Intensities in this MALDI mass-spectrum are roughly proportional to abundance of the neutral N-glycans. Note: single and double GlcNAc are not accounted for.

FIG. 23. Glycoforms observed for event 663 for IgG. All glycans were removed from glycopeptides by PNGase-A treatment. For single N, removal is incomplete. Codes: 'H'=hexose (Man, Gal, Glc); 'N'=HexNAc (GlcNAc or GalNac); 'X'=xylose; and 'F'=fucose.
Signal intensity:
*=S/N>3–5, but <10;
**=S/N>10;
***=intense signal, but less than "minor"; and
"significant signal"=intensity between "minor" and "major".

FIG. 25. Glycoforms observed for CHO-expressed IgG. All glycans were removed from glycopeptides by PNGase-A treatment. For single N, removal is incomplete. Codes: 'H'=hexose (Man, Gal, Glc); 'N'=HexNAc (GlcNAc or GalNac); 'X'=xylose; 'F'=fucose.
Signal intensity:
*=S/N>3–5, but <10;
**=S/N>10;
***=intense signal, but less than "minor"; and
"significant signal"=intensity between "minor" and "major".

DETAILED DESCRIPTION

Figure 1:
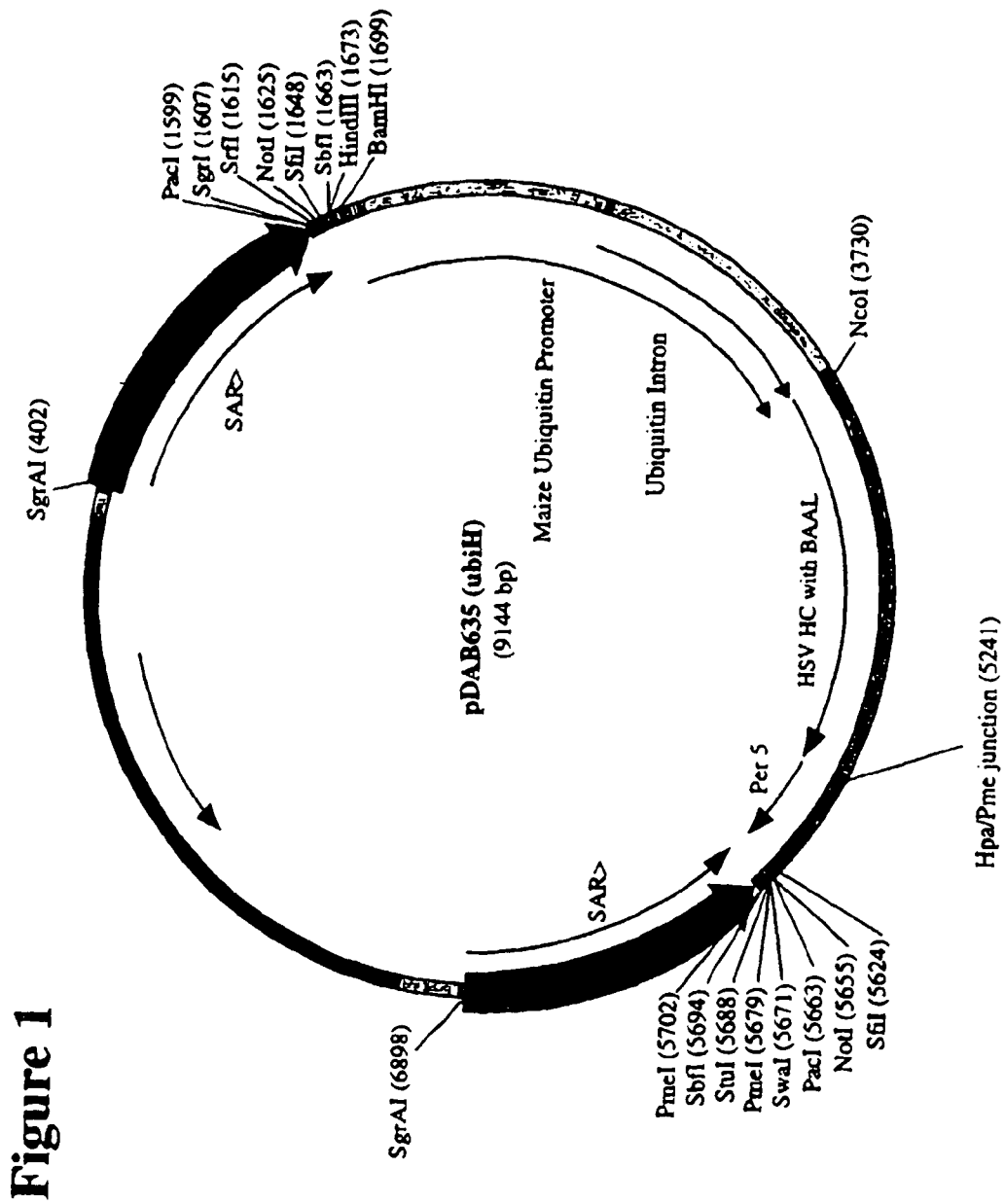
FIG. 1. Plasmid for pDAB635 (ubiH). (SEQ ID NO: 15).
SAR nucleotides: 424-1589
Maize ubiquitin promoter/intron nucleotides: 1717-3730
Anti-HSV heavy chain nucleotides: 3732-5240
(w/barley alpha amylase leader)
Maize per5 3' UTR nucleotides: 5248-5612
SAR nucleotides: 5720-6885

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

I. Definitions

As used herein, the terms "afucosylated" and "afucosylation" refer to situations where fucose is absent from a particular glycan, glycan fraction, glycopeptide or glycopeptide fraction which is attached to an immunoglobulin, portion of an immunoglobulin, an antibody or a portion of an antibody. The use of the terms "afucosylated" and "afucosylation" herein is not meant to imply any specific mechanism, molecular or otherwise, by which a fucose is either prevented from attaching or removed after attachment. Thus, the use of the terms herein is not meant to imply that the fucose has been eliminated by any particular one of the following mechanisms: transcriptionally, translationally or post-translationally.

As used herein, the term "agronomic crop plant" refers to any crop plant grown on a production scale, most typically for the harvest of seed, silage or hay. Examples include, but are not limited to maize, soybeans, rye, wheat, oats, barley, lentils, dry peas, rape, sorghum, alfalfa, triticale, clover, and the like.

As used herein, the term "allele" refers to any of several alternative forms of a gene.

As used herein, the term "amino acid" refers to the aminocarboxylic acids that are components of proteins and peptides. The amino acid abbreviations used in Tables 6 and 7 and elsewhere herein are as follows:

| | | | | | | | | | |
|---|---|---|---|---|---|---|---|---|---|
| A | (Ala) | C | (Cys) | D | (Asp) | E | (Glu) | F | (Phe) |
| G | (Gly) | H | (His) | I | (Iso) | K | (Lys) | L | (Leu) |
| M | (Met) | N | (Asn) | P | (Pro) | Q | (Gln) | R | (Arg) |
| S | (Ser) | T | (Thr) | V | (Val) | W | (Trp) | Y | (Tyr) |

As used herein, an "anti-alpha-v-beta3, alpha-v-beta5 dual integrin antibody," "anti-dual integrin antibody," "anti-dual integrin antibody portion," "anti-$\alpha V\beta 3$, anti-$\alpha V\beta 5$," "anti-$\alpha_v\beta_3$, anti-$\alpha_v\beta_5$," or "anti-dual integrin antibody fragment" and/or "anti-dual integrin antibody variant" and the like include any protein or peptide containing molecule that comprises at least a portion of an immunoglobulin molecule, such as but not limited to at least one complementarity determining region (CDR) of a heavy or light chain or a ligand binding portion thereof, a heavy chain or light chain variable region, a heavy chain or light chain constant region, a framework region, or any portion thereof, or at least one portion of an dual integrin receptor or binding protein, which can be incorporated into an antibody of the present invention.

As used herein, the term "antibody" refers to a protein normally produced in the body (human or animal) in response to contact with a pathogen or other moiety not recognized as "self." Antibodies (such as, for example, IgG and sIgA) and antibody fragments (such as, for example, Fab and ScFv) have the specific capacity of neutralizing, hence creating immunity to, the pathogen. An antibody molecule is composed of four polypeptide chains: two identical heavy chains (HC) and two identical light chains (LC). Each "arm" of the Y antibody configuration comprises one light chain and part of one heavy chain; the hinge region allows the arms to move; and the "stem" is formed by the rest of the two heavy chains (See FIG. 13). Each arm region of the Y serves as an antigen-binding site, with the binding sites associated with the variable regions of the polypeptide. The HC and LC are held together by disulfide bridges. Secretory antibodies are also comprised of a joining chain (JC) and a secretory component (SC).

As used herein, the term "antigen" refers to any substance capable of inducing a specific immune response and of reacting with the resulting antibodies produced by that response.

As used herein, the term "antiviral" refers to a substance that interferes with the replication of a virus.

As used herein, the terms "backbone plasmids" or "backbone vectors" refer to plasmids that contain all of the necessary elements for expression of the gene(s) of interest, including MAR sequences, promoter, 3' UTR, selectable marker gene cassette and unique restriction sites for the single-step addition of the antibody coding regions. Another characteristic of the backbone vectors is the presence of unique restriction sites for the efficient removal of the antibiotic resistance gene.

As used herein, the terms "beta-glucuronidase" or "GUS" refer to the screenable marker gene routinely used in plant transformation studies that comes from *Escherichia coli*. See, for example, Jefferson, R., et al., Proc. Nat. Acad. Sci. USA 83: 8447-8451 (1986); Jefferson, R., et al., EMBO J. 6: 3901-3907 (1987); Jefferson, R., Plant Mol. Biol. Rep. 5: 387-405 (1987); and Jefferson, R., Plant Mol. Biol. Rep. 5:387-405 (1988).

As used herein, the term "crop plant" refers to any plant grown for any commercial purpose, including, but not limited to the following purposes: seed production, hay production, ornamental use, fruit production, berry production, vegetable production, oil production, protein production, forage production, animal grazing, golf courses, lawns, flower production, landscaping, erosion control, green manure, improving soil tilth/health, producing pharmaceutical products/drugs, producing food additives, smoking products, pulp production and wood production.

As used herein, the term "cross pollination" or "cross-breeding" when used in reference to plants means the process by which the pollen of one flower on one plant is applied (artificially or naturally) to the ovule (stigma) of a flower on another plant.

As used herein, the term "cultivar" when referring to plants means a variety, strain or race of plant that has been produced by horticultural or agronomic techniques and is not normally found in wild populations.

As used herein, the terms "dicotyledon" and "dicot" refer to a flowering plant having an embryo containing two seed halves or cotyledons. Examples include tobacco; tomato; the legumes, including peas, alfalfa, clover and soybeans; oaks; maples; roses; mints; squashes; daisies; walnuts; cacti; violets and buttercups.

As used herein, the term "dimeric antibody" or "dIgA" refers to an antibody comprising two monomeric antibodies linked by a J chain. Thus, a "dimeric IgA" or "dIgA" comprises two monomeric IgA antibodies linked by a J chain (See FIG. 13B); and, a "dimeric anti-HSV IgA" or "anti-HSV dIgA" comprises two monomeric IgA antibodies to a herpes simplex virus linked by a J chain.

As used herein, the term "endosperm" refers to a triploid structure resulting from the development of a fusion between two polar nuclei of the embryo sac and one of the sperm nucleus from the pollen found in many plant seeds. The endosperm frequently stores food materials, which are broken down during germination.

As used herein, the term "filial generation" refers to any of the generations of plant cells, tissues or organisms following a particular parental generation. The generation resulting from a mating of the parent plants is the first filial generation (designated as "F1" or "$F_1$"), while that resulting from crossing of F1 plants is the second filial generation (designated as "F2" or "$F_2$").

The term "gamete" refers to a reproductive cell whose nucleus (and often cytoplasm) fuses with that of another gamete of similar origin but of opposite sex to form a zygote, which has the potential to develop into a new individual plant. Gametes are typically haploid and are differentiated into male and female.

The term "gene" refers to any segment of DNA associated with a biological function. Thus, genes include, but are not limited to, coding sequences and/or the regulatory sequences required for their expression. Genes can also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "genotype" refers to the genetic makeup of a cell, cell culture, tissue, whole organism (e.g., a whole plant or animal), or group of whole organisms (e.g., a group of plants or animals).

As used herein, the term "glycan", which is synonymous with "polysaccharide", refers to any linear or branched polymer consisting of monosaccharide (i.e., glucose) residues joined to each other by glycosidic linkages. Examples of glycans include glycogen, starch, hyaluronic acid, and cellulose.

As used herein, the term "glycoside" refers to any compound containing a carbohydrate molecule (sugar), particularly any such natural product in plants, convertible by hydrolytic cleavage, into a sugar and a non-sugar component.

As used herein, the term "glycopeptide" refers to a compound or composition in which carbohydrate is covalently attached to a peptide or oligopeptide.

As used herein, the term "glycoprotein" refers to a compound or composition in which carbohydrate is covalently attached to a protein.

As used herein, the term "glycosylation" refers to the addition of oligosaccharides to particular residues on a protein. This modification can be both co-translational and post-translational, occurring in the endoplasmic reticulum and golgi. Three different forms of glycosylation can be distinguished: N-linked oligosaccharides, O-linked oligosaccharides and glycosyl-phosphatidylinositol (GPI-) anchors.

As used herein, the term "hemizygous" refers to a cell, tissue or organism in which a gene is present only once in a genotype, as a gene in a haploid cell or organism, a sex-linked gene in the heterogametic sex, or a gene in a segment of chromosome in a diploid cell or organism where its partner segment has been deleted.

As used herein, the term "herpes" means an inflammatory skin disease caused by herpes simplex virus or varicella-zoster virus.

As used herein, the term "herpes simplex" refers to a variety of infections caused by "Herpes Simplex Virus 1", also referred to as "HSV1" and "herpes simplex virus type 1", and "Herpes Simplex Virus 2", also referred to as "HSV2" and "herpes simplex virus type 2", all refer to any of several acute, inflammatory virus diseases. The diseases are characterized by the eruption of small blisters, usually on the mouth, lips, face and genitals. The locations of the blisters caused by HSV1 and HSV2 are not location specific.

As used herein, "herpes virus" refers to any virus belonging to the family Herpesviridae.

As used herein, the terms "heteroglycan" or "heteropolysaccharide" refer to a glycan composed of two or more different kinds of monosaccharide residues.

A "heterologous polynucleotide" or a "heterologous nucleic acid" or an "exogenous DNA segment" refer to a polynucleotide, nucleic acid or DNA segment that originates from a source foreign to the particular host cell, or, if from the same source, is modified from its original form. Thus, a heterologous gene in a host cell includes a gene that is endogenous to the particular host cell, but has been modified. Thus, the terms refer to a DNA segment that is either (i) foreign or heterologous to the cell, or (ii) homologous to the cell but in a position within the host cell nucleic acid in which the element is not ordinarily found. Exogenous DNA segments may be expressed to yield exogenous polypeptides.

A "heterologous trait" refers to a phenotype imparted to a transformed host cell or transgenic organism by an exogenous DNA segment, heterologous polynucleotide or heterologous nucleic acid.

As used herein, the term "heterozygote" refers to a diploid or polyploid individual plant cell or plant having different alleles (forms of a given gene) present at least at one locus.

As used herein, the term "heterozygous" refers to the presence of different alleles (forms of a given gene) at a particular gene locus.

As used herein, the term "HPLC" refers to High Performance Liquid Chromatography.

As used herein, the term "homozygote" refers to an individual plant cell or plant having the same alleles at one or more loci.

As used herein, the term "homozygous" refers to the presence of identical alleles at one or more loci in homologous chromosomal segments.

As used herein, the term "hybrid" refers to any cell, tissue or whole organisms (e.g., a whole plant or animal) resulting from a cross between parents that differ in one or more genes.

As used herein, the term "HX8" or "HX-8" refers to the identification code for an IgA antibody, wherein H=herpes, X=simplex and 8=the sample number. HX8 is a human monoclonal antibody (sample number 8) which neutralizes both Herpes simplex virus (HSV) Type 1 and Type 2, binds to an epitope present on glycoprotein D, has the binding specificity of an Fab fragment produced by ATCC 69522, and has heavy chains with a CDR3 of SEQ ID NO:1 as set forth in U.S. Pat. No. 6,156,313, the entire patent of which is specifically incorporated herein. The entire nucleotide for the heavy chain and light chain of the HX8 antibody is shown as SEQ ID Nos: 1 and 9, respectively.

As used herein, the terms "immunoglobulin" or "Ig" refer to a class of structurally related protein products or portion of the proteins found in plasma and other body fluids that are immunologically active and are capable of specifically binding with antigen. Each Ig consists of two pairs of immunologically active portions of an immunoglobulin light chain (LC) (κ, λ), and an immunoglobulin heavy chain (HC) (γ, α, μ, δ and ε) (See FIG. 13A). There are five major classes of antibody proteins, or immunoglobulins classified on the basis of their structure and biological activity: IgM, IgG, IgA, IgD, and IgE. While most antibody classes are secreted as single molecules, IgA and IgM antibodies form associations into larger polymers, stabilized in part by other protein chains.

As used herein, the terms "immunoglobulin product" or "Ig product" refer to a polypeptide, protein or multimeric protein capable of specifically combining with an antigen. Exemplary immunoglobulin products are an immunoglobulin heavy chain, immunoglobulin molecules, substantially intact immunoglobulin molecules, any portion of an immunoglobulin that contains the paratope, including those portions known in the art as Fab fragments.

As used herein, the terms "inbred" or "inbred line" refers to a relatively true-breeding strain.

As used herein, the terms "integrin" or "integrins" refer to any member of the large family of transmembrane proteins that act as receptors for cell-adhesion molecules. Integrins are heterodimeric molecules in which the α and β subunits are noncovalently bonded.

As used herein, the terms "joining chain", "J chain" or "JC" refer to a polypeptide that is involved in the polymerization of immunoglobulins and transport of polymerized immunoglobulins through epithelial cells. See, for example, The Immunoglobulin Helper: The J Chain in Immunoglobulin Genes, at pg. 345, Academic Press (1989). The JC is found in pentameric IgM and dimeric IgA (See FIG. 13B) and typically attached via disulfide bonds.

As used herein, the term "locus" (plural: "loci") refers to any site that has been defined genetically. A locus may be a gene, or part of a gene, or a DNA sequence that has some regulatory role, and may be occupied by different sequences.

As used herein, the term "MALDI" refers to Matrix-Assisted Laser Desorption Ionization.

As used herein, the terms "MALDI-Tof mass spectrum" or "MALDI-Tof MS" refer to matrix-assisted laser desorption/ionization time-of-flight mass spectrometry. An example of equipment used to determine the MALDI-Tof mass-spectrum is the Applied Biosystems Voyager DE-STR MALDI time-of-flight (MALDI-Tof) mass-spectrometer.

As used herein, the term "matrix attachment regions" or "MAR", also called "scaffold attachment regions" or "SAR", refer to specific DNA sequences at which attachment to the nuclear scaffold network occurs. Information on the MAR sequences used in this invention is available in U.S. Pat. Nos. 5,773,689 and 6,239,328, each of which is herein incorporated in its entirety.

As used herein, the term "mass selection" when used to describe a plant breeding process refers to a form of selection in which individual plants are selected and the next generation propagated from the aggregate of their seeds.

As used herein, the term "monoclonal antibody" or "MAb" refer to antibodies derived from a single antibody-producing cell that recognizes a specific antigen. MAbs are produced by hybridoma cells, which are a fusion of a cell that produces the antibody and a multiple myeloma cell. The myeloma cell can continuously produce the antibody.

As used herein, the term "monocotyledon" or "monocot" refer to any of a subclass (Monocotyledoneae) of flowering plants having an embryo containing only one seed leaf and usually having parallel-veined leaves, flower parts in multiples of three, and no secondary growth in stems and roots. Examples include lilies; orchids; rice; corn, grasses, such as tall fescue, goat grass, and Kentucky bluegrass; grains, such as wheat, oats and barley; irises; onions and palms.

Figure 13A:
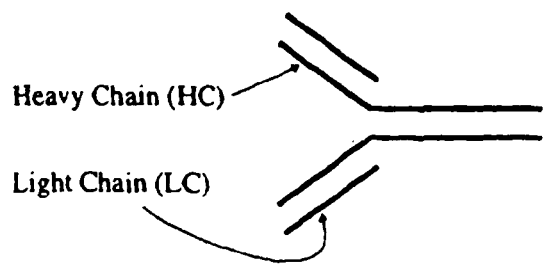
FIG. 13. Pictorial representation of a monomeric, dimeric and secretory antibody.
Figure 13B:
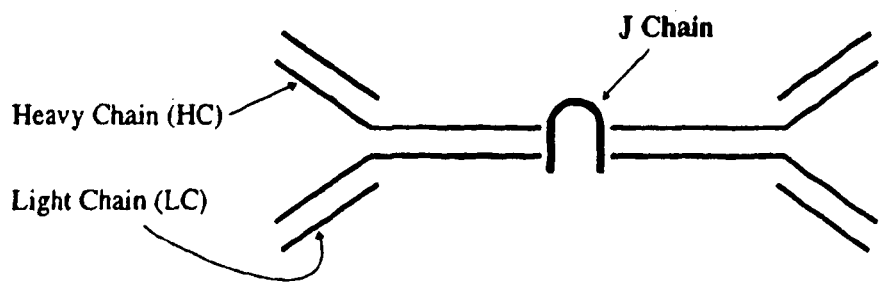

As used herein, the term "monomeric antibody" refers to an antibody comprising two light and two heavy chains linked to each other by disulfide bridges (See FIG. 13A). Thus, a "monomeric IgA" or "mIgA" comprises two light and two heavy chains of an IgA antibody; and, a "monomeric HSV IgA" or "HSV mIgA" comprises the two light and two heavy chains of an IgA antibody to a herpes simplex virus.

As used herein, the term "multimeric protein" refers to a globular protein containing more than one separate polypeptide or protein chain associated with each other to form a single globular protein. Both heterodimeric and homodimeric proteins are multimeric proteins.

As used herein, the term "nucleic acid" or "polynucleotide" refer to deoxyribonucleotides or ribonucleotides and polymers thereof in either single- or double-stranded form. Unless specifically limited, the terms encompass nucleic acids containing known analogues of natural nucleotides that have similar binding properties as the reference nucleic acid and are metabolized in a manner similar to naturally occurring nucleotides. Specifically, degenerate codon substitutions may be achieved by generating sequences in which the third position of one or more selected (or all) codons is substituted with mixed-base and/or deoxyinosine residues. See, for example, Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994). The term nucleic acid is used interchangeably with gene, cDNA, and mRNA encoded by a gene.

As used herein, the term "oligosaccharide" refers to any molecule that contains a small number (2 to about 20) of monosaccharide residues connected by glycosidic linkages.

As used herein, a DNA segment is referred to as "operably linked" when it is in a functional relationship with another DNA segment. For example, DNA encoding a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Generally, DNA sequences that are operably linked are contiguous, and in the case of a signal sequence both contiguous and in reading phase. However, promoters and enhancers need not be contiguous with the coding sequences whose transcription they control. Linking is accomplished by ligation at convenient restriction sites or at adapters or linkers inserted in lieu thereof.

As used herein, the term "open pollination" when used in reference to plants means a plant population that is freely exposed to some gene flow, as opposed to a closed one in which there is an effective barrier to gene flow.

As used herein, the terms "open-pollinated population" or "open-pollinated variety" when used in reference to plants refers to plants normally capable of at least some cross-fertilization, selected to a standard, that may show variation but that also have one or more genotypic or phenotypic characteristics by which the population or the variety can be differentiated from others. A hybrid, which has no barriers to cross-pollination, is an open-pollinated population or an open-pollinated variety.

As used herein, the term "ovule" refers to the female gametophyte, whereas the term "pollen" means the male gametophyte.

As used herein, the term "ovule-specific promoter" refers broadly to a nucleic acid sequence that regulates the expression of nucleic acid sequences selectively in the cells or tissues of a plant essential to ovule formation and/or function and/or limits the expression of a nucleic acid sequence to the period of ovule formation in a plant.

As used herein, the term "peptide" refers to a class of compounds of low molecular weight which yield two or more amino acids on hydrolysis and form the constituent parts of proteins. As used herein, an "oligopeptide" refers to any molecule that contains a small number (two to about 20) of amino-acid residues connected by peptide linkages.

As used herein, the term "peptide bond" refers to an amide bond linking amino acids between their COOH and NH2 groups; this is essentially a planar bond having some double bond character, so free rotation is not possible.

As used herein, the term "phenotype" refers to the observable characters of a cell, cell culture, tissue, whole organism (e.g., a whole plant or animal), or group of whole organisms (e.g., a group of whole plants or animals) which results from the interaction between the genetic makeup (i.e., genotype) of the cell, cell culture, tissue or organism and the environment.

As used herein, the term "plant" refers to whole plants and progeny of the whole plants, plant cells, plant tissue, plant calli, seeds and pollen. The class of plants that can be used in the methods of the invention is generally as broad as the class of higher plants amenable to transformation techniques, including both monocotyledonous and dicotyledonous plants.

As used herein, the term "plant line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses effected such that a gene or a combination of genes, in heterozygous (hemizygous) or homozygous condition, imparts a desired trait to the plant.

As used herein, the term "plant organ" refers to any part of a plant. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath.

As used herein, "plantibody™" refers to an antibody including individual antibody chains, monomeric, dimeric or secretory antibodies or antibody fragments produced by a plant, plant organ or plant cell.

As used herein, the terms "plant transcription unit" or "PTU" refer to a nucleic acid sequence encoding a promoter sequence, a coding sequence and a 3' termination sequence.

As used herein, the term "polypeptide" refers to a linear polymer of amino acids linked via peptide bonds. A polypeptide may be as short as 2 amino acids to virtually any length.

As used herein, the term "promoter" refers to a recognition site on a DNA sequence or group of DNA sequences that provide an expression control element for a gene and to which RNA polymerase specifically binds and initiates RNA synthesis (transcription) of that gene.

As used herein, the term "recombinant" refers to a cell, cell culture, tissue or organism that has undergone transformation with recombinant DNA. The original recombinant is designated as "R0" or "$R_0$" Selfing the $R_0$ produces a first transformed generation designated as "R1" or "$R_1$"

As used herein, the terms "secretory component" or "SC" refer to a polypeptide that is present at the N-terminus of a chimeric immunoglobulin chain useful in aiding in the secretion of the chain to the outside of the host.

Figure 13C:
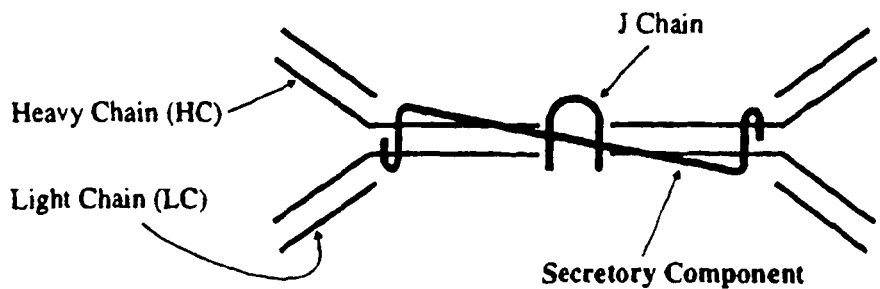
Figure 14:
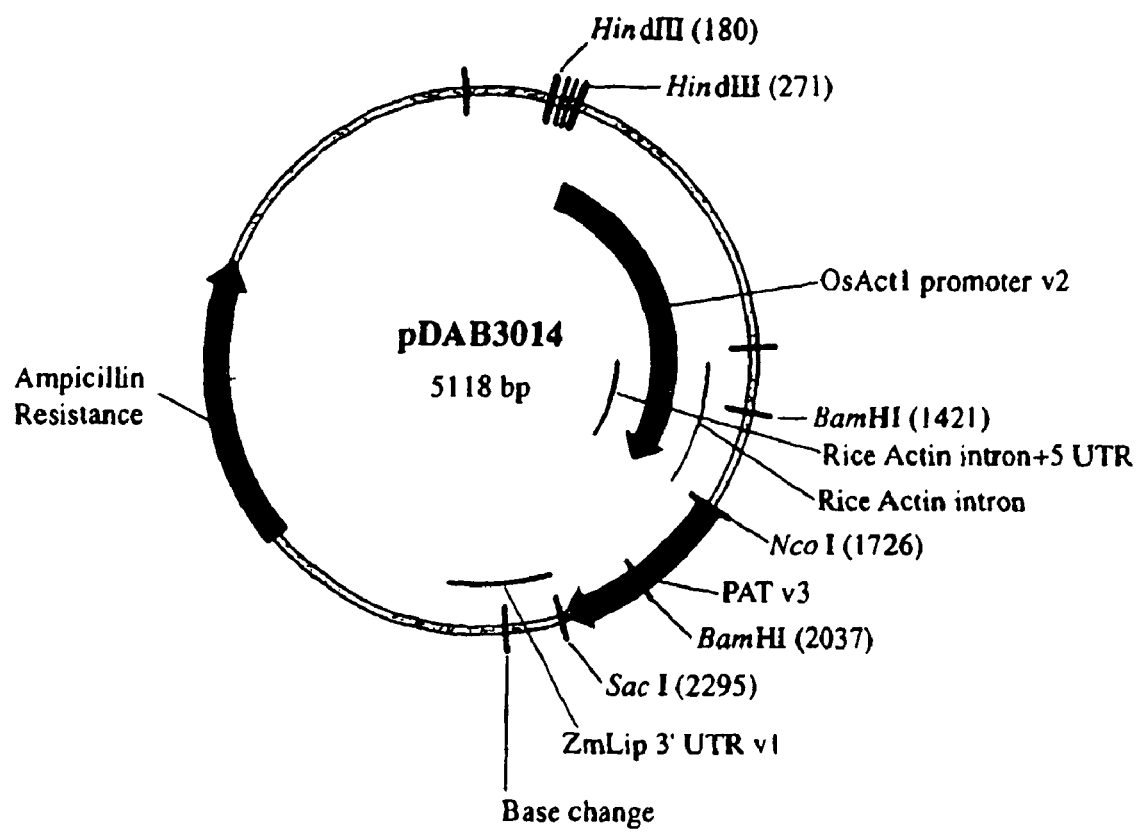
FIG. 14. Plasmid for pDAB3014. (SEQ ID NO: 84).
Rice actin promoter: nucleotides 1172-1724;
PAT (phosphinothricin
acyltransferase gene): nucleotides 1727-2281;
maize lipase 3' UTR: nucleotides 2296-6652.

As used herein, the terms "secretory IgA antibodies" and ("sIg") refer to antibodies that are comprised of 10 protein chains encoded by four genes: the heavy chain ("HC") and the light ("LC") which combine to form monomeric IgA ("mIgA") (See FIG. 13A); the joining chain ("JC") which joins two monomeric IgA monomers into a dimeric IgA ("dIgA")(See, FIG. 13B); and the secretory component ("SC") which wraps around the dIgA molecule (See FIG. 13C).

As used herein, the term "self pollinated" or "self-pollination" when used in reference to plants means the pollen of one flower on one plant is applied (artificially or naturally) to the ovule (stigma) of the same or a different flower on the same plant.

As used herein, the terms "sexually transmitted infections" or "STIs" refer to a class of diseases and infections that are passed from one person to the next by sexual intercourse or contact; also known as STDs or sexually transmitted diseases.

As used herein, the term "signal sequence" refers to an amino acid sequence (the signal peptide) attached to the polypeptide which binds the polypeptide to the endoplasmic reticulum and is essential for protein secretion.

As used herein, the term "synthetic variety" when referring to plants means a set of progenies derived by intercrossing a specific set of clones or seed-propagated lines. A synthetic may contain mixtures of seed resulting from cross-, self-, and sib-fertilization.

As used herein, the term "tailpiece" refers to that portion of the heavy chain comprising an Asn residue which is normally fucosylated. For example, in the IgA HX8 antibody, the tailpiece comprises amino acid residues 476-497 of SEQ ID NO: 1. The Asn residue is at position 484 in the HX8 antibody.

As used herein, the term "transcript" refers to a product of a transcription process.

As used herein, the term "transformation" refers to the transfer of nucleic acid (i.e., a nucleotide polymer) into a cell. As used herein, the term "genetic transformation" refers to the transfer and incorporation of DNA, especially recombinant DNA, into a cell.

As used herein, the term "transformation" refers to a cell, tissue or organism that has undergone transformation. The original transformant is designated as "T0" or "$T_0$." Selfing the T0 produces a first transformed generation designated as "T1" or $T_1$.

As used herein, the term "transgene" refers to a nucleic acid that is inserted into an organism, host cell or vector in a manner that ensures its function.

As used herein, the term "transgenic" refers to cells, cell cultures, tissues, organisms (e.g., plants or animals), and their progeny which have received a foreign or modified gene by one of the various methods of transformation, wherein the foreign or modified gene is from the same or different species than the species of the cell, cell culture, tissue or organism, receiving the foreign or modified gene.

As used herein, the terms "untranslated region" or "UTR" refer to any part of a mRNA molecule not coding for a protein (e.g., in eukaryotes the poly(A) tail).

As used herein, the term "vector" refers broadly to any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al., Proc. Natl. Acad. Sci. U.S.A. 94:12744-12746 (1997). Examples of viral vectors include, but are not limited to, a recombinant vaccinia virus, a recombinant adenovirus, a recombinant retrovirus, a recombinant adeno-associated virus, a recombinant avian pox virus, and the like. See, for example, Cranage et al., EMBO J. 5:3057-3063 (1986); International Patent Application No. WO94/17810, published Aug. 18, 1994; and, International Patent Application No. WO94/23744, published Oct. 27, 1994. Examples of non-viral vectors include, but are not limited to, liposomes, polyamine derivatives of DNA, and the like.

The term "virus" refers to any of a group of ultramicroscopic or submicroscopic infective agents that cause various diseases in animals, such as measles, mumps, etc., or in plants, such as mosaic diseases; viruses are capable of multiplying only in connection with living cells and are regarded both as living organisms and as packages of nucleic acids, sometimes involving complex proteins, enzymes, etc.

The present invention includes a plant cell, plant callus, plantlet, whole plant or seed comprising an afucosylated monomeric antibody. In one embodiment, the plant is a maize plant. In another embodiment, the antibody is located in the seed's endosperm. In a different embodiment, the antibody is a human antibody. In a preferred embodiment, the antibody comprises a heavy chain comprising the amino acid sequence of SEQ ID NO: 6. In another preferred embodiment, the antibody comprises a light chain comprising the amino acid sequence of SEQ ID NO: 14. In a highly preferred embodiment, the heavy chain lacks a tailpiece. In another preferred embodiment, the antibody is an IgA antibody. In a highly preferred embodiment, the antibody is an anti-herpes simplex virus antibody.

Another aspect of the invention also includes an isolated nucleic acid molecule comprising a nucleic acid sequence encoding the amino acid encoded by SEQ ID NO: 2 or SEQ ID NO: 6; an isolated nucleic acid molecule comprising a nucleic acid sequence encoding the amino acid encoded by SEQ ID NO: 10 or SEQ ID NO: 14; an isolated nucleic acid molecule comprising SEQ ID NO: 1 or SEQ ID NO: 5; and, an isolated nucleic acid molecule comprising SEQ ID NO: 9 or SEQ ID NO: 13.

Another aspect of the invention includes an isolated vector or plasmid comprising SEQ ID NO: 1 or SEQ ID NO: 5; and, an isolated vector or plasmid comprising SEQ ID NO: 9 or SEQ ID NO: 13.

Figure 12:
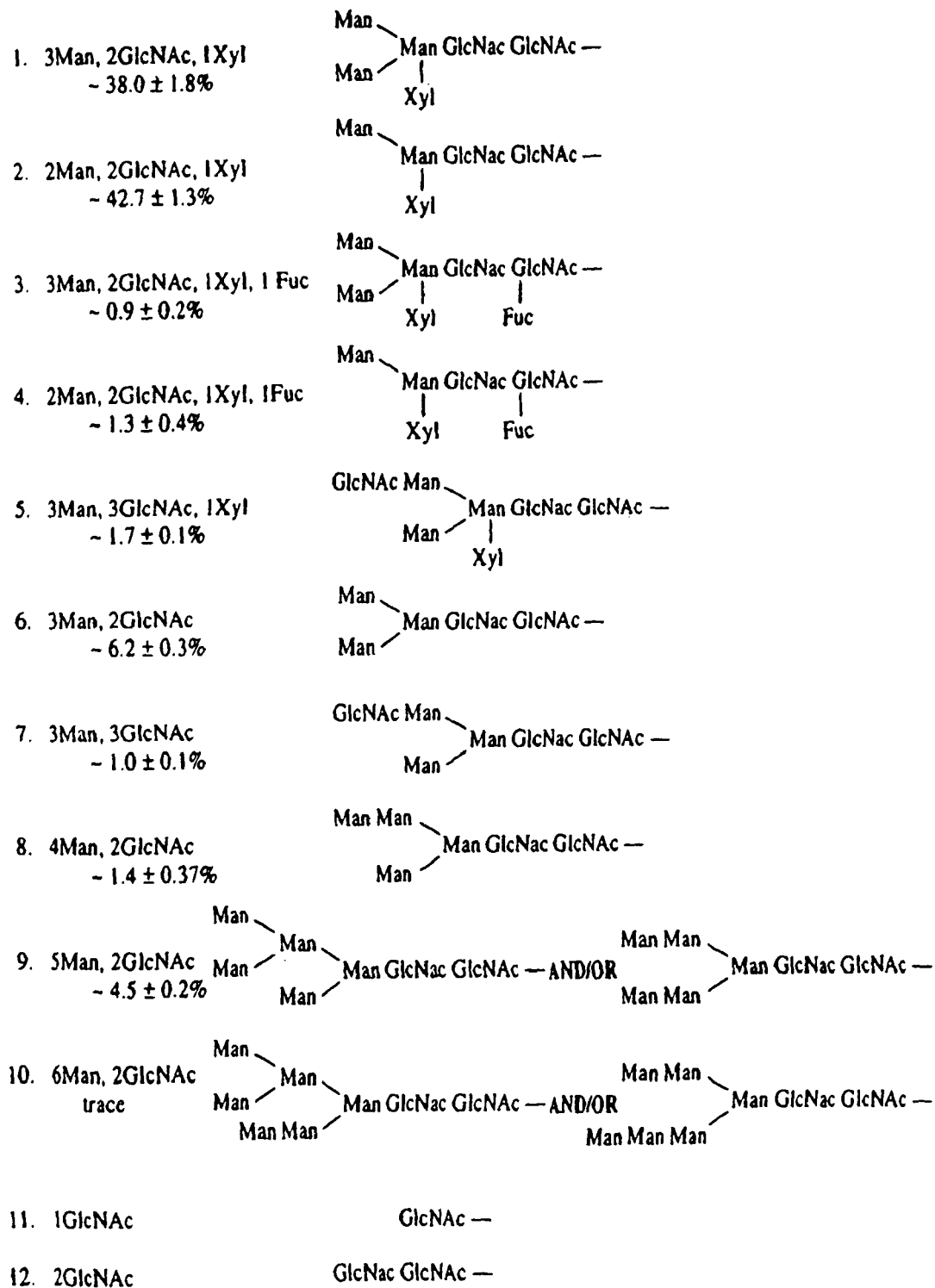
FIG. 12. Structures of IgA glycans isolated from plants. Single and double GlcNAc species (structures 11 and 12) were not detected as free glycans due to inaccessibility of MALDI MS to the molecular mass region below 500 Daltons (Da).

The invention also includes an antibody composition comprising two or more different glycan structures selected from the group consisting of the structures in FIG. 12, wherein at least one of the selected glycan structures from FIG. 12 is afucosylated.

Also included in the invention is plant material comprising the antibody composition comprising two or more different glycan structures selected from the group consisting of the structures in FIG. 12, wherein at least one of the selected glycan structures from FIG. 12 is afucosylated. In one embodiment, the composition is isolated from plant material. In another embodiment, the plant material is from maize.

The invention also comprises a monomeric antibody composition comprising at least one glycan having the structure of structure 1 as listed in FIG. 12; a monomeric antibody composition comprising at least one glycan having the structure of structure 2 as listed in FIG. 12; and, a monomeric antibody composition comprising at least one glycan having the structure of structure 1 as listed in FIG. 16 and at least one glycan having the structure of structure 2 as listed in FIG. 16.

Further included in the invention is a plant callus, plantlet, whole plant or seed comprising a monomeric antibody composition wherein the monomeric antibody composition is a monomeric antibody composition comprising at least one glycan having the structure of structure 1 as listed in FIG. 12; a monomeric antibody composition comprising at least one glycan having the structure of structure 2 as listed in FIG. 12; or a monomeric antibody composition comprising at least one glycan having the structure of structure 1 as listed in FIG. 16 and at least one glycan having the structure of structure 2 as listed in FIG. 16.

The invention also includes an isolated afucosylated monomeric anti-herpes simplex virus antibody produced by a method comprising: (i) introducing into a plant cell nucleic acids having SEQ ID NO: 1 or SEQ ID NO: 5 and SEQ ID NO: 9 or SEQ ID NO: 13, each of which is operably-linked to a promoter; (ii) culturing the plant cell to express the introduced nucleic acids; and (iii) isolating the afucosylated monomeric anti-herpes simplex virus antibody produced by the plant cell. Also included in the invention is a method of producing an isolated afucosylated monomeric anti-herpes simplex virus antibody comprising: (i) introducing into a plant cell nucleic acids having SEQ ID NO: 1 or SEQ ID NO: 5 and SEQ ID NO: 9 or SEQ ID NO: 13, each of which is operably-linked to a promoter; (ii) culturing the plant cell to express the introduced nucleic acids; and (iii) isolating the afucosylated monomeric anti-herpes simplex virus antibody produced by the plant cell.

Preferred embodiments of the invention include a nucleic acid molecule comprising a nucleic acid sequence selected from the group consisting of SEQ ID NO: 15 (pDAB635), SEQ ID NO: 16 (pDAB16), SEQ ID NO: 17 (pDAB637), SEQ ID NO: 84 (pDAB3014) and SEQ ID NO: 85 (pDAB8505).

The invention is also directed to a method of producing a transformed plant cell expressing an afucosylated antibody comprising introducing a single vector comprising a nucleic acid sequence encoding an immunoglobulin heavy chain and an immunoglobulin light chain into a plant cell and culturing the transformed plant cell to produce a plant expressing an afucosylated antibody. In one embodiment, a transformed plant is regenerated from the transformed plant cell. In a preferred embodiment, the vector is pDAB8505.

II. Background for Production of IgA in Plants

A. Examples of Suitable IgAs to Utilize

Any IgA antibody can be used in the methods of the instant invention. IgA is an immunoglobulin found in human plasma. It is the major immunoglobulin of seromucous secretions and is involved in the defense of external body surfaces against attack by microorganisms.

Immunoglobulin A (IgA) proteins are well known and characterized, including their nucleic acid and amino acid sequences. Examples of IgA immunoglobulins that can be used in the compositions and methods of the instant invention include but are not limited to the following: *Entamoeba histolytica* antigens recognized by human secretory IgA antibodies (Carrero et al., Parasitol Res. 86(4):330-4 (2000)); transforming growth factor-beta-inducible mouse germ line Ig alpha constant region gene (Zhang et al., J Biol. Chem. 275(22):16979-85 (2000)); immunoglobulin A (IgA) and IgM antibodies against human cytomegalovirus in solid-organ transplant recipients (Eing et al., Clin Diagn Lab Immunol. 6(4):621-3 (1999)); excretion of secretory IgA in the postischemic kidney (Rice et al, Am J. Physiol. 276(5 Pt 2):F666-73 (1999)); secretory immunoglobulin A release by Calu-3 airway epithelial cells (Loman et al., Immunology. 96(4):537-43 (1999)); specific IgA in the sera of HBsAg chronic carriers (Elsana et al., J Hum Virol. 1(1):52-7 (1997)); anti-*Toxoplasma gondii* IgA antibodies (Ronday et al., Am J.

Ophthalmol. 127(3):294-300 (1999)); secretory immunoglobulins A from human milk (Kit et al., Biochemistry (Mosc). 64(1):40-6 (1999)); anti-Kp 90 IgA antibodies in the diagnosis of active tuberculosis (Arikan et al., Chest. 114(5):1253-7 (1998)); cloning of IgA from the marsupial *Monodelphis domestica* (Aveskogh et al., Eur J. Immunol. 28(9):2738-50 (1998)); germline and full-length IgA RNA transcripts among peritoneal B-1 cells (deWaard et al., Dev Immunol. 6(1-2):81-7 (1998)); and the constant region of the immunoglobulin A heavy chain (C alpha) from a marsupial: *Trichosurus vulpecula* (common brushtail possum) (Belov et al., Immunol Lett. 60(2-3): 165-70 (1998). Erratum in: Immunol Lett 63(3):175-6 (1998)).

B. Herpes Simplex Virus (HSV)

Herpes simplex refers to a variety of infections caused by herpesvirus type 1 (HSV 1) and type 2 (HSV 2). Herpes simplex viruses subtypes 1 and 2 (HSV-1, HSV-2), are herpes viruses that are among the most common infectious agents encountered by humans. Type 1 infections are marked most commonly by the eruption of one or more groups of vesicles on the vermilion border of the lips or at the external nares with lesions occurring also on the genitalia. Type 2 is characterized by such lesions on the genitalia with lesions often occurring on the vermilion border of the lips or at the external nares. The viruses frequently become latent and may not be expressed for years.

These viruses cause a broad spectrum of diseases which range from relatively insignificant and nuisance infections such as recurrent herpes simplex labialis, to severe and life-threatening diseases such as herpes simplex encephalitis (HSE) of older children and adults, or the disseminated infections of neonates. Clinical outcome of herpes infections is dependent upon early diagnosis and prompt initiation of antiviral therapy. However, despite some successful therapy, dermal and epidermal lesions recur, and HSV infections of neonates and infections of the brain are associated with high morbidity and mortality. Improved treatments are desperately needed.

Exemplary strains of herpes simplex virus-1 include, but are not limited to HSV-1716, HSV-3410, HSV-3616, HSV-R3616, HSV-R47, HSV-G207, HSV-7020, HSV-NVR10, HSV-G92A, HSV-3616-IL-4, and HSV-hrR3. Exemplary strains of herpes simplex virus-2 include, but are not limited to strain 2701, strain 2616, and strain 2604. U.S. Pat. No. 6,156,313 provides the amino acid residue sequence of the heavy chain variable region sequence for an antibody which targets and neutralizes Herpes simplex virus Type-1 and Type-2 (SEQ D NO: 2 of the '313 patent) as well as the nucleic acid sequence that encodes the heavy chain CDR3 amino acid sequence (SEQ ID NO: 1 of the '313 patent).

C. Formulations for Anti-HSV Antibodies

The anti-HSV antibodies of the present invention are produced in plants, at least partially purified, and can then be formulated into a topical application. The anti-HSV antibodies of the present invention can be used in the treatment of the skin of terrestrial mammals, including for example humans, domestic pets, and livestock and other farm animals. A preferred use of the anti-HSV antibodies of the present invention is to prevent transmission of the HSV.

For such therapy, the compounds of the invention can be formulated for a variety of loads of administration, including systemic and topical or localized administration. Techniques and formulations generally may be found in Remington's Pharmaceutical Sciences, Meade Publishing Co., Easton, Pa., which is incorporated in its entirety herein. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution. (Hanks' Solution: Potassium Phosphate 0.44 mM, Potassium Chloride 5.37 mM, Sodium Phosphate, Dibasic 0.34 mM 136.89, Sodium Chloride mM, D-Glucose 5.55 mM. The reagent is ready for use. The pH of the diluted Hanks' Salt Solution is 6.7 plus or minus 0.2. Sodium Bicarbonate can be added to the solution (0.35g/L). The pH of the solution can be adjusted with 1N HCl or 1N NaOH). In addition, the compounds may be formulated in solid form and redissolved or suspended immediately prior to use. Lyophilized forms are also included.

In a preferred practice of this invention, the anti-HSV antibodies of the present invention can be administered as active ingredients in a formulation that is pharmaceutically acceptable for topical administration. Topical formulations, including those that are useful for transdermal drug release, are well-known to those of skill in the art and are suitable in the context of the present invention for application to skin. Formulations suitable for topical or intranasal application include ointments, drops, creams, solutions, tinctures, lotions, pastes, gels, sprays, aerosols and oils containing the active ingredient and various supports and vehicles. These formulations may or may not contain a vehicle or carrier, although the use of a vehicle or carrier is preferred. Suitable carriers for such formulations include petroleum jelly, lanolin, polyethyleneglycols, alcohols, and combinations thereof. Preferred vehicles are non-lipid vehicles, particularly a water-miscible liquid or mixture of liquids. Examples are methanol, ethanol, isopropanol, ethylene glycol, propylene glycol, and butylene glycol, and mixtures of two or more of these compounds. The active ingredient is typically present in such formulations at a concentration of from 0.1 to 15% w/w.

Formulations such as discussed herein can be prepared by any suitable method, typically by uniformly and intimately admixing the active compound with liquids or finely divided solid carriers or both, in the required proportions and then, if necessary, shaping the resulting mixture into the desired shape.

For example a tablet may be prepared by compressing an intimate mixture comprising a powder or granules of the active ingredient and one or more optional ingredients, such as a binder, lubricant, inert diluent, or surface active dispersing agent, or by molding an intimate mixture of powdered active ingredient and inert liquid diluent.

A topical semi-solid ointment formulation typically contains a concentration of the active ingredient from about 1 to 20%, e.g., 5 to 10% in a carrier such as a pharmaceutical cream base, although the concentration may vary outside this range. The optimum amounts in any given instance will be readily apparent to those skilled in the art or are capable of determination by routine experimentation.

Topical formulations containing the anti-HSV antibodies of the present invention can be formulated as lotions, solutions, gels, creams, emollient creams, unguents, sprays, or any other form that will permit topical application. The formulation may also contain one or more agents that promote the spreading of the formulation over the affected area, but are otherwise biologically inactive. Examples of these agents are surfactants, humectants, wetting agents, emulsifiers, or propellants.

The anti-HSV antibodies of the present invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference in its entirety.

Optimal methods and frequency of administration will be readily apparent to those skilled in the art or are capable of determination by routine experimentation. Effective results in most cases are achieved by topical application of a thin layer over the affected area, or the area where one seeks to achieve the desired effect. Depending on the condition being addressed, its stage or degree, and whether application is done for therapeutic or preventive reasons, effective results are achieved with application rates of from one application every two or three days to four or more applications per day.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

D. Summary List of SEQ ID NOs. for Anti-HSV Antibodies

| SEQ ID NUMBER | DESCRIPTION |
|---|---|
| 1 | Heavy Chain Sequence (nucleic acid) (mouse leader sequence), 1494 nt |
| 2 | Heavy Chain Sequence (amino acid), 497 a.a. |
| 3 | Heavy Chain signal peptide (nucleic acid), 57 nt |
| 4 | Heavy Chain signal peptide (amino acid) (mouse leader sequence), 19 a.a. |
| 5 | Mature Heavy Chain (nucleic acid), 1368 nt |
| 6 | Mature Heavy Chain (amino acid), 456 a.a. |
| 7 | Heavy Chain Tailpiece (nucleic acid), 69 nt |
| 8 | Heavy Chain Tailpiece (amino acid), 22 a.a. |
| 9 | Light Chain Sequence (nucleic acid), 702 nt |
| 10 | Light Chain Sequence (amino acid) (mouse leader sequence), 233 a.a. |
| 11 | Light Chain signal peptide (nucleic acid), 57 nt |
| 12 | Light Chain signal peptide (amino acid) (mouse leader sequence), 19 a.a. |
| 13 | Mature Light Chain (nucleic acid), 642 nt |
| 14 | Mature Light Chain (amino acid), 214 a.a. |
| 15 | pDAB635 (ubiH) sequence (barley leader sequence), 9144 nt |
| 16 | pDAB636 (ubiL) sequence (barley leader sequence), 8352 nt |
| 17 | pDAB637 (ubi H + L) sequence (barley leader sequence), 12380 nt |
| 18 | CDR3 region of heavy chain FabHSV 8-CDR3, 16 a.a. |
| 19 | Heavy Chain V region FabSHV 8, 122 a.a. |
| 20 | Tryptic+ Asp-N peptide of N269, 18 a.a. |
| 21-48 | Peptide Tryptic fragments in Table 6 |
| 49-83 | Peptide Tryptic fragments in Table 7 |
| 84 | pDAB3014 |
| 85 | pDAB8505 (mouse leader sequence for HC and LC) |

E. Amino Acid Sequences of Anti-HSV Heavy Chain, Light Chain and Monomeric IgA Antibodies Isolated From Plants The present invention provides the polypeptides for the heavy chain, light chain and monomeric IgA for anti-HSV antibodies, wherein such polypeptides are isolated from plants.

As used herein, "protein" or "polypeptide" refers, in part, to an amino acid that has the amino acid sequence depicted in SEQ ID NOs: 2, 4, 6, 8, 10, 12, and 14. The terms also refer to naturally occurring allelic variants and proteins that have a slightly different amino acid sequence than that specifically provided in SEQ ID NOs: 2, 4, 6, 8, 10, 12 and 14. Allelic variants, though possessing a slightly different amino acid sequence than those recited herein, will still have the same or similar biological functions associated with these proteins.

As used herein, the family of proteins related to the amino acid sequences having SEQ ID NOs: 2, 4, 6, 8, 10, 12 and 14 refers to proteins that have been isolated from organisms in addition to humans.

The anti-HSV antibody polypeptides of the present invention are preferably in isolated form. As used herein, a polypeptide is said to be isolated when physical, mechanical or chemical methods are employed to remove the protein from cellular constituents that are normally associated with the protein. A skilled artisan can readily employ standard purification methods to obtain an isolated protein.

The proteins of the present invention further include insertion, deletion or conservative amino acid substitution variants of SEQ ID NOs: 2, 4, 6, 8, 10, 12 and 14. As used herein, a conservative variant refers to alterations in the amino acid sequence that do not adversely affect the biological functions of the protein. A substitution, insertion or deletion is said to adversely affect the protein when the altered sequence prevents or disrupts a biological function associated with the protein. For example, the overall charge, structure or hydrophobic/hydrophilic properties of the protein, in certain instances, may be altered without adversely affecting a biological activity. Accordingly, the amino acid sequence can be altered, for example to render the peptide more hydrophobic or hydrophilic, without adversely affecting the biological activities of the protein.

Ordinarily, the allelic variants, the conservative substitution variants, and the members of the protein family, will have an amino acid sequence having at least about 50%, 60%, 70% or 75% amino acid sequence identity with the sequence set forth in SEQ ID NOs: 2, 4, 6, 8, 10, 12 and 14; more preferably at least about 80%; even more preferably at least about 90-95%; and most preferably at least about 99 or 99.5% sequence identity. Identity or homology with respect to such sequences is defined herein as the percentage of amino acid residues in the candidate sequence that are identical with SEQ ID NOs: 2, 4, 6, 8, 10, 12 and 14, after aligning the sequences and introducing gaps, if necessary, to achieve the maximum percent homology, and not considering any conservative substitutions as part of the sequence identity. Fusion proteins, or N-terminal, C-terminal or internal extensions, deletions, or insertions into the peptide sequence shall not be construed as affecting homology.

Thus, the proteins of the present invention include molecules having the amino acid sequence disclosed in SEQ ID NOs: 2, 4, 6, 8, 10, 12 and 14; fragments thereof having a consecutive sequence of at least about 3, 4, 5, 6, 10, 15, 20, 25, 30, 35 or more amino acid residues of these proteins; amino acid sequence variants wherein one or more amino acid residues has been inserted N- or C-terminal to, or within, the disclosed coding sequence; and amino acid sequence variants of the disclosed sequence, or their fragments as defined above, that have been substituted by at least one residue. Such fragments, also referred to as peptides or polypeptides, may contain antigenic regions, functional regions of the protein identified as regions of the amino acid sequence which correspond to known protein domains, as well as regions of pronounced hydrophilicity. The regions are all easily identifiable by using commonly available protein sequence analysis software such as, for example, MacVector (Oxford Molecular). Other protein analysis software, useful in the practice of the invention, is known in the art.

Contemplated variants further include those containing predetermined mutations by, e.g., homologous recombination, site-directed or PCR mutagenesis, and the corresponding proteins of other animal species, including but not limited to rabbit, mouse, rat, porcine, bovine, ovine, equine and non-human primate species, and the alleles or other naturally occurring variants of the family of HSV-related proteins; and derivatives wherein the protein has been covalently modified by substitution, chemical, enzymatic, or other appropriate means with a moiety other than a naturally occurring amino acid (for example a detectable moiety such as an enzyme or radioisotope).

The present invention further provides compositions comprising a protein or polypeptide of the invention and a diluent. Suitable diluents can be aqueous or non-aqueous solvents or a combination thereof, and can comprise additional components, for example water-soluble salts or glycerol, that contribute to the stability, solubility, activity, and/or storage of the protein or polypeptide.

F. Nucleic Acid Sequences of Anti-HSV Heavy Chain, Light Chain and Monomeric IgA Antibodies The present invention utilizes nucleic acid molecules that encode the heavy chain (SEQ ID NOs: 1 and 5) and light chain (SEQ ID NOs: 9 and 13) of anti-HSV antibodies and the related polypeptides herein described, preferably in isolated form.

As used herein, "nucleic acid" is defined as RNA or DNA that encodes a protein or peptide as defined herein, is complementary to a nucleic acid sequence encoding such peptides, hybridizes to the nucleic acid of SEQ ID NOs: 1, 3, 5, 7, 9, 11 and 13 and remains stably hybridized to it under appropriate stringency conditions, encodes a polypeptide sharing at least about 50%, 60%, 70% or 75%, preferably at least about 80%, more preferably at least about 85%, and most preferably at least about 90%, 95%, 98%, 99%, 99.5% or more identity with the peptide sequence of SEQ ID NOs: 1, 3, 5, 7, 9, 11 and 13, or exhibits at least 50%, 60%, 70% or 75%, preferably at least about 80%, more preferably at least about 85%, and even more preferably at least about 90%, 95%, 98%, 99%, 99.5% or more nucleotide sequence identity over the open reading frames of SEQ ID NOs: 1, 3, 5, 7, 9, 11 and 13.

The present invention further includes isolated nucleic acid molecules that specifically hybridize to the complement of SEQ ID NOs: 1, 3, 5, 7, 9, 11 and 13, particularly molecules that specifically hybridize over the open reading frames. Such molecules that specifically hybridize to the complement of SEQ ID NOs: 1, 3, 5, 7, 9, 11 and 13 typically do so under stringent hybridization conditions, such conditions being described below.

Specifically contemplated are genomic DNA, cDNA, mRNA and antisense molecules, as well as nucleic acids based on alternative backbones or including alternative bases whether derived from natural sources or synthesized.

Homology or identity at the nucleotide or amino acid sequence level is determined by BLAST (Basic Local Alignment Search Tool) analysis using the algorithm employed by the programs blastp, blastn, blastx, tblastn and tblastx. See, for example, Altschul et al., Nucleic Acids Res. 25: 3389-3402 (1997) and Karlin et al., Proc. Natl. Acad. Sci. USA 87: 2264-2268 (1990), both fully incorporated by reference, which are tailored for sequence similarity searching. The approach used by the BLAST program is to first consider similar segments, with and without gaps, between a query sequence and a database sequence, then to evaluate the statistical significance of all matches that are identified and finally to summarize only those matches which satisfy a pre-selected threshold of significance. For a discussion of basic issues in similarity searching of sequence databases, see, for example, Altschul et al., Nat. Genet. 6: 119-129 (1994), which is fully incorporated by reference. The search parameters for histogram, descriptions, alignments, expect (i.e., the statistical significance threshold for reporting matches against database sequences), cutoff, matrix and filter (low complexity) are at the default settings. The default scoring matrix used by blastp, blastx, tblastn, and tblastx is the BLOSUM62 matrix (see, for example, Henikoff et al., Proc. Natl. Acad. Sci. USA 89: 10915-10919 (1992), fully incorporated by reference), recommended for query sequences over 85 nucleotides or amino acids in length.

For blastn, the scoring matrix is set by the ratios of M (i.e., the reward score for a pair of matching residues) to N (i.e., the penalty score for mismatching residues), wherein the default values for M and N are 5 and −4, respectively. Four blastn parameters were adjusted as follows: Q=10 (gap creation penalty); R=10 (gap extension penalty); wink=1 (generates word hits at every $wink^{th}$ position along the query); and gapw=16 (sets the window width within which gapped alignments are generated). The equivalent Blastp parameter settings were Q=9; R=2; wink=1; and gapw=32. A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

"Stringent conditions" are those that (1) employ low ionic strength and high temperature for washing, for example, 0.015 M NaCl/0.0015 M sodium citrate/0.1% SDS (sodium dodecyl sulfate) at 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42□C. Another example is hybridization in 50% formamide, 5×SSC solution (0.75 M NaCl, 0.075 M sodium citrate), 50 mM sodium phosphate (pH 6.8), 0.1% sodium pyrophosphate, 5× Denhardt's solution (50× Denhards's Reagent: 1% (w/v) Ficoll 400, 1% (w/V) polyvinylpyrrolidone, 1% (w/v) bovine serum albumin (Sigma, Fraction V)), sonicated salmon sperm DNA (50 µg/ml), 0.1% SDS, and 10% dextran sulfate at 42° C., with washes at 42° C. in 0.2×SSC solution and 0.1% SDS. A skilled artisan can readily determine and vary the stringency conditions appropriately to obtain a clear and detectable hybridization signal. Preferred molecules are those that hybridize under the above conditions to the complement of SEQ ID NOs: 1, 3, 5, 7, 9, 11 and 13 and which encode a functional or full-length protein. Even more preferred hybridizing molecules are those that hybridize under the above conditions to the complement strand of the open reading frame of SEQ ID NOs: 1, 3, 5, 7, 9, 11 and 13.

As used herein, a nucleic acid molecule is said to be "isolated" when the nucleic acid molecule is substantially separated from contaminant nucleic acid molecules encoding other polypeptides.

The present invention further utilizes fragments of the disclosed nucleic acid molecules. As used herein, a fragment of a nucleic acid molecule refers to a small portion of the coding or non-coding sequence. The size of the fragment will be determined by the intended use. If the fragment is to be used as a nucleic acid probe or PCR primer, then the fragment length is chosen so as to obtain a relatively small number of false positives during probing/priming. If the fragment is chosen so as to encode an active portion of the protein, the fragment will need to be large enough to encode the functional region(s) of the protein. For instance, fragments which encode peptides corresponding to predicted antigenic regions may be prepared. For example, the present invention utilizes fragments that encode the amino acid sequence for the CDR3 region of the heavy chain of clone FabHSV8 as provided by SEQ ID NO: 1 of U.S. Pat. No. 6,156,313 (set forth herein as SEQ ID NO: 18). Furthermore, the present invention utilizes a human monoclonal antibody which neutralizes both HSV Type-1 and Type-2, binds to an epitope present on glycoprotein D, has the binding specificity of an Fab fragment produced by ATCC 69522, and has heavy chains with a CDR3 of SEQ ID NO:2 as provided by U.S. Pat. No. 6,156,313 (set forth herein as SEQ ID NO: 19).

Fragments of the nucleic acid molecules of the present invention (i.e., synthetic oligonucleotides) that are used as probes or specific primers for the polymerase chain reaction (PCR), or to synthesize gene sequences encoding proteins of the invention, can easily be synthesized by chemical techniques, for example, the phosphoramidite method of Matteucci et al. (J. Am. Chem. Soc. 103: 3185-3191 (1981) or using automated synthesis methods. In addition, larger DNA segments can readily be prepared by well known methods, such as synthesis of a group of oligonucleotides that define various modular segments of the gene, followed by ligation of oligonucleotides to build the complete modified gene.

The nucleic acid molecules of the present invention may further be modified so as to contain a detectable label for diagnostic and probe purposes. A variety of such labels are known in the art and can readily be employed with the encoding molecules herein described. Suitable labels include, but are not limited to, biotin, radiolabeled or fluorescently labeled nucleotides and the like. A skilled artisan can readily employ any such label to obtain labeled variants of the nucleic acid molecules of the invention.

II. Background for Production of IgG in Plants

A. Examples of Suitable IgGs to Utilize

Any IgG antibody can be used in the methods of the instant invention. IgG is the principal immunoglobulin of human plasma and other internal body fluids. It is also the most commonly seen myeloma protein. A myeloma protein designated Eu from a human protein was the first immunoglobulin to be completely sequenced (Edelman et al., Proc. Natl. Acad. Sci. USA 63:78 (1969)).

Immunoglobulin G (IgG) proteins are well known and characterized, including their nucleic acid and amino acid sequences. Examples of IgG immunoglobulins that can be used in the compositions and methods of the instant invention include but are not limited to the following: human antibodies reacting with different epitopes on integrin beta 3 of platelets and endothelial cells (Jallu et al., Eur J. Biochem. 222(3):743-51 (1994)); high affinity recombinant human IgG1 anti-RhD antibody (Miescher et al., Br J Haematol. 111(1):157-66 (2000)); synovial IgG against the EF-Tu of *M. tuberculosis* (Adachi et al., J Dent Res. 79(10):1752-7(2000)); binding to endogenous retroviral antigens in HIV-1 infected persons (Lawoko et al., J Med Virol. 62(4):43544 (2000)); immunoglobulin G antibody to human immunodeficiency virus type 1 (Hashinaka et al., Clin Diagn Lab Immunol. (6):967-76 (2000)); a recombinant human CCR5-specific antibody (Steinberger et al., J Biol Chem. 275(46):36073-8 (2000)); a cDNA sequence encoding the immunoglobulin heavy chain of the Antarctic teleost *Trematonmus bernacchii* (Coscia et al., Fish Shellfish Immunol. 10(4):343-57 (2000)); expression and regulation of immunoglobulin heavy chain gene transfected into lymphoid cells (Neuberger, EMBO J. 2(8):1373-8 (1983)); a murine monoclonal IgG that participates in the neutralization of *Androctonus australis* hector scorpion venom (Devaux et al., Eur J. Biochem. 268(3):694-702 (2001)); truncated forms of humanized L243 IgG1 (Lund et al., Eur J. Biochem. 267(24):7246-57.(2000)); single-chain Fv-Fc fusions in *Pichia pastoris* (Powers et al., J Immunol Methods. 1; 251(1-2):123-35 (2001)); immunoglobulin G (IgG) autoantibody specific for CRMP-5 (Yu et al., Ann Neurol. 49(2): 146-54 (2001)); IgG antibodies specific for Wolbachia surface protein in rhesus monkeys infected with *Brugia malayi* (Punkosdy et al., J Infect Dis. 184(3):385-9. Epub 2001 Jul. 3 (2001)); human IgG monoclonal anti-alpha(IIb) beta(3)-binding fragments (Jacobin et al., J. Immunol. 168 (4), 2035-2045 (2002)); systemic sclerosis immunoglobulin G autoantibodies (Lunardi et al., Nat. Med. 6(10):1183-6 (2000)); human monoclonal antibody specific for the leucine-33 (P1A1, HPA-1a) (Griffin et al., Blood. 15; 86(12):4430-6 (1995)); humanized anti-CD18 murine immunoglobulin G (Ipp et al., Arch Biochem Biophys. 308(2):387-99 (1994); and antibodies to GPIIb alpha (300-312) (Taylor et al., Proc Soc Exp Biol Med. 205(1):35-43 (1994)).

B. Integrins

Integrin receptors (also called integrins) are a class of molecules mediating cell adhesion to the extracellular matrix, and cell recognition and transmembrane responses in a wide array of physiological contexts (Clarke et al., Science 285:1028-1032 (1995)). Integrins $\alpha V\beta 3$ and $\alpha V\beta 5$ have been shown to have strong involvement in new blood vessel growth. Each of these integrins binds specific molecules in the extracellular matrix: $\alpha V\beta 3$ binds vitronectin plus other extracellular matrix proteins including fibrinogen; $\alpha V\beta 5$ is a vitronectin receptor. The primary medical target of the anti-integrin $\alpha V\beta 3/\alpha V\beta 5$ antibody is vascular recruitment by tumors ("tumor angiogenesis"). During angiogenesis, blood vessel endothelial cells leave pre-existing vessels and form new tubules, which will develop into capillaries. When this process is proceeding normally, vitronectin binding to $\alpha V\beta 5$ expressed in the vascular endothelial cells induces expression of $\alpha V\beta 3$ and promotes angiogenesis by a cascade of signals and interactions. Vitronectin binding to endothelial $\alpha V\beta 3$ also suppresses protein kinase A. When anti-$\alpha V\beta 3$ antibody blocks that binding to vitronectin, protein kinase A perturbs the cells so that vessel development, tumor cell migration and metastasis are inhibited. Cell death will occur in such antibody-blocked cells of angiogenic systems.

An antibody generated against $\alpha V\beta 3$ blocked basic fibroblast growth factor (bFGF) induced angiogenesis, whereas an antibody specific to $\alpha V\beta 5$ inhibited vascular endothelial growth factor (VEGF) induced angiogenesis (Eliceiri, et al., J. Clin. Invest. 103: 1227-1230 (1999); Friedlander et al., Science 270: 1500-1502 (1995)). In addition to those discussed above, other examples of integrin-related immunoglobulins that can be used in the compositions and methods of the instant invention include but are not limited to the following: monoclonal antibodies to ligand-occupied conformers of integrin alpha IIb beta 3 (glycoprotein IIb-IIIa) (Frelinger et al, J Biol. Chem. 266(26):17106-11 (1991)); human autoantibody 2E7 specific for the platelet integrin IIb heavy chain (Kunicki et al., J. Autoimmun. (3):433-46 (1991)); a murine monoclonal antibody directed against the CD18 component of leukocyte integrins (Daugherty et al., Nucleic Acids Res. 19(9):2471-6 (1991)); anti-integrin (alpha 5 beta 1) antibodies (Fogerty et al., J. Cell Biol. 111(2):699-708 (1990)); a monoclonal antibody against platelet GPIIb (Golino et al., J Biol. Chem. 265(16):9575-81 (1990)); human monoclonal autoantibody specific for human platelet glycoprotein IIb (integrin alpha IIb) heavy chain (Kunicki et al., Hum Antibodies Hybridomas 1(2):83-95 (1990)); humanized antibody specific for the platelet integrin gpIIb/IIIa (Co et al., J Immunol. 15; 152(6):2968-76 (1994)); bioactive Arg-Gly-Asp conformations in anti-integrin GPIIb-IIIa antibodies (Prammer et al., Receptor. 4(2):93-108 (1994)); humanized anti-beta 1 integrin chain mAb (Poul et al., Mol Immunol. 32(2):101-16 (1995)); leukocyte integrin lymphocyte function-associated antigen 1 (Holness et al., J Biol. Chem. 270(2):877-84 (1995)); synthetic antibodies as adhesive ligands for integrins (Smith et al., J Biol. Chem. 269(52):32788-95 (1994)); monoclonal antibodies to platelet integrin alpha IIb beta 3 (Yano et al., J Biochem (Tokyo). 116(4):778-86 (1994)); recombinant murine Fab fragment specific for the integrin alpha IIb beta 3 (Kunicki et al., J Biol. Chem. 270(28):16660-5 (1995)); IgG anti-phospholipid antibody with platelet glycoprotein IIIa (Tokita et al., Thromb Haemost. 75(1): 168-74 (1996)); and human monoclonal Fab fragments that bind specifically to the platelet HPA-1a alloantigen on glycoprotein IIb-IIIa (Proulx et al., Vox Sang. 72(1): 52-60 (1997)).

Examples of anti-dual integrin antibodies that can be used in the compositions and methods of the instant invention include but are not limited to those disclosed in U.S. Patent Application No. 2003/0040044 and International Published Patent Application No. WO 02/12501. See also ATCC Deposit Numbers AX472604, AX472605, AX472606, AX472607, AX472608, and AX47209.

III. General Background for Production for Either IgA and IgG in Plants

A. Recombinant DNA (rDNA) Molecules Comprising a Nucleic Acid Molecule

The present invention further provides recombinant DNA molecules (rDNAs) that contain a coding sequence. As used herein, a rDNA molecule is a DNA molecule that has been subjected to molecular manipulation. Methods for generating rDNA molecules are well known in the art, for example, see Sambrook et al., *Molecular Cloning—A Laboratory Manual, Third Ed.*, Cold Spring Harbor Laboratory Press, Cold Spring Harbor, N.Y., 2001. In the preferred rDNA molecules, a coding DNA sequence is operably linked to expression control sequences and/or vector sequences.

The choice of vector and/or expression control sequences to which one of the protein family encoding sequences of the present invention is operably linked depends directly, as is well known in the art, on the functional properties desired, e.g., protein expression, and the host cell to be transformed. A vector contemplated by the present invention is at least capable of directing the replication or insertion into the host chromosome, and preferably also expression, of the structural gene included in the rDNA molecule.

Expression control elements that are used for regulating the expression of an operably linked protein encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium.

B. Production of Recombinant Proteins using a rDNA Molecule

The present invention further provides methods for producing a protein of the invention using nucleic acid molecules herein described. In general terms, the production of a recombinant form of a protein typically involves the following steps:

First, a nucleic acid molecule is obtained that encodes a protein of the invention, such as a nucleic acid molecule comprising, consisting essentially of or consisting of SEQ ID NO: 1 or SEQ ID NO: 9.

If the encoding sequence is uninterrupted by introns, as are these open-reading-frames, it is directly suitable for expression in any host.

The nucleic acid molecule is then preferably placed in operable linkage with suitable control sequences, as described above, to form an expression unit containing the protein open reading frame. The expression unit is used to transform a suitable host and the transformed host is cultured under conditions that allow the production of the recombinant protein. Optionally the recombinant protein is isolated from the medium or from the cells; recovery and purification of the protein may not be necessary in some instances where some impurities may be tolerated.

Each of the foregoing steps can be done in a variety of ways. For example, the desired coding sequences may be obtained from genomic fragments and used directly in appropriate hosts. The construction of expression vectors that are operable in a variety of hosts is accomplished using appropriate replicons and control sequences, as set forth above. The control sequences, expression vectors, and transformation methods are dependent on the type of host cell used to express the gene and were discussed in detail earlier. Suitable restriction sites can, if not normally available, be added to the ends of the coding sequence so as to provide an excisable gene to insert into these vectors. A skilled artisan can readily adapt any host/expression system known in the art for use with the nucleic acid molecules of the invention to produce recombinant protein.

C. Promoters

An inducible promoter is a promoter where the rate of RNA polymerase binding and initiation is modulated by external stimuli. Such stimuli include light, heat, anaerobic stress, alteration in nutrient conditions, presence or absence of a metabolite, presence of a ligand, microbial attack, wounding and the like.

A viral promoter is a promoter with a DNA sequence substantially similar to the promoter found at the 5' end of a viral gene. For example, a typical viral promoter is found at the 5' end of the gene coding for the p2I protein of MMTV described by Huang et al., Cell 27:245 (1981).

A synthetic promoter is a promoter that was chemically synthesized rather than biologically derived. Usually synthetic promoters incorporate sequence changes that optimize the efficiency of RNA polymerase initiation.

A constitutive promoter is a promoter that promotes the expression of a gene product throughout an organism, such as a plant. Examples of constitutive promoters include the cauliflower mosaic virus 35S and 19S promoters (for example, Poszkowski et al., EMBO J. 3:2719 (1989); Odell et al., Nature 313:810 (1985)); and the maize ubiquitin-1 promoter (for example, U.S. Pat. Nos. 5,510,474; 5,614,399; 6,020,190 and 6,054,574).

A temporally regulated promoter is a promoter where the rate of RNA polymerase binding and initiation is modulated at a specific time during development. Examples of temporally regulated promoters are given in, for example, Chua et al., Science, 244:174-181 (1989).

A spatially regulated promoter is a promoter where the rate of RNA polymerase binding and initiation is modulated in a specific structure of the organism such as the leaf, stem, seed or root. Examples of spatially regulated promoters are given in Chua et al., Science 244:174-181 (1989). Such tissue-specific or organ-specific promoters are well known in the art and include but are not limited to seed-specific promoters, organ-primordia specific promoters, stem-specific promoters, leaf specific promoters, mesophyl-specific promoters (such as the light-inducible Rubisco promoters), root-specific promoters, tuber-specific promoters, vascular tissue specific promoters, stamen-selective promoters, dehiscence zone specific promoters and the like. The most preferred promoters for use in the instant invention will be most active in seed, fruit and tuber.

A spatiotemporally regulated promoter is a promoter where the rate of RNA polymerase binding and initiation is modulated in a specific structure of the organism at a specific time during development. An example of a typical spatiotemporally regulated promoter is the EPSP synthase-35S promoter described by Chua et al., Science 244:174-181 (1989).

For this invention, maize endosperm was determined to be the target tissue for gene expression, although the present invention is applicable to expression of the selected sIgA throughout the whole plant or in any specific tissue(s) of the plant. Gene expression in the maize endosperm ensures accumulation of high levels of the target protein and simplifies protein storage, shipment, extraction and purification. In one embodiment of the invention, an endosperm-specific promoter is used to drive expression of the HC and LC of anti-HSV antibodies.

Expression of seed-specific genes has been studied in great detail (see reviews, for example, by Goldberg et al., Cell 56:149-160 (1989) and Higgins et al., Ann. Rev. Plant Physiol. 35:191-221 (1984)). Promoter analysis of seed-specific genes is reviewed in Goldberg et al., Cell 56: 149-160 (1989) and Thomas, Plant Cell 5: 1401-1410 (1993). Research indicates that no plant gene is more tightly regulated in terms of spatial expression than those encoding seed storage proteins.

Many seed storage protein genes have been cloned from diverse plant species, and their promoters have been analyzed in detail (Thomas, Plant Cell 5: 1401-1410 (1993)). There are currently numerous examples of seed-specific expression of seed storage protein genes in transgenic plants. See, for example, b-phaseolin (Sengupta-Gopalan et al., Proc. Natl. Acad, Sci. USA 82:3320-3324 (1985); Hoffman et al., Plant Mol. Biol. 11, 717-729 (1988)); bean lectin (Voelker et al., EMBO J. 6:3571-3577 (1987)); soybean lectin (Okamuro et al., Proc. Natl. Acad. Sci. USA 83:8240-8244 (1986)); soybean Kunitz trypsin inhibitor (Perez-Grau et al., Plant Cell 1:095-1109 (1989)); soybean b-conglycinin (Beachy et al., EMBO J. 4:3047-3053 (1985); pea vicilin (Higgins et al., Plant Mol. Biol. 11:683-695 (1988)); pea convicilin (Newbigin et al., Planta 180:461-470 (1990)); pea legumin (Shirsat et al., Mol. Gen. Genetics 215:326-331 (1989)); rapeseed napin (Radke et al., Theor. Appl. Genet. 75:685-694(1988)); maize 18 kD oleosin (Lee et al., Proc Natl. Acad. Sci. USA 888: 6181-6185 (1991)); barley b-hordein (Marris et al., Plant Mol. Biol. 10:359-366 (1988); wheat glutenin (Colot et al., EMBO J. 6:3559-3564 (1987)). For additional sources of seed-specific promoters, see, for example, U.S. Pat. Nos. 5,623,067; 6,100,450; 6,177,613; 6,225,529; 6,342,657 and 6,403,371; Knutzon et al., Proc. Natl. Acad. Sci. USA 89:2624 (1992); Bustos et al., EMBO J. 10:1469 (1991), Lam and Chua, Science 248:471(1991); Stayton et al., Aust. J. Plant. Physiol. 18:507 (1991), each of which is incorporated by reference in its entirety. Moreover, seed-specific promoter genes operably linked to heterologous coding sequences in chimeric gene constructs also maintain their temporal and spatial expression pattern in transgenic plants. Such examples include use of *Arabidopsis thaliana* 2S seed storage protein gene promoter to express enkephalin peptides in *Arabidopsis* and *B. napus* seeds (see, for example, Vandekerckhove et al., Bio/Technology 7:929-932 (1989)); bean lectin and bean b-phaseolin promoters to express luciferase (see, for example, Riggs et al., Plant Sci. 63:47-57 (1989)); and wheat glutenin promoters to express chloramphenicol acetyl transferase (see, for example, Colot et al., EMBO J. 6:3559-3564 (1987)).

D. Vectors

As provided elsewhere herein, several embodiments of the present invention employ expression units (or expression vectors or systems) to express an exogenously supplied nucleic acid sequence in a plant. Methods for generating expression units/systems/vectors for use in plants are well known in the art and can readily be adapted for use in the instant invention. A skilled artisan can readily use any appropriate plant/vector/expression system in the present methods following the outline provided herein.

A gamete-specific promoter, a constitutive promoter (such as the CaMV or Nos promoter), an organ-specific promoter (such as the E8 promoter from tomato) or an inducible promoter is typically ligated to the protein or antisense encoding region using standard techniques known in the art. The expression unit may be further optimized by employing supplemental elements such as transcription terminators and/or enhancer elements.

The expression control elements used to regulate the expression of the protein can either be the expression control element that is normally found associated with the coding sequence (homologous expression element) or can be a heterologous expression control element. A variety of homologous and heterologous expression control elements are known in the art and can readily be used to make expression units for use in the present invention.

Transcription initiation regions, for example, can include any of the various opine initiation regions, such as octopine, mannopine, nopaline and the like that are found in the Ti plasmids of *Agrobacterium tumefacians*.

Plant viral promoters can also be used, such as, for example, the cauliflower mosaic virus 35S (CaMV 35S) promoter, to control gene expression in a plant.

Plant promoters such as prolifera promoter, fruit-specific promoters, Ap3 promoter, heat shock promoters, seed-specific promoters, etc. can also be used. The most preferred promoters for use in the instant invention will be most active in seed, fruit and tuber.

Thus, for expression in plants, the expression units will typically contain, in addition to the protein sequence, a plant promoter region, a transcription initiation site and a transcription termination sequence. Unique restriction enzyme sites at the 5' and 3' ends of the expression unit are typically included to allow for easy insertion into a preexisting vector.

In the construction of heterologous promoter/structural gene or antisense combinations, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette can also contain a transcription termination region downstream of the structural gene to provide for efficient termination. The termination region may be obtained from the same gene as the promoter sequence or may be obtained from different genes. If the mRNA encoded by the structural gene is to be efficiently processed, DNA sequences which direct polyadenylation of the RNA are also commonly added to the vector construct. Polyadenylation sequences include, but are not limited to the *Agrobacterium octopine* synthase signal (Gielen et al., EMBO J 3:835-846 (1984)) or the nopaline synthase signal (Depicker et al., Mol. and Appl. Genet. 1:561-573 (1982)).

The resulting expression unit is ligated into or otherwise constructed to be included in a vector that is appropriate for higher plant transformation. The vector will also typically contain a selectable marker gene by which transformed plant cells can be identified in culture. Antibiotic resistance markers could be used. These markers include, but are not limited to, resistance to G418, hygromycin, bleomycin, kanamycin, and gentamicin. More preferably, herbicide resistance markers are utilized. See, for example, U.S. Pat. Nos. 5,879,903; 5,637,489 and 5,276,268 for phosphinothricin (PTC)-resistance to phosphinothricyl-alanyl-alanine (PTT). Also see, for example, U.S. Pat. Nos. 5,767,361; 5,928,937 and 6,444,875 for acetohydroxy acid synthase (AHAS) resistant to imidazolinone herbicides. After transforming the plant cells, those cells having the vector will be identified by their ability to grow on a medium containing the particular antibiotic. Replication sequences, of bacterial or viral origin, are generally also included, but are not limited to, to allow the vector to be cloned in a bacterial or phage host, preferably a broad host range prokaryotic origin of replication is included. A selectable marker for bacteria should also be included, to allow selection of bacterial cells bearing the desired construct. Suitable prokaryotic selectable markers also include, but are not limited to, resistance to antibiotics such as ampicillin, kanamycin or tetracycline.

Other DNA sequences encoding additional functions may also be present in the vector, as is known in the art. For instance, in the case of *Agrobacterium* transformations, T-DNA sequences will also be included for subsequent transfer to plant chromosomes.

The sequences of the present invention can also be fused to various other nucleic acid molecules such as Expressed Sequence Tags (ESTs), epitopes or fluorescent protein markers.

ESTs are gene fragments, typically 300 to 400 nucleotides in length, sequenced from the 3' or 5' end of complementary-DNA (cDNA) clones. Nearly 30,000 *Arabidopsis thaliana* ESTs have been produced by a French and an American consortium (Delseny et al., FEBS Lett. 405(2):129-132 (1997); *Arabidopsis thaliana* Database, http://genome.www-.stanford.edu/Arabidopsis). For a discussion of the analysis of gene-expression patterns derived from large EST databases, see, e.g., M. R. Fannon, TIBTECH 14:294-298 (1996).

Biologically compatible fluorescent protein probes, particularly the self-assembling green fluorescent protein (GFP) from the jellyfish *Aequorea victoria*, have revolutionized research in cell, molecular and developmental biology because they allow visualization of biochemical events in living cells (see, for example, Murphy et al., Curr. Biol. 7(11): 870-876 (1997); Grebenok et al., Plant J. 11(3):573-586 (1997); Chiu et al., Curr. Biol. 6(3):325-330 (1996); and, Plautz et al., Gene 173(1):83-87 (1996); and, Sheen et al., Plant J. 8(5):777-784 (1995)).

Site-directed mutagenesis has been used to develop a more soluble version of the codon-modified GFP called soluble-modified GFP (smGFP). When introduced into *Arabidopsis*, greater fluorescence was observed when compared to the codon-modified GFP, implying that smGFP is 'brighter' because more of it is present in a soluble and functional form (Davis et al., Plant Mol. Biol. 36(4):521-528 (1998)). By fusing genes encoding GFP and beta-glucuronidase (GUS), researchers were able to create a set of bifunctional reporter constructs which are optimized for use in transient and stable expression systems in plants, including *Arabidopsis*. See, for example, Quaedvlieg et al., Plant Mol. Biol. 37(4):715-727 (1998).

Berger et al. (Dev. Biol. 194(2):226-234 (1998)) report the isolation of a GFP marker line for *Arabidopsis* hypocotyl epidermal cells. GFP-fusion proteins have been used to localize and characterize a number of *Arabidopsis* genes, including geranylgeranyl pyrophosphate (GGPP) (Zhu et al., Plant Mol. Biol. 35(3):331-341 (1997)).

E. Disabling Genes

It may be desirable to disable certain plant genes to gain the expression of the transgene and/or to obtain the desired protein produced as a result of the expression of the transgene. For example, in the instant invention, it may be desirable to disable certain enzymes that are native to the transgenic plant, for example one or more specific plant transferases. Methods of disabling genes are well known to those of ordinary skill in the art.

For example, an effective disabling modification is the introduction of a single nucleotide deletion occurring at the beginning of a gene that would produce a translational reading frameshift. Such a frameshift would disable the gene, resulting in non-expressible gene product and thereby disrupting functional protein production by that gene. If the unmodified gene encodes a protease, for example, protease production by the gene could be disrupted if the regulatory regions or the coding regions of the protease gene are disrupted.

In addition to disabling genes by deleting nucleotides, causing a transitional reading frameshift, disabling modifications would also be possible by other techniques well known to those of ordinary skill, including insertions, substitutions, inversions or transversions of nucleotides within the gene's DNA that would effectively prevent the formation of the protein encoded by the DNA.

It is also within the capabilities of one skilled in the art to disable genes by the use of less specific methods. Examples of less specific methods would be the use of chemical mutagens such as hydroxylamine or nitrosoguanidine or the use of radiation mutagens such as gamma radiation or ultraviolet radiation to randomly mutate genes. Such mutated strains could, by chance, contain disabled genes such that the genes were no longer capable of producing functional proteins for any one or more of the domains. The presence of the desired disabled genes could be detected by routine screening techniques. For further guidance, see, for example, U.S. Pat. No. 5,759,538.

F. Antisense Encoding Vectors

As discussed above, it may be desirable to inhibit the expression of certain native plant genes, such as specific plant transferases, in order to obtain expression of the transgene and/or to obtain the desired protein coded by the transgene. Methods for inhibiting expression in plants using antisense constructs, including generation of antisense sequences in situ are well known to those of ordinary skill in the art and are described, for example, in U.S. Pat. Nos. 5,107,065; 5,254, 800; 5,356,799; 5,728,926; and 6,184,439.

Other methods that can be used to inhibit expression of an endogenous gene in a plant may also be used in the present methods. For example, formation of a triple helix at an essential region of a duplex gene serves this purpose. The triplex code, permitting design of the proper single stranded participant is also known in the art. (See, for example, H. E. Moser et al., Science 238:645-650 (1987) and M. Cooney et al., Science 241:456-459 (1988)). Regions in the control sequences containing stretches of purine bases are particularly attractive targets. Triple helix formation along with photocrosslinking is described, e.g., in D. Praseuth et al., Proc. Nat'l Acad. Sci. USA 85:1349-1353 (1988).

G. Transformation

To introduce a desired gene or set of genes by conventional methods requires a sexual cross between two lines, and then repeated back-crossing between hybrid offspring and one of the parents until a plant with the desired characteristics is obtained. This process, however, is restricted to plants that can sexually hybridize, and genes in addition to the desired gene will be transferred.

Recombinant DNA techniques allow plant researchers to circumvent these limitations by enabling plant geneticists to identify and clone specific genes for desirable traits, such as resistance to an insect pest, and to introduce these genes into already useful varieties of plants. Once the foreign genes have been introduced into a plant, that plant can then be used in conventional plant breeding schemes (e.g., pedigree breeding, single-seed-descent breeding schemes, reciprocal recurrent selection) to produce progeny which also contain the gene of interest.

Genes can be introduced in a site directed fashion using homologous recombination. Homologous recombination permits site-specific modifications in endogenous genes and thus inherited or acquired mutations may be corrected, and/or novel alterations may be engineered into the genome. Homologous recombination and site-directed integration in plants are discussed in, for example, U.S. Pat. Nos. 5,451,513; 5,501,967 and 5,527,695.

Methods of producing transgenic plants are well known to those of ordinary skill in the art. Transgenic plants can now be produced by a variety of different transformation methods including, but not limited to, electroporation; microinjection; microprojectile bombardment, also known as particle acceleration or biolistic bombardment; viral-mediated transformation; and *Agrobacterium*-mediated transformation. See, for example, U.S. Pat. Nos. 5,405,765; 5,472,869; 5,538,877; 5,538,880; 5,550,318; 5,641,664; 5,736,369 and 5,736,369; Watson et al., Recombinant DNA, Scientific American Books (1992); Hinchee et al., Bio/Tech. 6:915-922 (1988); McCabe et al., Bio/Tech. 6:923-926 (1988); Toriyama et al., Bio/Tech. 6:1072-1074 (1988); From et al., Bio/Tech. 8:833-839 (1990); Mullins et al., Bio/Tech. 8:833-839 (1990); Hiei et al., Plant Molecular Biology 35:205-218 (1997); Ishida et al., Nature Biotechnology 14:745-750 (1996); Zhang et al., Molecular Biotechnology 8:223-231 (1997); Ku et al., Nature Biotechnology 17:76-80 (1999); and, Raineri et al., Bio/Tech. 8:33-38 (1990)), each of which is expressly incorporated herein by reference in their entirety.

*Agrobacterium tumefaciens* is a naturally occurring bacterium that is capable of inserting its DNA (genetic information) into plants, resulting in a type of injury to the plant known as crown gall. Most species of plants can now be transformed using this method, including alfalfa. See, for example, Wang et al., Australian Journal of Plant Physiology 23(3): 265-270 (1996); Hoffman et al., Molecular Plant-Microbe Interactions 10(3): 307-315 (1997); and, Trieu et al., Plant Cell Reports 16:6-11 (1996).

Microprojectile bombardment is also known as particle acceleration, biolistic bombardment, and the gene gun (Biolistic® Gene Gun). The gene gun is used to shoot pellets that are coated with genes (e.g., for desired traits) into plant seeds or plant tissues in order to get the plant cells to then express the new genes. The gene gun uses an actual explosive (0.22 caliber blank) to propel the material. Compressed air or steam may also be used as the propellant. The Biolistic® Gene Gun was invented in 1983-1984 at Cornell University by John Sanford, Edward Wolf, and Nelson Allen. It and its registered trademark are now owned by E.I. du Pont de Nemours and Company. Most species of plants have been transformed using this method, including alfalfa (U.S. Pat. No. 5,324,646) and clover (Voisey et al., Biocontrol Science and Technology 4(4): 475-481 (1994); Quesbenberry et al., Crop Science 36(4): 1045-1048 (1996); Khan et al., Plant Physiology 105 (1): 81-88 (1994); and, Voisey et al., Plant Cell Reports 13(6): 309-314 (1994)).

Developed by ICI Seeds Inc. (Garst Seed Company) in 1993, WHISKERS™ is an alternative to other methods of inserting DNA into plant cells (e.g., the Biolistic® Gene Gun, *Agrobacterium tumefacien*, the "Shotgun" Method, etc.); and it consists of needle-like crystals ("whiskers") of silicon carbide. The fibers are placed into a container along with the plant cells, then mixed at high speed, which causes the crystals to pierce the plant cell walls with microscopic "holes" (passages). Then the new DNA (gene) is added, which causes the DNA to flow into the plant cells. The plant cells then incorporate the new gene(s); and thus they have been genetically engineered.

The essence of the WHISKERS™ technology is the small needle-like silicon carbide "whisker" (0.6 microns in diameter and 5-80 microns in length) which is used in the following manner. A container holding a "transformation cocktail" composed of DNA (e.g., agronomic gene plus a selectable marker gene), embryogenic corn tissue, and silicon carbide "whiskers" is mixed or shaken in a robust fashion on either a dental amalgam mixer or a paint shaker. The subsequent collisions between embryogenic corn cells and the sharp silicon carbide "whiskers" result in the creation of small holes in the plant cell wall through which DNA (the agronomic gene) is presumed to enter the cell. Those cells receiving and incorporating a new gene are then induced to grow and ultimately develop into fertile transgenic plants.

Silicon carbide "whisker" transformation has now produced stable transformed calli and/or plants in a variety of plants species such as *Zea mays*. See, for example, U.S. Pat. Nos. 5,302,523 and 5,464,765, each of which is incorporated herein by reference in their entirety; Frame et al., The Plant Journal 6: 941-948 (1994); Kaeppler et al., Plant Cell Reports 9:415-418 (1990); Kaeppler et al., Theoretical and Applied Genetics 84:560-566 (1992); Petolino et al., Plant Cell Reports 19(8):781-786 (2000); Thompson et al., Euphytica 85:75-80 (1995); Wang et al., In Vitro Cellular and Developmental Biology 31:101-104 (1995); Song et al., Plant Cell Reporter 20:948-954 (2002); Petolino et al., Molecular Methods of Plant Analysis, In Genetic Transformation of Plants, Vol. 23, pp. 147-158, Springer-Verlag, Berlin (2003). Other examples include *Lolium multiflorum, Lolium perenne, Festuca arundinacea, Agrostis stolonifera* (Dalton et al., Plant Science 132:3143 (1997)), *Oryza sativa* (Nagatani et al., Biotechnology Techniques 11:471-473 (1997)), and *Triticum aestivum* and *Nicotiana tobacum* (Kaeppler et al., Theoretical and Applied Genetics 84:560-566 (1992)). Even *Chlamydomonas* (see, for example, Dunahay, T. G., Biotechniques 15:452-460 (1993)) can be transformed with a "whiskers" approach. As it is currently practiced on higher plants, the "whisker" system is one of the least complex ways to transform some plant cells.

Genes successfully introduced into plants using recombinant DNA methodologies include, but are not limited to, those coding for the following traits: seed storage proteins, including modified 7S legume seed storage proteins (see, for example, U.S. Pat. Nos. 5,508,468, 5,559,223 and 5,576, 203); herbicide tolerance or resistance (see, for example, De Greef et al., Bio/Technology 7:61 (1989); U.S. Pat. No. 4,940, 835; U.S. Pat. No. 4,769,061; U.S. Pat. No. 4,975,374; Marshall et al. (1992) Theor. Appl. Genet. 83, 435; U.S. Pat. No. 5,489,520; U.S. Pat. No. 5,498,544; U.S. Pat. No. 5,554,798; Powell et al., Science 232:738-743 (1986); Kaniewski et al., Bio/Tech. 8:750-754 (1990)); Day et al., Proc. Natl. Acad. Sci. USA 88:6721-6725 (1991)); phytase (see, for example, U.S. Pat. No. 5,593,963); resistance to bacterial, fungal, nematode and insect pests, including resistance to the lepidoptera insects conferred by the Bt gene (see, for example, U.S. Pat. Nos. 5,597,945 and 5,597,946; Johnson et al., Proc. Natl. Acad. Sci. USA, 86:9871-9875 (1989); Perlak et al., Bio/Tech. 8:939-943 (1990)); lectins (U.S. Pat. No. 5,276, 269); flower color (Meyer et al, Nature 330:677-678 (1987); Napoli et al., Plant Cell 2:279-289 (1990); van der Krol et al., Plant Cell 2:291-299 (1990)); Bt genes (Voisey et al., supra); neomycin phosphotransferase II (Quesbenberry et al., supra); the pea lectin gene (Diaz et al., Plant Physiology 109(4): 1167-1177 (1995); Eijsden et al., Plant Molecular Biology 29(3):431-439 (1995)); the auxin-responsive promoter GH3 (Larkin et al., Transgenic Research 5(5):325-335 (1996)); seed albumin gene from sunflowers (Khan et al., Transgenic Research 5(3):179-185 (1996)); and genes encoding the enzymes phosphinothricin acetyl transferase, beta-glucuronidase (GUS) coding for resistance to the Basta® herbicide, neomycin phosphotransferase, and an alpha-amylase inhibitor (Khan et al., supra), each of which is expressly incorporated herein by reference in their entirety.

For certain purposes, different antibiotic or herbicide selection markers may be preferred. Selection markers used routinely in transformation include the nptII gene which confers resistance to kanamycin and related antibiotics (see, for example, Messing & Vierra, Gene 19: 259-268 (1982); Bevan et al., Nature 304:184-187 (1983)), the bar gene which confers resistance to the herbicide phosphinothricin (White et al., Nucl Acids Res 18:1062 (1990), Spencer et al., Theor Appl Genet 79:625-631(1990)), and the dhfr gene, which confers resistance to methotrexate (Bourouis et al., EMBO J. 2(7): 1099-1104 (1983)).

Transgenic alfalfa plants have been produced using a number of different genes isolated from both alfalfa and non-alfalfa species including, but not limited to, the following: the promoter of an early nodulin gene fused to the reporter gene gusA (Bauer et al., The Plant Journal 10(1):91-105 (1996)); the early nodulin gene (Charon et al., Proc. Natl. Acad. of Sci. USA 94(16):8901-8906 (1997); Bauer et al., Molecular Plant-Microbe Interactions 10(1):39-49 (1997)); NADH-dependent glutamate synthase (Gantt, The Plant Journal 8(3): 345-358 (1995)); promoter-gusA fusions for each of three lectin genes (Bauchrowitz et al., The Plant Journal 9(1):31-43 (1996)); the luciferase enzyme of the marine soft coral *Renilla reniforms* fused to the CaMV promoter (Mayerhofer et al., The Plant Journal 7(6):1031-1038 (1995)); Mn-superoxide dismutase cDNA (McKersie et al., Plant Physiology 111(4): 1177-1181 (1996)); synthetic cryIC genes encoding a *Bacillus thuringiensis* delta-endotoxin (Strizhov et al., Proc. Natl. Acad. Sci. USA 93(26):15012-15017 (1996)); glucanse (Dixon et al., Gene 179(1):61-71 (1996); and leaf senescence gene (U.S. Pat. No. 5,689,042).

Genetic transformation has also been reported in numerous forage and turfgrass species (Conger B. V., Genetic Transformation of Forage Grasses in Molecular and Cellular Technologies for Forage Improvement, CSSA Special Publication No. 26, Crop Science Society of America, Inc. E. C. Brummer et al. Eds. 1998, pages 49-58). These include, but are not limited to, orchardgrass (*Dactylis glomerata* L.), tall fescue (*Festuca arundinacea* Schreb.) red fescue (*Festuca rubra* L.), meadow fescue (*Festuca pratensis* Huds.) perennial ryegrass (*Lolium perenne* L.) creeping bentgrass (*Agrostis palustris* Huds.) and redtop (*Agrostis alba* L.).

Transgenic plants have been utilized for the molecular farming ("phaming") of industrial proteins. For example, recombinant egg white avidin and bacterial B-glucuronidase (GUS) from transgenic maize have been commercially produced, with high levels of expression being obtained in seed by employing the ubiquitin promoter from maize (Hood et al., Adv Exp Med Biol 464:127-147 (1999)).

H. Hemizygosity

A transgenic plant formed using *Agrobacterium* transformation methods typically contains a single gene on one chromosome, although multiple copies are possible. Such transgenic plants can be referred to as being hemizygous for the added gene. A more accurate name for such a plant is an independent segregant, because each transformed plant represents a unique T-DNA integration event (see, for example, U.S. Pat. No. 6,156,953). A transgene locus is generally characterized by the presence and/or absence of the transgene. A heterozygous genotype in which one allele corresponds to the absence of the transgene is also designated hemizygous (see, for example, U.S. Pat. No. 6,008,437).

Assuming normal hemizygosity, selfing will result in maximum genotypic segregation in the first selfed recombinant generation, also known as the R1 or $R_1$ generation. The $R_1$ generation is produced by selfing the original recombinant line, also known as the R0 or $R_0$ generation. Because each insert acts as a dominant allele, in the absence of linkage and assuming only one hemizygous insert is required for tolerance expression, one insert would segregate 3:1, two inserts, 15:1, three inserts, 63:1, etc. Therefore, relatively few $R_1$ plants need to be grown to find at least one resistance phenotype (see, for example, U.S. Pat. Nos. 5,436,175 and 5,776, 760).

As mentioned above, self-pollination of a hemizygous transgenic regenerated plant should produce progeny equivalent to an $F_2$ in which approximately 25% should be homozygous transgenic plants. Self-pollination and testcrossing of the $F_2$ progeny to non-transformed control plants can be used to identify homozygous transgenic plants and to maintain the line. If the progeny initially obtained for a regenerated plant were from cross pollination, then identification of homozygous transgenic plants will require an additional generation of self-pollination (see, for example, U.S. Pat. No. 5,545,545).

I. Breeding Methods

Open-Pollinated Populations. The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes for flow from one population to another. Plants in one population (cultivar, strain, ecotype, or any germplasm source) are crossed either naturally (e.g., by wind) or by hand or by bees (commonly *Apis mellifera* L. or *Megachlile rotundata* F.) with plants from other populations. Selection is applied to improve one (or sometimes both) population(s) by isolating plants with desirable traits from both sources.

There are basically two primary methods of open-pollinated population improvement. First, there is the situation in which a population is changed ell masse by a chosen selection procedure. The outcome is an improved population that is indefinitely propagable by random-mating within itself in isolation. Second, the synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including but not limited to: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988).

Mass Selection. In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

Synthetics. A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (*Vicia*) or clones, as in herbage grasses, clovers and alfalfa, makes no difference in principle. Parents are selected on general combining ability, sometimes by test crosses or topcrosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enter a synthetic vary widely. In practice, numbers of parental lines range from 10 to several hundred, with 100-200 being the average. Broad based synthetics formed from 100 or more clones would be expected to be more stable during seed multiplication than narrow based synthetics.

Hybrids. A hybrid is an individual plant resulting from a cross between parents of differing genotypes. Commercial hybrids are now used extensively in many crops, including corn (maize), sorghum, sugarbeet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individual plants in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

The production of hybrids is a well-developed industry, involving the isolated production of both the parental lines and the hybrids which result from crossing those lines. For a detailed discussion of the hybrid production process, see, for example, Wright, H., Commercial Hybrid Seed Production, volume 8, pages 161-176, In *Hybridization of Crop Plants*, supra.

EXAMPLES

I. Examples for the Production of IgA in Plants

Two basic strategies were employed to produce anti-HSV monomeric IgA in maize:
constitutive expression of IgA; and
endosperm-specific expression of IgA.

Experiments also compared the efficacy of expression of the heavy chain ("HC") and light chain ("LC") on a single plasmid versus HC and LC on two separate plasmids.

Example 1

Construction of Ubiquitin/HC, LC Plasmids

Constitutive expression of anti-HSV antibody genes was chosen so as to enable the rapid analysis of protein production on callus tissue. More specifically, maize ubiquitin-1 promoter-driven HSV heavy chain HC and LC plasmid constructions and transgenic events were made to demonstrate correct assembly and accumulation of heavy chain and light chain genes from certain plasmid configurations.

Maize ubiquitin-1 ('ubi') is described, for example, in U.S. Pat. Nos. 5,510,474; 5,614,399; 6,020,190; and 6,054,574, each of which is herein incorporated in its entirety. MAR (matrix association region) is described in U.S. Pat. Nos. 5,773,689 and 6,239,328, each of which is herein incorporated in its entirety. Maize per5 UTR is described in U.S. Pat. No. 6,384,207, which is herein incorporated in its entirety. The genes used in this experiment were not rebuilt for plant codon-bias, and they contain the barley alpha-amylase leader sequence for targeting protein to the endoplasmic reticulum.

Figure 2:
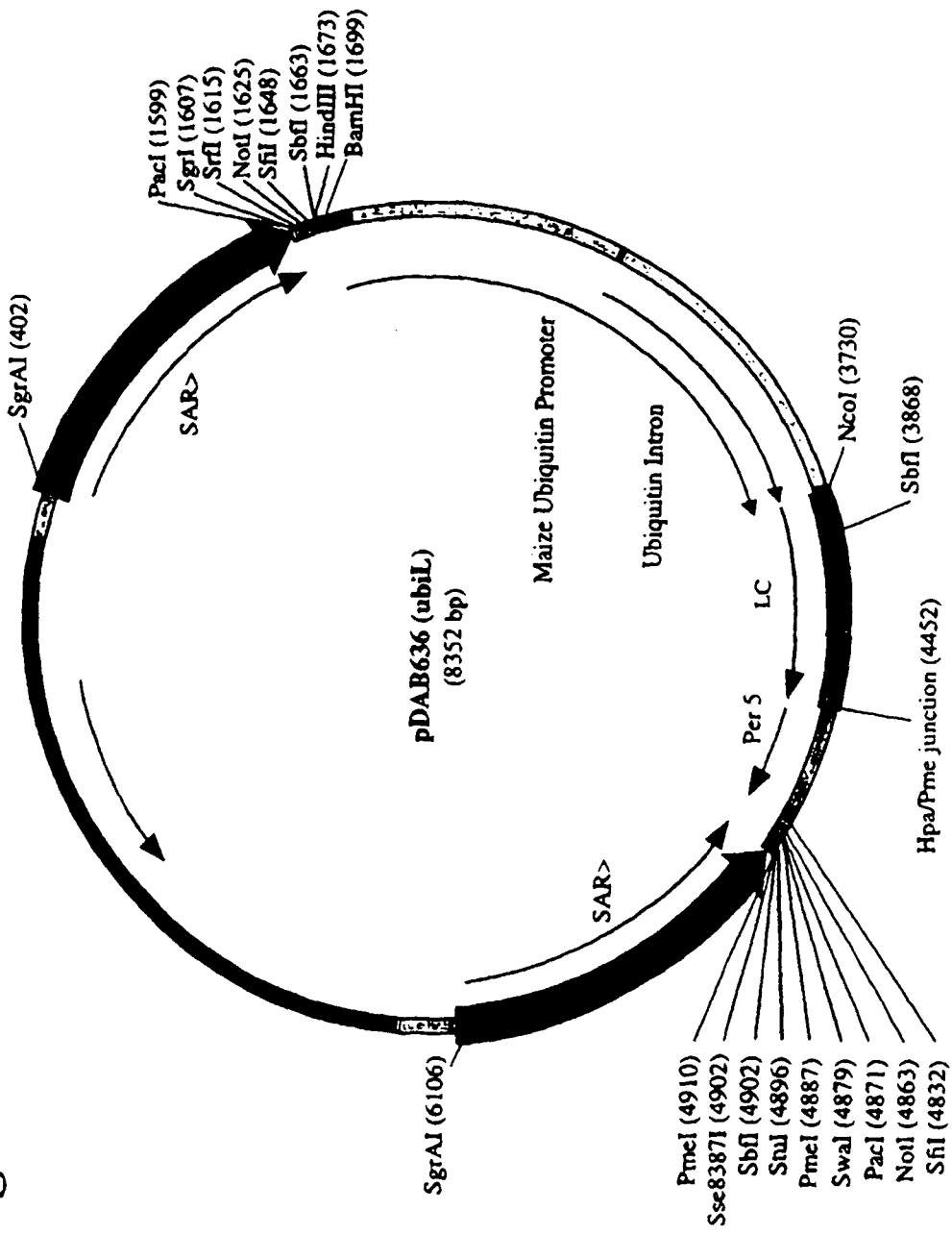
FIG. 2. Plasmid for pDAB636 (ubiL). (SEQ ID NO: 16).
SAR nucleotides: 424-1589
Maize ubiquitin promoter/intron nucleotides: 1717-3730
Anti-HSV light chain nucleotides: 3732-4448
(w/barley alpha amylase leader)
Maize per5 3' UTR nucleotides: 4456-4820
SAR nucleotides: 4928-6093
Figure 3:
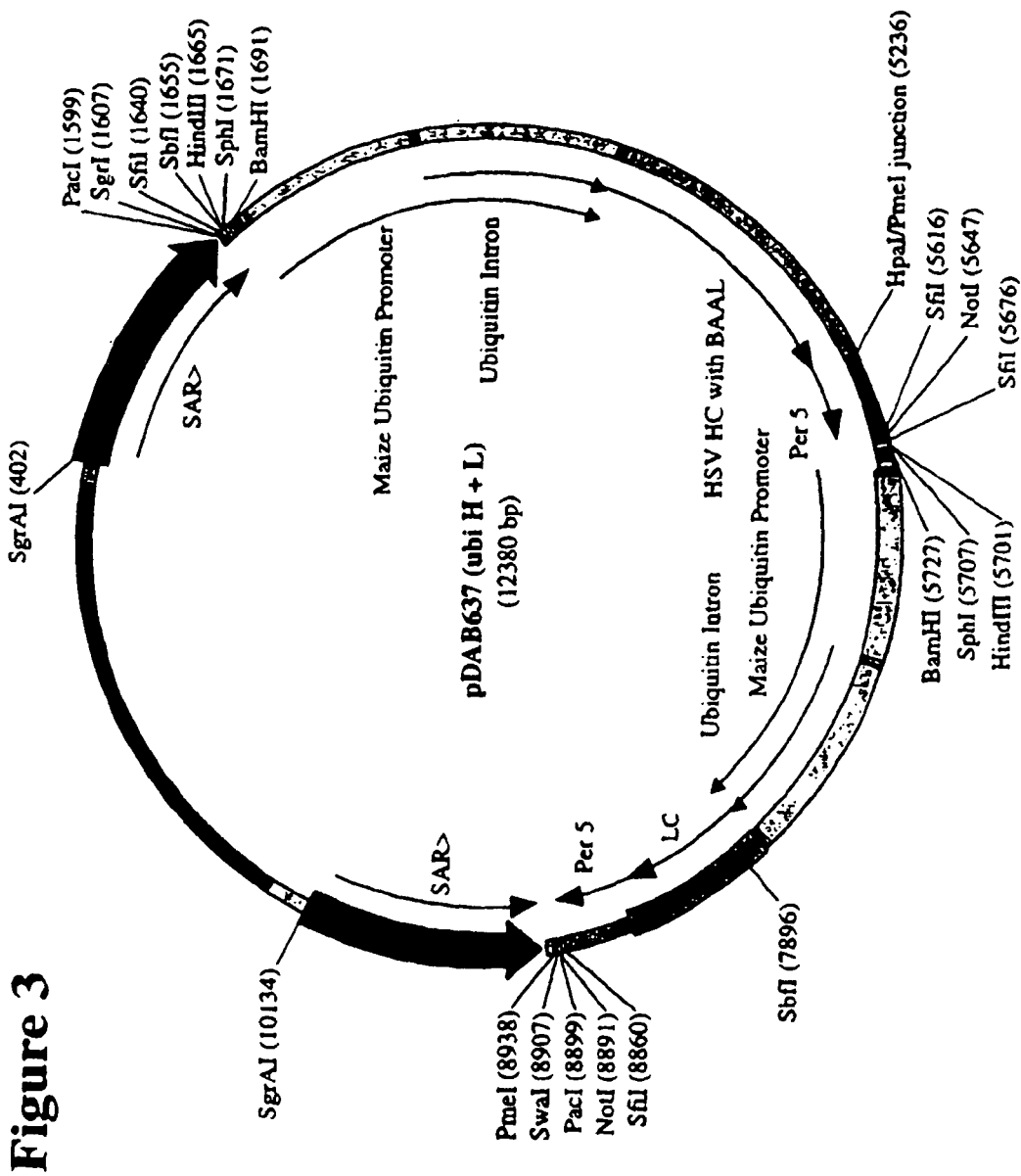
FIG. 3. Plasmid for pDAB637 (ubiH+L). (SEQ ID NO: 17)
SAR nucleotides: 424-1589
Maize ubiquitin promoter/intron nucleotides: 1709-3722
Anti-HSV heavy chain nucleotides: 724-5232
(w/barley alpha amylase leader)
Maize per5 3' UTR nucleotides: 5240-5604
Maize ubiquitin promoter/intron nucleotides: 5745-7758
Anti-HSV light chain nucleotides: 7760-8476
(w/barley alpha amylase leader)
Maize per5 3' UTR nucleotides: 8484-8848
SAR nucleotides: 8956-10121

The following vectors were assembled:
pDAB635 (MAR::ubi/HC/per5::MAR) (FIG. 1; SEQ ID NO: 15);
pDAB636 (MAR::ubi/LC/per5::MAR) (FIG. 2; SEQ ID NO: 16); and
pDAB637 (MAR::ubi/HC/per5::ubi/LC/per5::MAR) (FIG. 3; SEQ ID NO: 17).

The antibody genes were liberated from source vectors on NcoI-HpaI fragments and cloned into NcoI-PmeI sites of vector pDAB4005, between the maize ubiquitin promoter and the maize per5 3' UTR, replacing the GUS coding region. The entire ubi promoter/antibody gene/per5 cassette was then liberated on a NotI fragment and inserted into the NotI site of the inverse MAR vector 252-4. Plasmid pDAB637 was constructed by liberating the ubi/HC/per5 cassette on a NotI fragment from an intermediate vector, and blunt ending the fragment with T4 polymerase for insertion into a unique SrfI site in pDAB636. All three plasmids were bulked up in preparation for maize transformation with pDAB3014, which contains the selectable marker cassette rice actin/pat/lipase.

Example 2

Alternative Methods of Delivering Multiple Plasmids

Because of the extreme differences in the size between the PAT plasmid (pDAB3014) and the antibody plasmids, there was concern that the use of equal mass amounts of DNA for co-transformation would result in inefficient delivery of each of the plasmids into the maize cells. In an effort to evaluate certain parameters for the delivery of multiple plasmids into maize cells, the use of molar equivalent amounts of DNA was compared to the use of mass equivalent amounts of DNA to determine if there is any effect on the efficiency at which the cells receive all of the necessary plasmids.

A total of 106 events were available for PCR and 10 events that were analyzed to be positive were regenerated.

Figure 4:
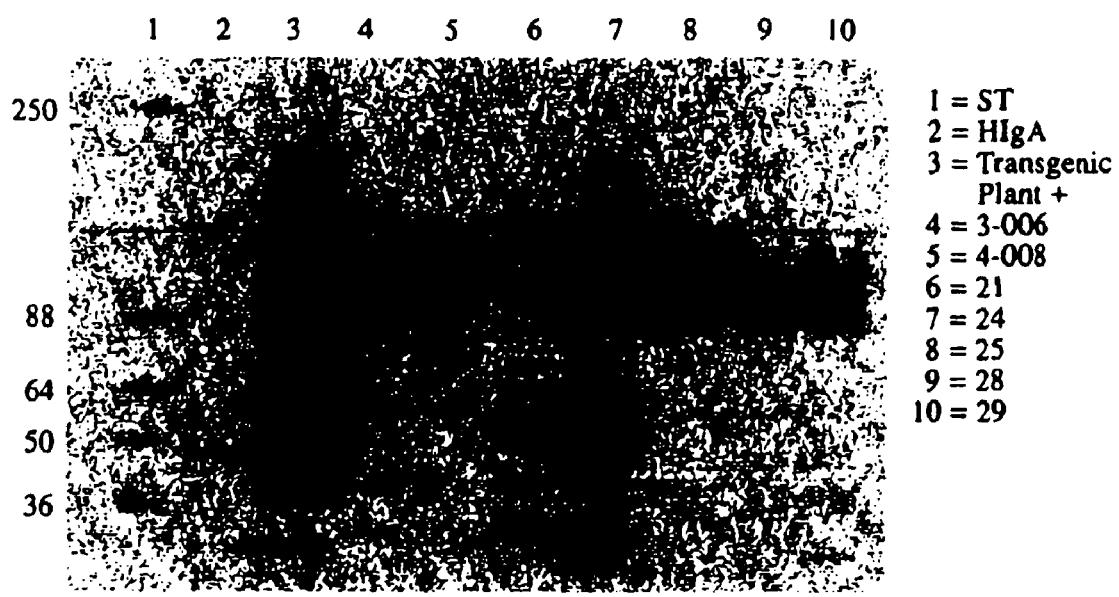
FIG. 4. A native Western blot using the IgA kappa chain as the detection antibody to detect protein expression from ubiquitin HSV-IgA (HC/LC) antibody produced by transgenic maize calli. A total of 53 transgenic calli derived from the two-way transformation (pDAB637 (SEQ ID NO: 17) and pDAB3014 (SEQ ID NO: 84)) and 23 transgenic calli derived from the three-way transformation (pDAB635 (SEQ ID NO: 15) and pDAB3014 (SEQ ID NO: 84)) were analyzed by PCR to detect the presence of PTUs for the transgene. Callus events that were both PTU positive and negative underwent Western and ELISA analysis. Protein analysis data was generated using events from the ubiquitin/HC, LC transformations that are described above. The goal of the experiment was to compare the efficacy of expression of the HC and LC on a single plasmid versus HC and LC on two separate plasmids. Callus material was collected and frozen at −70° C. before shipment for protein analysis. An initial screen of the events was performed with a capture ELISA assay using an IgA heavy chain capture antibody and an IgA kappa chain detection antibody. Only ELISA positive samples were evaluated with a Native Western Blot, also using the IgA kappa chain as the detection antibody. Of the 54 events screened by ELISA, 26 were positive (Table 1). Lane 1: Molecular weight standards; Lane 2: Heavy chain IgA; Lane 3: Callus material from transgenic plants; Lane 4: IgA detected from sample 3-006 (Table 1); Lane 5: IgA detected from sample 4-008 (Table 1); Lanes 6-10: IgA detected from samples 21, 24, 25, 28 and 29, respectively (Table 1). Western blot conditions were: 4-12% GEL nonreducing sample buffer 62 ng total protein each well; 1:5000 Goat anti-Human Kappa-HRP one hour RT; and a five minute exposure period.

Analysis of the transgenic callus events transformed with the ubiquitin/HC, LC plasmids was performed in two stages: 1) PCR identification of those events that contained intact genes of interest; and 2) Western and ELISA analysis of PCR positive events for protein expression and IgA assembly. FIG. 4 shows a native Western blot using the IgA kappa chain as the detection antibody to detect protein expression from ubiquitin HSV-IgA (HC/LC) monomeric antibody produced by transgenic maize calli.

PCR identification of intact PTUs (plant transcription units:promoter/coding region/3' UTR) was particularly challenging because of the repeated regulatory elements contained within the three plasmids and the resultant difficulty of designing primers that would specifically and accurately amplify the desired PTU. Several amplification strategies, PCR systems and amplification conditions were tested including eight different primers sets. It was determined that both the HC PTU (ubi/HC/per5) and the LC PTU (ubi/LC/per5) could be amplified with a single set of primers in a single PCR reaction. By taking advantage of several base pairs that were different in the regions flanking HC and LC, a second and third set of primers was also found that could recognize and specifically amplify the HC or LC PTU separately.

A total of 53 transgenic calli derived from the two-way transformation (pDAB637 (SEQ ID NO: 17) and pDAB3014 (SEQ ID NO: 84)) and 23 transgenic calli derived from the three-way transformation (pDAB635 (SEQ ID NO: 15) and pDAB3014 (SEQ ID NO: 84)) were PCR analyzed to detect the presence of PTUs for the transgene. The strategy to amplify both HC and LC in a single PCR reaction was employed. Among the callus lines derived from 2-way, 79% were PCR positive, while 78% of callus lines derived from 3-way were PCR positive. To verify the results from the first amplification strategy, a subset of 16 samples were analyzed using the alternative strategy, which could amplify the PTU of HC and LC separately. The results were consistent with the first PCR analysis in which HC and LC PTU were detected in the same PCR reaction. These 16 subset samples were further analyzed with primers to amplify only the coding region of HC and LC. Although the amplification was successful, the result was not an exact match with the PTU analysis. This difference can be a result of fragmented PTUs, which would be detected by the coding-region-specific primers but not the PTU-specific primers. Callus events that were both PTU positive and negative underwent Western and ELISA analysis.

Protein analysis data was generated using events from the ubiquitin/HC, LC transformations that are described above. The goal of the experiment was to compare the efficacy of expression of the HC and LC on a single plasmid versus HC and LC on two separate plasmids. Callus material was collected and frozen at −70° C. before shipment for protein analysis. An initial screen of the events was performed with a capture ELISA assay using an IgA heavy chain capture antibody and an IgA kappa chain detection antibody. Only ELISA positive samples were evaluated with a Native Western Blot, also using the IgA kappa chain as the detection antibody.

Of the 54 events screened by ELISA, 26 were positive (Table 1). All of these 26 positive samples produced assembled IgA monomers with an approximate mole weight of 160,000 kd. Eighteen of the events also include some non-assembled IgA. Both of the transformation methods, two-plasmid and three-plasmid, produced assembled IgA with the 3-way strategy producing 60% positives and the two-way strategy producing 38% positives. The difference in the frequency of expressing lines is not believed to be a function of the plasmid configuration, but rather a result of the small data set submitted for analysis.

TABLE 1

Protein and PCR Results for the Ubi/HC, LC Events.

| Sample | Transformation Strategy | Protein Analysis Results ELISA O.D. Western | | PCR Results | |
|---|---|---|---|---|---|
| | | | | PCR: H | PCR: L |
| 180/300(3)-006 | H + L same plasmid | 0.527 | A/N | + | + |
| 180/300(4)-008 | H + L same plasmid | 0.41 | A/N | − | + |
| 21 | H, L two plasmids | 1.4 | A/N | + | + |
| 24 | H, L two plasmids | 1.5 | A/N | N.T. | N.T. |
| 25 | H, L two plasmids | 0.322 | A | N.T. | N.T. |
| 28 | H, L two plasmids | 0.333 | A | N.T. | N.T. |
| 29 | H, L two plasmids | 0.825 | A/N | + | + |
| 37 | H, L two plasmids | 0.303 | A | + | − |
| 38 | H, L two plasmids | 0.3 | A/N | + | − |
| 39 | H, L two plasmids | 0.418 | A/N | + | + |
| 41 | H, L two plasmids | 1.18 | A/N | + | + |
| 42 | H, L two plasmids | 0.309 | A/N | N.T. | N.T. |
| 43 | H, L two plasmids | 1.5 | A/N | N.T. | N.T. |
| 44 | H, L two plasmids | 0.332 | A | N.T. | N.T. |
| TS2 | H + L same plasmid | 0.562 | A | − | + |

TABLE 1-continued

Protein and PCR Results for the Ubi/HC, LC Events.

| Sample | Transformation Strategy | Protein Analysis Results ELISA O.D. Western | PCR Results PCR: H | PCR: L |
|---|---|---|---|---|
| TS6 | H + L same plasmid | 0.436 A/N | + | + |
| TS9 | H + L same plasmid | 0.345 A | + | + |
| TS11 | H + L same plasmid | 2.221 A/N | + | + |
| TS12 | H + L same plasmid | 4 A/N | + | + |
| TS19 | H + L same plasmid | 4 A/N | + | + |
| TS22 | H + L same plasmid | 0.348 A/N | + | + |
| TS25 | H + L same plasmid | 0.393 A | + | + |
| TS27 | H + L same plasmid | 0.351 A/N | + | + |
| TS30 | H + L same plasmid | 0.695 A | + | + |
| TS32 | H + L same plasmid | 1.087 A/N | + | + |
| TS34 | H + L same plasmid | 4 A/N | + | + |
| 151 | non-transformed | | | |
| 630-307 | GUS transformed | | | |

H = HC
L = LC
N.T. = not tested
N = non-assembled IgA
A = assembled IgA

These experiments demonstrate that there is no significant difference in protein expression and assembly when HC and LC reside on a single plasmid or on two separate plasmids. On average the same number of events were generated for each strategy regardless of adding the DNA in mass equivalent amounts or molar equivalent amounts. Additionally, both DNA delivery strategies resulted in the same number of events containing all genes of interest. Based on these results, DNA was added in mass equivalent amounts for subsequent work.

Example 3

Vector Construction for Endosperm-Specific Anti-HSV Antibody Expression in Plants The following examples involve a monomeric IgA antibody for control of the Herpes simplex Virus (HSV). The two genes coding for HC and LC were introduced into plants in one vector for seed-specific expression of monomeric antibodies with functionality against HSV.

The two antibody genes (HC and LC) were redesigned for optimal expression in plants using a method analogous to that taught in U.S. Pat. No. 5,380,831, which is herein incorporated in its entirety. Thus, the two human HSV antibody genes HC (SEQ ID NO: 1) and LC (SEQ ID NO: 9), as well as nucleotide sequences SEQ ID NOs: 3, 5, 7, 9, 11 and 13, have a codon-bias that most closely resembles plant codons than human codons for enhanced gene expression in maize.

Plasmid construction for the anti-HSV project required the assembly of four complex plasmids, each of which contain MAR sequences flanking two antibody plant transcription units (PTU). The antibody genes are under control of the maize gamma-zein ('gz' or 'γ-zein') promoter for endosperm-specific expression (Ueda, T. et al., Mol. Cell. Biol. 14(7): 4350-9 (1994)) and terminate with the maize peroxidase 3' UTR (per5).

Backbone Vector Construction. The first phase of plasmid construction involved the preparation of backbone vectors. Backbone plasmids contain all the necessary elements for expression of the gene(s) of interest including MAR sequences, promoter, 3' UTR, selectable marker gene cassette and unique restriction sites for the single-step addition of the antibody coding regions. Another characteristic of the backbone vectors is the presence of unique restriction sites for the efficient removal of the antibiotic resistance gene. Another characteristic of the antibody-specific backbone vectors is the absence of sites that may interfere with cloning of antibody gene segments for future product concept vectors.

Antibody vector construction was performed in two phases: step 1=insertion of the antibody genes between the γ-zein promoter and the per5 3' UTR; and step 2=insertion of the γ-zein: antibody gene:per5 cassette into the inverse MAR vector. Several modifications were made to the two backbone vectors to facilitate sub-cloning variable region motifs, to enable ampicillin-free fragment purification, and to support Southern analysis and PTU identification. An AvrII site was removed from the "step 1" vector by nucleotide removal with T4 polymerases. Additionally, a PmeI site was removed from the "step 1" vector by the replacement of the existing per5 fragment with a similar fragment cured of the PmeI site. An FspI site was added to the "step 2" MAR vector by the addition of a synthetic adapter into a unique SapI site. And finally, the γ-zein promoter was inserted into the "step 1" vector by removing the ubiquitin promoter from pDAB4005 and replacing it with the γ-zein promoter which was PCR amplified from W22 genomic DNA. The modified backbone vectors were sequenced to verify the changes. Additionally, thorough sequencing of the γ-zein promoter was completed to ensure there were no PCR induced errors.

Table 2 lists the backbone vectors that have been constructed and the modifications that have been performed to accommodate the antibody genes.

TABLE 2

Backbone Vectors.

| New Plasmid # | Modification | Original Plasmid # | Plasmid Parts |
|---|---|---|---|
| pDAB8506 | Cured AvrII | pDAB4005 | ubi/GUS/per5 |
| pDAB634 | Replace ubi with gamma zein | pDAB8506 | gz/GUS/per5 |
| pDAB1416 | Remove PmeI | pDAB634 | gz/GUS/per5 |
| pDAB8504 | add FspI site | 254-3 | MAR::ra/PAT/lip::MAR |
| pDAB1414 | Remove ra/PAT/lip | pDAB8504 | MAR::MAR |

A more detailed description of the backbone vectors and the strategy used to construct them follows.

pDAB8506 is a modified pDAB4005 vector which was designed to be a standard testing vector. It contains the maize ubi/GUS/per5 cassette and was the basis for subsequent backbone vectors. An AvrII site was removed from pDAB4005 using T4 DNA polymerase.

pDAB634 contains a maize gamma zein-promoter/GUS/per5 ('gz/GUS/per5') cassette. This plasmid was created by replacing the ubiquitin promoter of DAB8506 with the gamma zein promoter on a HindIII-NcoI fragment. The gamma zein promoter was PCR amplified from W22 genomic DNA with primers designed based upon GenBank Accession #MZEZEIN27.

pDAB1416 is a modification of pDAB634 where the PmeI site was deleted by removing the existing per5 3'UTR from the SacI-FseI fragment. The PmeI site was removed from the per5 3'UTR by PCR amplification using primers designed to cure the site. PmeI was outside of the per5 functional sequence, therefore removal of this site will not interfere with the functionality of the element.

pDAB8504 is a modification of MAR vector p254-3 which contains the Rb7 MARs in an inverse orientation relative to each other and flanking the rice actin/PAT/lipase 3' UTR cassette, and a multiple cloning region for the insertion of genes of interest. Plasmid pDAB8504 is essentially p254-3 except for the addition of an FspI site in the plasmid backbone. A 9-bp adapter containing FspI site was inserted into SapI site in the MAR vector and resulted in the addition of three FspI sites in the backbone region of the MAR vector. These FspI sites will be used to remove the ampicillin resistance gene from the bulked-up plasmid prep before transformation.

pDAB1414 is a modified version of pDAB8504 where the rice actin/PAT/lipase cassette has been removed by digestion with PmeI to delete the PTU.

Antibody Vector Construction. Three cloning steps and the preparation of two intermediate vectors were required to complete the assembly of the final antibody plasmids. The three cloning steps are as follows:

1. Subclone the antibody gene between the gamma zein promoter and the per5 3' UTR to create a "gamma zein/antibody cassette" (Step 1 vector).
2. Subclone the "gamma-zein/antibody cassette" containing antibody gene #1 into the vector containing the MAR sequences (Step 2 vector).
3. Subclone the "gamma-zein cassette" containing antibody gene #2 into the MAR vector created in step #2. (Step 3 vector=Final vector)

Vector assembly began with producing the codon-optimized genes for HC and LC, as discussed previously. All of the vectors were bulked-up and independently cloned into the backbone plasmid pDAB1416. New plasmid numbers were assigned to each of these intermediate vectors (Table 3).

TABLE 3

Intermediate and final antibody constructs.

| Step # | Plasmid # | Plasmid Components |
|---|---|---|
| 1 | pDAB1415 | gz/LC/per5 |
| 1 | pDAB1417 | gz/LC/nosA |
| 1 | pDAB8501 | gz/HC/per5 |
| 1 | pDAB8502 | gz/HC/nosA |
| 2 | pDAB8503 | MAR::gz/LC/per5::ra/PAT/lip::MAR |
| 2 | pDAB2100 | MAR::gz/LC/per5::MAR |
| 3 Final | pDAB8505 | MAR::gz/HC/per5::gz/LC/per5::ra/PAT/lip::MAR |

Figure 5:
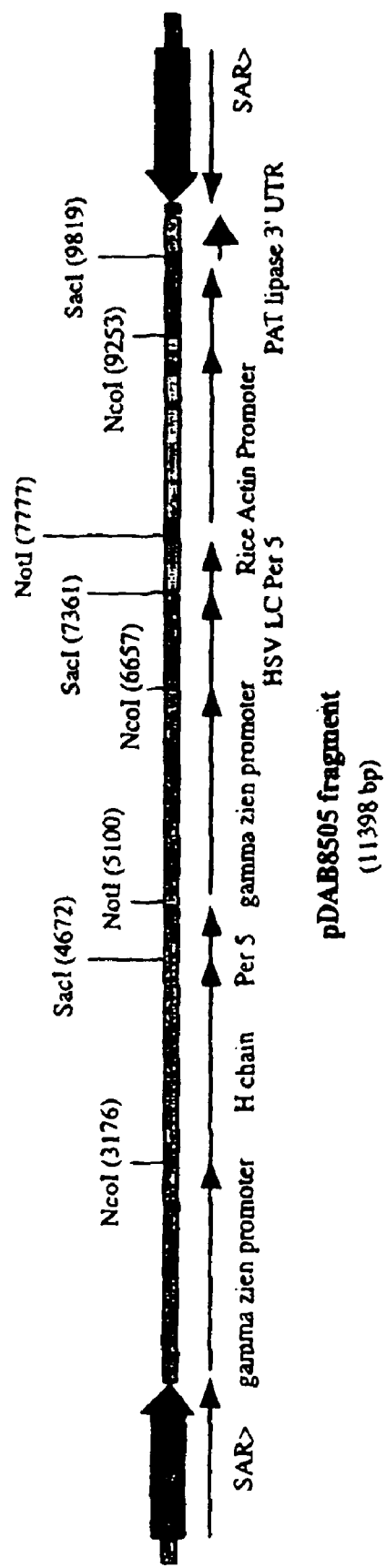
FIG. 5. Linear plasmid for pDAB8505 fragment (11398 bp). (SEQ ID NO: 85).
Figure 15:
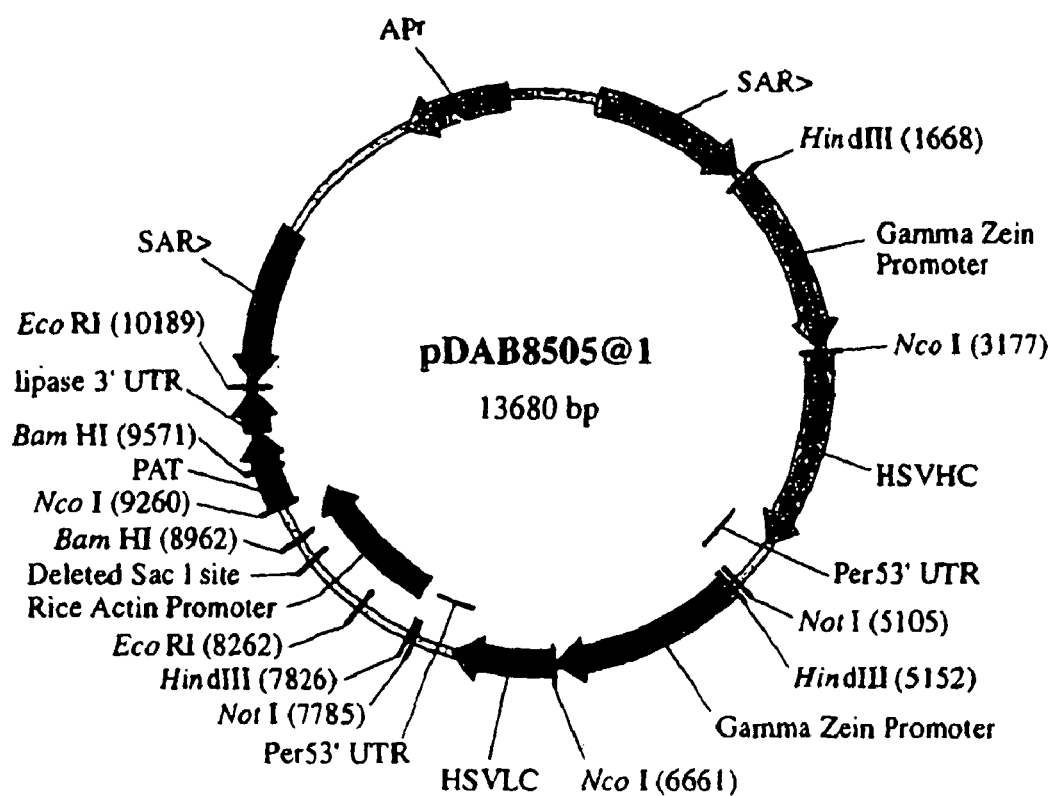
FIG. 15. Circular plasmid for pDAB8505. (SEQ ID NO: 85).
SAR: nucleotides 424-1589;
maize γ zein promoter: nucleotides 1673-3175;
anti-HSV heavy chain gene: nucleotides 3178-4668;
maize per5 3' UTR: nucleotides 4678-5045;
maize γ zein promoter: nucleotides 5157-6659;
anti-HSV light chain: nucleotides 6662-7360;
maize per5 3' UTR: nucleotides 7370-7737;
rice actin promoter with intron: nucleotides 7889-9258;
PAT coding region: nucleotides 9260-9820;
maize lipase 3' UTR: nucleotides 9831-10162;
SAR: nucleotides 10229-11394.
Note: the anti-HSV heavy chain gene and the anti-HSV light chain both include a mouse leader sequence.

Plasmid pDAB8505 (FIG. 15) contains gz/HC/per5::gz/LC/per5 expression cassette flanked with reverse orientated MAR sequences (Rb7) and plasmid pDAB2101 contains MAR::gz/LC/per5::gz/HC/per5::MAR. Plasmid pDAB8505 was used in both the co-transformation and the crossing strategies. The details of vector construction are described below:

pDAB1415 has a cassette containing gz/LC/per5. To build this construct, the GUS gene in pDAB 1416 was cut out with NcoI and SacI and replaced with the LC gene, which was also cut out from its donor vector with NcoI and SacI.

pDAB 1417 has a cassette containing gz/LC/nosA. To build this construct, the GUS gene in pDAB 1416 was cut out with NcoI and SacI and replaced with the LC gene, which also cut out from its donor vector with NcoI and SacI.

pDAB8501 has a cassette containing gz/HC/per5. To build this construct, the GUS gene in pDAB 1416 was cut out with NcoI and SacI and replaced with the HC gene, which was also cut out from its donor vector with NcoI and SacI.

pDAB8502 has a cassette containing gz/HC/nosA. To build this construct, the LC gene in pDAB1417 was cut out with NcoI and SacI and replaced with the HC gene, which was also cut out from its donor vector with NcoI and SacI.

pDAB8503 has a cassette containing MAR/gz/LC/per5:: rice actin/PAT/lipase::MAR. To build this construct, the gz/LC/per5 cassette from pDAB 1415 was cut out with NotI and inserted into NotI site of pDAB8504.

pDAB8505 (FIG. 5) is one of the two final vectors. It has a cassette containing MAR::gz/HC/per5::gz/LC/per5::rice actin/PAT/lipase::MAR. To build this construct, the gz/HC/per5 cassette was cut out of pDAB8501 with NotI followed by treatment with T4 DNA polymerase to create blunt ends and finally ligation into the SrfI site of pDAB8503.

The final plasmids underwent a large-scale DNA purification and fragment purification to remove the ampicillin gene. Approximately 15 mg of each final plasmid (without the amp fragment) was available for transformation.

The tail-less heavy chain antibody could also be obtained by making vectors which do not include the coding region for the tail.

Example 4

Large-Scale DNA Fragment Purification of Plant Transformation Vectors for Removal of Ampicillin Resistance Gene As described previously, the removal of plasmid backbone sequences from plant transformation vectors is necessary to ensure that transformed plant material is free of any contaminating antibiotic resistance genes. A gel-based strategy for the large-scale removal of DNA fragments has been an effective method for producing transformation-quality fragment, however the process is labor intensive and time consuming.

The first step in separation is to use restriction enzymes to cut out the gene construct fragment from the vector and bring down unwanted DNA fragments to the smallest unit possible. Fsp was used to remove the Amp fragment. With this strategy, the ampicillin resistance gene-containing region could be broken down into two fragments with sizes of 1023 and 1236 bp, respectively.

In total, over 34.8 mg of amp-free pDAB8505 was produced. Quality control was performed using restriction digestion for each batch of DNA fragment produced to ensure there was no parent plasmid or partially digested fragment remaining in the prep. PCR amplification was used to determine the purity of processed DNA fragment before delivery. The overall purity ranged from about 98% to about 99.5%. In most cases, about 99% or higher purity was achieved. FPLC-based technique is more cost efficient than the gel purification protocol.

Large-scale DNA fragment separation process using a FPLC-packed Sephacryl S-1000 column. A 2.6/100 cm column was packed with Sephacryl S-1000 using FPLC system at a constant rate. TE buffer supplemented with 150 mM NaCl was used for filtration media pre-washing and column packing as well as DNA elution. Two milligrams (1 mg/mL) of FspI-digested pDAB3016 DNA was loaded to the column. A total of 500 mL elution were collected with 8 mL per collection tube. The elution process was monitored at 260, 280 and 320 nm. To examine the result of the separation, 20 µL of aliquot from each collection was loaded onto agarose gel followed by electrophoresis.

A 1 kb plus DNA ladder, which contained DNA fragments with sizes ranging from 100 bp to 12 kb was tested. Results suggested that DNA fragments with a size of 7 kb or above could be separated from the 1.0 and 1.2 kb ampicillin resistance fragments with the current procedure.

To improve reproducibility and further enhance separation efficiency, several factors were studied, including DNA pre-heat temperatures and duration, amount of DNA per load and stability of column performance after continued use. A pretreatment of 55° C. for 15-20 minutes was found to be most desirable for the best resolution (i.e., best separation efficiency). Additionally, it was determined that the column should be reconditioned after being used consecutively used for 34 times. Although as high as 25 ml (25 mg) could be loaded onto the column, the fragment recovery efficiency decreased with increased DNA loads. Greater than about 95% of DNA fragment could be recovered with 2 mg DNA loading. However, this recovery rate dropped to about 70% when the amount of DNA loaded increased to 5 mg (Table 4). The 3-mg load level is the typical scale used, which has an average recovery rate of about 85% in the first round of column purification. Results show that FPLC column chromatography is an effective technique for the removal of ampicillin gene fragments from plasmids prior to maize transformation.

TABLE 4

Average DNA fragment recovery rate using FPLC-based column purification.

| Amount of DNA loaded | Recovery rate after 1 round of column purification | Recovery rate after 2 round of column purification |
| --- | --- | --- |
| 2 mg | 95% | N/A |
| 3 mg | 85% | >90% |
| 5 mg | 70% | 90% |

Example 5

Estimating Transgene Copy Number by Quantitative Real Time PCR (qRT-PCR)

The majority of transgenic events generated by direct-DNA delivery methods display complex insertion patterns. These multiple copy insertions make breeding increasingly difficult and also lead to an increase in the frequency of silenced events. Thus, these should be eliminated in early stages of the transformation process. Transgene insertion patterns are usually determined by Southern blot analysis. However, this method is rather labor-intensive, lengthy and unfeasible to be adapted into a high-throughput analysis process. To circumvent these problems, techniques that provide quick estimation of copy number were used to discern events to discard early in the process. Quantitative Real Time PCR (qRT-PCR) has been developed and implemented to predict transgene copy number for the HSV constructs.

Quantitative Real Time PCR (qRT-PCR). Quantitative real time PCR (qRT-PCR) has been proven to be an efficient method to estimate the transgene copy number of transgenic maize calli.

Validation of this technology with the AO and IMT genes showed that the copy number estimated by qRT-PCR and the insertion bands determined by southern blot analysis was very close and highly correlated.

Validations of qRT-PCR analysis with pDAB8505 (HC+LC+PAT) were performed. Two pairs of primers for each of the two genes, i.e., HC and LC, were designed and tested with both regular PCR and qRT-PCR. To estimate transgene copy number in HSV transgenic maize calli, only LC was analyzed for pDAB8505 events.

The reproducibility of qRt-PCR was also studied. This method was found to be highly reproducible. The estimated copy numbers obtained by different researchers or several times by a single researcher were very close and highly correlated. Therefore, no replication of analysis was found to be necessary unless unusual data was observed. In addition, uneven distribution of events with low copy number and high copy number was observed. Blocks of simple events and complex events were found in some orders. This suggest that clones of events might exist as multiple isolates.

Example 6

Transformations for Monomeric IgA Production in Maize Seed

Plant cells of corn inbred line 'HiII' were treated via direct-DNA delivery with pDAB8505 using the WHISKERS™ transformation method (Song et al., Plant Cell Reporter 20:948-954 (2002)). The "small-scale" WHISKERS™ method utilized was able to treat about 2 ml of packed plant cells at one time. Of 541 callus events analyzed, about 67% (360/541) had more than 5 copies of the transcript; about 5% (29/541) had 5 copies; about 5% (27/541) had 4 copies; about 6% (33/541) had 3 copies; about 8% (45/541) had 2 copies; about 7% (36/541) had 1 copy; and about 2% (11/541) had 0 copies. A total of 871 plants representing 126 events were regenerated, transferred to the greenhouse and grown to maturity.

Seed production. The anti-HSV transformed plants were planted in 5-gallon pots and pollinated by inbred corn line 'OQ414' to produce the progeny seed that was analyzed for antibody production.

Herbicide resistance, as well as being a selectable marker in vitro, is an important tool in field studies and trait introgression activities in *planta*. Leaf paint tests for herbicide tolerance are performed on every plant after they are established in 5-gallon pots, along with a positive control (4XH753) and a negative control (Hi II F1). The protocol involved applying 10 µL of 2.0% Finale® solution (1" square) per plant, 20 cm up from the tip of the leaf. The results demonstrated that the 4XH753 plants were clearly sensitive and that the Hi II F1 plants appeared tolerant to the herbicide. All of the anti-HSV transformed plants except one were resistant.

In summary, the plants believed to be transformed were painted with the 2% Finale® and plants resistant to the herbicide were selected for further reproduction and characterization. Leaf samples of every anti-HSV plant were also collected for use in Southern analysis.

Example 7

Protein Analysis in Maize Endosperm

HC/LC transformants. $T_1$, seeds were analyzed for the γ-zein/HC/LC construct (pDAB8505) by ELISA and SDS non-reduced Western blot. This method also required determining sample weight and total extractable protein in the extracts. An event was selected for analysis if at least 25 seeds were produced for the event—10 and 20 kernels were tested for low and high seed count events, respectively. Kernels were selected from one or two ear families for testing. An ear family is the progeny of a single pollinated ear.

Samples were chipped from the seed nondestructively, preserving the option of germinating positive seeds. The ELISA was designed to capture the heavy chain and detect the light chain of the IgA monomer. The standard used for all of these events was a sIgA antibody (I1890-10 from U.S. Biological).

Western analysis showed that all of the expressing events produced assembled IgA monomer along with unassembled or degraded heavy and light chains. Seeds were considered positive if both the ELISA and Western analyses produced a positive result. Events were recommended to proceed to the field based on the protein expression and the segregation ratio observed within the tested kernels.

A total of 930 individual seeds were analyzed for the pDAB8505 construct, representing 66 events with a high enough seed count to test. In summary, 33 events (50%) were advanced based on favorable expression and segregation data; expression was found for another 8 events (12%) that had problems, such as poor segregation data; and 25 events (38%) were found not to be expressing IgA.

Example 8

Oligosaccharide Profile of Asn-269 (CH2 Region of Alpha Heavy Chain) of Monomeric IgA-HX8 Expressed in Maize by MALDI-TOF MS Typical procedures used in glycan analysis of monomeric IgA-HX8 are described below.

Tryptic digest of reduced/alkylated IgA-HX8. 100 µg of affinity-purified IgA-HX8 was dried in a centrifugal evaporator in a microcentrifuge tube (0.6 mL, low protein binding). The pellet was resuspended in 100 µL of protein dissolution buffer containing 6M Guanidine hydrochloride and 0.4M ammonium bicarbonate. The sample was reduced by addition of 10 µL of 0.1M DTT and incubation at 65° C. for 1 hour. After reduction, the protein sample was alkylated by addition of 20 µL of 0.2M iodoacetamide and incubation at room temperature for 2 hours in the dark. Alkylation reaction was quenched by addition of 40 µL of 0.1M DTT and incubation at room temperature for 30 minutes. The protein was then desalted using a reversed phase cartridge (Protein Macro Trap, Michrom Bioresources) according to the manufacturer's procedure and eluted with 150 µL of 80% acetonitrile/ 0.2% TFA, then 100% acetonitrile/0.2% TFA and the eluted protein was dried in a centrifugal evaporator. The desalted reduced/alkylated protein was resuspended in 50 µL of digestion buffer (100 mM Tris-HCl, pH 8.5) and solution of trypsin (sequencing grade, Roche) was added at trypsin:protein ratio of 1:100. The sample was incubated for 16 hours at 37° C. The tryptic digest was then stored at −20° C. before further steps were performed.

(Alternatively) In-gel tryptic digest of IgA-HX8 heavy chain isolated by SDS-PAGE. 70-100 µg of IgA-HX8 was dried in centrifugal evaporator, the pellet was resuspended in 120 µL of Laemmli sample buffer (Bio-Rad) containing 1:19 v/v µ-mercaptoethanol and the resulting solution was heated for 10 min at 95° C. The resulting reduced and denatured IgA-HX8 sample was loaded onto 4-20% SDS-PAGE gel (Bio-Rad) (6 lanes, 20 µL per lane) and the gel was run at 60 mA constant current for approximately 1 hour. The gel was stained with Coomassie Blue stain. Bands corresponding to IgA-HX8 heavy chain at ~50 kDa were excised from gel and destained with destain buffer (50% acetonitrile, 50% ammonium bicarbonate buffer, pH 8.5). The destained gel pieces were dried in a centrifugal evaporator and rehydrated with solution of trypsin (31.25 µg/mL in 25 mM ammonium bicarbonate, pH 8.5). The samples were incubated at 37° C. for 16 hours. Tryptic peptides were extracted from gel with 400 µL of 50% acetonitrile/1% TFA, then 400 µL of 70% acetonitrile/ 25% 25 mM ammonium bicarbonate buffer/5% formic acid. The extracts were combined, filtered and dried in a centrifugal evaporator. The resulting isolated tryptic peptides were desalted with a C18 cartridge (Peptide Macro Trap, Michrom Bioresources) and dried in a centrifugal evaporator before digestion with peptide-N-glycanase A (PNGase A).

(Alternatively) Digestion of IgA-HX8 with pepsin. 25 µg of affinity-purified IgA-HX8 was resuspended in 200 µL of 20 mM ammonium acetate buffer, pH 3.5. 10 µL of pepsin (Roche) solution (2 mg/mL in 10 mM HCl) was added to the protein sample and the sample was incubated at 37° C. for 16 hours. Reaction was quenched by addition of 5 µL of 1M NaOH and sample was heated at 95° C. for 30 min to completely inactivate pepsin. The sample was dried in a centrifugal evaporator and re-dissolved in 50 µL of 20 mM ammonium acetate buffer, pH 5.0, before addition of PNGase A.

Enzymatic release of N-linked oligosaccharides. Proteolytic peptides (whole digests after digestion with trypsin or pepsin, or tryptic glycopeptides isolated by RP-HPLC) were dissolved in 5-50 µL of 20 mM ammonium acetate buffer, pH 5.0, and 5-10 µL of peptide-N-glycosidase A solution (PNGase A, Roche) was added. The samples were incubated at 37° C. for 16 hours.

Isolation of released oligosaccharides from proteolytic peptides. The proteolytic/PNGase-A digest was passed through C18 cartridge (Peptide Macro Trap, Michrom Bioresources; pre-conditioned according to manufacturer's procedure) and the flow-through fraction was collected. The cartridge was washed with 0.5 mL of 0.1% aqueous TFA and the wash was combined with the first flow-through fraction. These fractions, containing released oligosaccharides, were further purified using a porous graphitic carbon cartridge (PGC) (GlycoClean-H, Glyko) according to the manufacturer's procedure. Oligosaccharides were eluted from PGC cartridge with 50% acetonitrile/0.1% TFA and dried to completeness in a centrifugal evaporator. The glycan samples were re-dissolved in 2.5 µL of high-purity water and passed through C18 ZipTips (Millipore). C18 ZipTips were pre-conditioned according to the manufacturer's procedure. Purified glycan samples were then ready for analysis by MALDI-Tof MS.

Liquid chromatography separation of tryptic peptides. Tryptic peptides resulting from approximately 100 µg of affinity-purified IgA-HX8 were separated by reversed-phase C18 chromatography. A Magic C18, 2 mm ID×150 mm length (Michrom Bioresources) and a Perkin Elmer 200 LC system was used for the separation. Constant flow rate of 0.5 mL/min was used for the separation. 100-120 µL of the tryptic digest mixture was injected. The separation of peptides was accomplished using the following gradient: 100% solvent A (3% acetonitrile/0.06% TFA) isocratic for 10 min, 0 to 50% solvent B (80% acetonitrile/0.05% TFA) in 165 min, 50 to 100% solvent B in 10 min. The column was then washed with 100% solvent B for 2 min, and then re-equilibrated in 100% solvent A and washed with 100% solvent A for 5 min. The separation was performed at room temperature. Elution of peptides was monitored by UV absorption at 205 nm. 2-mL fractions were collected in siliconized microcentrifuge tubes and the fractions were dried in a centrifugal evaporator following the separation. Before analysis by MALDI-Tof MS, first four fractions were desalted using C18 ZipTips (Millipore) according to the manufacturer's procedure. The rest of the fractions were re-dissolved in 2 µL of 50% acetonitrile/ 0.1% TFA and 1 µL of the material in each fraction was examined by MALDI-Tof MS.

MALDI-Tof MS of released N-linked oligosaccharides. Voyager DE-STR (Applied BioSystems) MALDI-Tof mass spectrometer operated in reflectron mode was used. The acceleration voltage was set to 20 kV. The grid voltage was set to 69% of the acceleration voltage. The delay time was set to 215 nsec. The laser setting was approximately 3000. 500 acquisitions were averaged in each spectrum. The mass scale was calibrated with the following standard oligosaccharides: $(GlcNAc)_2(Man)_5$, m/z $(MNa^+)$=1257.46; $(GlcNAc)_4(Man)_3(Fuc)$, m/z $(MNa^+)$=1485.56; $(Gal)(GlcNAc)_4(Man)_3(Fuc)$, m/z $(MNa^+)$=1647.62; $(Gal)_2(GlcNAc)_4(Man)_3(Fuc)$, m/z $(MNa^+)$=1809.68. 1 µL of sample of purified glycans was deposited onto a MALDI sample plate, overlaid with 1 µL of sDHB matrix (9:1 v/v mixture of 18 mg/mL 2,5-dihydroxybenzoic acid in 66% acetonitrile and 15 mg/mL 2-hydroxy-5-methoxybenzoic acid in 66% acetonitrile) and air-dried.

MALDI-Tof MS of peptides. Voyager DE-STR (Applied BioSystems) MALDI-Tof mass spectrometer operated in reflectron mode was used. The acceleration voltage was set to 20 kV. The grid voltage was set to 66% of the acceleration voltage. The delay time varied between 215 and 350 nsec. The laser setting varied between 2200 and 2500. 500 acquisitions were averaged in each spectrum. The mass scale was calibrated with the following standard peptides (Applied BioSystems): des-Arg[1]-Bradykinin, m/z 904.4; Angiotensin I, m/z 1,296.6; Glu[1]-Fibrinopeptide B, m/z 1570.6; Neurotensin, m/z 1672.9; ACTH (clip 1-17), m/z 2093.0; ACTH (clip 18-39), m/z 2465.1; ACTH (clip 7-38), m/z 5730.6. 1 µL of sample of purified peptides was deposited onto a MALDI sample plate, overlaid with 1 µL of CHCA matrix (α-cyanohydroxycinnamic acid) and air-dried.

Analysis of MALDI-Tof MS data. MS data were analyzed using Data Explorer v4.0 software (Applied BioSystems). Peptides and glycopeptides: molecular weights and amino acid sequences were attributed to the sequence of IgA-HX8 using MassLynx v3.4 software (Micromass). Oligosaccharides: home-written software (The Dow Chemical Company) was used to interpret mass-spectra of oligosaccharides.

Example 9

Glycan Profile of N269 (CH2 Region of IgA Alpha Heavy Chain) Maize HX8 Event 81 (self) by ESI-MS Purification of Maize HX8.
Process 1. Obtain powder of maize endosperm
Product 1. Powder of maize endosperm
Process 2. 1 XPBS, 1 hr stirring RM
Product 2. Extraction Slurry
Process 3. Centrifugation, 5000×g, 15 min.
Product 3. Crude maize extract
Process 4. 0.22 µm CA microfiltration
Product 4. Filtered maize extract
Process 5. Affinity purification (check overflow; if no, then discard)
Product 5. Purified HX8-IgA antibody Affinity column preparation—antibody immobilization on POROS matrix. The column was prepared mixing in a 15 ml conical tube 2 ml of POROS 20 resin (Applied Biosystems). The resin was rinsed with buffer (10 mM phosphate 0.15 M NaCl, pH 7.2) and 8 mg of each polyclonal IgG goat anti-human IgA and polyclonal IgG goat anti-human kappa (both from Southern Biotech) were added and allowed to react for 30 min at room temperature. The Ab-resin mixture was then rinsed with 15 ml 1×PBS (phosphate buffered saline: 137 mM NaCl; 2.7 mM KCl; 10 mM $Na_2HPO_4$; 2 mM $KH_2PO_4$; pH7.4)). The anti-IgA antibodies were then crosslinked to the resin by the addition of 15 ml cross-linking solution (10 ml of 100 mM triethanolamine, pH 8.5 and 117 mg of dimethyl pimelimidate) and incubated for 1 hour while slowly shaking. The cross-linking solution was removed by centrifugation. The reaction was quenched by the addition of 5 ml of monoethanolamine (100 mM, pH 9.0) followed by incubation for 30 minutes at room temperature while gently shaking. The slurry was then washed repeatedly with 15 ml 1×PBS. The affinity resin was then gravity packed into columns (2.1×75 mM).

Extraction of transgenic maize. Five grams maize grain degermed and milled to an average particle size of 150 µm was added to 50 ml 1×PBS. The extraction slurry was slowly stirred for 1 at room temperature. The slurry was then centrifuged (5000×g for 15 min.) and the supernatant recovered. The supernatant was filtered (0.22 µm) prior to affinity purification.

Affinity column purification conditions. The anti-α/anti-β affinity column was pre-equilibrated at 1 ml/min with 1×PBS (pH 7.4) until a stable baseline as monitored at UV 280 nm was observed. The supernatant containing antibody (45 ml) was applied to the column at a flow rate of 0.5 ml/min. The column was then washed with 10 column volumes of 1×PBS where a stable baseline was again observed. The IgA was eluted from the column with 12 column volumes of glycine (100 mM, pH 2.5) while collecting 5 ml fractions. Prior to the elution step, each fraction tube contained 500 µl neutralizing buffer (1 M TRIS-HCL, pH 9.0). The column was then re-equilibrated with 10 column volumes of 1×PBS. IgA containing fractions were quantified by UV absorbance at 280 nm.

Sequential tryptic and aspartic acid-N digest of HX8. 50 µg in 250 µl of affinity purified IgA was centrifugal vacuum dried in a microcentrifuge tube (1.7 ml low protein binding buffer). The pellet was resuspended in 35 µL protein dissolution buffer (7.5 ml 8 M Guanidine HCL, 316 mg ammonium bicarbonate adjusted to pH 7.8, dilute to 10 ml final volume with water). The resuspended sample was reduced by the addition of 1.75 µl DTT (1M) and incubation at 75° C. for 40 min. After reduction the tube was allowed to cool to room temperature. The sample was alkylated by the addition of 4.2 µl iodoacetic acid (1M, prepared in 1N NaOH). The alkylation reaction was performed in the dark at room temperature for 40 mins. The alkylation reaction was quenched by the addition of 1 µl of DDT (1M). The sample was desalted on C18 cartridge (Michrom Protein Macro Trap, Michrom Bioresources, Inc.) and eluted with 250 µl elution buffer (Acetonitrile, 0.1% TFA). The eluted reduced-alkylated sample was dried by centrifugal vacuum. The resulting pellet was resuspended in 20 µl trypsin digestion buffer (100 mM TRIS-HCL, pH8.1, 10 mM $CaCl_2$). Trypsin (sequencing grade, Progmega) was added at a ratio of 1:100 (trypsin: sample) and incubated for 16 hours at 37° C. Heating the mixture at 95° C. for 3 mins halted the reaction. Ten microliters of the tryptic digest was removed for sequential digestion with aspartic acid-N protease (1:100 ratio enzyme:substrate, Roche). The Asp-N reaction mixture was incubated at 30° C. for 20 hours.

Liquid chromatography and nano-electrospray ionization ion trap mass spectrometry of tryptic and tryptic+Asp-N peptides. Approximately 16 pmol (1 µl) of either tryptic or tryptic+Asp-N peptide fragment were separated by reverse phase C18 chromatography (Magic C18, 0.02 ID×150 mm length, Michrom Bioresources). A Capillary HPLC (Agilent) plumbed with 50 µm ID tubing throughout and running at a flow rate 0.3 µl/min was used for separation. The separation of peptides was accomplished using a gradient of 0% solvent A (0.05% TFA) isocratic for 10 min followed by a gradient to 40% solvent B (Acetonitrile+0.04% TFA) in 165 min. The gradient was then increased to 50% solvent B in 15 mins and held at 50% for 20 mins for column cleaning. The column temperature was maintained at 35° C. and peptides were monitored by absorbance at 215 nm and by electrospray ionization mass spectrometer.

Nano-electrospray ionization mass spectrometry (NESI) was performed on a Finnigan LCQ™ Deca ion trap mass spectrometer (San Jose, Calif.) fitted with a nanospray ion source (New Objective, Inc., Woburn, Mass.). The electrospray ion source was operated at a potential difference of between 1.3-1.8 kV for a flow rate of 3 µl/min. The NSI source was operated with a capillary temperature of 135° C. with the capillary voltage at 42 Volts and the tube lens offset at 10 volts. The automatic gain control was set with full MS target 8×10$^7$, Msn target 6×10$^7$ and zoom target 3×10$^7$. LC NESI-MS and LC NESI-MS/MS were run in an automated LC/MS-LC/MS/MS mode that monitored for a signal threshold and performed MS/MS on the base peak when the threshold criterion was exceeded. The ion trap parameters were employed as follows. The trap was run with automatic gain controls for all experiments. In this mode, the system automatically selects the trapping parameters to keep the ions present in the trap to a constant preset value. The number of "microscans" collected were three and two for full MS and MS/MS, respectively. For MS/MS signal the normalized collision energy was set to 35% with an activation Q of 0.250.

Peptide and glycopeptide assignments. Molecular weights and amino acid sequences were attributed to the sequence of HX8 IgA using GPMAW (Light House Data, Version 5.01), and BioWorks Software (as supplied with LCQ Deca).

```
Sequence of tryptic + Asp-N peptide of N269
(monoisotopic).

MH+            1948.01
        M2H+            974.51
        M3H+            650.01

Sequence   DLLLGSEANLTCTLTGLR    (SEQ ID NO: 20)
```

TABLE 5

Monoisotopic masses of glycopeptides vs. theoretical masses.

| Structure | Theoretical Glycopeptide Mass | Actual Glycopeptide Mass | Difference (m/z) |
|---|---|---|---|
| N2M2X | 2811.4 | 2811.8 | 0.38 |
| N2M3 | 2841.4 | 2842.0 | 0.58 |
| N2M2FX | 2957.5 | 2975.4 | −0.07 |
| N2M3X | 2973.5 | 2974.0 | 0.53 |
| N2M3FX | 3120.8 | 3119.5 | 1.27 |
| N2M5 | 3165.5 | 3165.6 | 0.07 |

Example 10

Glycan Structures of IgA Anti-HSV Antibodies Produced in Plants

Figure 6:
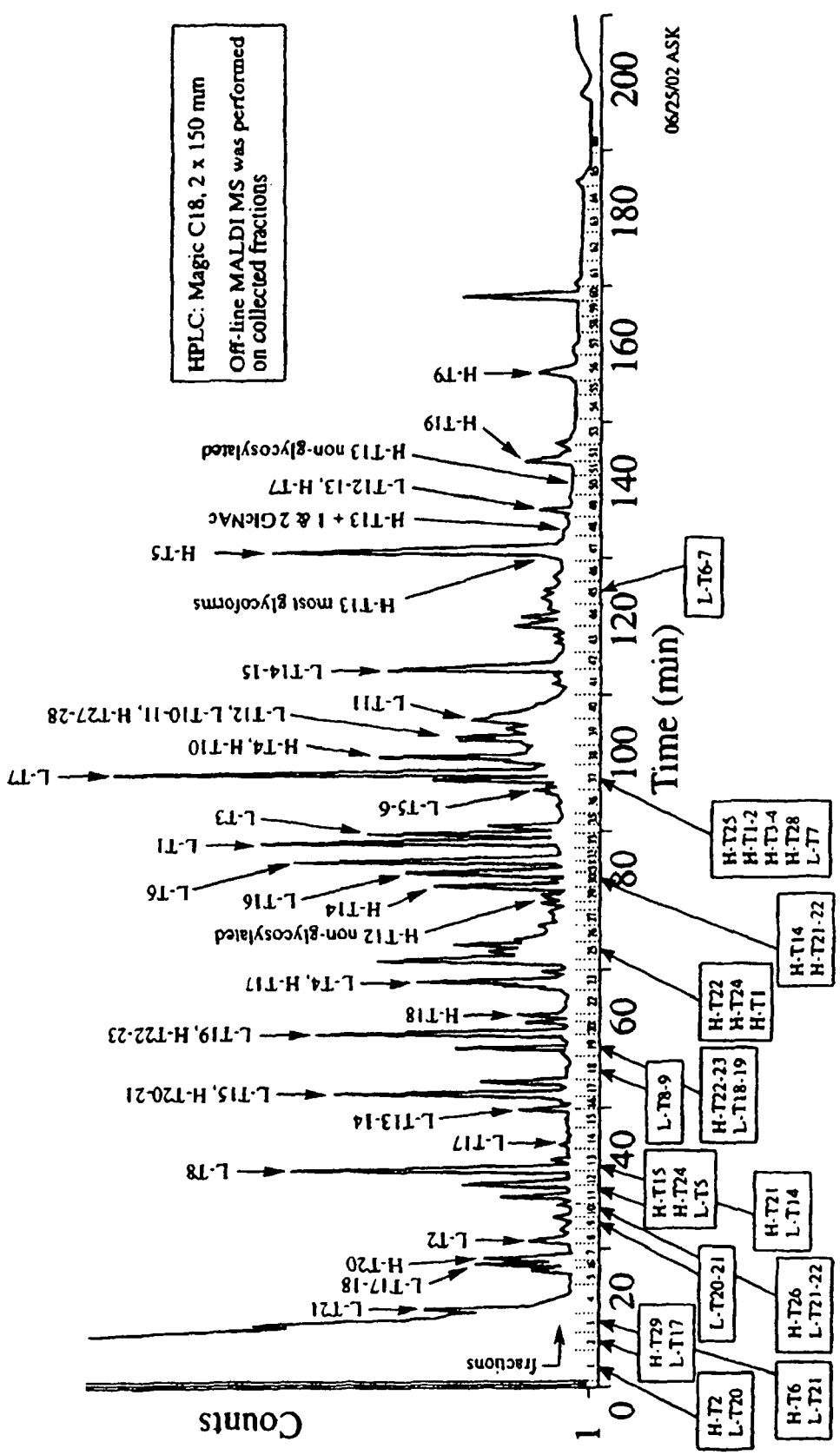
FIG. 6. A representative C18-HPLC chromatogram of tryptic digest of reduced and alkylated IgA-HX8 (event 193 self). Peak assignment was based on analysis of HPLC fractions by matrix-assisted laser desorption/ionization time-of-flight mass spectrometry ("MALDI-Tof MS"). Peaks labeled with "L" correspond to peptides resulting from light chain of IgA-HX8. Peaks labeled with "H" correspond to peptides resulting from heavy chain of IgA-HX8. Refer to Tables 1 and 2 and the accompanying text for more detail. Fractions containing glycopeptides were further treated with peptide-N-glycosidase-A (PNGase-A) and resulting deglycosylated peptides and released glycans were analyzed separately by MALDI-Tof MS. HPLC: Magic C18, 2×150 mm. Off-line MALDI MS was performed on collected fractions.
Figure 7:
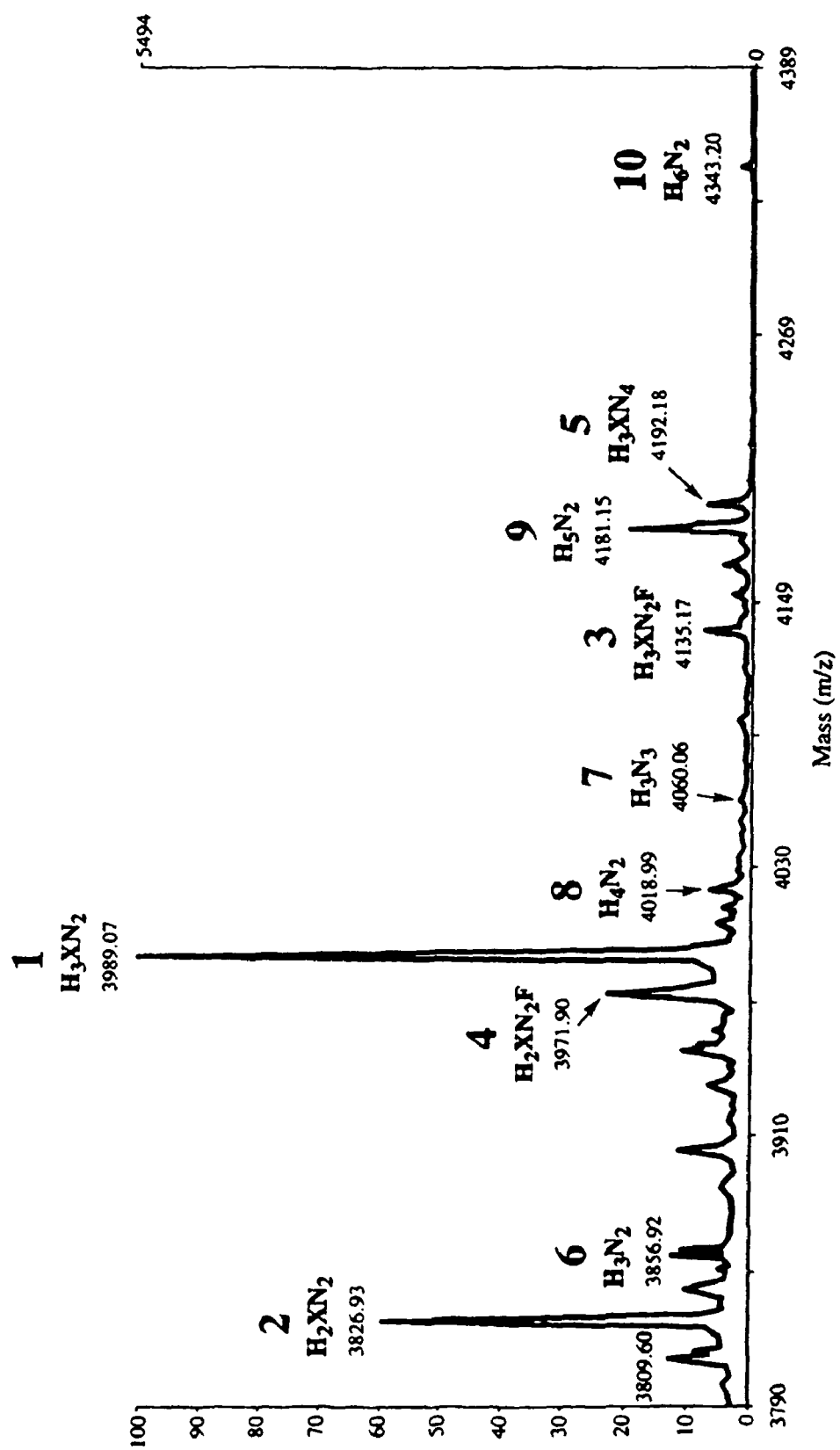
FIG. 7. A representative MAIDI-Tof MS of glycoforms of H-T13 peptide of IgA-HX8 heavy chain generated by tryptic digestion of reduced and alkylated IgA-HX8 (event 193 self). Monoisotopic masses of the glycopeptides are indicated. Large numbers above peaks correspond to glycan species summarized in Table 8. Short abbreviations for monosaccharide units are as follows: H, hexose; N,N-acetyl-glucosamine (GlcNAc); X, pentose (Xylose).
Figure 8:
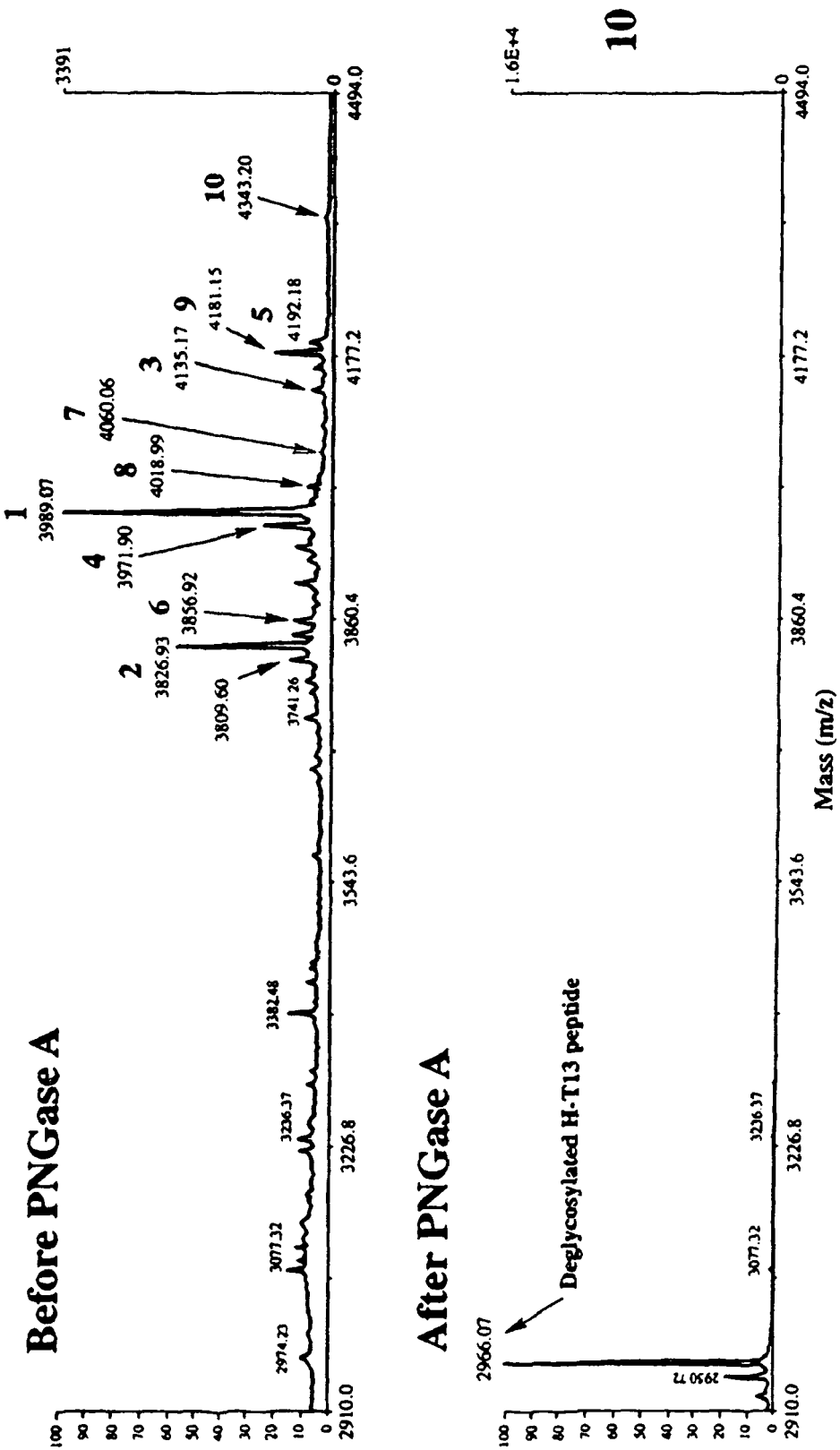
FIG. 8. Heterogeneity of glycoforms of H-T13 peptide of IgA-HX8 heavy chain is removed by enzymatic release (PNGase-A) of glycans. After treatment with PNGase-A, signals corresponding to glycoforms of H-T13 peptide disappear and a strong signal corresponding to deglycosylated peptide H-T13 appears in the mass-spectrum. Note that PNGase-A converts Asn (N) to Asp (D) during deglycosylation reaction; correspondingly, the deglycosylated H-T13 peptide appears with a mass-shift of ~+1 Da. Large numbers above peaks in mass-spectrum of glycopeptides (before PNGase-A treatment) correspond to glycan species listed in Table 8.
Figure 9:
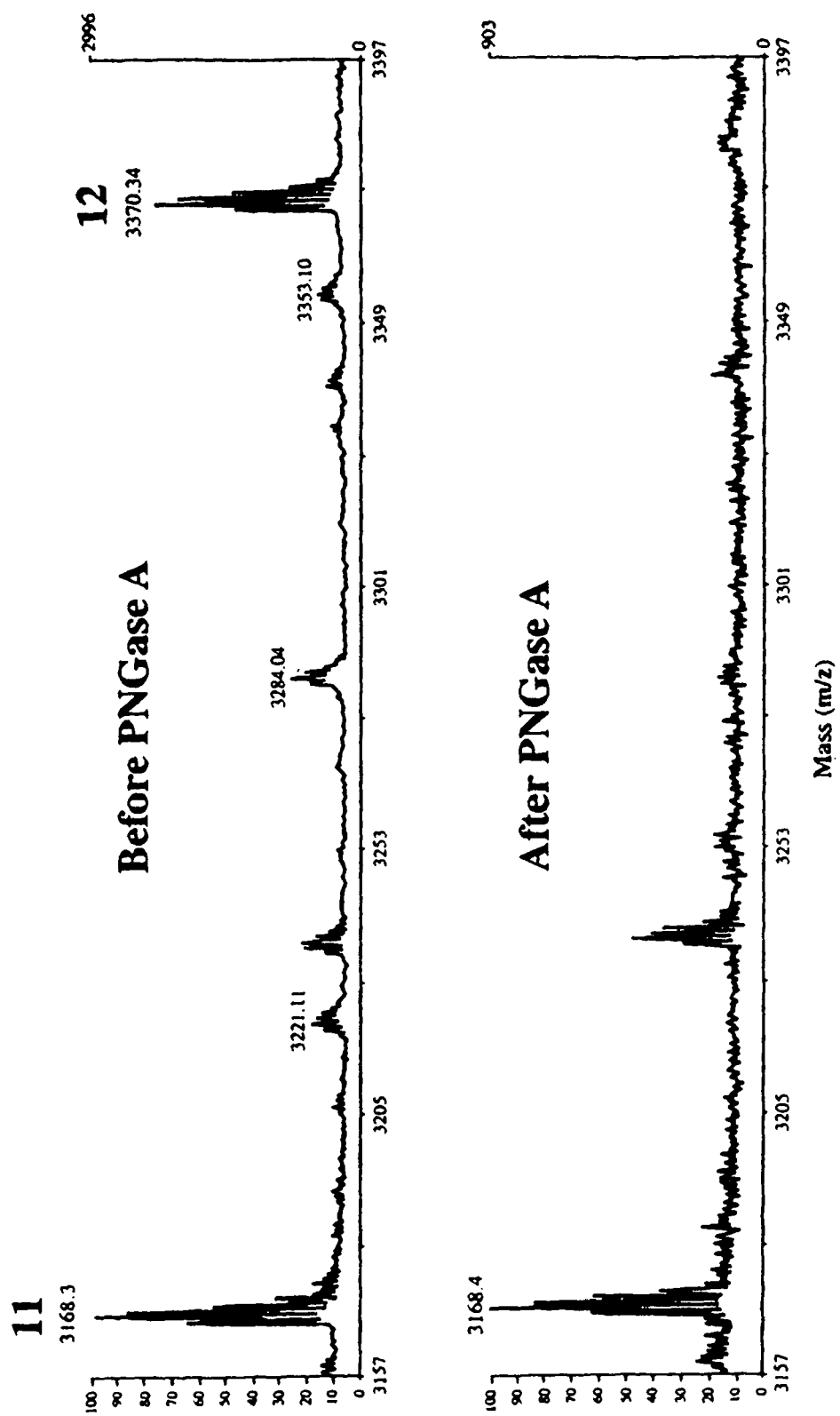
FIG. 9. Two additional glycoforms of H-T13 peptide of maize-expressed IgA-HX8 heavy chain are observed: single and double GlcNAc residue attached to N269. Large numbers above peaks in mass-spectrum of glycopeptides (before PNGase-A treatment) correspond to glycan species in Table 8. Treatment with PNGase-A results in removal of (GlcNAc)2 and partial removal of single GlcNAc residue. Peak corresponding to deglycosylated peptide H-T13 appears in the mass-spectrum after treatment of sample with PNGase-A (not shown).
Figure 10:
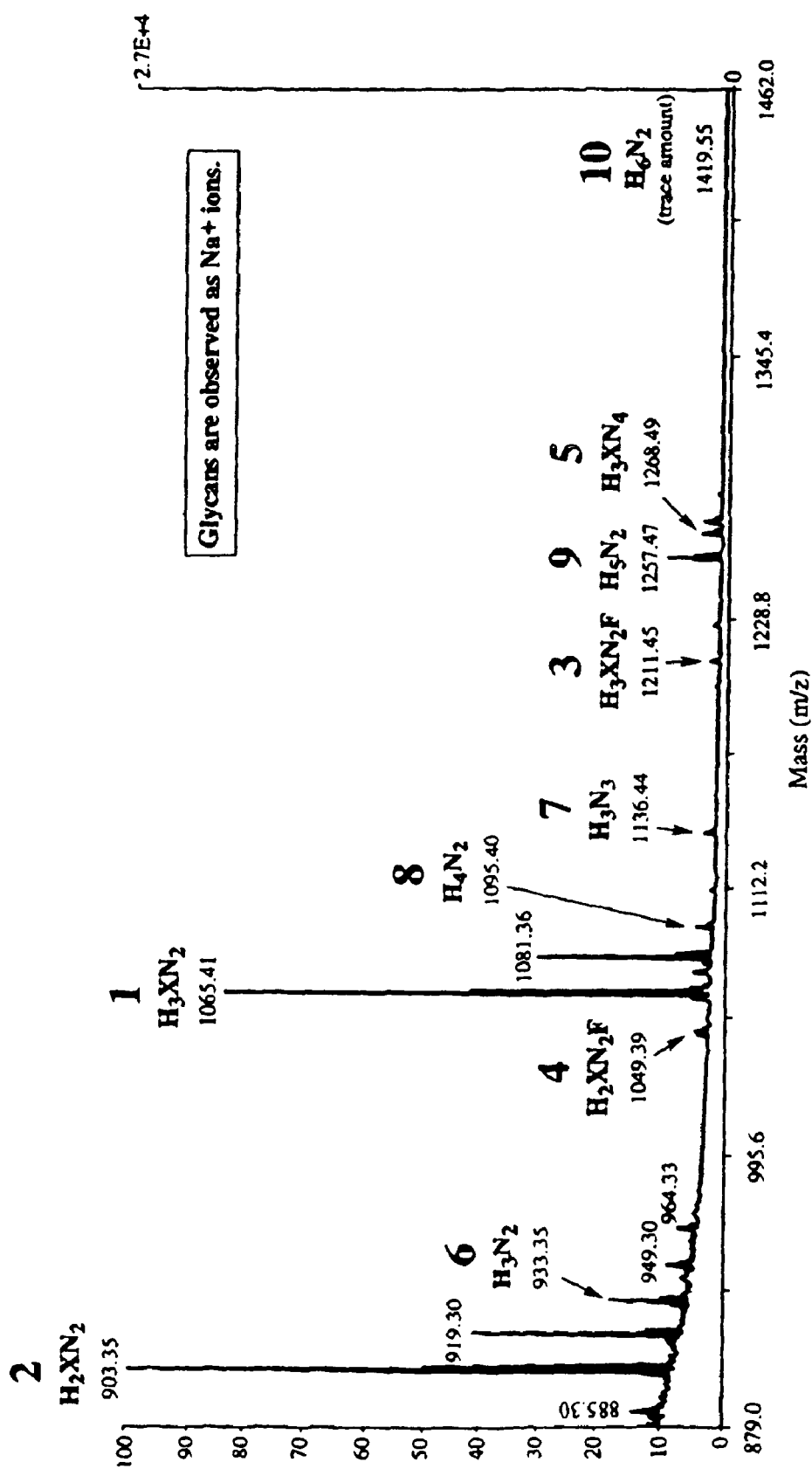
FIG. 10. A representative MALDI-Tof MS profile of free N-linked glycans enzymatically released from monomeric IgA-HX8 (event 193 self). Large numbers above peaks correspond to glycan species summarized in Table 8. Short abbreviation for monosaccharide units is as follows: H, hexose; N,N-acetyl-glucosamine (GlcNAc); X, pentose (Xylose). Single and double GlcNAc species (structures 11 and 12 in Table 8) were not detected as free glycans due to inaccessibility of MALDI MS to the molecular mass region below 500 Daltons (Da). Glycan species are observed as sodiated ions.

FIG. 6 provides a representative C18-HPLC chromatogram of the tryptic digest of reduced and alkylated IgA-HX8. FIG. 7 provides a representative MALDI-Tof mass-spectrum of glycoforms of HC-T13 peptide of IgA-HX8 HC generated by tryptic digestion of reduced and alkylated IgA-HX8. The heterogeneity of glycoforms of HC-T13 peptide of IgA-HX8 HC is removed by enzymatic release (PNGase-A) of glycans (FIG. 8). As shown in FIG. 9, two additional glycoforms of HC-T13 peptide of maize-expressed IgA-HX8 HC are observed. FIG. 10 provides a representative MALDI-Tof MS profile of free N-linked glycans enzymatically released from IgA-HX8.

Table 6 provides the peptide tryptic fragments observed for the light chain of IgA-HX8 expressed in maize (event 193 self) by MALDI-Tof MS. Total peptide mass coverage is 100%. "L"=LC.

TABLE 6

Observed peptide tryptic fragments of IgA-HX8 Light Chain (a representative peptide map for IgA-HX8LC, event 193)

| Fragment | Amino acid Residues | Sequence | [M + H] (theor.) | [M + H] (observed) | SEQ ID NO. |
|---|---|---|---|---|---|
| L-T1 | 1-18 | EIVLTQSPGTLSLSPGER | 1884.01 | 1884.20 | 21 |
| L-T2 | 19-24 | ATLSCR | 708.34 | 708.00 | 22 |
| L-T3 | 25-46 | ASQSVSSAYLAWYQQKPGQAPR | 2423.21 | 2423.50 | 23 |
| L-T4 | 47-55 | LLIYGASSR | 979.56 | 979.24 | 24 |
| L-T5 | 56-62 | ATGIPDR | 729.39 | 729.56 | 25 |
| L-T6 | 63-78 | FSGSGSGTDFTLTISR | 1632.79 | 1633.00 | 26 |
| L-T7 | 79-94 | LEPEDFAVYYCQQYGR | 2038.89 | 2038.60 | 27 |
| L-T8 | 95-103 | SPTFGQGTK | 922.46 | 922.70 | 28 |
| L-T11 | 109-126 | TVAAPSVFIFPPSDEQLK | 1946.03 | 1946.30 | 29 |
| L-T12 | 127-142 | SGTASVVCLLNFYPR | 1798.88 | 1799.10 | 30 |
| L-T14 | 146-149 | VQWK | 560.32 | 560.40 | 31 |
| L-T15 | 150-169 | VDNALQSGNSQESVTEQDSK | 2135.97 | 2136.27 | 32 |
| L-T16 | 170-183 | DSTYSLSNTLTLSK | 1529.77 | 1530.20 | 33 |
| L-T17 | 184-188 | ADYEK | 625.28 | 625.24 | 34 |
| L-T19 | 191-202 | VYACEVTHQGLR | 1433.68 | 1433.10 | 35 |
| L-T20 | 203-207 | SPVTK | 531.31 | 531.24 | 36 |
| L-T21 | 208-211 | SFNR | 523.26 | 523.40 | 37 |
| L-T5-6 | 56-78 | ATGIPDRFSGSGSGTDFTLTISR | 2343.16 | 2343.90 | 38 |
| L-T6-7 | 63-94 | FSGSGSGTDFTLTISRLEPEDFAVYYCQQYGR | 3652.65 | 3652.85 | 39 |
| L-T8-9 | 95-107 | SPTFGQGTKVEIK | 1391.75 | 1391.80 | 40 |

TABLE 6-continued

Observed peptide tryptic fragments of IgA-HX8 Light Chain (a representative peptide map for IgA-HX8LC, event 193)

| Fragment | Amino acid Residues | Sequence | [M + H] (theor.) | [M +H] (observed) | SEQ ID NO. |
|---|---|---|---|---|---|
| L-T10-11 | 108-126 | RTVAAPSVFIFPPSDEQLK | 2102.13 | 2102.40 | 41 |
| L-T12-13 | 127-145 | SGTASVVCLLNNFYPREAK | 2127.05 | 2127.40 | 42 |
| L-T13-14 | 143-149 | EAKVQWK | 888.49 | 888.45 | 43 |
| L-T14-15 | 146-169 | VQWKVDNALQSGNSQESVTE-QDSK | 2677.77 | 2676.90 | 44 |
| L-T17-18 | 184-190 | ADYEKHK | 890.44 | 890.50 | 45 |
| L-T18-19 | 189-202 | HKVYACEVTHQGLR | 1698.84 | 1698.40 | 46 |
| L-T20-21 | 203-211 | SPVTKSFNR | 1035.56 | 1035.61 | 47 |
| L-T21-22 | 208-214 | SFNRGEC | 870/34 | 870.48 | 48 |

Table 7 provides the peptide tryptic fragments observed for the heavy chain of IgA-HX8 expressed in maize (event 193 self) by MALDI-Tof mass-spectrum. Total peptide mass coverage is 93.8%. Observed glycopeptides are included. "ND"=not detected and "H"=HC.

TABLE 7

Observed peptide tryptic fragments of IgA-HX8 Heavy Chain (a representative peptide map for IqA-HX8 HC, event 193)

| SEQ ID No. | Fragment | Amino acid residues | Sequence | [M + H] (theor.) | [M + H] (observed) | Notes | Glycan entry in Table 3 |
|---|---|---|---|---|---|---|---|
| 49 | H-T1 | 1-12 | EVQLVQSGAEVK | 1268.68 | 1268.80 | Pyro-Glu on N-terminus | |
| 51 | H-T2 | 13-19 | KPGSSVK | 702.42 | 702.33 | | |
| 51 | H-T4 | 24-38 | ASGGFSSYAINWVR | 1601.77 | 1601.30 | | |
| 52 | H-T5 | 39-63 | QAPGQGLEWMGGLMPIFGTTNYAQK | 2695.30 | 2695.50 | | |
| 53 | H-T6 | 64-67 | FQDRLTITADVSTSTAYMQLSGLTYEDTAMYY | 562.27 | 565.33 | | |
| 54 | H-T7 | 68-98 | LTITADVSTSTAYMQLSGLTYEDTAMYYCAR | 3497.58 | 3497.60 | | |
| 55 | H-T8 | 99-132 | VAYMLEPTVTAGGLDVWGQGTLVTVSSASPTSPK | 3419.74 | 3420.30 | | |
| 56 | H-T9 | 133-176 | VFPLSLCSTQPDGNVVIACLVQGFFPQEPLSVTWSESGQGVTAV | 4780.33 | 4780.30 | | |
| 57 | H-T10 | 177-206 | NFPPSQDASGDLYTTSSQLTLPATQCLAGK | 3169.50 | 3169.40 | | |
| 58 | H-T11 | 207-213 | SVTCHVK | 831.40 | ND | | |
| 59 | H-T12 | 214-251 | HYTNPSQDVTVPCPVPSTPPTPSPSTPPTPSPSCCHPR | 4139.84 | 4138.55 | Non-glycosylated N217 | |
| 60 | H-T13 | 252-278 | LSLHRPALEDLLLGSEANLTCTLTGLR | 2964.58 | 2964.43 | Non-glycosylated N265 | |

TABLE 7-continued

Observed peptide tryptic fragments of IgA-HX8 Heavy Chain (a representative peptide map for IgA-HX8 HC, event 193)

| SEQ ID No. | Fragment | Amino acid residues | Sequence | [M + H] (theor.) | [M + H] (observed) | Notes | Glycan entry in Table 3 |
|---|---|---|---|---|---|---|---|
| 60 | H-T-13-a | 252-278 | LSLHRPALEDLLLGSEANLTCTLTGLR | 3168.08 | 3168.30 | +GlcNAc | 11 |
| 60 | H-T-13-b | 252-278 | LSLHRPALEDLLLGSEANLTCTLTGLR | 3371.50 | 3370.50 | +(GlcNAc)2 | 12 |
| 60 | H-T-13-c | 252-278 | LSLHRPALEDLLLGSEANLTCTLTGLR | 3827.05 | 3826.93 | +(GlcNAc)2 (Hex)2(Xyl) | 2 |
| 60 | H-T-13-d | 252-278 | LSLHRPALEDLLLGSEANLTCTLTGLR | 3857.07 | 3856.92 | +(GlcNAc)2 (Hex)3 | 6 |
| 60 | H-T-13-e | 252-278 | LSLHRPALEDLLLGSEANLTCTLTGLR | 3972.96 | 3971.90 | +(GlcNAc)2 (Hex)2(Xyl) (Fuc) | 4 |
| 60 | H-T-13-f | 252-278 | LSLHRPALEDLLLGSEANLTCTLTGLR | 3989.08 | 3989.07 | +(GlcNAc)2 (Hex)3(Xyl) | 1 |
| 60 | H-T-13-g | 252-278 | LSLHRPALEDLLLGSEANLTCTLTGLR | 4018.98 | 4018.99 | +(GlcNAc)2 (Hex)4 | 8 |
| 60 | H-T-13-h | 252-278 | LSLHRPALEDLLLGSEANLTCTLTGLR | 4060.02 | 4060.06 | +(GlcNAc)3 (Hex)3 | 7 |
| 60 | H-T-13-i | 252-278 | LSLHRPALEDLLLGSEANLTCTLTGLR | 4134.79 | 4135.17 | +(GlcNAc)2 (Hex)3(Xyl) (Fuc) | 3 |
| 60 | H-T-13-j | 252-278 | LSLHRPALEDLLLGSEANLTCTLTGLR | 4180.78 | 4181.15 | +(GlcNAc)2 (Hex)5 | 9 |
| 60 | H-T-13-k | 252-278 | LSLHRPALEDLLLGSEANLTCTLTGLR | 4192.07 | 4192.18 | +(GlcNAc)3 (Hex)3(Xyl) | 5 |
| 60 | H-T-13-l | 252-278 | LSLHRPALEDLLLGSEANLTCTLTGLR | 4342.83 | 4343.20 | +(GlcNac)2 (Hex)6 | 10 |
| 61 | H-T-14 | 279-293 | DASGVTFTWTPSSGK | 1540.73 | 1541.00 | | |
| 62 | H-T-15 | 294-302 | SAVQGPPER | 940.49 | 940.70 | | |
| 63 | H-T-16 | 203-325 | DLCGCYSVSSVLPGCAEPWNHGK | 2596.08 | 2596.20 | | |
| 64 | H-T-17 | 326-337 | TFTCTAAYPESK | 1376.60 | 1376.04 | | |
| 65 | H-T-18 | 338-346 | TPLTATLSK | 931.55 | 931.80 | | |
| 66 | H-T-19 | 347-378 | SGNTFRPEVHLLPPPSEELALNELVTLTCLAR | 3574.86 | 3575.20 | | |
| 67 | H-T-20 | 379-383 | GFSPK | 535.29 | 535.25 | | |
| 68 | H-T-21 | 384-388 | DVLVR | 601.37 | 601.50 | | |

TABLE 7-continued

Observed peptide tryptic fragments of IgA-HX8 Heavy Chain (a representative peptide map for IgA-HX8 HC, event 193)

| SEQ ID No. | Fragment | Amino acid residues | Sequence | [M + H] (theor.) | [M + H] (observed) | Notes | Glycan entry in Table 3 |
|---|---|---|---|---|---|---|---|
| 69 | H-T-22 | 389-398 | WLQGSQELPR | 1213.63 | 1213.79 | | |
| 70 | H-T-24 | 401-407 | YLTWASR | 896.46 | 896.57 | | |
| 71 | H-T-25 | 408-424 | QEPSQGTTTFAVTSILR | 1835.95 | 1835.50 | | |
| 72 | H-T-26 | 425-431 | VAAEDWK | 818.40 | 818.45 | | |
| 73 | H-T-28 | 433-452 | GDTFSCMVGHEALPLAFTQK | 2210.03 | 2209.80 | | |
| 74 | H-T-29 | 453-456 | TIDR | 504.28 | 504.27 | | |
| 75 | H-T-30 | 457-478 | LAGKPTHVNVSVVMAEVDGTCY | 2348.13 | ND | C-terminal peptide | |
| 76 | H-T1-2 | 1-19 | EVQLVQSGAEVKKPGSSVK | 1952.08 | 1951.60 | Pyro-Glu on N-teminus | |
| 77 | H-T2-3 | 13-23 | KPGSSVKVSCK | 1177.63 | 1177.71 | | |
| 78 | H-T3-4 | 20-28 | VSCKASGGSFSSYAINWVR | 2076.98 | 2076.50 | | |
| 79 | H-T17-18 | 326-346 | TFTCTAAYPESKTPLTATLSK | 2289.13 | 2289.90 | | |
| 80 | H-T20-21 | 379-388 | GFSPKDVLVR | 1117.64 | 1117.90 | | |
| 81 | H-T21-22 | 384-398 | DVLVRWLQGSQELPR | 1795.98 | 1796.20 | | |
| 82 | H-T22-23 | 389-400 | WLQGSQELPREK | 1470.77 | 1471.07 | | |
| 83 | H-T27-28 | 432-452 | KGDTFSCMVGHEALPLAFTQK | 2338.12 | 2338.50 | | |

ND = not detected.

FIG. 12 provides the suggested putative glycan structures identified on IgA-HX8 expressed in transgenic maize based on results of MALDI-Tof mass-spectrum. Abundances of glycan species were estimated using intensities of the corresponding ions in MALDI-Tof mass-spectra of free glycans enzymatically reduced from IgA-HX8. FIG. 16 provides a summary of glycan profiling of IgA-HX8 expressed in transgenic maize (different events).

Example 11

Neutralization of HSV-2 by Endosperm-Derived HX8

Transgenic corn seed was milled to isolate the endosperm. The endosperm was milled to a fine powder and the antibody was dissolved in 0.15 M PBS. The Crude HX8 containing endosperm extracts were clarified by low speed centrifugation and affinity purified using a goat anti-human IgA affinity column. The endosperm extract was tested for their ability to neutralize HSV-2.

Figure 11:
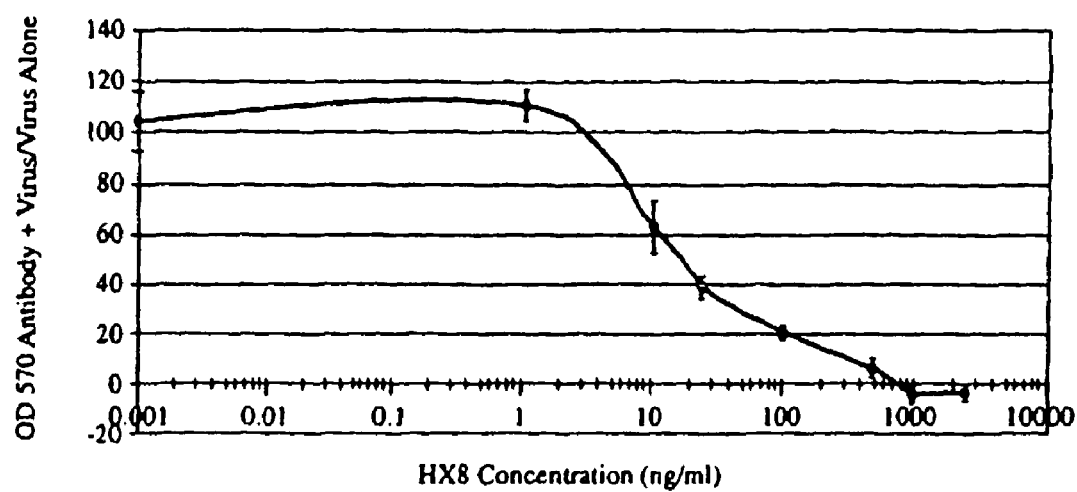
FIG. 11. Neutralization of HSV-2 using endosperm-derived HX8.

190 plaque forming units per well of a HSV-2 viral stock was incubated with serial dilutions of endosperm derived human monoclonal antibody HX8 for 1 hr at 37° C., 5% $CO_2$ in a 96 well format. Neutralization activity of the HX8 antibody was measured using a pre-CPE assay using ELVIS HSV cells commercially available from Diagnostic Hybrids, Inc., Athens, Ohio. This cell line was derived from baby hamster kidney cells (BHK) co-transfected with a plasmid which contains the G418 antibiotic resistance marker and a plasmid which contains the E. coli lacZ gene placed behind an inducible HSV promoter from the HSV-1 UL39 gene which encodes ICP6, the large subunit of HSV ribo-nucleotide reductase (E. C. Stabell and P. D. Olivo, "Isolation of a Cell Line for Rapid and Sensitive Histochemical Assay for the Detection of Herpes Simplex Virus," J. Virological Methods 38: 195-204 (1992)). ELVIS HSV cell monolayers were plated in a 96 well format and infected with the antibody-viral inoculum for 24 hours at 37° C., 5% $CO_2$. The supernatant was removed and the cells were lysed with ELVIRA lysis buffer purchased from Diagnostic Hybrids, Inc., Athens, Ohio. β-galactosidase activity was detected by adding the ELVIRA Detection Buffer purchased from Diagnostic Hybrids, Inc., Athens, Ohio. The concentration of β-galactosidase was detected by a spectrophometer OD 570 which corresponds to the level of HSV infection. The percent of virus neutralized by HX8 was calculated as a percentage of antibody minus negative control. Results obtained using this assay, which are also included in FIG. 11, indicate that at the given viral concentration, the antibody completely neutralizes the virus at 1 µg/ml.

II. Examples for Plant Production of Anti-Dual Integrin Antibody

Except as described herein, antibodies to IgG were produced in plant cells, plant calli and whole plants using all of the basic experimental protocols detailed above, including those related to plasmid construction (examples 1 and 2), vector construction (Examples 3 and 4), and transformation and regeneration (Example 6). Molecular and biochemical analysis of the IgG antibodies produced using such methods were determined according to the basic protocols provided in Examples 5 and 7-11.

Example 12

Plasmids and Vectors Utilized to Produce IgG

The specific IgG utilized in these experiments is one that is directed against the integrin receptors αVβ3 and αVβ5, also known as an anti-αVβ3, αVβ5 dual integrin antibody.

Figure 18A:
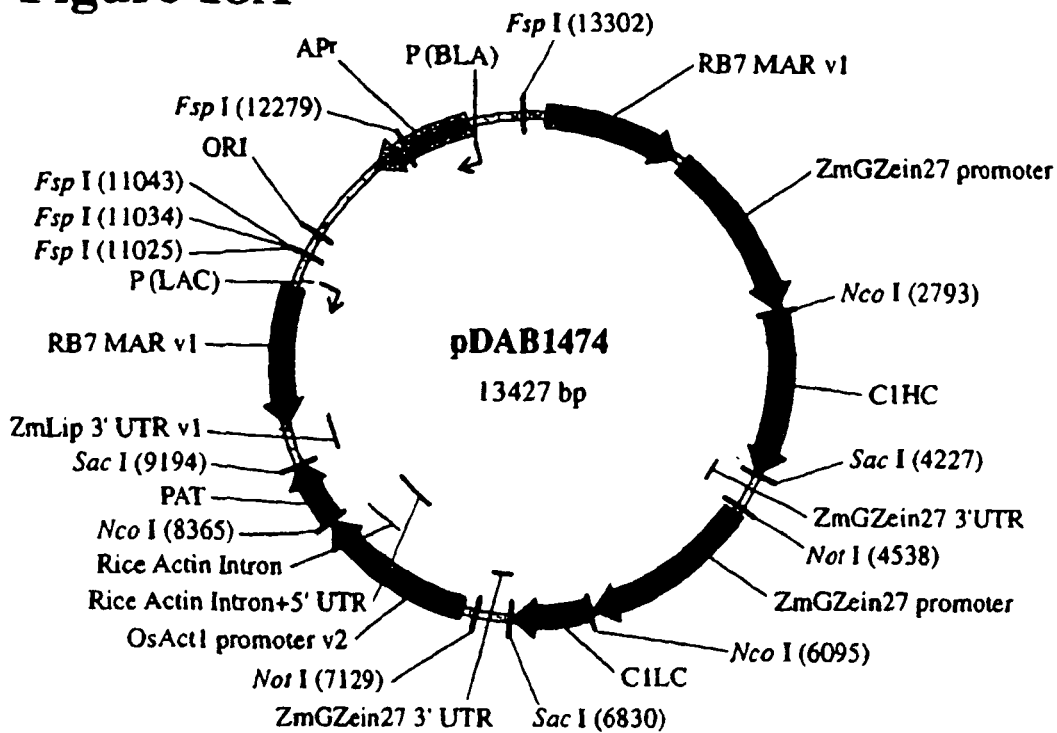
FIG. 18A. Plasmid pDAB1474 (FIG. 18A) and pDAB1475 (FIG. 18B).
Figure 18B:
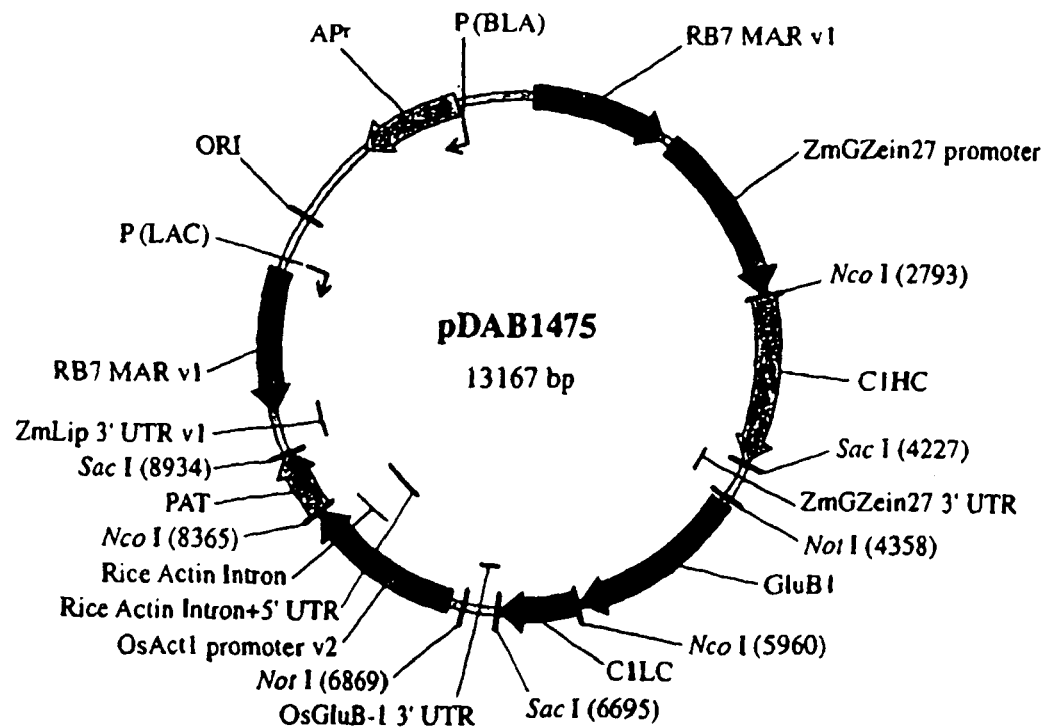

The following plasmids were utilized ("HC"=heavy chain; "LC"=light chain):

| Plasmid | Promoter-Gene-Terminator | Event No. or Sample No. | Figure |
|---|---|---|---|
| pDAB1472 | GluB1-HC-gluB1 GluB1-LC-gluB1 | 660 | FIG. 17A |
| pDAB1473 | Gzein-HC-gzein Gzein-LC-gzein | 661 | FIG. 17B |
| pDAB1474 | Gzein-HC-gzein Gzein-LC-gzein | 662 | FIG. 18A |
| pDAB1475 | Gzein-HC-gzein GluB1-LC-gluB1 | 663 | FIG. 18B |

Example 13

Plant Cell Transformation and Regeneration of IgG

Plant cells of corn inbred line 'HiII' were treated via direct-DNA delivery with pDAB1472, pDAB1473, pDAB1474 or pDAB1475 using the WHISKERS™ transformation method. These plasmids differed in the regulatory elements that were used to drive expression of the genes encoding the antibodies as a "test" to see which of the element combinations would result in the highest expression levels and accumulation of antibodies.

The "large-scale" WHISKERS™ method utilized treats about 18 ml of packed plant cells at one time (Petolino et al., Molecular Methods of Plant Analysis, In Genetic Transformation of Plants, Vol. 23, pp. 147-158, Springer-Verlag, Berlin (2003)). The anti-dual integrin transformed plants were planted and pollinated by inbred corn line '5XH751' so as to produce the progeny seed that was analyzed for antibody production.

Example 14

Estimating Transgene Copy Number of IgG

The Invader® assay platform from Third Wave Molecular Diagnostics was used to predict transgene copy number for the anti-dual integrin constructs. This method, unlike the one used for the IgA protocol discussed above, is based on a hybridization assay rather than a polymerase. Plant cells with 1-2 copies of the transcript were regenerated for further testing.

Example 15

Reduction and Carboxymethylation of Purified IgG, Followed by Proteolysis

A 25 µL sample was aliquoted for measurements of mass of "intact" protein by MALDI MS. The rest of the protein solution was dried in a siliconized microcentrifuge tube to completeness using a centrifugal evaporator. 180 µL of protein dissolution buffer (6M guanidine hydrochloride/0.4M ammonium bicarbonate, pH 7.8) was added to dry protein and sample was mixed by pipette action to achieve complete dissolution. 20 µl of 100 mM DTT (reducing reagent) solution was added to the tube.

The tube was sealed, vortexed, and incubated at 65° C. for 1 hour. It was then cooled to room temperature, centrifuged for 30 sec, and 40 µL of 200 mM IAA (alkylating reagent) solution was added to the tube. The tube was incubated in the dark at room temperature for 1 hour. 60 µL of DTT solution was added to consume unreacted IAA, and the tube was allowed to stand for 30 min at room temperature.

Desalting of the reduced/alkylated protein sample was performed as follows. A Protein Trap cartridge (Michrom BioResources, cat. no. 004-25108-53) was washed with 2×500 µL 100% acetonitrile ("ACN")/0.1% TFA and equilibrated with 500 µL of 2% ACN/0.1% TFA. 4 µL of ACN and 0.25 µL TFA was added to the reduced/alkylated protein solution (to a final concentration 2% of ACN and 0.2% TFA) and the solution was loaded onto the Protein Trap cartridge. The tube that contained the reduced/alkylated protein was rinsed with 100 µL of 2% ACN/0.1% TFA and the rinse was loaded onto the cartridge. The Protein Trap cartridge with bound protein was washed with 500 µL of 2% ACN/0.1% TFA. Desalted protein was eluted with 400 µL of 80% ACN/0.1% TFA into a 0.6-mL siliconized microcentrifuge tube.

The desalted protein sample was digested with trypsin as follows. The sample was dried in a centrifugal evaporator to completeness, and re-dissolved in 100 µL of 100 mM Tris buffer, pH 8-8.5. 50 µL of trypsin solution (Roche, cat. no. 1-418-025; 25 µg dissolved in 0.5 mL of 25 mM ammonium bicarbonate buffer immediately prior to digestion procedure) was added to the tube, and the sample was incubated for 16 hours at 37° C. After digestion, the sample was stored at −20° C. before HPLC separation and/or MALDI MS analysis.

Example 16

HPLC Fractionation of IgG Tryptic Digest

System Settings
HPLC system: Hitachi LC (L-7100 pump, L-7200 autosampler, L-7420 UV/Vis is detector).
Column: Magic C18, 2.0 mm (ID)×150 mm (Microm BioResources, cat. no. 901-61221-00).
UV detection: at 205 nm.
Automatic injection: using 200 µL sample loop; injection volume 100 □L.
Flow rate: 0.5 mL/min, constant.
Back pressure: reading should be approximately 2050-2100 psi (at 100% A).

Mobile Phases
A: 3% ACN, 97% Milli-Q water, 0.06% TFA.
B: 80% ACN, 20% Milli-Q water, 0.05% TFA.
Method

| Step | Time (min.) | % B | Comments |
| --- | --- | --- | --- |
| 1 | 5 | 0 | elution salts |
| 2 | 165 | 0 to 50 (linear) | main separation |
| 3 | 10 | 50 to 100 (linear) | ACN wash |
| 4 | 2 | 100 | ACN wash |
| 5 | 1 | 100 to 0 (linear) | re-equilibration |
| 6 | 5 | 0 | equilibration |

1-mL fractions were collected in siliconized microcentrifuge tubes and the fractions were dried in a centrifugal evaporator following the separation. A Gilson FC-203 fraction collector was used to collect fractions.

Example 17

Enzymatic Deglycosylation (PNGase-A Procedure)

In the separated tryptic digest, fractions containing glycopeptides were identified by MALDI MS. The remaining material in these fractions (~50%) was combined, dried in a centrifugal evaporator, and re-dissolved in 10 µL of 20 mM ammonium acetate buffer, pH 5.0. 10 µL of peptide-N-glycosidase A (PNGase-A) solution (Roche, cat. no. 1-642-995) was added, and the tubes were incubated at 37° C. for 16 hours.

Example 18

Purification of Released N-Glycans

The proteolytic/PNGase-A digest was passed through C18 cartridge (Peptide Macro Trap, Michrom Bioresources (cat no. 004-25108-52), pre-conditioned according to manufacturer's procedure) and the flow-through fraction was collected. The cartridge was washed with 0.5 mL of 0.1% aqueous TFA and the wash was combined with the first flow-through fraction. These fractions, containing released oligosaccharides, were further purified using an E-cartridge (QA-Bio, cat. no. C-E001, lot no. A2AA-01) according to the manufacturer's procedure. Oligosaccharides were eluted from E-cartridge with 50% acetonitrile/0.1% TFA and dried to completeness in a centrifugal evaporator. The glycan samples were re-dissolved in 2.5 µL of high-purity Milli-Q water and passed through C18 ZipTips (Millipore), according to the manufacturer's procedure. Purified glycan samples were ready for analysis by MALDI MS.

The deglycosylated peptides captured on the C18 cartridge were eluted with 100% ACN/0.1% TFA, concentrated in centrifugal evaporator, and examined by MALDI MS.

Example 19

MALDI MS and PSD

Voyager DE-STR (Applied BioSystems, serial no. 4260) MALDI-Tof mass spectrometer operated in positive reflectron mode was used to obtain data for peptides and oligosaccharides (glycans). The instrument was operated in positive linear mode to obtain data for intact proteins.

The first 4 HPLC fractions (those that eluted in the front of the chromatogram and contained salts) of the separated tryptic digests were dissolved in 10 µL of 0.1% TFA and combined; peptides were desalted using C18 zip tips according to standard protocol. The remaining HPLC fractions were dissolved in 3 µL of 50% ACN/0.1% TFA, and some fractions were combined. 50% of each fraction (after combining) was deposited onto a MALDI plate (in 1.5 µL), overlaid with 1 µL of CHCA matrix solution and air-dried. The remaining 50% of the fractions that were found to contain glycopeptides were further treated with PNGase-A as described above.

Settings used to obtain MALDI spectra of peptides. The acceleration voltage was set to 20 kV. The grid voltage was set to 66% of the acceleration voltage. The delay time varied between 215 and 350 nsec. The laser setting varied between 2200 and 3000. 500 acquisitions were averaged in each spectrum. The mass scale was calibrated with the following standard peptides (Applied BioSystems): des-Arg$^1$-Bradykinin, m/z 904.4; Angiotensin I, m/z 1,296.6; Glu$^1$-Fibrinopeptide B, m/z 1570.6; Neurotensin, m/z 1672.9; ACTH (clip 1-17), m/z 2093.0; ACTH (clip 18-39), m/z 2465.1; ACTH (clip 7-38), m/z 5730.6.

MALDI-PSD spectra were recorded using mirror voltage ratio 1.12; the following minor ratios were used: 1, 0.85, 0.75, 0.65, 0.55, 0.4, 0.3, 0.2, 0.1, 0.05.

Settings used to obtain MALDI spectra of oligosaccharides (glycans). The acceleration voltage was set to 20 kV. The grid voltage was set to 69% of the acceleration voltage. The delay time was set to 215 nsec. The laser setting was approximately 3000. 500 acquisitions were averaged in each spectrum.

The mass scale was calibrated with the following standard oligosaccharides: $(GlcNAc)_2(Man)_5$, m/z $(MNa^+)$=1257.46; $(GlcNAc)_4(Man)_3(Fuc)$, m/z $(MNa^+)$=1485.56; (Gal) $(GlcNAc)_4(Man)_3(Fuc)$, m/z $(MNa^+)$=1647.62; $(Gal)_2$ $(GlcNAc)_4(Man)_3(Fuc)$, m/z $(MNa^+)$=1809.68. 1 µL of sample of purified glycans was deposited onto a MALDI sample plate, overlaid with 1 µL of sDHB matrix (9:1 v/v mixture of 18 mg/mL 2,5-dihydroxybenzoic acid in 66% acetonitrile and 15 mg/mL 2-hydroxy-5-methoxybenzoic acid in 66% acetonitrile) and air-dried.

Conditions used to obtain MALDI spectra of intact proteins. The instrument was operated in positive linear mode. The acceleration voltage was set to 25 kV. The grid voltage was set to 89% of the acceleration voltage. The extraction delay time was varied between 750 and 1500 nsec. The laser setting was approximately 3300. The low mass gate was set to 5000 Da. Two sets of 500 acquisitions each were averaged in each spectrum.

The mass scale was calibrated with the following standard (Sequazyme IgG1, Applied BioSystems, cat no. GEN602151): doubly charged Sequazyme IgG1 monomer at m/z 74249, singly charged Sequazyme IgG1 monomer at m/z 148500.

The following procedure was used to desalt protein sample before mass-spectrometry. A C4 zip-tip (Millipore) was primed with 50% ACN, then equilibrated with 0.1% TFA; an aliquot of the protein sample was passed through zip-tip 10 times, then the spent solution was returned to the original vial; the zip-tip with bound protein was washed with 0.1% TFA and protein was eluted with 3 µL of 80% ACN/0.1% TFA directly onto the MALDI plate (dropwise). Desalted protein sample was overlaid with 1 µL of matrix (sinapinic acid, from Sequazyme kit, Applied BioSystems, cat no. P2-3143-00) and air-dried.

Analysis of MALDI MS data. MALDI MS and MALDI-PSD data were analyzed using Data Explorer v4.0 software (Applied BioSystems). Molecular weights and amino acid sequences of peptides and glycopeptides were attributed to the sequence of the IgG samples using MassLynx v3.4 software (Micromass).

Example 20

MALDI MS of Intact IgG

MALDI MS experiments were conducted with samples of "intact" affinity-purified IgG protein from maize-expressed IgG for three separate transformation events (i.e., events 660, 661 and 663) and for CHO-expressed IgG (data not shown).

Measured mass for the antibody light chain (LC) was within ~1.0% of theoretical average mass (M=23486 Da). Measured mass for intact assembled antibody was about 1.7 to 2.0% higher than expected theoretical average mass (M=145612 Da for non-glycosylated protein). This discrepancy is probably explained by glycosylation of the heavy chain.

Overall, the MALDI mass-spectrum for all four samples of "intact" antibody (three maize-expressed and the CHO-expressed) were typical of an assembled IgG.

Example 21

Peptide Mapping Results

Peptide mapping results were obtained for all three maize-expressed IgG samples and for the CHO-expressed IgG sample (data not shown). Sequence mass coverages (combined tryptic and Asp-N peptide maps) and tryptic peptide maps were also obtained for all samples (data not shown). Briefly, overall sequence mass coverage was about 90% to about 100% for heavy and light chains in all of the antibody samples. N-terminal fragments were detected in all heavy and light chains. In all samples, the N-terminal fragment of heavy chain contained pyro-Glu as the N-terminal residue, which is a typical post-translational modification in antibodies. Weak signals consistent with a trace content of non-processed N-terminal heavy chain fragments (containing Gln as N-terminal residue) were also detected. C-terminal fragments of light chains were detected in all samples. In maize-expressed antibody samples for events 660 and 663, C-terminal fragments of heavy chains were represented by a mixture of a full-size C-terminal fragment (with Lys449 as C-terminal residue) and a C-terminal fragment with Lys449 deleted ("no K"). Only the truncated ("no K", i.e. without Lys449) version of the C-terminal heavy chain fragment was detected in the C1-661 sample. Only the truncated ("no K", i.e. without Lys449) version of the C-terminal heavy chain fragment was detected in CHO-expressed antibody. Sequences of all N-terminal tryptic fragments and heavy chain C-terminal fragments were confirmed by MALDI-PSD experiments.

Example 22

Glycosylation Profiling

Primary structure and glycosylation of the three maize-expressed and one CHO-expressed IgG antibodies were examined and compared to each other. Full profiles of the N-linked glycans observed (as glycopeptides) in the antibody samples are provided in FIG. 19 (event 660), FIG. 21 (event 661), FIG. 23 (event 663) and FIG. 25 (CHO-expression). As discussed above, fucosylation is α1,6 for mammalian-produced glycoproteins and α1,3 for plant-produced glycoproteins.

Figure 20A:
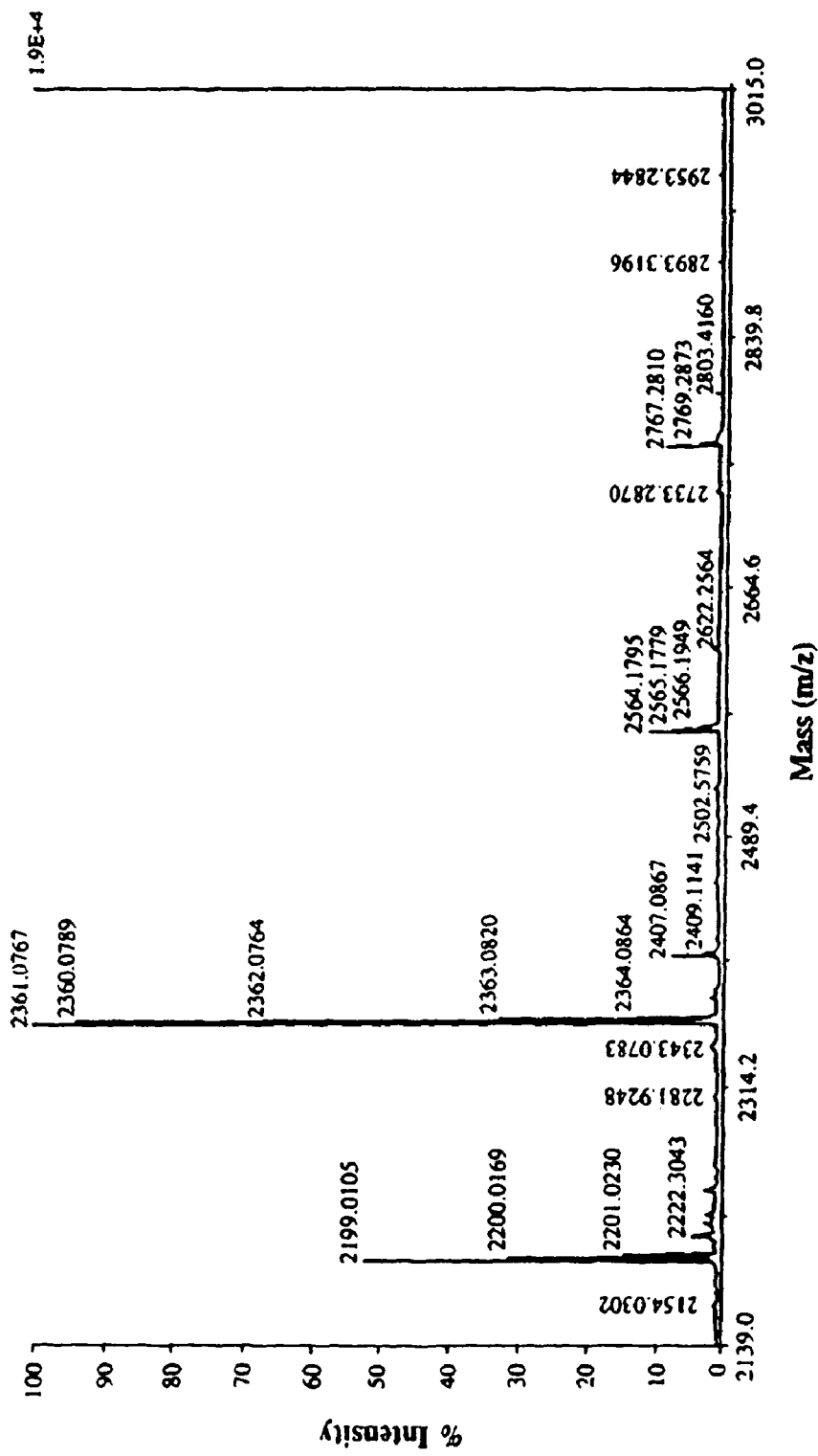
FIG. 20A. A representative MALDI-TOF of MS profile of glycoforms of H-T27 peptide (N299 site of heavy chain) for event 660.
Figure 20B:
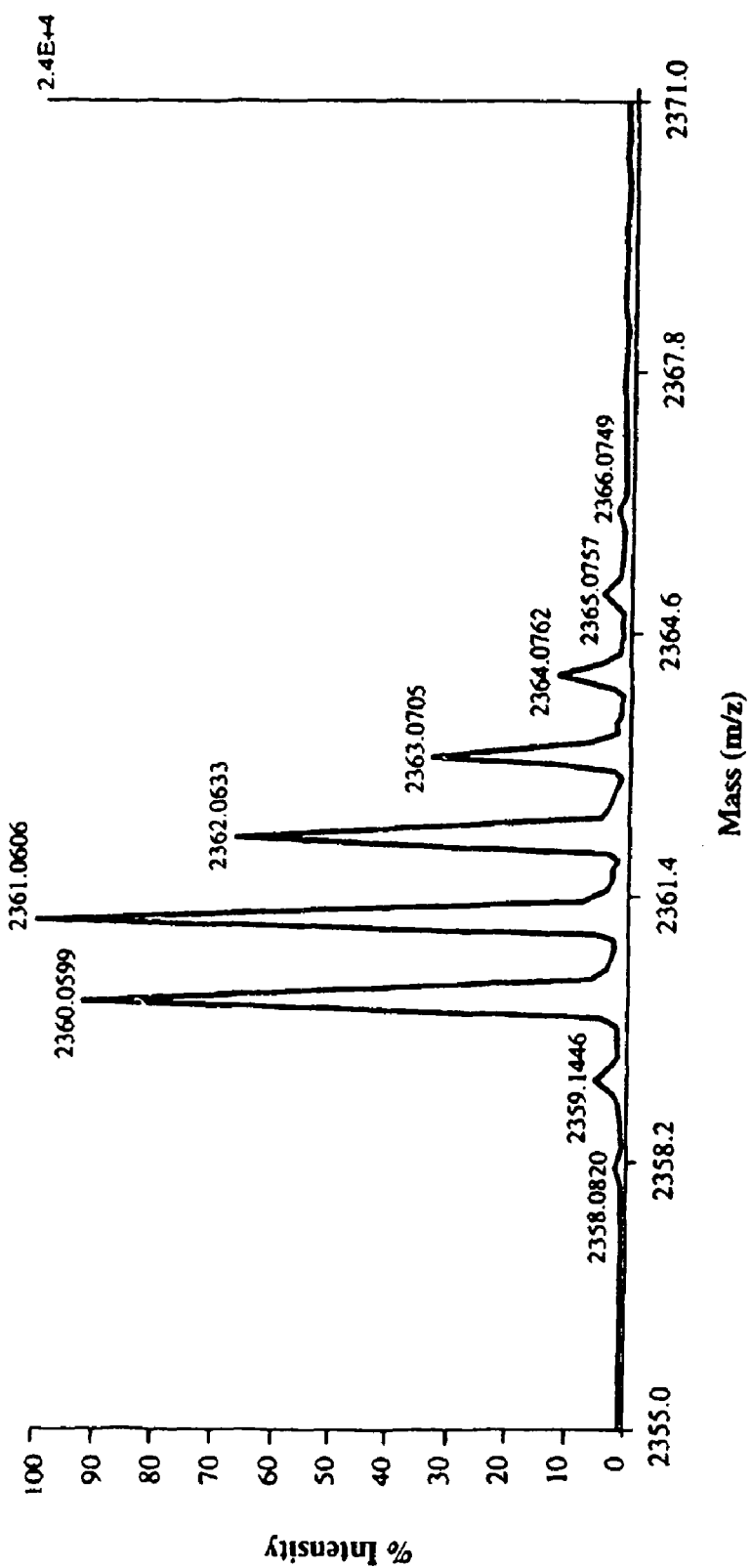
FIG. 20B. Zoom-in on m/z 2360.06 (major glycoform, N2H3XF) for event 660. Note isotopic resolution.
Figure 22A:
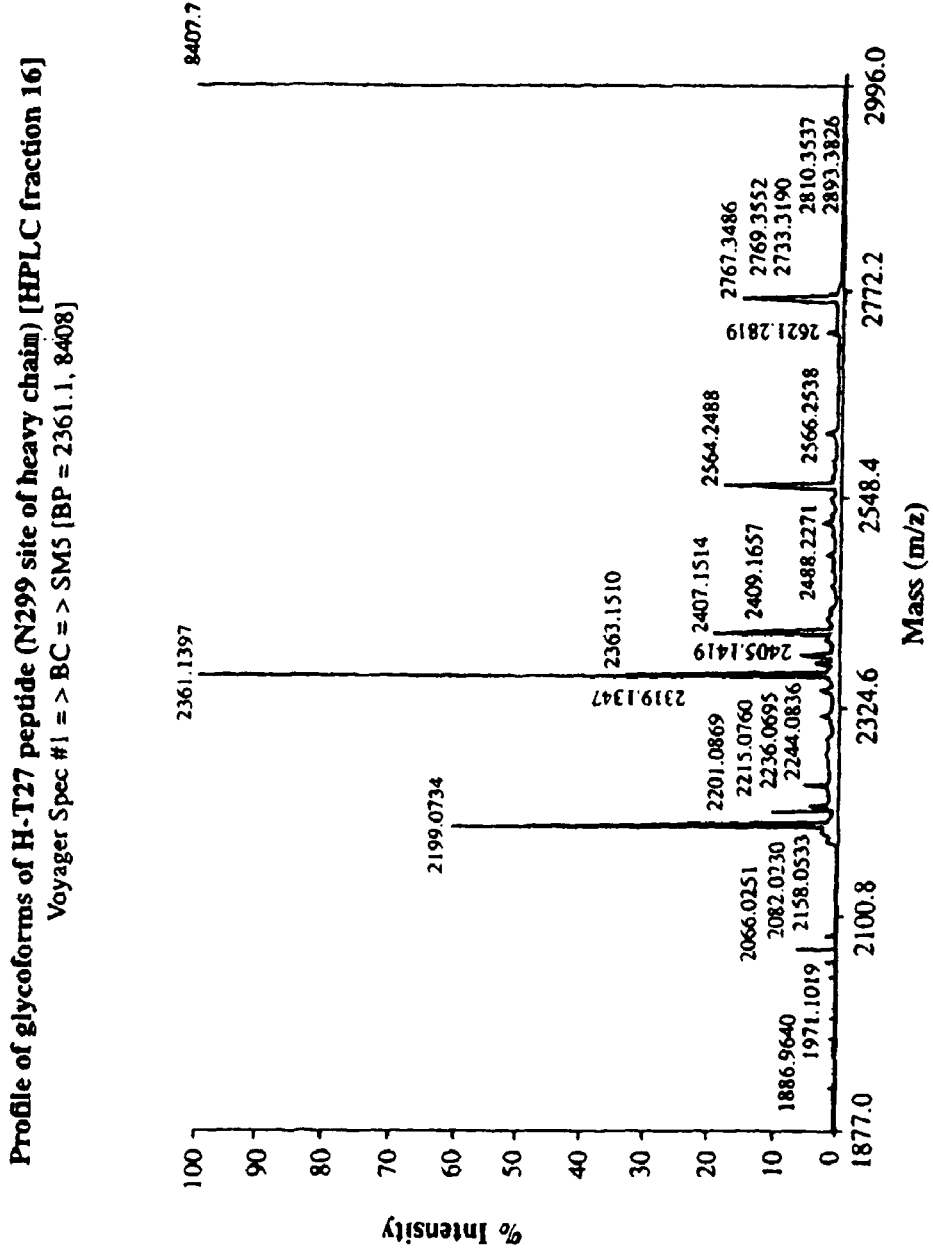
FIG. 22A. A representative MALDI-TOF of MS profile of glycoforms of H-T27 peptide (N299 site of heavy chain) for event 661. HPLC fraction 16.
Figure 22B:
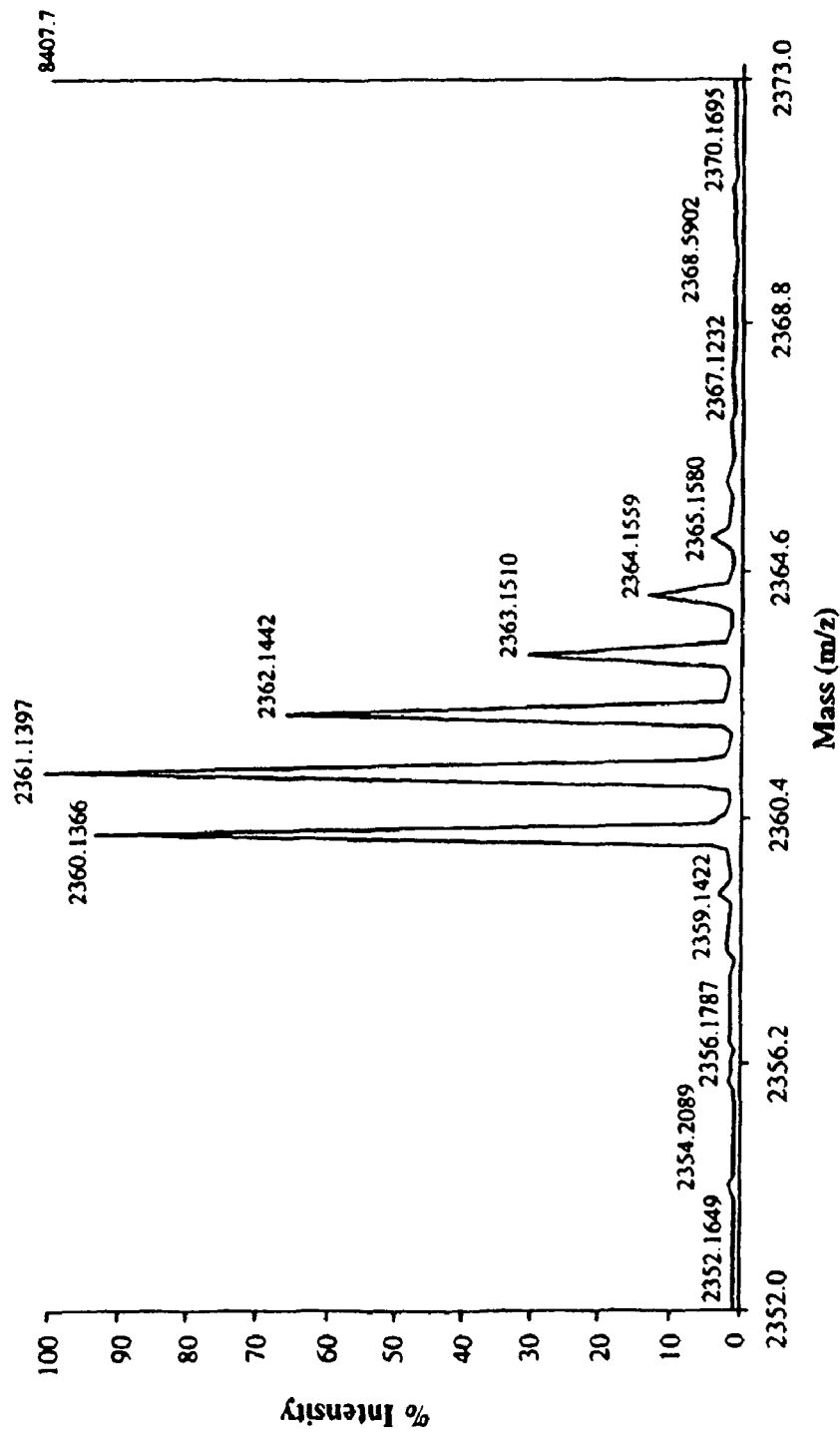
FIG. 22B. Zoom-in on m/z 2360.06 (major glycoform, N2H3XF) for event 661. Note isotopic resolution.
Figure 22C:
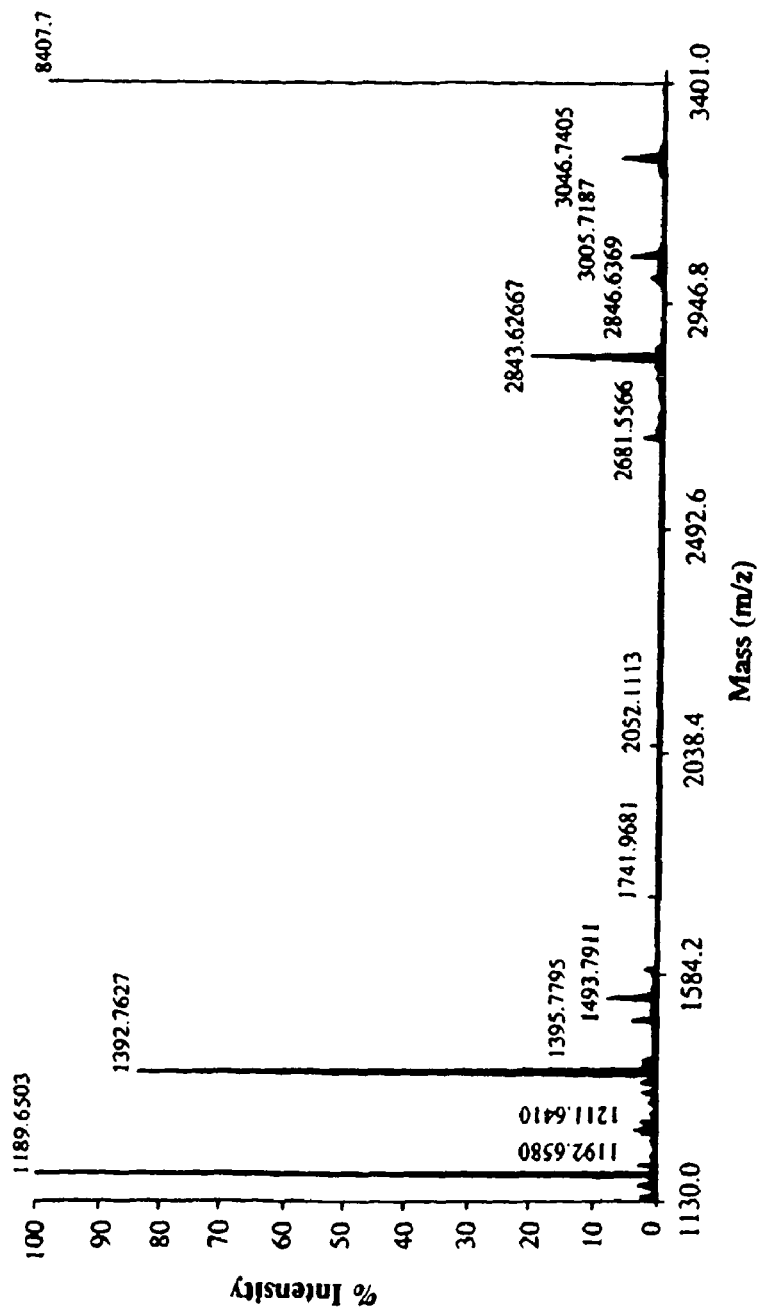
FIG. 22C. A representative MALDI-TOF of MS profile of glycoforms of H-T27 peptide (non-glycosylated at m/z 1189.65, and with single HexNAc at m/z 1392.76, plus some N-glycoforms on H-T26-27 peptide at higher m/z) for event 661. HPLC fraction 17.
Figure 22D:
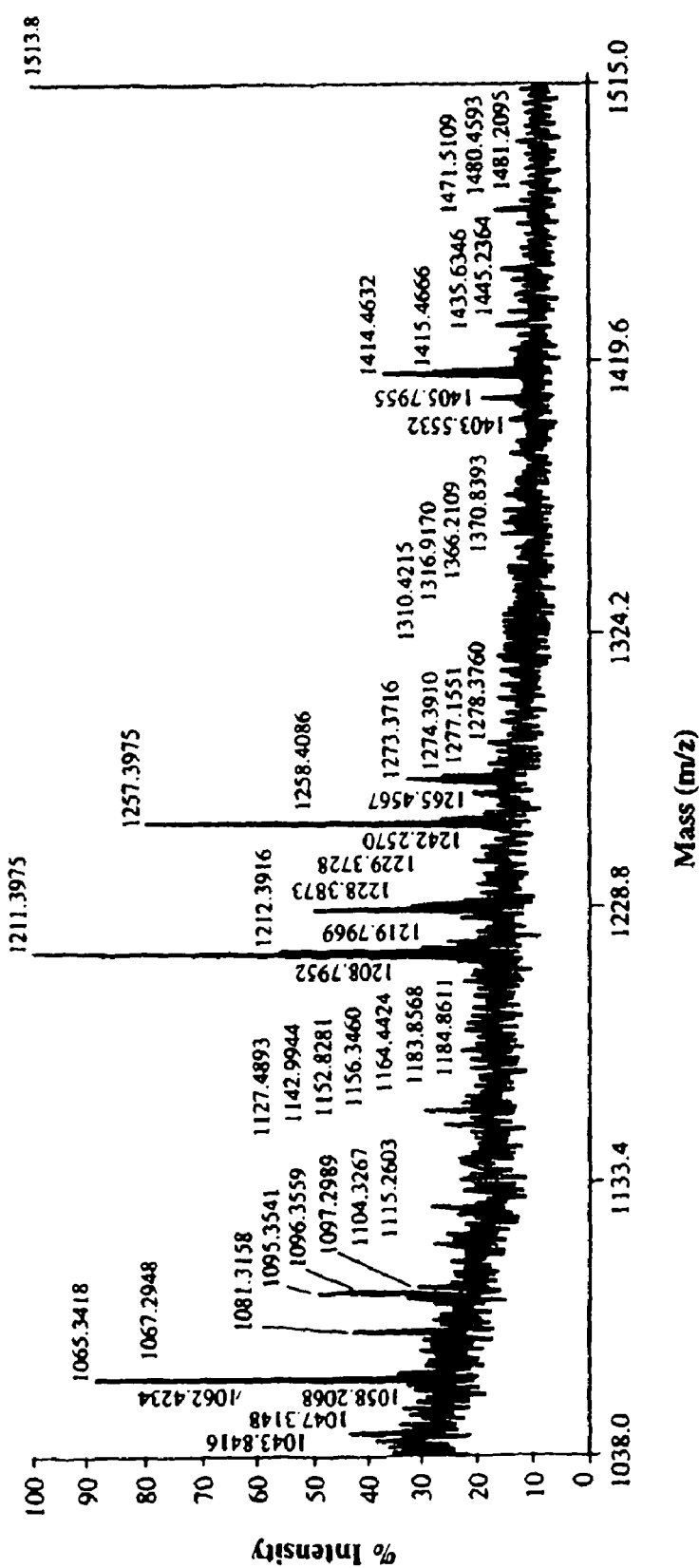
Figure 24A:
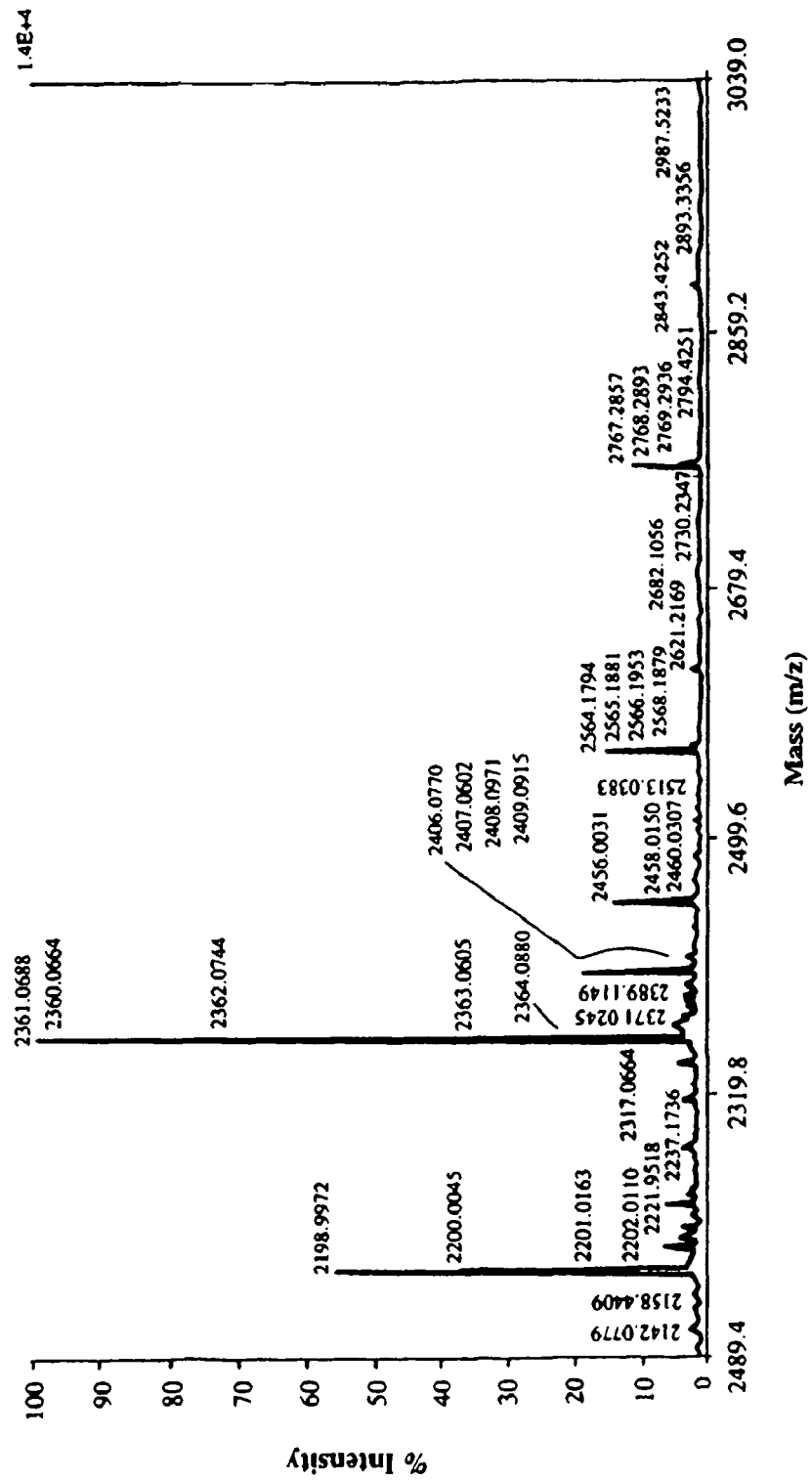
FIG. 24A. A representative MALDI-TOF of MS profile of glycoforms of H-T27 peptide (N299 site of heavy chain) for event 663.
Figure 24B:
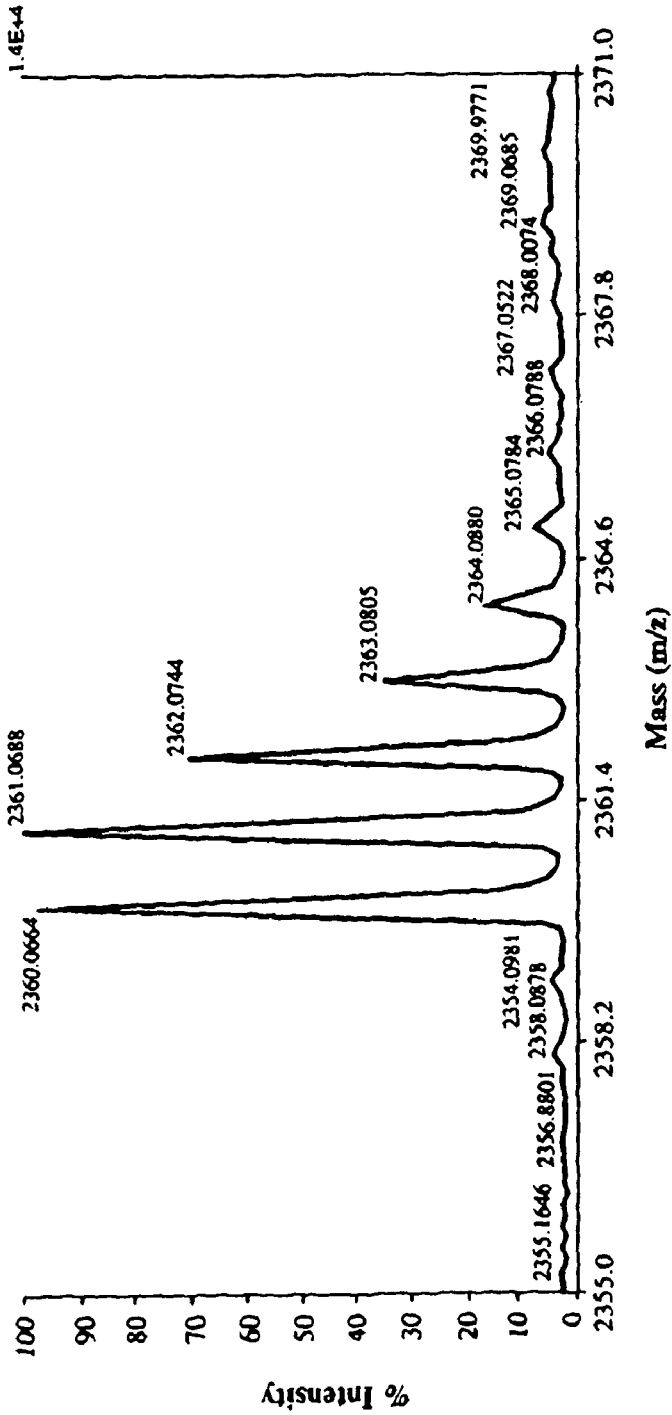
FIG. 24B. Zoom-in on m/z 2360.07 (major glycoform, N2H3XF) for event 663. Note isotopic resolution.
Figure 26A:
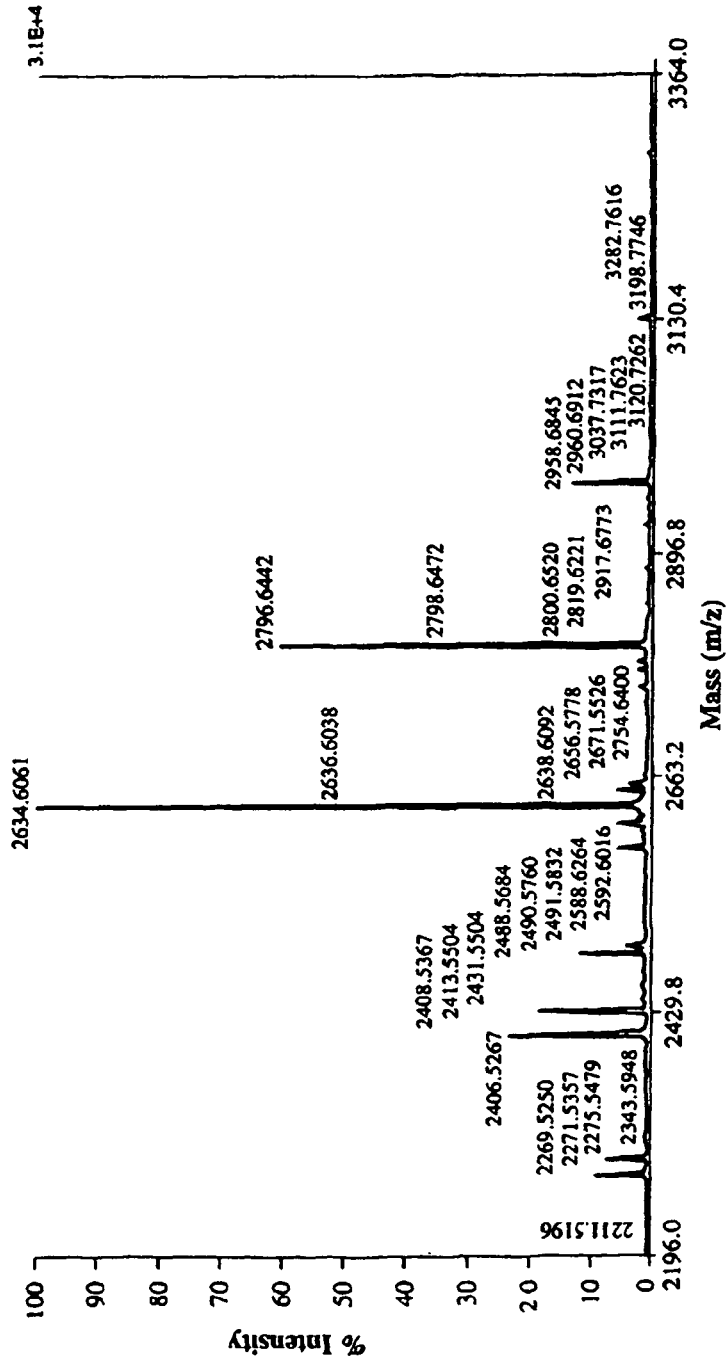
FIG. 26A. A representative MALDI-TOF of MS profile of glycoforms of H-T27 peptide (N299 site of heavy chain) for CHO-expressed IgG.
Figure 26B:
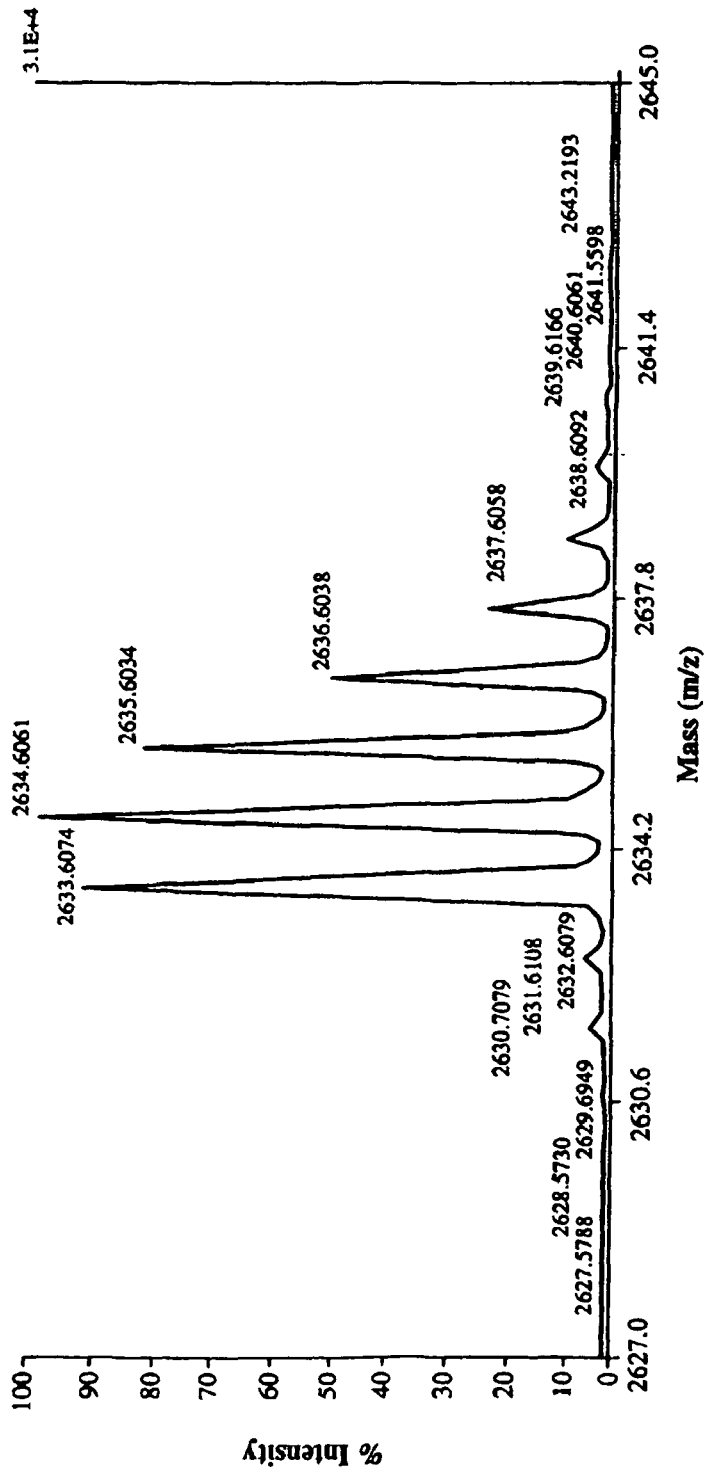
FIG. 26B. Zoom-in on m/z 2633.61 (major glycoform, N4H3F) for CHO-expressed IgG. Note isotopic resolution.

Representative MALDI-TOF of MS profiles are provided for event 660 in FIGS. 20A-B; event 661 in FIGS. 22A-C; event 663 in FIGS. 24A-B; and for the CHO expression in FIGS. 26A-B. FIG. 22D provides the mass-spectrum results of the N-glycans released from H-T27 glycopeptide. Intensities in this MALDI mass-spectrum are roughly proportional to abundance of the neutral N-glycans. The MALDI mass-spectra for all samples of intact antibodies were typical of an assembled IgG.

The two most abundant glycans observed on Asn299 of the maize-expressed heavy chain samples have the composition $HexNAc_2$-$Hex_2$-Xyl-Fuc (or N2H2XF) and $HexNAc_2$-$Hex_3$-Xyl-Fuc (or N2H3XF), whereas the most abundant glycans in CHO-expressed have the composition $HexNAc_4$-$Hex_3$-Fuc (or N4H3F) and $HexNAc_4$-$Hex_4$-Fuc (or N4H4F). The level of heavy chain modified with a single HexNAc monosaccharide appears to be higher in maize-expressed antibody samples than in the CHO-expressed antibody samples. N-glycosylation in the CHO-expressed samples appear more heterogeneous (diverse) than that in maize-expressed antibody samples.

Sequences of H-T27 heavy chain tryptic fragment (i.e., the fragment containing Asn299 glycosylation site) and its variant modified with a single HexNAc monosaccharide were confirmed by MALDI-PSD experiments for all antibody samples examined in this work. However, the signal intensities of glycoforms observed as free N-glycans were somewhat different from those observed as glycopeptides. In the MALDI mass-spectrum of H-T27 peptide glycoforms, glycopeptides with the glycans $HexNAc_2$-$Hex_2$-Xyl-Fuc (or N2H2XF) and $HexNAc_2$-$Hex_3$-Xyl-Fuc (or N2H3XF) produced the most intense signals. In contrast, in the MALDI mass-spectrum of enzymatically released free oligosaccharides, glycans $HexNAc_2$-$Hex_3$-Xyl (or N2H3X), $HexNAc_2$-$Hex_3$-Xyl-Fuc (or N2H3XF), and $HexNAc_2$-$Hex_5$ (or N2H5) appeared as major species. According to literature reports (D. Harvey, Mass Spectrometry Reviews 18:349-451 (1999)) and our own findings, MALDI MS of free glycans should give a generally more accurate estimate of relative quantities of N-glycans. In any case, by both approaches (i.e., glycopeptides and free glycans), the N-glycan $HexNAc_2$-$Hex_3$-Xyl-Fuc (or N2H3XF) was observed as the most abundant species.

No evidence of O-linked glycosylation was found in the antibody samples examined in this work.

The foregoing detailed description has been given for clearness of understanding only and no unnecessary limitations should be understood therefrom as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A plant-produced heavy chain (HC) or light chain (LC) of an immunoglobulin, wherein the immunoglobulin is an IgA molecule specific to herpes simplex virus; and wherein the HC or LC has a glycopeptide profile comprising at least one glycopeptide which lacks fucose, the at least one glycopeptide containing a glycan that is 2Man, 2GlcNAc, 1Xyl, in which Man=Mannose, GlcNAc=N-acetylglucosamine, and Xyl=xylose, wherein 2Man, 2GlcNAc, 1Xyl has the structure set forth in FIG. 12, item 2.

2. The HC of claim 1, wherein the at least one glycopeptide comprises an asparagine (Asn) residue in a CH2 region of the plant-produced heavy chain.

3. A plant-produced immunoglobulin, wherein the immunoglobulin has a free glycan profile comprising at least one glycan which lacks fucose, the glycan being 2Man, 2GlcNAc, 1Xyl, in which Man=Mannose, GlcNAc=N-acetylglucosamine, and Xyl=xylose, wherein 2Man, 2GlcNAc, 1Xyl has the structure set forth in FIG. 12, item 2, and wherein the immunoglobulin is an IgA molecule specific to herpes simplex virus.

4. The immunoglobulin of claim 3, wherein the plant-produced immunoglobulin comprises an asparagine (Asn) residue.

5. The immunoglobulin of claim 3, wherein the free glycan profile is the same as or substantially the same as that provided in FIG. 12.

6. The immunoglobulin of claim 3, wherein the free glycan profile further comprises a glycan selected from the group consisting of 3Man, 2GlcNAc, 1Xyl having the structure set forth in FIG. 12, item 1; 3Man, 3GlcNAc, 1Xyl having the structure set forth in FIG. 12, item 5; 3Man, 2GlcNAc having the structure set forth in FIG. 12, item 6; 3Man, 3GlcNAc having the structure set forth in FIG. 12, item 7; 4Man, 2GlcNAc having the structure set forth in FIG. 12, item 8; 5 Man, 2GlcNAc having the structure set forth in FIG. 12, item 9; and 6Man, 2GlcNAc having the structure set forth in FIG. 12, item 10, wherein Man=Mannose, GlcNAc=N-acetylglucosamine and Xyl=xylose.

7. The immunoglobulin of claim 3, wherein the free glycan profile is the same as or substantially the same as one of the glycan profiles provided in FIG. 16.

8. The immunoglobulin of claim 3, wherein the free glycan profile further comprises 3Man, 2GlcNAc having the structure set forth in FIG. 12, item 6; and 3Man, 2GlcNAc, 1 Xyl having the structure set forth in FIG. 12, item 1, wherein Man=Mannose, GlcNAc=N-acetylglucosamine and Xyl=xylose.

9. The immunoglobulin of claim 3, wherein the free glycan profile further comprises 8Man, 2GlcNAc; 3Man, 2GlcNAc, 1Xyl; 4Man, 2GlcNAc, 1Xyl; 5Man, 2GlcNAc; 6Man, 2GlcNAc; 7Man, 2GlcNAc; 3Man, 3GlcNAc, 1Xyl; or 4Man, 2GlcNAc, wherein Man=Mannose, GlcNAc=N-acetylglucosamine and Xyl=xylose, and wherein 3Man, 2GlcNAc, 1Xyl has the structure set forth in FIG. 12, item 1, 5Man, 2GlcNAc has the structure set forth in FIG. 12, item 9, 6Man, 2GlcNAc has the structure set forth in FIG. 12, item 10, 3Man, 3GlcNAc, 1 Xyl has the structure set forth in FIG. 12, item 5, and 4Man, 2GlcNAc has the structure set forth in FIG. 12, item 8.

10. The immunoglobulin of claim 3, wherein the plant-produced immunoglobulin comprises an asparagine (Asn) residue in its CH2 region.

11. The immunoglobulin of claim 3, wherein its free glycan profile is determined using matrix-assisted laser desorption/ionization time-of-flight mass spectrometry (MALDI-Tof MS) analysis of free N-linked glycans enzymatically-released from the immunoglobulin.

12. The immunoglobulin of claim 3, wherein the plant-produced immunoglobulin is a human immunoglobulin.

13. The immunoglobulin of claim 3, wherein the plant-produced immunoglobulin comprises a heavy chain lacking a tailpiece.

14. The plant-produced immunoglobulin heavy chain (HC) or light chain (LC) of claim 1, wherein the heavy chain of the immunoglobulin lacks a tailpiece.

15. The immunoglobulin of claim 3, wherein the plant-produced immunoglobulin is isolated from the plant used to produce the immunoglobulin.

16. The immunoglobulin of claim 3, comprising an amino acid fragment lacking an attached glycan with fucose, wherein the plant-produced immunoglobulin has an attached glycan with fucose on the same amino acid fragment or on substantially the same amino acid fragment when the immunoglobulin is mammalian-produced.

17. The immunoglobulin of claim 3, comprising an amino acid fragment having an attached glycan lacking fucose, wherein the plant-produced immunoglobulin also lacks an attached glycan with fucose on the same amino acid fragment or on substantially the same amino acid fragment when the immunoglobulin is mammalian-produced.

18. The immunoglobulin of claim 16, wherein the plant-produced immunoglobulin is produced in a maize cell.

19. A method of producing an isolated a monomeric anti-herpes simplex virus antibody comprising: (i) introducing into a plant cell nucleic acids having either SEQ ID NO: 1 or either SEQ ID NO: 5 and SEQ ID NO: 9 or SEQ ID NO: 13, each of which is operably-linked to a promoter, to produce a transformed plant cell; (ii) culturing the transformed plant cell to express the introduced nucleic acids; and (iii) isolating the monomeric anti-herpes simplex virus antibody produced by the plant cell.

20. The method of claim 19 further comprising regenerating a transformed plant from the transformed plant cell.

21. The immunoglobulin of claim 3, wherein the plant-produced immunoglobulin comprises a heavy chain comprising the amino acid sequence of SEQ ID NO: 6.

22. The immunoglobulin of claim 3, wherein the plant-produced immunoglobulin comprises a light chain comprising the amino acid sequence of SEQ ID NO: 14.

* * * * *

SEQUENCE LISTING

<160> NUMBER OF SEQ ID NOS: 85

<210> SEQ ID NO 1
<211> LENGTH: 1494
<212> TYPE: DNA
<213> ORGANISM: Herpes simplex virus
<220> FEATURE:
<221> NAME/KEY: CDS
<222> LOCATION: (1)..(1494)
<220> FEATURE:
<221> NAME/KEY: misc_feature
<223> OTHER INFORMATION: HSV Heavy Chain sequence

<400> SEQUENCE: 1

| | | | | | | | | | | | | | | | | |
|---|---|---|---|---|---|---|---|---|---|---|---|---|---|---|---|---|
| atg | gga | tgg | agc | tgg | atc | ttt | ctc | ttc | ctc | ctg | tca | gga | gct | gca | ggt | 48 |
| Met | Gly | Trp | Ser | Trp | Ile | Phe | Leu | Phe | Leu | Leu | Ser | Gly | Ala | Ala | Gly | |
| 1 | | | | 5 | | | | | 10 | | | | | 15 | | |
| gtc | cat | tgc | cag | gtt | cag | ctc | gtg | cag | tca | ggt | gct | gag | gtg | aag | aag | 96 |
| Val | His | Cys | Gln | Val | Gln | Leu | Val | Gln | Ser | Gly | Ala | Glu | Val | Lys | Lys | |
| | | 20 | | | | | 25 | | | | | 30 | | | | |
| cct | ggc | tcc | tcg | gtg | aag | gtc | tcc | tgc | aag | gct | tct | gga | ggt | tcc | ttc | 144 |
| Pro | Gly | Ser | Ser | Val | Lys | Val | Ser | Cys | Lys | Ala | Ser | Gly | Gly | Ser | Phe | |
| | | | 35 | | | | | 40 | | | | | 45 | | | |
| agc | tcc | tat | gct | atc | aac | tgg | gtg | agg | caa | gct | cct | gga | caa | ggg | ctt | 192 |
| Ser | Ser | Tyr | Ala | Ile | Asn | Trp | Val | Arg | Gln | Ala | Pro | Gly | Gln | Gly | Leu | |
| 50 | | | | | 55 | | | | | 60 | | | | | | |
| gag | tgg | atg | gga | ggg | ctc | atg | cct | atc | ttt | ggg | aca | aca | aac | tac | gcg | 240 |
| Glu | Trp | Met | Gly | Gly | Leu | Met | Pro | Ile | Phe | Gly | Thr | Thr | Asn | Tyr | Ala | |
| 65 | | | | | 70 | | | | | 75 | | | | | 80 | |
| cag | aag | ttc | cag | gac | agg | ctc | acg | att | acc | gcg | gac | gta | tcc | acg | agt | 288 |
| Gln | Lys | Phe | Gln | Asp | Arg | Leu | Thr | Ile | Thr | Ala | Asp | Val | Ser | Thr | Ser | |
| | | | | 85 | | | | | 90 | | | | | 95 | | |
| aca | gcc | tac | atg | caa | ctg | agc | ggc | ctg | aca | tat | gaa | gac | acg | gcc | atg | 336 |
| Thr | Ala | Tyr | Met | Gln | Leu | Ser | Gly | Leu | Thr | Tyr | Glu | Asp | Thr | Ala | Met | |
| | | | 100 | | | | | 105 | | | | | 110 | | | |
| tat | tac | tgt | gcg | aga | gtt | gcc | tac | atg | ctt | gaa | cct | acc | gtc | act | gca | 384 |
| Tyr | Tyr | Cys | Ala | Arg | Val | Ala | Tyr | Met | Leu | Glu | Pro | Thr | Val | Thr | Ala | |
| | | | | 115 | | | | | 120 | | | | | 125 | | |
| ggt | ggt | ttg | gac | gtc | tgg | ggc | caa | ggg | acc | ttg | gtc | acc | gtc | tcc | tcc | 432 |
| Gly | Gly | Leu | Asp | Val | Trp | Gly | Gln | Gly | Thr | Leu | Val | Thr | Val | Ser | Ser | |
| | 130 | | | | | 135 | | | | | 140 | | | | | |
| gca | tcc | ccg | acc | agc | ccg | aag | gtc | ttc | ccg | ctg | agc | ctc | tgt | agc | acc | 480 |
| Ala | Ser | Pro | Thr | Ser | Pro | Lys | Val | Phe | Pro | Leu | Ser | Leu | Cys | Ser | Thr | |
| 145 | | | | | 150 | | | | | 155 | | | | | 160 | |
| cag | cca | gat | ggg | aac | gtg | gtc | atc | gcc | tgc | ctg | gtc | cag | ggc | ttc | ttc | 528 |
| Gln | Pro | Asp | Gly | Asn | Val | Val | Ile | Ala | Cys | Leu | Val | Gln | Gly | Phe | Phe | |
| | | | | 165 | | | | | 170 | | | | | 175 | | |
| cct | cag | gag | cca | ctc | agt | gtg | acc | tgg | agc | gaa | agc | gga | cag | ggc | gtg | 576 |
| Pro | Gln | Glu | Pro | Leu | Ser | Val | Thr | Trp | Ser | Glu | Ser | Gly | Gln | Gly | Val | |
| | | | 180 | | | | | 185 | | | | | 190 | | | |
| acc | gcc | agg | aac | ttc | cca | ccc | agc | cag | gat | gcc | tcc | gga | gac | ctg | tac | 624 |
| Thr | Ala | Arg | Asn | Phe | Pro | Pro | Ser | Gln | Asp | Ala | Ser | Gly | Asp | Leu | Tyr | |
| | | | | 195 | | | | | 200 | | | | | 205 | | |
| acc | acg | tcc | agc | cag | ctg | acc | ctt | ccg | gcc | aca | cag | tgc | cta | gcg | ggc | 672 |
| Thr | Thr | Ser | Ser | Gln | Leu | Thr | Leu | Pro | Ala | Thr | Gln | Cys | Leu | Ala | Gly | |
| | | | 210 | | | | | 215 | | | | | 220 | | | |
| aag | tcc | gtg | aca | tgc | cac | gtg | aag | cac | tac | acg | aat | ccc | agc | cag | gat | 720 |
| Lys | Ser | Val | Thr | Cys | His | Val | Lys | His | Tyr | Thr | Asn | Pro | Ser | Gln | Asp | |
| 225 | | | | | 230 | | | | | 235 | | | | | 240 | |
| gtg | act | gtg | ccc | tgc | cca | gtt | ccc | tca | act | cca | cct | acc | cca | tct | ccc | 768 |
| Val | Thr | Val | Pro | Cys | Pro | Val | Pro | Ser | Thr | Pro | Pro | Thr | Pro | Ser | Pro | |

```
                 245                 250                 255
tcg act cca cct acc cca tct ccc tca tgc tgc cac ccc agg ctg tca        816
Ser Thr Pro Pro Thr Pro Ser Pro Ser Cys Cys His Pro Arg Leu Ser
        260                 265                 270 ctg cac agg cct gcc ctc gag gac ctg ctc tta ggt tcg gaa gcg aac        864
Leu His Arg Pro Ala Leu Glu Asp Leu Leu Leu Gly Ser Glu Ala Asn
            275                 280                 285 ctc acg tgc aca ctc acc ggc ctg aga gat gcg tca ggt gtc acc ttc        912
Leu Thr Cys Thr Leu Thr Gly Leu Arg Asp Ala Ser Gly Val Thr Phe
    290                 295                 300 acc tgg acg ccc tca agt ggt aag agc gct gtt caa ggc cca cct gag        960
Thr Trp Thr Pro Ser Ser Gly Lys Ser Ala Val Gln Gly Pro Pro Glu
305                 310                 315                 320 cgt gac ctc tgt ggc tgc tac agc gtg tcc agt gtc ctt ccg ggc tgt       1008
Arg Asp Leu Cys Gly Cys Tyr Ser Val Ser Ser Val Leu Pro Gly Cys
                325                 330                 335 gcc gag cct tgg aat cat ggg aag acc ttc act tgc act gct gcc tac       1056
Ala Glu Pro Trp Asn His Gly Lys Thr Phe Thr Cys Thr Ala Ala Tyr
            340                 345                 350 ccc gag agc aag acc ccg cta acc gcc acc ctc tcg aaa tcc ggc aac       1104
Pro Glu Ser Lys Thr Pro Leu Thr Ala Thr Leu Ser Lys Ser Gly Asn
    355                 360                 365 aca ttc cgg ccc gag gtc cac ctg ctg ccg ccg ccg tcg gag gag ctg       1152
Thr Phe Arg Pro Glu Val His Leu Leu Pro Pro Pro Ser Glu Glu Leu
370                 375                 380 gcc ctg aac gag ctg gtg acg ctg acg tgc ctg gcg cgc ggc ttc agc       1200
Ala Leu Asn Glu Leu Val Thr Leu Thr Cys Leu Ala Arg Gly Phe Ser
385                 390                 395                 400 ccc aag gac gtg ctg gtt cgc tgg ctg cag ggc tca cag gag ctg cct       1248
Pro Lys Asp Val Leu Val Arg Trp Leu Gln Gly Ser Gln Glu Leu Pro
                405                 410                 415 agg gag aag tac ctg act tgg gca tcc cgg cag gag ccc agc caa ggc       1296
Arg Glu Lys Tyr Leu Thr Trp Ala Ser Arg Gln Glu Pro Ser Gln Gly
            420                 425                 430 acc acc acc ttc gct gtg acc tcg ata ctg cgc gtg gca gcc gag gac       1344
Thr Thr Thr Phe Ala Val Thr Ser Ile Leu Arg Val Ala Ala Glu Asp
    435                 440                 445 tgg aag aag ggt gac acc ttc tcc tgc atg gtg ggc cac gag gcc ctt       1392
Trp Lys Lys Gly Asp Thr Phe Ser Cys Met Val Gly His Glu Ala Leu
450                 455                 460 ccg ctg gcc ttc aca cag aag acc atc gac cgc ttg gcg ggt aaa ccc       1440
Pro Leu Ala Phe Thr Gln Lys Thr Ile Asp Arg Leu Ala Gly Lys Pro
465                 470                 475                 480 acc cat gtc aat gtg tct gtt gtc atg gcg gag gtg gac ggc acc tgc       1488
Thr His Val Asn Val Ser Val Val Met Ala Glu Val Asp Gly Thr Cys
                485                 490                 495 tac tga                                                                1494
Tyr

<210> SEQ ID NO 2
<211> LENGTH: 497
<212> TYPE: PRT
<213> ORGANISM: Herpes simplex virus

<400> SEQUENCE: 2

Met Gly Trp Ser Trp Ile Phe Leu Phe Leu Leu Ser Gly Ala Ala Gly
1               5                   10                  15

Val His Cys Gln Val Gln Leu Val Gln Ser Gly Ala Glu Val Lys Lys
            20                  25                  30

Pro Gly Ser Ser Val Lys Val Ser Cys Lys Ala Ser Gly Gly Ser Phe
```

```
                 35                  40                  45
Ser Ser Tyr Ala Ile Asn Trp Val Arg Gln Ala Pro Gly Gln Gly Leu
            50                  55                  60

Glu Trp Met Gly Gly Leu Met Pro Ile Phe Gly Thr Thr Asn Tyr Ala
65                      70                  75                  80

Gln Lys Phe Gln Asp Arg Leu Thr Ile Thr Ala Asp Val Ser Thr Ser
                    85                  90                  95

Thr Ala Tyr Met Gln Leu Ser Gly Leu Thr Tyr Glu Asp Thr Ala Met
                100                 105                 110

Tyr Tyr Cys Ala Arg Val Ala Tyr Met Leu Glu Pro Thr Val Thr Ala
            115                 120                 125

Gly Gly Leu Asp Val Trp Gly Gln Gly Thr Leu Val Thr Val Ser Ser
130                 135                 140

Ala Ser Pro Thr Ser Pro Lys Val Phe Pro Leu Ser Leu Cys Ser Thr
145                 150                 155                 160

Gln Pro Asp Gly Asn Val Val Ile Ala Cys Leu Val Gln Gly Phe Phe
                165                 170                 175

Pro Gln Glu Pro Leu Ser Val Thr Trp Ser Glu Ser Gly Gln Gly Val
                180                 185                 190

Thr Ala Arg Asn Phe Pro Pro Ser Gln Asp Ala Ser Gly Asp Leu Tyr
            195                 200                 205

Thr Thr Ser Ser Gln Leu Thr Leu Pro Ala Thr Gln Cys Leu Ala Gly
            210                 215                 220

Lys Ser Val Thr Cys His Val Lys His Tyr Thr Asn Pro Ser Gln Asp
225                 230                 235                 240

Val Thr Val Pro Cys Pro Val Pro Ser Thr Pro Pro Thr Pro Ser Pro
                245                 250                 255

Ser Thr Pro Pro Thr Pro Ser Pro Ser Cys Cys His Pro Arg Leu Ser
                260                 265                 270

Leu His Arg Pro Ala Leu Glu Asp Leu Leu Leu Gly Ser Glu Ala Asn
            275                 280                 285

Leu Thr Cys Thr Leu Thr Gly Leu Arg Asp Ala Ser Gly Val Thr Phe
            290                 295                 300

Thr Trp Thr Pro Ser Ser Gly Lys Ser Ala Val Gln Gly Pro Pro Glu
305                 310                 315                 320

Arg Asp Leu Cys Gly Cys Tyr Ser Val Ser Ser Val Leu Pro Gly Cys
                325                 330                 335

Ala Glu Pro Trp Asn His Gly Lys Thr Phe Thr Cys Thr Ala Ala Tyr
                340                 345                 350

Pro Glu Ser Lys Thr Pro Leu Thr Ala Thr Leu Ser Lys Ser Gly Asn
            355                 360                 365

Thr Phe Arg Pro Glu Val His Leu Leu Pro Pro Pro Ser Glu Glu Leu
            370                 375                 380

Ala Leu Asn Glu Leu Val Thr Leu Thr Cys Leu Ala Arg Gly Phe Ser
385                 390                 395                 400

Pro Lys Asp Val Leu Val Arg Trp Leu Gln Gly Ser Gln Glu Leu Pro
                405                 410                 415

Arg Glu Lys Tyr Leu Thr Trp Ala Ser Arg Gln Glu Pro Ser Gln Gly
            420                 425                 430

Thr Thr Thr Phe Ala Val Thr Ser Ile Leu Arg Val Ala Ala Glu Asp
                435                 440                 445

Trp Lys Lys Gly Asp Thr Phe Ser Cys Met Val Gly His Glu Ala Leu
            450                 455                 460
```

```
Pro Leu Ala Phe Thr Gln Lys Thr Ile Asp Arg Leu Ala Gly Lys Pro
465                 470                 475                 480

Thr His Val Asn Val Ser Val Val Met Ala Glu Val Asp Gly Thr Cys
                485                 490                 495

Tyr

<210> SEQ ID NO 3
<211> LENGTH: 57
<212> TYPE: DNA
<213> ORGANISM: Artificial sequence
<220> FEATURE:
<223> OTHER INFORMATION: Heavy chain signal peptide
<220> FEATURE:
<221> NAME/KEY: CDS
<222> LOCATION: (1)..(57)

<400> SEQUENCE: 3 atg gga tgg agc tgg atc ttt ctc ttc ctc ctg tca gga gct gca ggt     48
Met Gly Trp Ser Trp Ile Phe Leu Phe Leu Leu Ser Gly Ala Ala Gly
1               5                   10                  15 gtc cat tgc                                                         57
Val His Cys <210> SEQ ID NO 4
<211> LENGTH: 19
<212> TYPE: PRT
<213> ORGANISM: Artificial sequence
<220> FEATURE:
<223> OTHER INFORMATION: Heavy chain signal peptide

<400> SEQUENCE: 4

Met Gly Trp Ser Trp Ile Phe Leu Phe Leu Leu Ser Gly Ala Ala Gly
1               5                   10                  15

Val His Cys

<210> SEQ ID NO 5
<211> LENGTH: 1368
<212> TYPE: DNA
<213> ORGANISM: Artificial sequence
<220> FEATURE:
<223> OTHER INFORMATION: Mature heavy chain sequence
<220> FEATURE:
<221> NAME/KEY: CDS
<222> LOCATION: (1)..(1368)

<400> SEQUENCE: 5 cag gtt cag ctc gtg cag tca ggt gct gag gtg aag aag cct ggc tcc     48
Gln Val Gln Leu Val Gln Ser Gly Ala Glu Val Lys Lys Pro Gly Ser
1               5                   10                  15 tcg gtg aag gtc tcc tgc aag gct tct gga ggt tcc ttc agc tcc tat     96
Ser Val Lys Val Ser Cys Lys Ala Ser Gly Gly Ser Phe Ser Ser Tyr
                20                  25                  30 gct atc aac tgg gtg agg caa gct cct gga caa ggg ctt gag tgg atg    144
Ala Ile Asn Trp Val Arg Gln Ala Pro Gly Gln Gly Leu Glu Trp Met
            35                  40                  45 gga ggg ctc atg cct atc ttt ggg aca aca aac tac gcg cag aag ttc    192
Gly Gly Leu Met Pro Ile Phe Gly Thr Thr Asn Tyr Ala Gln Lys Phe
        50                  55                  60 cag gac agg ctc acg att acc gcg gac gta tcc acg agt aca gcc tac    240
Gln Asp Arg Leu Thr Ile Thr Ala Asp Val Ser Thr Ser Thr Ala Tyr
65                  70                  75                  80 atg caa ctg agc ggc ctg aca tat gaa gac acg gcc atg tat tac tgt    288
Met Gln Leu Ser Gly Leu Thr Tyr Glu Asp Thr Ala Met Tyr Tyr Cys
                85                  90                  95
```

| | | |
|---|---|---|
| gcg aga gtt gcc tac atg ctt gaa cct acc gtc act gca ggt ggt ttg<br>Ala Arg Val Ala Tyr Met Leu Glu Pro Thr Val Thr Ala Gly Gly Leu<br>100                 105                 110 | | 336 |
| gac gtc tgg ggc caa ggg acc ttg gtc acc gtc tcc tca gca tcc ccg<br>Asp Val Trp Gly Gln Gly Thr Leu Val Thr Val Ser Ser Ala Ser Pro<br>      115                 120                 125 | | 384 |
| acc agc ccg aag gtc ttc ccg ctg agc ctc tgt agc acc cag cca gat<br>Thr Ser Pro Lys Val Phe Pro Leu Ser Leu Cys Ser Thr Gln Pro Asp<br>130                 135                 140 | | 432 |
| ggg aac gtg gtc atc gcc tgc ctg gtc cag ggc ttc ttc cct cag gag<br>Gly Asn Val Val Ile Ala Cys Leu Val Gln Gly Phe Phe Pro Gln Glu<br>145                 150                 155                 160 | | 480 |
| cca ctc agt gtg acc tgg agc gaa agc gga cag ggc gtg acc gcc agg<br>Pro Leu Ser Val Thr Trp Ser Glu Ser Gly Gln Gly Val Thr Ala Arg<br>                165                 170                 175 | | 528 |
| aac ttc cca ccc agc cag gat gcc tcc gga gac ctg tac acc acg tcc<br>Asn Phe Pro Pro Ser Gln Asp Ala Ser Gly Asp Leu Tyr Thr Thr Ser<br>                180                 185                 190 | | 576 |
| agc cag ctg acc ctt ccg gcc aca cag tgc cta gcg ggc aag tcc gtg<br>Ser Gln Leu Thr Leu Pro Ala Thr Gln Cys Leu Ala Gly Lys Ser Val<br>                195                 200                 205 | | 624 |
| aca tgc cac gtg aag cac tac acg aat ccc agc cag gat gtg act gtg<br>Thr Cys His Val Lys His Tyr Thr Asn Pro Ser Gln Asp Val Thr Val<br>210                 215                 220 | | 672 |
| ccc tgc cca gtt ccc tca act cca cct acc cca tct ccc tcg act cca<br>Pro Cys Pro Val Pro Ser Thr Pro Pro Thr Pro Ser Pro Ser Thr Pro<br>225                 230                 235                 240 | | 720 |
| cct acc cca tct ccc tca tgc tgc cac ccc agg ctg tca ctg cac agg<br>Pro Thr Pro Ser Pro Ser Cys Cys His Pro Arg Leu Ser Leu His Arg<br>                245                 250                 255 | | 768 |
| cct gcc ctc gag gac ctg ctc tta ggt tcg gaa gcg aac ctc acg tgc<br>Pro Ala Leu Glu Asp Leu Leu Leu Gly Ser Glu Ala Asn Leu Thr Cys<br>                260                 265                 270 | | 816 |
| aca ctc acc ggc ctg aga gat gcg tca ggt gtc acc ttc acc tgg acg<br>Thr Leu Thr Gly Leu Arg Asp Ala Ser Gly Val Thr Phe Thr Trp Thr<br>                275                 280                 285 | | 864 |
| ccc tca agt ggt aag agc gct gtt caa ggc cca cct gag cgt gac ctc<br>Pro Ser Ser Gly Lys Ser Ala Val Gln Gly Pro Pro Glu Arg Asp Leu<br>290                 295                 300 | | 912 |
| tgt ggc tgc tac agc gtg tcc agt gtc ctt ccg ggc tgt gcc gag cct<br>Cys Gly Cys Tyr Ser Val Ser Ser Val Leu Pro Gly Cys Ala Glu Pro<br>305                 310                 315                 320 | | 960 |
| tgg aat cat ggg aag acc ttc act tgc act gct gcc tac ccc gag agc<br>Trp Asn His Gly Lys Thr Phe Thr Cys Thr Ala Ala Tyr Pro Glu Ser<br>                325                 330                 335 | | 1008 |
| aag acc ccg cta acc gcc acc ctc tcg aaa tcc ggc aac aca ttc cgg<br>Lys Thr Pro Leu Thr Ala Thr Leu Ser Lys Ser Gly Asn Thr Phe Arg<br>                340                 345                 350 | | 1056 |
| ccc gag gtc cac ctg ctg ccg ccg ccg tcg gag gag ctg gcc ctg aac<br>Pro Glu Val His Leu Leu Pro Pro Pro Ser Glu Glu Leu Ala Leu Asn<br>                355                 360                 365 | | 1104 |
| gag ctg gtg acg ctg acg tgc ctg gcg cgc ggc ttc agc ccc aag gac<br>Glu Leu Val Thr Leu Thr Cys Leu Ala Arg Gly Phe Ser Pro Lys Asp<br>370                 375                 380 | | 1152 |
| gtg ctg gtt cgc tgg ctg cag ggc tca cag gag ctg cct agg gag aag<br>Val Leu Val Arg Trp Leu Gln Gly Ser Gln Glu Leu Pro Arg Glu Lys<br>385                 390                 395                 400 | | 1200 |
| tac ctg act tgg gca tcc cgg cag gag ccc agc caa ggc acc acc acc<br>Tyr Leu Thr Trp Ala Ser Arg Gln Glu Pro Ser Gln Gly Thr Thr Thr<br>                405                 410                 415 | | 1248 |

```
ttc gct gtg acc tcg ata ctg cgc gtg gca gcc gag gac tgg aag aag    1296
Phe Ala Val Thr Ser Ile Leu Arg Val Ala Ala Glu Asp Trp Lys Lys
        420                 425                 430 ggt gac acc ttc tcc tgc atg gtg ggc cac gag gcc ctt ccg ctg gcc    1344
Gly Asp Thr Phe Ser Cys Met Val Gly His Glu Ala Leu Pro Leu Ala
            435                 440                 445 ttc aca cag aag acc atc gac cgc                                    1368
Phe Thr Gln Lys Thr Ile Asp Arg
        450                 455

<210> SEQ ID NO 6
<211> LENGTH: 456
<212> TYPE: PRT
<213> ORGANISM: Artificial sequence
<220> FEATURE:
<223> OTHER INFORMATION: Mature heavy chain sequence

<400> SEQUENCE: 6
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ser Phe Ser Ser Tyr
            20                  25                  30

Ala Ile Asn Trp Val Arg Gln Ala Pro Gly Gln Gly Leu Glu Trp Met
        35                  40                  45

Gly Gly Leu Met Pro Ile Phe Gly Thr Thr Asn Tyr Ala Gln Lys Phe
    50                  55                  60

Gln Asp Arg Leu Thr Ile Thr Ala Asp Val Ser Thr Ser Thr Ala Tyr
65                  70                  75                  80

Met Gln Leu Ser Gly Leu Thr Tyr Glu Asp Thr Ala Met Tyr Tyr Cys
                85                  90                  95

Ala Arg Val Ala Tyr Met Leu Glu Pro Thr Val Thr Ala Gly Gly Leu
            100                 105                 110

Asp Val Trp Gly Gln Gly Thr Leu Val Thr Val Ser Ser Ala Ser Pro
        115                 120                 125

Thr Ser Pro Lys Val Phe Pro Leu Ser Leu Cys Ser Thr Gln Pro Asp
    130                 135                 140

Gly Asn Val Val Ile Ala Cys Leu Val Gln Gly Phe Phe Pro Gln Glu
145                 150                 155                 160

Pro Leu Ser Val Thr Trp Ser Glu Ser Gly Gln Gly Val Thr Ala Arg
                165                 170                 175

Asn Phe Pro Pro Ser Gln Asp Ala Ser Gly Asp Leu Tyr Thr Thr Ser
            180                 185                 190

Ser Gln Leu Thr Leu Pro Ala Thr Gln Cys Leu Ala Gly Lys Ser Val
        195                 200                 205

Thr Cys His Val Lys His Tyr Thr Asn Pro Ser Gln Asp Val Thr Val
    210                 215                 220

Pro Cys Pro Val Pro Ser Thr Pro Pro Thr Pro Ser Pro Ser Thr Pro
225                 230                 235                 240

Pro Thr Pro Ser Pro Ser Cys Cys His Pro Arg Leu Ser Leu His Arg
                245                 250                 255

Pro Ala Leu Glu Asp Leu Leu Leu Gly Ser Glu Ala Asn Leu Thr Cys
            260                 265                 270

Thr Leu Thr Gly Leu Arg Asp Ala Ser Gly Val Thr Phe Thr Trp Thr
        275                 280                 285

Pro Ser Ser Gly Lys Ser Ala Val Gln Gly Pro Pro Glu Arg Asp Leu
    290                 295                 300

Cys Gly Cys Tyr Ser Val Ser Ser Val Leu Pro Gly Cys Ala Glu Pro

```
                305                 310                 315                 320
Trp Asn His Gly Lys Thr Phe Thr Cys Thr Ala Ala Tyr Pro Glu Ser
                325                 330                 335

Lys Thr Pro Leu Thr Ala Thr Leu Ser Lys Ser Gly Asn Thr Phe Arg
            340                 345                 350

Pro Glu Val His Leu Leu Pro Pro Ser Glu Glu Leu Ala Leu Asn
        355                 360                 365

Glu Leu Val Thr Leu Thr Cys Leu Ala Arg Gly Phe Ser Pro Lys Asp
    370                 375                 380

Val Leu Val Arg Trp Leu Gln Gly Ser Gln Glu Leu Pro Arg Glu Lys
385                 390                 395                 400

Tyr Leu Thr Trp Ala Ser Arg Gln Glu Pro Ser Gln Gly Thr Thr Thr
                405                 410                 415

Phe Ala Val Thr Ser Ile Leu Arg Val Ala Ala Glu Asp Trp Lys Lys
            420                 425                 430

Gly Asp Thr Phe Ser Cys Met Val Gly His Glu Ala Leu Pro Leu Ala
        435                 440                 445

Phe Thr Gln Lys Thr Ile Asp Arg
    450                 455

<210> SEQ ID NO 7
<211> LENGTH: 69
<212> TYPE: DNA
<213> ORGANISM: Artificial sequence
<220> FEATURE:
<223> OTHER INFORMATION: heavy chain tailpiece
<220> FEATURE:
<221> NAME/KEY: CDS
<222> LOCATION: (1)..(69)

<400> SEQUENCE: 7 ttg gcg ggt aaa ccc acc cat gtc aat gtg tct gtt gtc atg gcg gag      48
Leu Ala Gly Lys Pro Thr His Val Asn Val Ser Val Val Met Ala Glu
1               5                   10                  15 gtg gac ggc acc tgc tac tga                                          69
Val Asp Gly Thr Cys Tyr
            20

<210> SEQ ID NO 8
<211> LENGTH: 22
<212> TYPE: PRT
<213> ORGANISM: Artificial sequence
<220> FEATURE:
<223> OTHER INFORMATION: heavy chain tailpiece

<400> SEQUENCE: 8

Leu Ala Gly Lys Pro Thr His Val Asn Val Ser Val Val Met Ala Glu
1               5                   10                  15

Val Asp Gly Thr Cys Tyr
            20

<210> SEQ ID NO 9
<211> LENGTH: 702
<212> TYPE: DNA
<213> ORGANISM: Herpes simplex virus
<220> FEATURE:
<221> NAME/KEY: CDS
<222> LOCATION: (1)..(702)
<220> FEATURE:
<221> NAME/KEY: misc_feature
<223> OTHER INFORMATION: HSV light chain sequence

<400> SEQUENCE: 9
```

```
atg gga tgg tcc tgg atc ttt ctc ttc ctt ctg tca gga gct gca ggt      48
Met Gly Trp Ser Trp Ile Phe Leu Phe Leu Leu Ser Gly Ala Ala Gly
1               5                   10                  15 gtc cac tgc gag atc gtg ctc acg cag tct cca ggc acc ctg tct ttg      96
Val His Cys Glu Ile Val Leu Thr Gln Ser Pro Gly Thr Leu Ser Leu
            20                  25                  30 tcg cca ggg gaa cgt gcc acc ctc tcc tgc cgg gcc agt cag tcc gtt     144
Ser Pro Gly Glu Arg Ala Thr Leu Ser Cys Arg Ala Ser Gln Ser Val
        35                  40                  45 tcc agc gcg tac ctt gcc tgg tac cag cag aag cct ggc caa gct ccc     192
Ser Ser Ala Tyr Leu Ala Trp Tyr Gln Gln Lys Pro Gly Gln Ala Pro
    50                  55                  60 agg ctc ctc atc tat ggt gcg tcc agc agg gct act ggc att cca gac     240
Arg Leu Leu Ile Tyr Gly Ala Ser Ser Arg Ala Thr Gly Ile Pro Asp
65                  70                  75                  80 cgc ttc tca ggc agt ggg tct ggg aca gac ttc acg ctc acc att agc     288
Arg Phe Ser Gly Ser Gly Ser Gly Thr Asp Phe Thr Leu Thr Ile Ser
                85                  90                  95 agg ctg gaa cct gag gat ttt gca gtg tac tac tgt cag cag tat ggt     336
Arg Leu Glu Pro Glu Asp Phe Ala Val Tyr Tyr Cys Gln Gln Tyr Gly
            100                 105                 110 cgc tca ccc acg ttc ggc cag ggg acc aag gtg gag atc aag cgc act     384
Arg Ser Pro Thr Phe Gly Gln Gly Thr Lys Val Glu Ile Lys Arg Thr
        115                 120                 125 gtg gct gca ccg tcg gtc ttc ata ttc ccg cca tcc gat gag cag ctg     432
Val Ala Ala Pro Ser Val Phe Ile Phe Pro Pro Ser Asp Glu Gln Leu
    130                 135                 140 aag tct ggc act gcc tct gtt gtg tgc ctg ctg aat aac ttc tat ccg     480
Lys Ser Gly Thr Ala Ser Val Val Cys Leu Leu Asn Asn Phe Tyr Pro
145                 150                 155                 160 aga gag gcg aag gta cag tgg aag gtg gat aac gcc ctc caa tcg ggt     528
Arg Glu Ala Lys Val Gln Trp Lys Val Asp Asn Ala Leu Gln Ser Gly
                165                 170                 175 aac tcc caa gag tcc gtt aca gag cag gac agc aag gac agc acc tac     576
Asn Ser Gln Glu Ser Val Thr Glu Gln Asp Ser Lys Asp Ser Thr Tyr
            180                 185                 190 agc ctc agc aac acc ttg acg ctg agc aaa gcg gac tac gag aaa cac     624
Ser Leu Ser Asn Thr Leu Thr Leu Ser Lys Ala Asp Tyr Glu Lys His
        195                 200                 205 aag gtc tac gcc tgc gaa gtc acc cat caa ggc ctg cgc tcg ccc gtc     672
Lys Val Tyr Ala Cys Glu Val Thr His Gln Gly Leu Arg Ser Pro Val
    210                 215                 220 aca aag agc ttc aac cgg gga gag tgt tga                             702
Thr Lys Ser Phe Asn Arg Gly Glu Cys
225                 230

<210> SEQ ID NO 10
<211> LENGTH: 233
<212> TYPE: PRT
<213> ORGANISM: Herpes simplex virus

<400> SEQUENCE: 10

Met Gly Trp Ser Trp Ile Phe Leu Phe Leu Leu Ser Gly Ala Ala Gly
1               5                   10                  15

Val His Cys Glu Ile Val Leu Thr Gln Ser Pro Gly Thr Leu Ser Leu
            20                  25                  30

Ser Pro Gly Glu Arg Ala Thr Leu Ser Cys Arg Ala Ser Gln Ser Val
        35                  40                  45

Ser Ser Ala Tyr Leu Ala Trp Tyr Gln Gln Lys Pro Gly Gln Ala Pro
    50                  55                  60
```

```
Arg Leu Leu Ile Tyr Gly Ala Ser Ser Arg Ala Thr Gly Ile Pro Asp
 65                  70                  75                  80

Arg Phe Ser Gly Ser Gly Ser Gly Thr Asp Phe Thr Leu Thr Ile Ser
                 85                  90                  95

Arg Leu Glu Pro Glu Asp Phe Ala Val Tyr Tyr Cys Gln Gln Tyr Gly
            100                 105                 110

Arg Ser Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Asn Thr Leu Thr Leu Ser Lys Ala Asp Tyr Glu Lys His
        195                 200                 205

Lys Val Tyr Ala Cys Glu Val Thr His Gln Gly Leu Arg Ser Pro Val
210                 215                 220

Thr Lys Ser Phe Asn Arg Gly Glu Cys
225                 230
```

<210> SEQ ID NO 11
<211> LENGTH: 57
<212> TYPE: DNA
<213> ORGANISM: Artificial sequence
<220> FEATURE:
<223> OTHER INFORMATION: Light chain signal peptide
<220> FEATURE:
<221> NAME/KEY: CDS
<222> LOCATION: (1)..(57)

<400> SEQUENCE: 11

```
atg gga tgg tcc tgg atc ttt ctc ttc ctt ctg tca gga gct gca ggt      48
Met Gly Trp Ser Trp Ile Phe Leu Phe Leu Leu Ser Gly Ala Ala Gly
1               5                   10                  15 gtc cac tgc                                                          57
Val His Cys
```

<210> SEQ ID NO 12
<211> LENGTH: 19
<212> TYPE: PRT
<213> ORGANISM: Artificial sequence
<220> FEATURE:
<223> OTHER INFORMATION: Light chain signal peptide

<400> SEQUENCE: 12

```
Met Gly Trp Ser Trp Ile Phe Leu Phe Leu Leu Ser Gly Ala Ala Gly
1               5                   10                  15

Val His Cys
```

<210> SEQ ID NO 13
<211> LENGTH: 642
<212> TYPE: DNA
<213> ORGANISM: Artificial sequence
<220> FEATURE:
<223> OTHER INFORMATION: Mature light chain sequence
<220> FEATURE:
<221> NAME/KEY: CDS
<222> LOCATION: (1)..(642)

<400> SEQUENCE: 13

| | | | | | | | | | | | | | | | | |
|---|---|---|---|---|---|---|---|---|---|---|---|---|---|---|---|---|
| gag | atc | gtg | ctc | acg | cag | tct | cca | ggc | acc | ctg | tct | ttg | tcg | cca | ggg | 48 |
| Glu | Ile | Val | Leu | Thr | Gln | Ser | Pro | Gly | Thr | Leu | Ser | Leu | Ser | Pro | Gly | |
| 1 | | | | 5 | | | | | 10 | | | | | 15 | | |
| gaa | cgt | gcc | acc | ctc | tcc | tgc | cgg | gcc | agt | cag | tcc | gtt | tcc | agc | gcg | 96 |
| Glu | Arg | Ala | Thr | Leu | Ser | Cys | Arg | Ala | Ser | Gln | Ser | Val | Ser | Ser | Ala | |
| | | | 20 | | | | | 25 | | | | | 30 | | | |
| tac | ctt | gcc | tgg | tac | cag | cag | aag | cct | ggc | caa | gct | ccc | agg | ctc | ctc | 144 |
| Tyr | Leu | Ala | Trp | Tyr | Gln | Gln | Lys | Pro | Gly | Gln | Ala | Pro | Arg | Leu | Leu | |
| | | 35 | | | | | 40 | | | | | 45 | | | | |
| atc | tat | ggt | gcg | tcc | agc | agg | gct | act | ggc | att | cca | gac | cgc | ttc | tca | 192 |
| Ile | Tyr | Gly | Ala | Ser | Ser | Arg | Ala | Thr | Gly | Ile | Pro | Asp | Arg | Phe | Ser | |
| | 50 | | | | | 55 | | | | | 60 | | | | | |
| ggc | agt | ggg | tct | ggg | aca | gac | ttc | acg | ctc | acc | att | agc | agg | ctg | gaa | 240 |
| Gly | Ser | Gly | Ser | Gly | Thr | Asp | Phe | Thr | Leu | Thr | Ile | Ser | Arg | Leu | Glu | |
| 65 | | | | | 70 | | | | | 75 | | | | | 80 | |
| cct | gag | gat | ttt | gca | gtg | tac | tac | tgt | cag | cag | tat | ggt | cgc | tca | ccc | 288 |
| Pro | Glu | Asp | Phe | Ala | Val | Tyr | Tyr | Cys | Gln | Gln | Tyr | Gly | Arg | Ser | Pro | |
| | | | | 85 | | | | | 90 | | | | | 95 | | |
| acg | ttc | ggc | cag | ggg | acc | aag | gtg | gag | atc | aag | cgc | act | gtg | gct | gca | 336 |
| Thr | Phe | Gly | Gln | Gly | Thr | Lys | Val | Glu | Ile | Lys | Arg | Thr | Val | Ala | Ala | |
| | | | 100 | | | | | 105 | | | | | 110 | | | |
| ccg | tcg | gtc | ttc | ata | ttc | ccg | cca | tcc | gat | gag | cag | ctg | aag | tct | ggc | 384 |
| Pro | Ser | Val | Phe | Ile | Phe | Pro | Pro | Ser | Asp | Glu | Gln | Leu | Lys | Ser | Gly | |
| | | 115 | | | | | 120 | | | | | 125 | | | | |
| act | gcc | tct | gtt | gtg | tgc | ctg | ctg | aat | aac | ttc | tat | ccg | aga | gag | gcg | 432 |
| Thr | Ala | Ser | Val | Val | Cys | Leu | Leu | Asn | Asn | Phe | Tyr | Pro | Arg | Glu | Ala | |
| | 130 | | | | | 135 | | | | | 140 | | | | | |
| aag | gta | cag | tgg | aag | gtg | gat | aac | gcc | ctc | caa | tcg | ggt | aac | tcc | caa | 480 |
| Lys | Val | Gln | Trp | Lys | Val | Asp | Asn | Ala | Leu | Gln | Ser | Gly | Asn | Ser | Gln | |
| 145 | | | | | 150 | | | | | 155 | | | | | 160 | |
| gag | tcc | gtt | aca | gag | cag | gac | agc | aag | gac | agc | acc | tac | agc | ctc | agc | 528 |
| Glu | Ser | Val | Thr | Glu | Gln | Asp | Ser | Lys | Asp | Ser | Thr | Tyr | Ser | Leu | Ser | |
| | | | | 165 | | | | | 170 | | | | | 175 | | |
| aac | acc | ttg | acg | ctg | agc | aaa | gcg | gac | tac | gag | aaa | cac | aag | gtc | tac | 576 |
| Asn | Thr | Leu | Thr | Leu | Ser | Lys | Ala | Asp | Tyr | Glu | Lys | His | Lys | Val | Tyr | |
| | | | 180 | | | | | 185 | | | | | 190 | | | |
| gcc | tgc | gaa | gtc | acc | cat | caa | ggc | ctg | cgc | tcg | ccc | gtc | aca | aag | agc | 624 |
| Ala | Cys | Glu | Val | Thr | His | Gln | Gly | Leu | Arg | Ser | Pro | Val | Thr | Lys | Ser | |
| | | 195 | | | | | 200 | | | | | 205 | | | | |
| ttc | aac | cgg | gga | gag | tgt | | | | | | | | | | | 642 |
| Phe | Asn | Arg | Gly | Glu | Cys | | | | | | | | | | | |
| | | 210 | | | | | | | | | | | | | | |

<210> SEQ ID NO 14
<211> LENGTH: 214
<212> TYPE: PRT
<213> ORGANISM: Artificial sequence
<220> FEATURE:
<223> OTHER INFORMATION: Mature light chain sequence

<400> SEQUENCE: 14

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ala
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu

```
                65                  70                  75                  80
Pro Glu Asp Phe Ala Val Tyr Tyr Cys Gln Gln Tyr Gly Arg Ser Pro
                    85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Asn Thr Leu Thr Leu Ser Lys Ala Asp Tyr Glu Lys His Lys Val Tyr
                180                 185                 190

Ala Cys Glu Val Thr His Gln Gly Leu Arg Ser Pro Val Thr Lys Ser
        195                 200                 205

Phe Asn Arg Gly Glu Cys
    210

<210> SEQ ID NO 15
<211> LENGTH: 9144
<212> TYPE: DNA
<213> ORGANISM: Artificial sequence
<220> FEATURE:
<223> OTHER INFORMATION: pDAB635 (ubiH) sequence

<400> SEQUENCE: 15
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt acaccggtgt gatcatgggc     420
cgcgattaaa atcccaatt atatttggtc taatttagtt tggtattgag taaaacaaat      480
tcgaaccaaa ccaaaatata aatatatagt ttttatatat atgcctttaa gactttttat     540
agaattttct ttaaaaaata tctagaaata tttgcgactc ttctggcatg taatatttcg     600
ttaaatatga agtgctccat ttttattaac tttaaataat tggttgtacg atcacttttct    660 tatcaagtgt tactaaaatg cgtcaatctc tttgttcttc catattcata tgtcaaaatc     720
tatcaaaatt cttatatatc tttttcgaat ttgaagtgaa atttcgataa tttaaaatta     780
aatagaacat atcattattt aggtatcata ttgattttta tacttaatta ctaaatttgg     840
ttaactttga agtgtacat caacgaaaaa ttagtcaaac gactaaaata aataaatatc      900
atgtgttatt aagaaaattc tcctataaga atattttaat agatcatatg tttgtaaaaa     960
aaattaattt ttactaacac atatatttac ttatcaaaaa tttgacaaag taagattaaa    1020
ataatattca tctaacaaaa aaaaaaccag aaaatgctga aaacccggca aaaccgaacc    1080
aatccaaacc gatatagttg gtttggttg attttgatat aaaccgaacc aactcggtcc     1140
atttgcaccc ctaatcataa tagctttaat atttcaagat attattaagt taacgttgtc    1200
aatatccctg gaaattttgca aaatgaatca agcctatatg gctgtaatat gaatttaaaa    1260
```

```
gcagctcgat gtggtggtaa tatgtaattt acttgattct aaaaaaatat cccaagtatt    1320
aataatttct gctaggaaga aggttagcta cgatttacag caaagccaga atacaaagaa    1380
ccataaagtg attgaagctc gaaatatacg aaggaacaaa tattttttaaa aaaatacgca   1440 atgacttgga acaaaagaaa gtgatatatt ttttgttctt aaacaagcat cccctctaaa    1500
gaatggcagt tttcctttgc atgtaactat tatgctccct tcgttacaaa aattttggac    1560
tactattggg aacttcttct gaaaatagtg gccaccgctt aattaacacc ggtggcccgg    1620
gcaagcggcc gcattcccgg gaagctaggc accgtggcc cgcctgcagg ggaagcttgc     1680
atgcctgcag atccccgggg atcctctaga gtcgacctgc agtgcagcgt gacccggtcg    1740
tgcccctctc tagagataat gagcattgca tgtctaagtt ataaaaaatt accacatatt    1800 tttttgtca cacttgtttg aagtgcagtt tatctatctt tatacatata tttaaacttt     1860
aatctacgaa taatataatc tatagtacta caataatatc agtgttttag agaatcatat    1920
aaatgaacag ttagacatgg tctaaaggac aattgagtat tttgacaaca ggactctaca    1980
gttttatctt tttagtgtgc atgtgttctc cttttttttt gcaaatagct tcacctatat    2040
aatacttcat ccattttatt agtacatcca tttagggttt agggttaatg gttttttatag   2100 actaattttt ttagtacatc tattttattc tattttagcc tctaaattaa gaaaactaaa    2160
actctatttt agttttttta tttaataatt tagatataaa atagaataaa ataaagtgac    2220
taaaaattaa acaaataccc tttaagaaat taaaaaaact aaggaaacat ttttcttgtt    2280
tcgagtagat aatgccagcc tgttaaacgc cgtcgacgag tctaacggac accaaccagc    2340
gaaccagcag cgtcgcgtcg ggccaagcga agcagacggc acggcatctc tgtcgctgcc    2400
tctggacccc tctcgagagt tccgctccac cgttggactt gctccgctgt cggcatccag    2460
aaattgcgtg gcggagcggc agacgtgagc cggcacggca ggcggcctcc tcctcctctc    2520
acggcacggc agctacgggg gattcctttc ccaccgctcc ttcgctttcc cttcctcgcc    2580
cgccgtaata aatagacacc ccctccacac cctctttccc caacctcgtg ttgttcggag    2640
cgcacacaca cacaaccaga tctcccccaa atccacccgt cggcacctcc gcttcaaggt    2700
acgccgctcg tcctcccccc ccccccctct ctaccttctc tagatcggcg ttccggtcca    2760
tgcatggtta gggcccggta gttctacttc tgttcatgtt tgtgttagat ccgtgtttgt    2820
gttagatccg tgctgctagc gttcgtacac ggatgcgacc tgtacgtcag acacgttctg    2880
attgctaact tgccagtgtt tctctttggg gaatcctggg atggctctag ccgttccgca    2940
gacgggatcg atttcatgat ttttttttgtt tcgttgcata gggtttggtt tgccctttttc  3000 ctttatttca atatatgccg tgcacttgtt tgtcgggtca tcttttcatg cttttttttg    3060
tcttggttgt gatgatgtgg tctggttggg cggtcgttct agatcggagt agaattctgt    3120
ttcaaactac ctggtggatt tattaatttt ggatctgtat gtgtgtgcca tacatattca    3180
tagttacgaa ttgaagatga tggatggaaa tatcgatcta ggataggtat acatgttgat    3240
gcgggtttta ctgatgcata tacagagatg cttttttgttc gcttggttgt gatgatgtgg   3300
tgtggttggg cggtcgttca ttcgttctag atcggagtag aatactgttt caaactacct    3360
ggtgtattta ttaattttgg aactgtatgt gtgtgtcata catcttcata gttacgagtt    3420
taagatggat ggaaatatcg atctaggata ggtatacatg ttgatgtggg ttttactgat    3480
gcatatacat gatggcatat gcagcatcta ttcatatgct ctaaccttga gtacctatct    3540
attataataa acaagtatgt tttataatta ttttgatctt gatatacttg gatgatggca    3600
tatgcagcag ctatatgtgg attttttttag ccctgccttc atacgctatt tatttgcttg   3660
```

```
gtactgtttc ttttgtcgat gctcaccctg ttgtttggtg ttacttctgc agggtacccc    3720
cggggtcgac catggccaac aagcacctga gcctctccct cttcctcgtg ctcctcggcc    3780
tctccgcctc cctcgccagc ggccaggttc agctcgtgca gtcagggct gaggtgaaga     3840 agcctgggtc ctcggtgaag gtctcctgca aggcttctgg aggttccttc agcagctatg    3900
ctatcaactg ggtgcgacag gcccctggac aagggcttga gtggatggga gggctcatgc    3960
ctatctttgg gacaacaaac tacgcacaga agttccagga cagactcacg attaccgcgg    4020
acgtatccac gagtacagcc tacatgcagc tgagcggcct gacatatgaa gacacggcca    4080
tgtattactg tgcgagagtt gcctatatgt tggaacctac cgtcactgca gggggtttgg    4140
acgtctgggg caaagggacc acggtcaccg tctccccagc atcccgacc agccccaagg     4200 tcttcccgct gagcctctgc agcacccagc cagatgggaa cgtggtcatc gcctgcctgg    4260
tccagggctt cttcccccag gagccactca gtgtgacctg agcgaaagc ggacagggcg     4320 tgaccgccag aaacttccca cccagccagg atgcctccgg ggacctgtac accacgagca    4380
gccagctgac cctgccggcc acacagtgcc tagccggcaa gtccgtgaca tgccacgtga    4440
agcactacac gaatcccagc caggatgtga ctgtgccctg cccagttccc tcaactccac    4500
ctaccccatc tccctcaact ccacctaccc catctccctc atgctgccac ccccgactgt    4560
cactgcaccg accggccctc gaggacctgc tcttaggttc agaagcgaac ctcacgtgca    4620
cactgaccgg cctgagagat gcctcaggtg tcaccttcac ctggacgccc tcaagtggga    4680
agagcgctgt tcaaggacca cctgagcgtg acctctgtgg ctgctacagc gtgtccagtg    4740
tcctgccggg ctgtgccgag ccttggaatc atgggaagac cttcacttgc actgctgcct    4800
accccgagtc caagacccg ctaaccgcca ccctctcaaa atccggaaac acattccggc     4860
ccgaggtcca cctgctgccg ccgccgtcgg aggagctggc cctgaacgag ctggtgacgc    4920
tgacgtgcct ggcacgtggc ttcagccca aggacgtgct ggttcgctgg ctgcaggggt     4980
cacaggagct gccccgcgag aagtacctga cttgggcatc ccggcaggag cccagccagg    5040
gcaccaccac cttcgctgtg accagcatac tgcgcgtggc agccgaggac tggaagaagg    5100
gggacacctt ctcctgcatg gtgggccacg aggccctgcc gctggccttc acacagaaga    5160
ccatcgaccg cttggcgggt aaacccaccc atgtcaatgt gtctgttgtc atggcggagg    5220
tggacggcac ctgctactga gttaaactga gggcactgaa gtcgcttgat gtgctgaatt    5280
gtttgtgatg ttggtggcgt attttgttta aataagtaag catggctgtg attttatcat    5340
atgatcgatc tttggggttt tatttaacac attgtaaaat gtgtatctat taataactca    5400
atgtataaga tgtgttcatt cttcggttgc catagatctg cttatttgac ctgtgatgtt    5460
ttgactccaa aaaccaaaat cacaactcaa taaactcatg aatatgtcc acctgtttct     5520 tgaagagttc atctaccatt ccagttggca tttatcagtg ttgcagcggc gctgtgcttt    5580
gtaacataac aattgttacg gcatatatcc aacggccggc ctaggccacg gtggccagat    5640
ccactagttc tagagcggcc gcttaattaa atttaaatgt ttaaactagg cctcctgcag    5700
ggtttaaact tgccgtggcc tattttcaga agaagttccc aatagtagtc caaaattttt    5760
gtaacgaagg gagcataata gttacatgca aaggaaaact gccattcttt agaggggatg    5820
cttgtttaag aacaaaaaat atatcacttt cttttgttcc aagtcattgc gtatttttt     5880 aaaaatattt gttccttcgt atatttcgag cttcaatcac tttatggttc tttgtattct    5940
ggctttgctg taaatcgtag ctaaccttct tcctagcaga aattattaat acttgggata    6000 ttttttttaga atcaagtaaa ttacatatta ccaccacatc gagctgcttt taaattcata    6060
```

```
ttacagccat ataggcttga ttcattttgc aaaatttcca ggatattgac aacgttaact    6120
taataatatc ttgaaatatt aaagctatta tgattagggg tgcaaatgga ccgagttggt    6180
tcggtttata tcaaaatcaa accaaaccaa ctatatcggt ttggattggt tcggttttgc    6240
cgggttttca gcattttctg gtttttttt tgttagatga atattattt aatcttactt    6300 tgtcaaattt ttgataagta aatatatgtg ttagtaaaaa ttaatttttt ttacaaacat    6360
atgatctatt aaaatattct tataggagaa ttttcttaat aacacatgat atttatttat    6420
tttagtcgtt tgactaattt ttcgttgatg tacactttca aagttaacca aatttagtaa    6480
ttaagtataa aaatcaatat gatacctaaa taatgatatg ttctatttaa ttttaaatta    6540
tcgaaatttc acttcaaatt cgaaaaagat atataagaat tttgatagat tttgacatat    6600
gaatatggaa gaacaaagag attgacgcat tttagtaaca cttgataaga aagtgatcgt    6660
acaaccaatt atttaaagtt aataaaaatg gagcacttca tatttaacga aatattacat    6720
gccagaagag tcgcaaatat ttctagatat tttttaaaga aaattctata aaaagtctta    6780
aaggcatata tataaaaact atatatttat attttggttt ggttcgaatt tgttttactc    6840
aataccaaac taaattagac caaatataat tgggattttt aatcgcggcc cactagtcac    6900
cggtgtgctt ggcgtaatca tggtcatagc tgtttcctgt gtgaaattgt tatccgctca    6960
caattccaca acatacga gccggaagca taaagtgtaa agcctggggt gcctaatgag    7020
tgagctaact cacattaatt gcgttgcgct cactgcccgc tttccagtcg gaaacctgt    7080 cgtgccagct gcattaatga atcggccaac gcgcggggag aggcggtttg cgtattgggc    7140
gctcttccgc ttcctcgctc actgactcgc tgcgctcggt cgttcggctg cggcgagcgg    7200
tatcagctca ctcaaaggcg gtaatacggt tatccacaga atcaggggat aacgcaggaa    7260
agaacatgtg agcaaaaggc cagcaaaagg ccaggaaccg taaaaaggcc gcgttgctgg    7320
cgtttttcca taggctccgc cccctgacg agcatcacaa aaatcgacgc tcaagtcaga    7380
ggtggcgaaa cccgacagga ctataaagat accaggcgtt tcccctgga agctccctcg    7440 tgcgctctcc tgttccgacc ctgccgctta ccggatacct gtccgccttt ctcccttcgg    7500
gaagcgtggc gctttctcat agctcacgct gtaggtatct cagttcggtg taggtcgttc    7560
gctccaagct gggctgtgtg cacgaacccc ccgttcagcc cgaccgctgc gccttatccg    7620
gtaactatcg tcttgagtcc aacccggtaa gacacgactt atcgccactg gcagcagcca    7680
ctggtaacag gattagcaga gcgaggtatg taggcggtgc tacagagttc ttgaagtggt    7740
ggcctaacta cggctacact agaaggacag tatttggtat ctgcgctctg ctgaagccag    7800
ttaccttcgg aaaagagtt ggtagctctt gatccggcaa acaaaccacc gctggtagcg    7860
gtggtttttt tgtttgcaag cagcagatta cgcgcagaaa aaaggatct caagaagatc    7920 ctttgatctt ttctacgggg tctgacgctc agtggaacga aaactcacgt taagggattt    7980
tggtcatgag attatcaaaa aggatcttca cctagatcct tttaaattaa aaatgaagtt    8040
ttaaatcaat ctaaagtata tatgagtaaa cttggtctga cagttaccaa tgcttaatca    8100
gtgaggcacc tatctcagcg atctgtctat ttcgttcatc catagttgcc tgactccccg    8160
tcgtgtagat aactacgata cgggagggct taccatctgg ccccagtgct gcaatgatac    8220
cgcgagaccc acgctcaccg gctccagatt tatcagcaat aaaccagcca gccggaaggg    8280
ccgagcgcag aagtggtcct gcaactttat ccgcctccat ccagtctatt aattgttgcc    8340
gggaagctag agtaagtagt tcgccagtta atagtttgcg caacgttgtt gccattgcta    8400
caggcatcgt ggtgtcacgc tcgtcgtttg gtatggcttc attcagctcc ggttcccaac    8460
```

```
gatcaaggcg agttacatga tcccccatgt tgtgcaaaaa agcggttagc tccttcggtc    8520
ctccgatcgt tgtcagaagt aagttggccg cagtgttatc actcatggtt atggcagcac    8580
tgcataattc tcttactgtc atgccatccg taagatgctt ttctgtgact ggtgagtact    8640
caaccaagtc attctgagaa tagtgtatgc ggcgaccgag ttgctcttgc ccggcgtcaa    8700
tacgggataa taccgcgcca catagcagaa ctttaaaagt gctcatcatt ggaaaacgtt    8760
cttcggggcg aaaactctca aggatcttac cgctgttgag atccagttcg atgtaaccca    8820
ctcgtgcacc caactgatct tcagcatctt ttactttcac cagcgtttct gggtgagcaa    8880
aaacaggaag gcaaaatgcc gcaaaaaagg gaataagggc gacacggaaa tgttgaatac    8940
tcatactctt cctttttcaa tattattgaa gcatttatca gggttattgt ctcatgagcg    9000
gatacatatt tgaatgtatt tagaaaaata aacaaatagg ggttccgcgc acatttcccc    9060
gaaaagtgcc acctgacgtc taagaaacca ttattatcat gacattaacc tataaaaata    9120
ggcgtatcac gaggccccttt cgtc                                            9144

<210> SEQ ID NO 16
<211> LENGTH: 8352
<212> TYPE: DNA
<213> ORGANISM: Artificial sequence
<220> FEATURE:
<223> OTHER INFORMATION: pDAB636 (ubiL) sequence

<400> SEQUENCE: 16
tcgcgcgttt cggtgatgac ggtgaaaacc tctgacacat gcagctcccg gagacggtca      60
cagcttgtct gtaagcggat gccggagcaga gcaagcccg tcagggcgcg tcagcgggtg    120
ttggcgggtg tcgggctgg cttaactatg cggcatcaga gcagattgta ctgagagtgc     180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt acaccggtgt gatcatgggc    420
cgcgattaaa atcccaatt atatttggtc taatttagtt tggtattgag taaaacaaat     480
tcgaaccaaa ccaaaatata aatatatagt ttttatatat atgcctttaa gacttttttat   540 agaattttct ttaaaaaata tctagaaata tttgcgactc ttctggcatg taatatttcg    600
ttaaatatga agtgctccat ttttattaac tttaaataat tggttgtacg atcactttct    660
tatcaagtgt tactaaaatg cgtcaatctc tttgttcttc catattcata tgtcaaaatc    720
tatcaaaatt cttatatatc tttttcgaat ttgaagtgaa atttcgataa tttaaaatta    780
aatagaacat atcattattt aggtatcata ttgattttta tacttaatta ctaaatttgg    840
ttaactttga agtgtacat caacgaaaaa ttagtcaaac gactaaaata aataaatatc      900
atgtgttatt aagaaaattc tcctataaga atatttaat agatcatatg tttgtaaaaa      960
aaattaattt ttactaacac atatattac ttatcaaaaa tttgacaaag taagattaaa    1020
ataatattca tctaacaaaa aaaaaaccag aaaatgctga aacccggca aaccgaacc      1080 aatccaaacc gatatagttg gtttggtttg atttgatat aaaccgaacc aactcggtcc    1140
atttgcaccc ctaatcataa tagctttaat atttcaagat attattaagt taacgttgtc    1200
aatatcctgg aaattttgca aaatgaatca agcctatatg gctgtaatat gaatttaaaa    1260
gcagctcgat gtggtggtaa tatgtaattt acttgattct aaaaaaatat cccaagtatt    1320
aataatttct gctaggaaga aggttagcta cgatttacag caaagccaga atacaaagaa    1380
```

```
ccataaagtg attgaagctc gaaatatacg aaggaacaaa tattttaaa aaaatacgca   1440 atgacttgga acaaaagaaa gtgatatatt ttttgttctt aaacaagcat cccctctaaa   1500
gaatggcagt tttcctttgc atgtaactat tatgctccct tcgttacaaa aattttggac   1560
tactattggg aacttcttct gaaaatagtg gccaccgctt aattaacacc ggtggcccgg   1620
gcaagcggcc gcattcccgg gaagctaggc accgtggcc cgcctgcagg ggaagcttgc    1680
atgcctgcag atccccgggg atcctctaga gtcgacctgc agtgcagcgt gacccggtcg   1740
tgcccctctc tagagataat gagcattgca tgtctaagtt ataaaaaatt accacatatt   1800 tttttgtca cacttgtttg aagtgcagtt tatctatctt tatacatata tttaaacttt    1860
aatctacgaa taatataatc tatagtacta caataatatc agtgttttag agaatcatat   1920
aaatgaacag ttagacatgg tctaaaggac aattgagtat tttgacaaca ggactctaca   1980
gttttatctt tttagtgtgc atgtgttctc ctttttttt gcaaatagct tcacctatat    2040
aatacttcat ccattttatt agtacatcca tttagggttt agggtaatg gtttttatag    2100 actaattttt ttagtacatc tattttattc tattttagcc tctaaattaa gaaaactaaa   2160
actctatttt agttttttta tttaataatt tagatataaa atagaataaa ataaagtgac   2220
taaaaattaa acaaataccc tttaagaaat taaaaaaact aaggaaacat ttttcttgtt   2280
tcgagtagat aatgccagcc tgttaaacgc cgtcgacgag tctaacggac accaaccagc   2340
gaaccagcag cgtcgcgtcg ggccaagcga agcagacggc acggcatctc tgtcgctgcc   2400
tctggacccc tctcgagagt tccgctccac cgttggactt gctccgctgt cggcatccag   2460
aaattgcgtg gcggagcggc agacgtgagc cggcacggca ggcggcctcc tcctcctctc   2520
acggcacggc agctacgggg gattcctttc ccaccgctcc ttcgctttcc cttcctcgcc   2580
cgccgtaata aatagacacc ccctccacac cctctttccc caacctcgtg ttgttcggag   2640
cgcacacaca cacaaccaga tctccccaa atccaccgt cggcacctcc gcttcaaggt     2700
acgccgctcg tcctcccccc ccccccctct ctaccttctc tagatcggcg ttccggtcca   2760
tgcatggtta gggcccggta gttctacttc tgttcatgtt tgtgttagat ccgtgtttgt   2820
gttagatccg tgctgctagc gttcgtacac ggatgcgacc tgtacgtcag acacgttctg   2880
attgctaact tgccagtgtt tctctttggg gaatcctggg atggctctag ccgttccgca   2940
gacgggatcg atttcatgat ttttttgtt tcgttgcata gggtttggtt tgcccttttc    3000
ctttatttca atatatgccg tgcacttgtt tgtcgggtca tcttttcatg cttttttttg   3060
tcttggttgt gatgatgtgg tctggttggg cggtcgttct agatcggagt agaattctgt   3120
ttcaaactac ctggtggatt tattaatttt ggatctgtat gtgtgtgcca tacatattca   3180
tagttacgaa ttgaagatga tggatggaaa tatcgatcta ggataggtat acatgttgat   3240
gcgggtttta ctgatgcata tacagagatg cttttttgttc gcttggttgt gatgatgtgg   3300
tgtggttggg cggtcgttca ttcgttctag atcggagtag aatactgttt caaactacct   3360
ggtgtattta ttaattttgg aactgtatgt gtgtgtcata catcttcata gttacgagtt   3420
taagatggat ggaaatatcg atctaggata ggtatacatg ttgatgtggg ttttactgat   3480
gcatatacat gatggcatat gcagcatcta ttcatatgct ctaaccttga gtacctatct   3540
attataataa acaagtatgt tttataatta ttttgatctt gatatacttg gatgatggca   3600
tatgcagcag ctatatgtgg atttttttag ccctgccttc atacgctatt tatttgcttg   3660
gtactgtttc ttttgtcgat gctcaccctg ttgtttggtg ttacttctgc agggtacccc   3720
cggggtcgac catggccaac aagcacctga gcctctccct cttcctcgtg ctcctcggcc   3780
```

```
tctccgcctc cctcgccagc ggcgaaattg tgctcacgca gtctccaggc accctgtctt    3840
tgtctccagg ggaaaaagcc accctctcct gcagggccag tcagagtgtt agtagcgcct    3900
acttagcctg gtaccagcag aaacctggcc aggctcccag gctcctcatc tatggtgcat    3960
ccagcagggc cactggcatc ccagacaggt tcagtggcag tgggtctggg acagacttca    4020
ctctcaccat cagcagactg gaacctgaag attttgcagt gtattactgt cagcagtatg    4080
gtaggtcacc cactttcggc ggagggacca aggtggagat caaacgaact gtggctgcac    4140
catctgtctt catcttcccg ccatctgatg agcagttgaa atctggaact gcctctgttg    4200
tgtgcctgct gaataacttc tatcccagag aggccaaagt acagtggaag gtggataacg    4260
ccctccaatc gggtaactcc caggagagtg tcacagagca ggacagcaag gacagcacct    4320
acagcctcag caacaccctg acgctgagca agcagactac cgagaaacac aaagtctacg    4380
cctgcgaagt cacccatcag ggcctgagat cgcccgtcac aaagagcttc aacaggggag    4440
agtgttgagt taaactgagg gcactgaagt cgcttgatgt gctgaattgt ttgtgatgtt    4500
ggtggcgtat tttgtttaaa taagtaagca tggctgtgat tttatcatat gatcgatctt    4560
tggggtttta tttaacacat tgtaaaatgt gtatctatta ataactcaat gtataagatg    4620
tgttcattct tcggttgcca tagatctgct tatttgacct gtgatgtttt gactccaaaa    4680
accaaaatca caactcaata aactcatgga atatgtccac ctgtttcttg aagagttcat    4740
ctaccattcc agttggcatt tatcagtgtt gcagcggcgc tgtgctttgt aacataacaa    4800
ttgttacggc atatatccaa cggccggcct aggccacggt ggccagatcc actagttcta    4860
gagcggccgc ttaattaaat ttaaatgttt aaactaggcc tcctgcaggg tttaaacttg    4920
ccgtggccta ttttcagaag aagttcccaa tagtagtcca aaattttgt aacgaaggga     4980
gcataatagt tacatgcaaa ggaaaactgc cattctttag aggggatgct tgtttaagaa    5040
caaaaaatat atcactttct tttgttccaa gtcattgcgt attttttaa aaatatttgt     5100
tccttcgtat atttcgagct tcaatcactt tatggttctt tgtattctgg ctttgctgta    5160
aatcgtagct aaccttcttc ctagcagaaa ttattaatac ttgggatatt tttttagaat    5220
caagtaaatt acatattacc accacatcga gctgctttta aattcatatt acagccatat    5280
aggcttgatt cattttgcaa aatttccagg atattgacaa cgttaactta ataatatctt    5340
gaaatattaa agctattatg attaggggtg caaatggacc gagttggttc ggtttatatc    5400
aaaatcaaac caaaccaact atatcggttt ggattggttc ggttttgccg ggttttcagc    5460
attttctggt ttttttttg ttagatgaat attatttaa tcttactttg tcaaattttt      5520
gataagtaaa tatatgtgtt agtaaaaatt aattttttt acaaacatat gatctattaa     5580
aatattctta taggagaatt ttcttaataa cacatgatat ttatttattt tagtcgtttg    5640
actaattttt cgttgatgta cacttttcaaa gttaaccaaa tttagtaatt aagtataaaa   5700
atcaatatga tacctaaata atgatatgtt ctatttaatt ttaaattatc gaaatttcac    5760
ttcaaattcg aaaagatat ataagaattt tgatagattt tgacatatga atatggaaga     5820
acaaagagat tgacgcattt tagtaacact tgataagaaa gtgatcgtac aaccaattat    5880
ttaaagttaa taaaatgga gcacttcata tttaacgaaa tattacatgc cagaagagtc     5940
gcaaatattt ctagatattt tttaaagaaa attctataaa aagtcttaaa ggcatatata    6000
taaaaactat atatttatat tttggtttgg ttcgaatttg ttttactcaa taccaaacta    6060
aattagacca aatataattg ggattttaa tcgcggccca ctagtcaccg gtgtgcttgg     6120
cgtaatcatg gtcatagctg tttcctgtgt gaaattgtta tccgctcaca attccacaca    6180
```

```
acatacgagc cggaagcata aagtgtaaag cctggggtgc ctaatgagtg agctaactca   6240
cattaattgc gttgcgctca ctgcccgctt tccagtcggg aaacctgtcg tgccagctgc   6300
attaatgaat cggccaacgc gcggggagag gcggtttgcg tattgggcgc tcttccgctt   6360
cctcgctcac tgactcgctg cgctcggtcg ttcggctgcg gcgagcggta tcagctcact   6420
caaaggcggt aatacggtta tccacagaat caggggataa cgcaggaaag aacatgtgag   6480
caaaaggcca gcaaaaggcc aggaaccgta aaaaggccgc gttgctggcg ttttTccata   6540
ggctccgccc ccctgacgag catcacaaaa atcgacgctc aagtcagagg tggcgaaacc   6600
cgacaggact ataaagatac caggcgtttc ccCCtggaag ctccctcgtg cgctctcctg   6660
ttccgaccct gccgcttacc ggatacctgt ccgcctttct cccttcggga agcgtggcgc   6720
tttctcatag ctcacgctgt aggtatctca gttcggtgta ggtcgttcgc tccaagctgg   6780
gctgtgtgca cgaaccCCCC gttcagcccg accgctgcgc cttatccggt aactatcgtc   6840
ttgagtccaa cccggtaaga cacgacttat cgccactggc agcagccact ggtaacagga   6900
ttagcagagc gaggtatgta ggcggtgcta cagagttctt gaagtggtgg cctaactacg   6960
gctacactag aaggacagta tttggtatct gcgctctgct gaagccagtt accttcggaa   7020
aaagagttgg tagctcttga tccggcaaac aaaccaccgc tggtagcggt ggtttttttg   7080
tttgcaagca gcagattacg cgcagaaaaa aaggatctca agaagatcct ttgatctttt   7140
ctacggggtc tgacgctcag tggaacgaaa actcacgtta agggattttg gtcatgagat   7200
tatcaaaaag gatcttcacc tagatccttt taaattaaaa atgaagtttt aaatcaatct   7260
aaagtatata tgagtaaact tggtctgaca gttaccaatg cttaatcagt gaggcaccta   7320
tctcagcgat ctgtctattt cgttcatcca tagttgcctg actccccgtc gtgtagataa   7380
ctacgatacg ggagggctta ccatctggcc ccagtgctgc aatgataccg cgagacccac   7440
gctcaccggc tccagattta tcagcaataa accagccagc cggaagggcc gagcgcagaa   7500
gtggtcctgc aactttatcc gcctccatcc agtctattaa ttgttgccgg gaagctagag   7560
taagtagttc gccagttaat agtttgcgca acgttgttgc cattgctaca ggcatcgtgg   7620
tgtcacgctc gtcgtttggt atggcttcat tcagctccgg ttcccaacga tcaaggcgag   7680
ttacatgatc ccccatgttg tgcaaaaaag cggttagctc cttcggtcct ccgatcgttg   7740
tcagaagtaa gttggccgca gtgttatcac tcatggttat ggcagcactg cataattctc   7800
ttactgtcat gccatccgta agatgctttt ctgtgactgg tgagtactca accaagtcat   7860
tctgagaata gtgtatgcgg cgaccgagtt gctcttgccc ggcgtcaata cgggataata   7920
ccgcgccaca tagcagaact ttaaaagtgc tcatcattgg aaaacgttct cggggcgaa    7980 aactctcaag gatcttaccg ctgttgagat ccagttcgat gtaacccact cgtgcaccca   8040
actgatcttc agcatctttt actttcacca gcgtttctgg gtgagcaaaa acaggaaggc   8100
aaaatgccgc aaaaaaggga ataagggcga cacggaaatg ttgaatactc atactcttcc   8160
tttttcaata ttattgaagc atttatcagg gttattgtct catgagcgga tacatatttg   8220
aatgtattta gaaaaataaa caaatagggg ttccgcgcac atttccccga aaagtgccac   8280
ctgacgtcta agaaaccatt attatcatga cattaaccta taaaaatagg cgtatcacga   8340
ggccctttcg tc                                                     8352
```

<210> SEQ ID NO 17
<211> LENGTH: 12380
<212> TYPE: DNA
<213> ORGANISM: Artificial sequence
<220> FEATURE:
<223> OTHER INFORMATION: pDAB637 (ubi H+L) sequence

<400> SEQUENCE: 17

```
tcgcgcgttt cggtgatgac ggtgaaaacc tctgacacat gcagctcccg gagacggtca        60
cagcttgtct gtaagcggat gccgggagca gacaagcccg tcagggcgcg tcagcgggtg       120
ttggcgggtg tcggggctgg cttaactatg cggcatcaga gcagattgta ctgagagtgc       180
accatatgcg gtgtgaaata ccgcacagat gcgtaaggag aaaataccgc atcaggcgcc       240
attcgccatt caggctgcgc aactgttggg aagggcgatc ggtgcgggcc tcttcgctat       300
tacgccagct ggcgaaaggg ggatgtgctg caaggcgatt aagttgggta acgccagggt       360
tttcccagtc acgacgttgt aaaacgacgg ccagtgaatt acaccggtgt gatcatgggc       420
cgcgattaaa aatcccaatt atatttggtc taatttagtt tggtattgag taaaacaaat       480
tcgaaccaaa ccaaaatata aatatatagt ttttatatat atgcctttaa gactttttat       540
agaattttct ttaaaaaata tctagaaata tttgcgactc ttctggcatg taatatttcg       600
ttaaatatga agtgctccat ttttattaac tttaataat tggttgtacg atcactttct        660
tatcaagtgt tactaaaatg cgtcaatctc tttgttcttc catattcata tgtcaaaatc       720
tatcaaaatt cttatatatc tttttcgaat ttgaagtgaa atttcgataa tttaaaatta       780
aatagaacat atcattattt aggtatcata ttgatttta tacttaatta ctaaatttgg        840
ttaactttga aagtgtacat caacgaaaaa ttagtcaaac gactaaaata aataaatatc       900
atgtgttatt aagaaaattc tcctataaga atattttaat agatcatatg tttgtaaaaa       960
aaattaattt ttactaacac atatatttac ttatcaaaaa tttgacaaag taagattaaa      1020
ataatattca tctaacaaaa aaaaaaccag aaaatgctga aacccggca aaaccgaacc        1080
aatccaaacc gatatagttg gtttggtttg attttgatat aaaccgaacc aactcggtcc      1140
atttgcaccc ctaatcataa tagctttaat atttcaagat attattaagt taacgttgtc      1200
aatatcctgg aaattttgca aaatgaatca agcctatatg gctgtaatat gaatttaaaa      1260
gcagctcgat gtggtggtaa tatgtaattt acttgattct aaaaaaatat cccaagtatt      1320
aataatttct gctaggaaga aggttagcta cgatttacag caaagccaga atacaaagaa      1380
ccataaagtg attgaagctc gaaatatacg aaggaacaaa tattttttaaa aaaatacgca      1440
atgacttgga acaaaagaaa gtgatatatt ttttgttctt aaacaagcat cccctctaaa      1500
gaatggcagt tttcctttgc atgtaactat tatgctcccc tcgttacaaa aatttttggac     1560
tactattggg aacttcttct gaaaatagtg gccaccgctt aattaacacc ggtggcccgg      1620
ccgcattccc gggaagctag gccaccgtgg cccgcctgca ggggaagctt gcatgcctgc      1680
agatccccgg ggatcctcta gagtcgacct gcagtgcagc gtgacccggt cgtgcccctc      1740
tctagagata atgagcattg catgtctaag ttataaaaaa ttaccacata ttttttttgt      1800
cacacttgtt tgaagtgcag tttatctatc tttatacata tatttaaact ttaatctacg      1860
aataatataa tctatagtac tacaataata tcagtgtttt agagaatcat ataaatgaac      1920
agttagacat ggtctaaagg acaattgagt attttgacaa caggactcta cagttttatc      1980
tttttagtgt gcatgtgttc tccttttttt ttgcaaatag cttcacctat ataatacttc      2040
atccatttta ttagtacatc catttagggt ttaggggtaa tggttttttat agactaattt     2100
ttttagtaca tctattttat tctatttttag cctctaaatt aagaaaacta aaactctatt     2160
ttagttttttt tatttaataa tttagatata aaatagaata aaataaagtg actaaaaatt     2220
aaacaaatac cctttaagaa attaaaaaaa ctaaggaaac attttttcttg tttcgagtag    2280
```

```
ataatgccag cctgttaaac gccgtcgacg agtctaacgg acaccaacca gcgaaccagc    2340
agcgtcgcgt cgggccaagc gaagcagacg gcacggcatc tctgtcgctg cctctggacc    2400
cctctcgaga gttccgctcc accgttggac ttgctccgct gtcggcatcc agaaattgcg    2460
tggcggagcg gcagacgtga gccggcacgg caggcggcct cctcctcctc tcacggcacg    2520
gcagctacgg gggattcctt tcccaccgct ccttcgcttt ccttcctcg cccgccgtaa     2580 taaatagaca cccctccac accctctttc cccaacctcg tgttgttcgg agcgcacaca    2640
cacacaacca gatctcccccc aaatccaccc gtcggcacct ccgcttcaag gtacgccgct   2700
cgtcctcccc cccccccct ctctaccttc tctagatcgg cgttccggtc catgcatggt    2760
tagggcccgg tagttctact tctgttcatg tttgtgttag atccgtgttt gtgttagatc    2820
cgtgctgcta gcgttcgtac acggatgcga cctgtacgtc agacacgttc tgattgctaa   2880
cttgccagtg tttctctttg gggaatcctg ggatggctct agccgttccg cagacgggat   2940
cgatttcatg atttttttg tttcgttgca tagggtttgg tttgcccttt tcctttattt    3000
caatatatgc cgtgcacttg tttgtcgggt catcttttca tgctttttttt tgtcttggtt  3060 gtgatgatgt ggtctggttg ggcggtcgtt ctagatcgga gtagaattct gtttcaaact   3120
acctggtgga tttattaatt ttggatctgt atgtgtgtgc catacatatt catagttacg   3180
aattgaagat gatggatgga aatatcgatc taggataggg atacatgttg atgcgggttt   3240
tactgatgca tatacagaga tgcttttttgt tcgcttggtt gtgatgatgt ggtgtggttg  3300
ggcggtcgtt cattcgttct agatcggagt agaatactgt ttcaaactac ctggtgtatt   3360
tattaatttt ggaactgtat gtgtgtgtca tacatcttca tagttacgag tttaagatgg   3420
atggaaatat cgatctagga taggtataca tgttgatgtg ggttttactg atgcatatac   3480
atgatggcat atgcagcatc tattcatatg ctctaacctt gagtacctat ctattataat   3540
aaacaagtat gttttataat tattttgatc ttgatatact tggatgatgg catatgcagc   3600
agctatatgt ggatttttttt agccctgcct tcatacgcta tttatttgct tggtactgtt   3660
tcttttgtcg atgctcaccc tgttgtttgg tgttacttct gcagggtacc cccggggtcg   3720
accatggcca acaagcacct gagcctctcc ctcttcctcg tgctcctcgg cctctccgcc    3780
tccctcgcca gcggccaggt tcagctcgtg cagtcagggg ctgaggtgaa gaagcctggg   3840
tcctcggtga aggtctcctg caaggcttct ggaggttcct tcagcagcta tgctatcaac   3900
tgggtgcgac aggcccctgg acaagggctt gagtggatgg gagggctcat gcctatcttt   3960
gggacaacaa actacgcaca gaagttccag gacagactca cgattaccgc ggacgtatcc   4020
acgagtacag cctacatgca gctgagcggc ctgacatatg aagacacggc catgtattac   4080
tgtgcgagag ttgcctatat gttggaacct accgtcactg caggggggttt ggacgtctgg   4140 ggcaaaggga ccacggtcac cgtctcccca gcatccccga ccagcccaa ggtcttcccg    4200 ctgagcctct gcagcaccca gccagatggg aacgtggtca tcgcctgcct ggtccagggc   4260
ttcttccccc aggagccact cagtgtgacc tggagcgaaa gcggacaggg cgtgaccgcc   4320
agaaacttcc cacccagcca ggatgcctcc ggggacctgt acaccacgag cagccagctg   4380
accctgccgg ccacacagtg cctagccggc aagtccgtga catgccacgt gaagcactac   4440
acgaatccca gccaggatgt gactgtgccc tgcccagttc cctcaactcc acctacccca   4500 tctcccctcaa ctccacctac cccatctccc tcatgctgcc accccgact gtcactgcac   4560 cgaccggccc tcgaggacct gctcttaggt tcagaagcga acctcacgtg cacactgacc   4620
ggcctgagag atgcctcagg tgtcaccttc acctggacgc cctcaagtgg gaagagcgct   4680
```

```
gttcaaggac cacctgagcg tgacctctgt ggctgctaca gcgtgtccag tgtcctgccg    4740
ggctgtgccg agccttggaa tcatgggaag accttcactt gcactgctgc ctaccccgag    4800
tccaagaccc cgctaaccgc caccctctca aaatccggaa acacattccg gcccgaggtc    4860
cacctgctgc cgccgccgtc ggaggagctg gccctgaacg agctggtgac gctgacgtgc    4920
ctggcacgtg gcttcagccc caaggacgtg ctggttcgct ggctgcaggg gtcacaggag    4980
ctgccccgcg agaagtacct gacttgggca tcccggcagg agcccagcca gggcaccacc    5040
accttcgctg tgaccagcat actgcgcgtg gcagccgagg actggaagaa ggggacacc     5100 ttctcctgca tggtgggcca cgaggccctg ccgctggcct tcacacagaa gaccatcgac    5160
cgcttggcgg gtaaacccac ccatgtcaat gtgtctgttg tcatggcgga ggtgacggc     5220 acctgctact gagttaaact gagggcactg aagtcgcttg atgtgctgaa ttgtttgtga    5280
tgttggtggc gtattttgtt taaataagta agcatggctg tgattttatc atatgatcga    5340
tctttggggt tttatttaac acattgtaaa atgtgtatct attaataact caatgtataa    5400
gatgtgttca ttcttcggtt gccatagatc tgcttatttg acctgtgatg ttttgactcc    5460
aaaaaccaaa atcacaactc aataaactca tggaatatgt ccacctgttt cttgaagagt    5520
tcatctacca ttccagttgg catttatcag tgttgcagcg gcgctgtgct ttgtaacata    5580
acaattgtta cggcatatat ccaacggccg gcctaggcca cggtggccag atccactagt    5640
tctagagcgg ccgcgggcaa attcccggga agctaggcca ccgtggcccg cctgcagggg    5700
aagcttgcat gcctgcagat ccccggggat cctctagagt cgacctgcag tgcagcgtga    5760
cccggtcgtg cccctctcta gagataatga gcattgcatg tctaagttat aaaaaattac    5820
cacatatttt ttttgtcaca cttgtttgaa gtgcagttta tctatctttta tacatatatt    5880 taaactttaa tctacgaata atataatcta tagtactaca ataatatcag tgttttagag    5940
aatcatataa atgaacagtt agacatggtc taaaggacaa ttgagtattt tgacaacagg    6000
actctacagt tttatctttt tagtgtgcat gtgttctcct ttttttttgc aaatagcttc    6060
acctatataa tacttcatcc attttattag tacatccatt tagggtttag ggttaatggt    6120
ttttatagac taatttttttt agtacatcta ttttattcta ttttagcctc taaattaaga    6180
aaactaaaac tctattttag tttttttatt taataattta gatataaaat agaataaaat    6240
aaagtgacta aaattaaac aaatacccct taagaaatta aaaaaactaa ggaaacattt     6300
ttcttgtttc gagtagataa tgccagcctg ttaaacgccg tcgacgagtc taacggacac    6360
caaccagcga accagcagcg tcgcgtcggg ccaagcgaag cagacggcac ggcatctctg    6420
tcgctgcctc tggaccccctc tcgagagttc cgctccaccg ttggacttgc tccgctgtcg    6480
gcatccagaa attgcgtggc ggagcggcag acgtgagccg gcacggcagg cggcctcctc    6540
ctcctctcac ggcacggcag ctacggggga ttccttttccc accgctcctt cgctttccct    6600
tcctcgcccg ccgtaataaa tagacacccc ctccacaccc tctttcccca acctcgtgtt    6660
gttcggagcg cacacacaca caaccagatc tcccccaaat ccaccccgtcg gcacctccgc    6720 ttcaaggtac gccgctcgtc ctccccccccc ccccctctct accttctcta gatcggcgtt    6780
ccggtccatg catggttagg gcccggtagt tctacttctg ttcatgtttg tgttagatcc    6840
gtgtttgtgt tagatccgtg ctgctagcgt tcgtacacgg atgcgacctg tacgtcagac    6900
acgttctgat tgctaacttg ccagtgtttc tctttgggga atcctgggat ggctctagcc    6960
gttccgcaga cgggatcgat ttcatgattt ttttgtttc gttgcatagg gtttggttttg    7020 ccctttttcct ttatttcaat atatgccgtg cacttgtttg tcgggtcatc ttttcatgct    7080
```

```
ttttttttgtc ttggttgtga tgatgtggtc tggttgggcg gtcgttctag atcggagtag   7140
aattctgttt caaactacct ggtggattta ttaattttgg atctgtatgt gtgtgccata   7200
catattcata gttacgaatt gaagatgatg gatggaaata tcgatctagg ataggtatac   7260
atgttgatgc gggttttact gatgcatata cagagatgct ttttgttcgc ttggttgtga   7320
tgatgtggtg tggttgggcg gtcgttcatt cgttctagat cggagtagaa tactgtttca   7380
aactacctgg tgtatttatt aattttggaa ctgtatgtgt gtgtcataca tcttcatagt   7440
tacgagttta agatggatgg aaatatcgat ctaggatagg tatacatgtt gatgtgggtt   7500
ttactgatgc atatacatga tggcatatgc agcatctatt catatgctct aaccttgagt   7560
acctatctat tataataaac aagtatgttt tataattatt ttgatcttga tatacttgga   7620
tgatggcata tgcagcagct atatgtggat ttttttagcc ctgccttcat acgctattta   7680
tttgcttggt actgtttctt ttgtcgatgc tcaccctgtt gtttggtgtt acttctgcag   7740
ggtaccccg gggtcgacca tggccaacaa gcacctgagc ctctccctct tcctcgtgct   7800
cctcggcctc tccgcctccc tcgccagcgg cgaaattgtg ctcacgcagt ctccaggcac   7860
cctgtctttg tctccagggg aaaaagccac cctctcctgc agggccagtc agagtgttag   7920
tagcgcctac ttagcctggt accagcagaa acctggccag gctcccaggc tcctcatcta   7980
tggtgcatcc agcagggcca ctggcatccc agacaggttc agtggcagtg ggtctgggac   8040
agacttcact ctcaccatca gcagactgga acctgaagat tttgcagtgt attactgtca   8100
gcagtatggt aggtcaccca ctttcggcgg agggaccaag gtggagatca aacgaactgt   8160
ggctgcacca tctgtcttca tcttcccgcc atctgatgag cagttgaaat ctggaactgc   8220
ctctgttgtg tgcctgctga ataacttcta tcccagagag gccaaagtac agtggaaggt   8280
ggataacgcc ctccaatcgg gtaactccca ggagagtgtc acagagcagg acagcaagga   8340
cagcacctac agcctcagca caccctgac gctgagcaaa gcagactacg agaaacacaa   8400
agtctacgcc tgcgaagtca cccatcaggg cctgagatcg cccgtcacaa agagcttcaa   8460
caggggagag tgttgagtta aactgagggc actgaagtcg cttgatgtgc tgaattgttt   8520
gtgatgttgg tggcgtattt tgtttaaata agtaagcatg gctgtgattt tatcatatga   8580
tcgatctttg gggttttatt taacacattg taaaatgtgt atctattaat aactcaatgt   8640
ataagatgtg ttcattcttc ggttgccata gatctgctta tttgacctgt gatgttttga   8700
ctccaaaaac caaaatcaca actcaataaa ctcatggaat atgtccacct gtttcttgaa   8760
gagttcatct accattccag ttggcattta tcagtgttgc agcggcgctg tgctttgtaa   8820
cataacaatt gttacggcat atatccaacg gccggcctag gccacggtgg ccagatccac   8880
tagttctaga gcggccgctt aattaaattt aaatgtttaa actaggcctc ctgcagggtt   8940
taaacttgcc gtggcctatt tcagaagaaa gttcccaata gtagtccaaa attttttgtaa   9000
cgaagggagc ataatagtta catgcaaagg aaaactgcca ttctttagag gggatgcttg   9060
tttaagaaca aaaatatat cactttcttt tgttccaagt cattgcgtat tttttaaaa   9120
atatttgttc cttcgtatat ttcgagcttc aatcacttta tggttctttg tattctggct   9180
ttgctgtaaa tcgtagctaa ccttcttcct agcagaaatt attaatactt gggatatttt   9240
tttagaatca agtaaattac atattaccac cacatcgagc tgcttttaaa ttcatattac   9300
agccatatag gcttgattca ttttgcaaaa tttccaggat attgacaacg ttaacttaat   9360
aatatcttga aatattaaag ctattatgat taggggtgca aatggaccga gttggttcgg   9420
tttatatcaa aatcaaacca aaccaactat atcggtttgg attggttcgg ttttgccggg   9480
```

```
ttttcagcat ttctggtttt ttttttttgtt agatgaatat tattttaatc ttactttgtc   9540 aaattttga taagtaaata tatgtgttag taaaaattaa ttttttttac aaacatatga     9600
tctattaaaa tattcttata ggagaattt cttaataaca catgatattt atttatttta     9660
gtcgtttgac taattttcg ttgatgtaca ctttcaaagt taaccaaatt tagtaattaa     9720
gtataaaaat caatatgata cctaaataat gatatgttct atttaatttt aaattatcga    9780
aatttcactt caaattcgaa aaagatatat aagaattttg atagattttg acatatgaat   9840
atggaagaac aaagagattg acgcatttta gtaacacttg ataagaaagt gatcgtacaa   9900
ccaattattt aaagttaata aaaatggagc acttcatatt taacgaaata ttacatgcca   9960
gaagagtcgc aaatatttct agatattttt taaagaaaat tctataaaaa gtcttaaagg  10020
catatatata aaaactatat atttatattt tggtttggtt cgaatttgtt ttactcaata  10080
ccaaactaaa ttagaccaaa tataattggg attttaatc gcggcccact agtcaccggt   10140
gtgcttggcg taatcatggt catagctgtt tcctgtgtga aattgttatc cgctcacaat  10200
tccacacaac atacgagccg gaagcataaa gtgtaaagcc tggggtgcct aatgagtgag  10260
ctaactcaca ttaattgcgt tgcgctcact gcccgctttc cagtcgggaa acctgtcgtg  10320
ccagctgcat taatgaatcg gccaacgcgc ggggagaggc ggtttgcgta ttgggcgctc  10380
ttccgcttcc tcgctcactg actcgctgcg ctcggtcgtt cggctgcggc gagcggtatc  10440
agctcactca aaggcggtaa tacggttatc cacagaatca ggggataacg caggaaagaa  10500
catgtgagca aaaggccagc aaaaggccag gaaccgtaaa aaggccgcgt tgctggcgtt  10560
tttccatagg ctccgccccc ctgacgagca tcacaaaaat cgacgctcaa gtcagaggtg  10620
gcgaaacccg acaggactat aaagatacca ggcgtttccc cctggaagct ccctcgtgcg  10680
ctctcctgtt ccgaccctgc cgcttaccgg atacctgtcc gcctttctcc cttcgggaag  10740
cgtggcgctt tctcatagct cacgctgtag gtatctcagt tcggtgtagg tcgttcgctc  10800
caagctgggc tgtgtgcacg aaccccccgt tcagcccgac cgctgcgcct tatccggtaa  10860
ctatcgtctt gagtccaacc cggtaagaca cgacttatcg ccactggcag cagccactgg  10920
taacaggatt agcagagcga ggtatgtagg cggtgctaca gagttcttga agtggtggcc  10980
taactacggc tacactagaa ggacagtatt tggtatctgc gctctgctga agccagttac  11040
cttcggaaaa agagttggta gctcttgatc cggcaaacaa accaccgctg gtagcggtgg  11100
tttttttgtt tgcaagcagc agattacgcg cagaaaaaaa ggatctcaag aagatccttt  11160
gatcttttct acggggtctg acgctcagtg gaacgaaaac tcacgttaag ggattttggt  11220
catgagatta tcaaaaagga tcttcaccta gatccttta aattaaaaat gaagttttaa   11280
atcaatctaa agtatatatg agtaaacttg gtctgacagt taccaatgct taatcagtga  11340
ggcacctatc tcagcgatct gtctatttcg ttcatccata gttgcctgac tccccgtcgt  11400
gtagataact acgatacggg agggcttacc atctggcccc agtgctgcaa tgataccgcg  11460
agacccacgc tcaccggctc cagatttatc agcaataaac cagccagccg aagggccga  11520 gcgcagaagt ggtcctgcaa ctttatccgc ctccatccag tctattaatt gttgccggga  11580
agctagagta agtagttcgc cagttaatag tttgcgcaac gttgttgcca ttgctacagg  11640
catcgtggtg tcacgctcgt cgtttggtat ggcttcattc agctccggtt cccaacgatc  11700
aaggcgagtt acatgatccc ccatgttgtg caaaaaagcg gttagctcct tcggtcctcc  11760
gatcgttgtc agaagtaagt tggccgcagt gttatcactc atggttatgg cagcactgca  11820
taattctctt actgtcatgc catccgtaag atgcttttct gtgactggtg agtactcaac  11880
```

```
caagtcattc tgagaatagt gtatgcggcg accgagttgc tcttgcccgg cgtcaatacg    11940
ggataatacc gcgccacata gcagaacttt aaaagtgctc atcattggaa aacgttcttc    12000
ggggcgaaaa ctctcaagga tcttaccgct gttgagatcc agttcgatgt aacccactcg    12060
tgcacccaac tgatcttcag catcttttac tttcaccagc gtttctgggt gagcaaaaac    12120
aggaaggcaa aatgccgcaa aaagggaat aagggcgaca cggaaatgtt gaatactcat     12180
actcttcctt tttcaatatt attgaagcat ttatcagggt tattgtctca tgagcggata    12240
catatttgaa tgtatttaga aaataaaca aataggggtt ccgcgcacat ttccccgaaa     12300
agtgccacct gacgtctaag aaaccattat tatcatgaca ttaacctata aaaataggcg    12360
tatcacgagg ccctttcgtc                                                 12380
```

```
<210> SEQ ID NO 18
<211> LENGTH: 16
<212> TYPE: PRT
<213> ORGANISM: Artificial sequence
<220> FEATURE:
<223> OTHER INFORMATION: CDR3 region of heavy chain FabHSV 8-CDR3

<400> SEQUENCE: 18

Val Ala Tyr Met Leu Glu Pro Thr Val Thr Ala Gly Gly Leu Asp Val
 1               5                  10                  15

<210> SEQ ID NO 19
<211> LENGTH: 122
<212> TYPE: PRT
<213> ORGANISM: Artificial sequence
<220> FEATURE:
<223> OTHER INFORMATION: Heavy chain V region FabSHV 8

<400> SEQUENCE: 19

Leu Glu Gln Ser Gly Ala Glu Val Lys Lys Pro Gly Ser Ser Val Lys
 1               5                  10                  15

Val Ser Cys Lys Ala Ser Gly Gly Ser Phe Ser Ser Tyr Ala Ile Asn
                20                  25                  30

Trp Val Arg Gln Ala Pro Gly Gln Gly Leu Glu Trp Met Gly Gly Leu
            35                  40                  45

Met Pro Ile Phe Gly Thr Thr Asn Tyr Ala Gln Lys Phe Gln Asp Arg
        50                  55                  60

Leu Thr Ile Thr Ala Asp Val Ser Thr Ser Thr Ala Tyr Met Gln Leu
65                  70                  75                  80

Ser Gly Leu Thr Tyr Glu Asp Thr Ala Met Tyr Tyr Cys Ala Arg Val
                85                  90                  95

Ala Tyr Met Leu Glu Pro Thr Val Thr Ala Gly Gly Leu Asp Val Trp
                100                 105                 110

Gly Gln Gly Thr Thr Val Thr Val Ala Ser
            115                 120

<210> SEQ ID NO 20
<211> LENGTH: 18
<212> TYPE: PRT
<213> ORGANISM: Artificial sequence
<220> FEATURE:
<223> OTHER INFORMATION: tryptic+ Asp-N peptide of N269

<400> SEQUENCE: 20

Asp Leu Leu Leu Gly Ser Glu Ala Asn Leu Thr Cys Thr Leu Thr Gly
 1               5                  10                  15

Leu Arg
```

```
<210> SEQ ID NO 21
<211> LENGTH: 18
<212> TYPE: PRT
<213> ORGANISM: Artificial sequence
<220> FEATURE:
<223> OTHER INFORMATION: peptide tryptic fragment L-T1

<400> SEQUENCE: 21

Glu Ile Val Leu Thr Gln Ser Pro Gly Thr Leu Ser Leu Ser Pro Gly
1               5                   10                  15

Glu Arg

<210> SEQ ID NO 22
<211> LENGTH: 6
<212> TYPE: PRT
<213> ORGANISM: Artificial sequence
<220> FEATURE:
<223> OTHER INFORMATION: peptide tryptic fragment L-T2

<400> SEQUENCE: 22

Ala Thr Leu Ser Cys Arg
1               5

<210> SEQ ID NO 23
<211> LENGTH: 22
<212> TYPE: PRT
<213> ORGANISM: Artificial sequence
<220> FEATURE:
<223> OTHER INFORMATION: peptide tryptic fragment L-T3

<400> SEQUENCE: 23

Ala Ser Gln Ser Val Ser Ser Ala Tyr Leu Ala Trp Tyr Gln Gln Lys
1               5                   10                  15

Pro Gly Gln Ala Pro Arg
            20

<210> SEQ ID NO 24
<211> LENGTH: 9
<212> TYPE: PRT
<213> ORGANISM: Artificial sequence
<220> FEATURE:
<223> OTHER INFORMATION: peptide tryptic fragment L-T4

<400> SEQUENCE: 24

Leu Leu Ile Tyr Gly Ala Ser Ser Arg
1               5

<210> SEQ ID NO 25
<211> LENGTH: 7
<212> TYPE: PRT
<213> ORGANISM: Artificial sequence
<220> FEATURE:
<223> OTHER INFORMATION: peptide tryptic fragment L-T5

<400> SEQUENCE: 25

Ala Thr Gly Ile Pro Asp Arg
1               5

<210> SEQ ID NO 26
<211> LENGTH: 16
<212> TYPE: PRT
<213> ORGANISM: Artificial sequence
<220> FEATURE:
<223> OTHER INFORMATION: peptide tryptic fragment L-T6

<400> SEQUENCE: 26
```

```
Phe Ser Gly Ser Gly Ser Gly Thr Asp Phe Thr Leu Thr Ile Ser Arg
1               5                   10                  15

<210> SEQ ID NO 27
<211> LENGTH: 16
<212> TYPE: PRT
<213> ORGANISM: Artificial sequence
<220> FEATURE:
<223> OTHER INFORMATION: peptide tryptic fragment L-T7

<400> SEQUENCE: 27

Leu Glu Pro Glu Asp Phe Ala Val Tyr Tyr Cys Gln Gln Tyr Gly Arg
1               5                   10                  15

<210> SEQ ID NO 28
<211> LENGTH: 9
<212> TYPE: PRT
<213> ORGANISM: Artificial sequence
<220> FEATURE:
<223> OTHER INFORMATION: peptide tryptic fragment L-T8

<400> SEQUENCE: 28

Ser Pro Thr Phe Gly Gln Gly Thr Lys
1               5

<210> SEQ ID NO 29
<211> LENGTH: 18
<212> TYPE: PRT
<213> ORGANISM: Artificial sequence
<220> FEATURE:
<223> OTHER INFORMATION: peptide tryptic fragment L-T11

<400> SEQUENCE: 29

Thr Val Ala Ala Pro Ser Val Phe Ile Phe Pro Pro Ser Asp Glu Gln
1               5                   10                  15

Leu Lys

<210> SEQ ID NO 30
<211> LENGTH: 16
<212> TYPE: PRT
<213> ORGANISM: Artificial sequence
<220> FEATURE:
<223> OTHER INFORMATION: peptide tryptic fragment L-T12

<400> SEQUENCE: 30

Ser Gly Thr Ala Ser Val Val Cys Leu Leu Asn Asn Phe Tyr Pro Arg
1               5                   10                  15

<210> SEQ ID NO 31
<211> LENGTH: 4
<212> TYPE: PRT
<213> ORGANISM: Artificial sequence
<220> FEATURE:
<223> OTHER INFORMATION: peptide tryptic fragment L-T14

<400> SEQUENCE: 31

Val Gln Trp Lys
1

<210> SEQ ID NO 32
<211> LENGTH: 20
<212> TYPE: PRT
<213> ORGANISM: Artificial sequence
<220> FEATURE:
<223> OTHER INFORMATION: peptide tryptic fragment L-T15

<400> SEQUENCE: 32
```

Val Asp Asn Ala Leu Gln Ser Gly Asn Ser Gln Glu Ser Val Thr Glu
1               5                   10                  15

Gln Asp Ser Lys
            20

<210> SEQ ID NO 33
<211> LENGTH: 14
<212> TYPE: PRT
<213> ORGANISM: Artificial sequence
<220> FEATURE:
<223> OTHER INFORMATION: peptide tryptic fragment L-T16

<400> SEQUENCE: 33

Asp Ser Thr Tyr Ser Leu Ser Asn Thr Leu Thr Leu Ser Lys
1               5                   10

<210> SEQ ID NO 34
<211> LENGTH: 5
<212> TYPE: PRT
<213> ORGANISM: Artificial sequence
<220> FEATURE:
<223> OTHER INFORMATION: peptide tryptic fragment L-T17

<400> SEQUENCE: 34

Ala Asp Tyr Glu Lys
1               5

<210> SEQ ID NO 35
<211> LENGTH: 12
<212> TYPE: PRT
<213> ORGANISM: Artificial sequence
<220> FEATURE:
<223> OTHER INFORMATION: peptide tryptic fragment L-T19

<400> SEQUENCE: 35

Val Tyr Ala Cys Glu Val Thr His Gln Gly Leu Arg
1               5                   10

<210> SEQ ID NO 36
<211> LENGTH: 5
<212> TYPE: PRT
<213> ORGANISM: Artificial sequence
<220> FEATURE:
<223> OTHER INFORMATION: peptide tryptic fragment L-T20

<400> SEQUENCE: 36

Ser Pro Val Thr Lys
1               5

<210> SEQ ID NO 37
<211> LENGTH: 4
<212> TYPE: PRT
<213> ORGANISM: Artificial sequence
<220> FEATURE:
<223> OTHER INFORMATION: peptide tryptic fragment L-T21

<400> SEQUENCE: 37

Ser Phe Asn Arg
1

<210> SEQ ID NO 38
<211> LENGTH: 23
<212> TYPE: PRT
<213> ORGANISM: Artificial sequence
<220> FEATURE:
<223> OTHER INFORMATION: peptide tryptic fragment L-T5-6

```
<400> SEQUENCE: 38

Ala Thr Gly Ile Pro Asp Arg Phe Ser Gly Ser Gly Ser Gly Thr Asp
1               5                   10                  15

Phe Thr Leu Thr Ile Ser Arg
            20

<210> SEQ ID NO 39
<211> LENGTH: 32
<212> TYPE: PRT
<213> ORGANISM: Artificial sequence
<220> FEATURE:
<223> OTHER INFORMATION: peptide tryptic fragment L-T6-7

<400> SEQUENCE: 39

Phe Ser Gly Ser Gly Ser Gly Thr Asp Phe Thr Leu Thr Ile Ser Arg
1               5                   10                  15

Leu Glu Pro Glu Asp Phe Ala Val Tyr Tyr Cys Gln Gln Tyr Gly Arg
                20                  25                  30

<210> SEQ ID NO 40
<211> LENGTH: 13
<212> TYPE: PRT
<213> ORGANISM: Artificial sequence
<220> FEATURE:
<223> OTHER INFORMATION: peptide tryptic fragment L-T8-9

<400> SEQUENCE: 40

Ser Pro Thr Phe Gly Gln Gly Thr Lys Val Glu Ile Lys
1               5                   10

<210> SEQ ID NO 41
<211> LENGTH: 19
<212> TYPE: PRT
<213> ORGANISM: Artificial sequence
<220> FEATURE:
<223> OTHER INFORMATION: peptide tryptic fragment L-T10-11

<400> SEQUENCE: 41

Arg Thr Val Ala Ala Pro Ser Val Phe Ile Phe Pro Pro Ser Asp Glu
1               5                   10                  15

Gln Leu Lys

<210> SEQ ID NO 42
<211> LENGTH: 19
<212> TYPE: PRT
<213> ORGANISM: Artificial sequence
<220> FEATURE:
<223> OTHER INFORMATION: peptide tryptic fragment L-T12-13

<400> SEQUENCE: 42

Ser Gly Thr Ala Ser Val Val Cys Leu Leu Asn Asn Phe Tyr Pro Arg
1               5                   10                  15

Glu Ala Lys

<210> SEQ ID NO 43
<211> LENGTH: 7
<212> TYPE: PRT
<213> ORGANISM: Artificial sequence
<220> FEATURE:
<223> OTHER INFORMATION: peptide tryptic fragment L-T13-14

<400> SEQUENCE: 43

Glu Ala Lys Val Gln Trp Lys
1               5
```

```
<210> SEQ ID NO 44
<211> LENGTH: 24
<212> TYPE: PRT
<213> ORGANISM: Artificial sequence
<220> FEATURE:
<223> OTHER INFORMATION: peptide tryptic fragment L-T14-15

<400> SEQUENCE: 44

Val Gln Trp Lys Val Asp Asn Ala Leu Gln Ser Gly Asn Ser Gln Glu
1               5                   10                  15

Ser Val Thr Glu Gln Asp Ser Lys
            20

<210> SEQ ID NO 45
<211> LENGTH: 7
<212> TYPE: PRT
<213> ORGANISM: Artificial sequence
<220> FEATURE:
<223> OTHER INFORMATION: peptide tryptic fragment L-T17-18

<400> SEQUENCE: 45

Ala Asp Tyr Glu Lys His Lys
1               5

<210> SEQ ID NO 46
<211> LENGTH: 14
<212> TYPE: PRT
<213> ORGANISM: Artificial sequence
<220> FEATURE:
<223> OTHER INFORMATION: peptide tryptic fragment L-T18-19

<400> SEQUENCE: 46

His Lys Val Tyr Ala Cys Glu Val Thr His Gln Gly Leu Arg
1               5                   10

<210> SEQ ID NO 47
<211> LENGTH: 9
<212> TYPE: PRT
<213> ORGANISM: Artificial sequence
<220> FEATURE:
<223> OTHER INFORMATION: peptide tryptic fragment L-T20-21

<400> SEQUENCE: 47

Ser Pro Val Thr Lys Ser Phe Asn Arg
1               5

<210> SEQ ID NO 48
<211> LENGTH: 7
<212> TYPE: PRT
<213> ORGANISM: Artificial sequence
<220> FEATURE:
<223> OTHER INFORMATION: peptide tryptic fragment L-T21-22

<400> SEQUENCE: 48

Ser Phe Asn Arg Gly Glu Cys
1               5

<210> SEQ ID NO 49
<211> LENGTH: 12
<212> TYPE: PRT
<213> ORGANISM: Artificial sequence
<220> FEATURE:
<223> OTHER INFORMATION: peptide tryptic fragment H-T1

<400> SEQUENCE: 49

Glu Val Gln Leu Val Gln Ser Gly Ala Glu Val Lys
1               5                   10
```

```
<210> SEQ ID NO 50
<211> LENGTH: 7
<212> TYPE: PRT
<213> ORGANISM: Artificial sequence
<220> FEATURE:
<223> OTHER INFORMATION: peptide tryptic fragment H-T2

<400> SEQUENCE: 50

Lys Pro Gly Ser Ser Val Lys
1               5

<210> SEQ ID NO 51
<211> LENGTH: 15
<212> TYPE: PRT
<213> ORGANISM: Artificial sequence
<220> FEATURE:
<223> OTHER INFORMATION: peptide tryptic fragment H-T4

<400> SEQUENCE: 51

Ala Ser Gly Gly Ser Phe Ser Ser Tyr Ala Ile Asn Trp Val Arg
1               5                   10                  15

<210> SEQ ID NO 52
<211> LENGTH: 25
<212> TYPE: PRT
<213> ORGANISM: Artificial sequence
<220> FEATURE:
<223> OTHER INFORMATION: peptide tryptic fragment H-T5

<400> SEQUENCE: 52

Gln Ala Pro Gly Gln Gly Leu Glu Trp Met Gly Gly Leu Met Pro Ile
1               5                   10                  15

Phe Gly Thr Thr Asn Tyr Ala Gln Lys
            20                  25

<210> SEQ ID NO 53
<211> LENGTH: 4
<212> TYPE: PRT
<213> ORGANISM: Artificial sequence
<220> FEATURE:
<223> OTHER INFORMATION: peptide tryptic fragment H-T6

<400> SEQUENCE: 53

Phe Gln Asp Arg
1

<210> SEQ ID NO 54
<211> LENGTH: 31
<212> TYPE: PRT
<213> ORGANISM: Artificial sequence
<220> FEATURE:
<223> OTHER INFORMATION: peptide tryptic fragment H-T7

<400> SEQUENCE: 54

Leu Thr Ile Thr Ala Asp Val Ser Thr Ser Thr Ala Tyr Met Gln Leu
1               5                   10                  15

Ser Gly Leu Thr Tyr Glu Asp Thr Ala Met Tyr Tyr Cys Ala Arg
            20                  25                  30

<210> SEQ ID NO 55
<211> LENGTH: 34
<212> TYPE: PRT
<213> ORGANISM: Artificial sequence
<220> FEATURE:
<223> OTHER INFORMATION: peptide tryptic fragment H-T8
```

-continued

```
<400> SEQUENCE: 55

Val Ala Tyr Met Leu Glu Pro Thr Val Thr Ala Gly Gly Leu Asp Val
1               5                   10                  15

Trp Gly Gln Gly Thr Leu Val Thr Val Ser Ser Ala Ser Pro Thr Ser
                20                  25                  30

Pro Lys

<210> SEQ ID NO 56
<211> LENGTH: 44
<212> TYPE: PRT
<213> ORGANISM: Artificial sequence
<220> FEATURE:
<223> OTHER INFORMATION: peptide tryptic fragment H-T9

<400> SEQUENCE: 56

Val Phe Pro Leu Ser Leu Cys Ser Thr Gln Pro Asp Gly Asn Val Val
1               5                   10                  15

Ile Ala Cys Leu Val Gln Gly Phe Phe Pro Gln Glu Pro Leu Ser Val
                20                  25                  30

Thr Trp Ser Glu Ser Gly Gln Gly Val Thr Ala Arg
        35                  40

<210> SEQ ID NO 57
<211> LENGTH: 30
<212> TYPE: PRT
<213> ORGANISM: Artificial sequence
<220> FEATURE:
<223> OTHER INFORMATION: peptide tryptic fragment H-T10

<400> SEQUENCE: 57

Asn Phe Pro Pro Ser Gln Asp Ala Ser Gly Asp Leu Tyr Thr Thr Ser
1               5                   10                  15

Ser Gln Leu Thr Leu Pro Ala Thr Gln Cys Leu Ala Gly Lys
                20                  25                  30

<210> SEQ ID NO 58
<211> LENGTH: 7
<212> TYPE: PRT
<213> ORGANISM: Artificial sequence
<220> FEATURE:
<223> OTHER INFORMATION: peptide tryptic fragment H-T11

<400> SEQUENCE: 58

Ser Val Thr Cys His Val Lys
1               5

<210> SEQ ID NO 59
<211> LENGTH: 38
<212> TYPE: PRT
<213> ORGANISM: Artificial sequence
<220> FEATURE:
<223> OTHER INFORMATION: peptide tryptic fragment H-T12

<400> SEQUENCE: 59

His Tyr Thr Asn Pro Ser Gln Asp Val Thr Val Pro Cys Pro Val Pro
1               5                   10                  15

Ser Thr Pro Pro Thr Pro Ser Pro Ser Thr Pro Pro Thr Pro Ser Pro
                20                  25                  30

Ser Cys Cys His Pro Arg
        35

<210> SEQ ID NO 60
<211> LENGTH: 27
```

```
<212> TYPE: PRT
<213> ORGANISM: Artificial sequence
<220> FEATURE:
<223> OTHER INFORMATION: peptide tryptic fragment H-T13

<400> SEQUENCE: 60

Leu Ser Leu His Arg Pro Ala Leu Glu Asp Leu Leu Gly Ser Glu
1               5                   10                  15

Ala Asn Leu Thr Cys Thr Leu Thr Gly Leu Arg
            20                  25

<210> SEQ ID NO 61
<211> LENGTH: 15
<212> TYPE: PRT
<213> ORGANISM: Artificial sequence
<220> FEATURE:
<223> OTHER INFORMATION: peptide tryptic fragment H-T14

<400> SEQUENCE: 61

Asp Ala Ser Gly Val Thr Phe Thr Trp Thr Pro Ser Ser Gly Lys
1               5                   10                  15

<210> SEQ ID NO 62
<211> LENGTH: 9
<212> TYPE: PRT
<213> ORGANISM: Artificial sequence
<220> FEATURE:
<223> OTHER INFORMATION: peptide tryptic fragment H-T15

<400> SEQUENCE: 62

Ser Ala Val Gln Gly Pro Pro Glu Arg
1               5

<210> SEQ ID NO 63
<211> LENGTH: 23
<212> TYPE: PRT
<213> ORGANISM: Artificial sequence
<220> FEATURE:
<223> OTHER INFORMATION: peptide tryptic fragment H-T16

<400> SEQUENCE: 63

Asp Leu Cys Gly Cys Tyr Ser Val Ser Ser Val Leu Pro Gly Cys Ala
1               5                   10                  15

Glu Pro Trp Asn His Gly Lys
            20

<210> SEQ ID NO 64
<211> LENGTH: 12
<212> TYPE: PRT
<213> ORGANISM: Artificial sequence
<220> FEATURE:
<223> OTHER INFORMATION: peptide tryptic fragment H-T17

<400> SEQUENCE: 64

Thr Phe Thr Cys Thr Ala Ala Tyr Pro Glu Ser Lys
1               5                   10

<210> SEQ ID NO 65
<211> LENGTH: 9
<212> TYPE: PRT
<213> ORGANISM: Artificial sequence
<220> FEATURE:
<223> OTHER INFORMATION: peptide tryptic fragment H-T18

<400> SEQUENCE: 65

Thr Pro Leu Thr Ala Thr Leu Ser Lys
1               5
```

<210> SEQ ID NO 66
<211> LENGTH: 32
<212> TYPE: PRT
<213> ORGANISM: Artificial sequence
<220> FEATURE:
<223> OTHER INFORMATION: peptide tryptic fragment H-T19

<400> SEQUENCE: 66

Ser Gly Asn Thr Phe Arg Pro Glu Val His Leu Leu Pro Pro Ser
1               5                   10                  15

Glu Glu Leu Ala Leu Asn Glu Leu Val Thr Leu Thr Cys Leu Ala Arg
            20                  25                  30

<210> SEQ ID NO 67
<211> LENGTH: 5
<212> TYPE: PRT
<213> ORGANISM: Artificial sequence
<220> FEATURE:
<223> OTHER INFORMATION: peptide tryptic fragment H-T20

<400> SEQUENCE: 67

Gly Phe Ser Pro Lys
1               5

<210> SEQ ID NO 68
<211> LENGTH: 5
<212> TYPE: PRT
<213> ORGANISM: Artificial sequence
<220> FEATURE:
<223> OTHER INFORMATION: peptide tryptic fragment H-T21

<400> SEQUENCE: 68

Asp Val Leu Val Arg
1               5

<210> SEQ ID NO 69
<211> LENGTH: 10
<212> TYPE: PRT
<213> ORGANISM: Artificial sequence
<220> FEATURE:
<223> OTHER INFORMATION: peptide tryptic fragment H-T22

<400> SEQUENCE: 69

Trp Leu Gln Gly Ser Gln Glu Leu Pro Arg
1               5                   10

<210> SEQ ID NO 70
<211> LENGTH: 7
<212> TYPE: PRT
<213> ORGANISM: Artificial sequence
<220> FEATURE:
<223> OTHER INFORMATION: peptide tryptic fragment H-T24

<400> SEQUENCE: 70

Tyr Leu Thr Trp Ala Ser Arg
1               5

<210> SEQ ID NO 71
<211> LENGTH: 17
<212> TYPE: PRT
<213> ORGANISM: Artificial sequence
<220> FEATURE:
<223> OTHER INFORMATION: peptide tryptic fragment H-T25

<400> SEQUENCE: 71

Gln Glu Pro Ser Gln Gly Thr Thr Thr Phe Ala Val Thr Ser Ile Leu

```
1               5                   10                  15
Arg

<210> SEQ ID NO 72
<211> LENGTH: 7
<212> TYPE: PRT
<213> ORGANISM: Artificial sequence
<220> FEATURE:
<223> OTHER INFORMATION: peptide tryptic fragment H-T26

<400> SEQUENCE: 72

Val Ala Ala Glu Asp Trp Lys
1               5

<210> SEQ ID NO 73
<211> LENGTH: 20
<212> TYPE: PRT
<213> ORGANISM: Artificial sequence
<220> FEATURE:
<223> OTHER INFORMATION: peptide tryptic fragment H-T28

<400> SEQUENCE: 73

Gly Asp Thr Phe Ser Cys Met Val Gly His Glu Ala Leu Pro Leu Ala
1               5                   10                  15

Phe Thr Gln Lys
            20

<210> SEQ ID NO 74
<211> LENGTH: 4
<212> TYPE: PRT
<213> ORGANISM: Artificial sequence
<220> FEATURE:
<223> OTHER INFORMATION: peptide tryptic fragment H-T29

<400> SEQUENCE: 74

Thr Ile Asp Arg
1

<210> SEQ ID NO 75
<211> LENGTH: 22
<212> TYPE: PRT
<213> ORGANISM: Artificial sequence
<220> FEATURE:
<223> OTHER INFORMATION: peptide tryptic fragment H-T30

<400> SEQUENCE: 75

Leu Ala Gly Lys Pro Thr His Val Asn Val Ser Val Val Met Ala Glu
1               5                   10                  15

Val Asp Gly Thr Cys Tyr
            20

<210> SEQ ID NO 76
<211> LENGTH: 19
<212> TYPE: PRT
<213> ORGANISM: Artificial sequence
<220> FEATURE:
<223> OTHER INFORMATION: peptide tryptic fragment H-T1-2

<400> SEQUENCE: 76

Glu Val Gln Leu Val Gln Ser Gly Ala Glu Val Lys Lys Pro Gly Ser
1               5                   10                  15

Ser Val Lys

<210> SEQ ID NO 77
<211> LENGTH: 11
```

```
<212> TYPE: PRT
<213> ORGANISM: Artificial sequence
<220> FEATURE:
<223> OTHER INFORMATION: peptide tryptic fragment H-T2-3

<400> SEQUENCE: 77

Lys Pro Gly Ser Ser Val Lys Val Ser Cys Lys
1               5                   10

<210> SEQ ID NO 78
<211> LENGTH: 19
<212> TYPE: PRT
<213> ORGANISM: Artificial sequence
<220> FEATURE:
<223> OTHER INFORMATION: peptide tryptic fragment H-T3-4

<400> SEQUENCE: 78

Val Ser Cys Lys Ala Ser Gly Gly Ser Phe Ser Ser Tyr Ala Ile Asn
1               5                   10                  15

Trp Val Arg

<210> SEQ ID NO 79
<211> LENGTH: 21
<212> TYPE: PRT
<213> ORGANISM: Artificial sequence
<220> FEATURE:
<223> OTHER INFORMATION: peptide tryptic fragment H-T17-18

<400> SEQUENCE: 79

Thr Phe Thr Cys Thr Ala Ala Tyr Pro Glu Ser Lys Thr Pro Leu Thr
1               5                   10                  15

Ala Thr Leu Ser Lys
            20

<210> SEQ ID NO 80
<211> LENGTH: 10
<212> TYPE: PRT
<213> ORGANISM: Artificial sequence
<220> FEATURE:
<223> OTHER INFORMATION: peptide tryptic fragment H-T20-21

<400> SEQUENCE: 80

Gly Phe Ser Pro Lys Asp Val Leu Val Arg
1               5                   10

<210> SEQ ID NO 81
<211> LENGTH: 15
<212> TYPE: PRT
<213> ORGANISM: Artificial sequence
<220> FEATURE:
<223> OTHER INFORMATION: peptide tryptic fragment H-T21-22

<400> SEQUENCE: 81

Asp Val Leu Val Arg Trp Leu Gln Gly Ser Gln Glu Leu Pro Arg
1               5                   10                  15

<210> SEQ ID NO 82
<211> LENGTH: 12
<212> TYPE: PRT
<213> ORGANISM: Artificial sequence
<220> FEATURE:
<223> OTHER INFORMATION: peptide tryptic fragment H-T22-23

<400> SEQUENCE: 82

Trp Leu Gln Gly Ser Gln Glu Leu Pro Arg Glu Lys
1               5                   10
```

<210> SEQ ID NO 83
<211> LENGTH: 21
<212> TYPE: PRT
<213> ORGANISM: Artificial sequence
<220> FEATURE:
<223> OTHER INFORMATION: peptide tryptic fragment H-T27-28

<400> SEQUENCE: 83

Lys Gly Asp Thr Phe Ser Cys Met Val Gly His Glu Ala Leu Pro Leu
1               5                   10                  15

Ala Phe Thr Gln Lys
            20

<210> SEQ ID NO 84
<211> LENGTH: 5118
<212> TYPE: DNA
<213> ORGANISM: Artificial sequence
<220> FEATURE:
<223> OTHER INFORMATION: pDAB3014 sequence

<400> SEQUENCE: 84

```
ctggcacgac aggtttcccg actggaaagc gggcagtgag cgcaacgcaa ttaatgtgag     60
ttagctcact cattaggcac cccaggcttt acactttatg cttccggctc gtatgttgtg    120
tggaattgtg agcggataac aatttcacac aggaaacagc tatgaccatg attacgccaa    180
gcttcccggg aatgcggccg ctagctagcg gccgcattcc cgggaagcta gcggccgcat    240
tcccgggaag ctagcggccg cttccccgga agcttgggct gcaggtcaat cccattgctt    300
ttgaagcagc tcaacattga tctctttctc gaggtcattc atatgcttga agagagagtc    360
gggatagtcc aaaataaaac aaaggtaaga ttacctggtc aaaagtgaaa acatcagtta    420
aaaggtggta taaagtaaaa tatcggtaat aaaaggtggc ccaaagtgaa atttactctt    480
ttctactatt ataaaaattg aggatgtttt tgtcggtact ttgatacgtc attttttgtat    540 gaattggttt ttaagtttat tcgcttttgg aaatgcatat ctgtatttga gtcgggtttt    600
aagttcgttt gcttttgtaa atacagaggg atttgtataa gaaatatctt taaaaaaacc    660
catatgctaa tttgacataa ttttttgagaa aaatatatat tcaggcgaat tctcacaatg    720
aacaataata agattaaaat agcttttcccc cgttgcagcg catgggtatt ttttctagta    780
aaaataaaag ataaacttag actcaaaaca tttacaaaaa caaccccctaa agttcctaaa    840 gcccaaagtg ctatccacga tccatagcaa gcccagccca acccaaccca acccaaccca    900
ccccagtcca gccaactgga caatagtctc cacacccccc cactatcacc gtgagttgtc    960
cgcacgcacc gcacgtctcg cagccaaaaa aaaaaaaaga agaaaaaaaa agaaaaagaa   1020
aaaacagcag gtgggtccgg gtcgtggggg ccggaaacgc gaggaggatc gcgagccagc   1080
gacgaggccg gccctccctc cgcttccaaa gaaacgcccc ccatcgccac tatatacata   1140
cccccccctc tcctcccatc cccccaaccc taccaccacc accaccacca cctccacctc   1200 ctccccccctc gctgccggac gacgcctccc ccctccccct ccgccgccgc cgcgccggta   1260
accaccccgc ccctctcctc tttctttctc cgttttttttt ttccgtctcg gtctcgatct   1320
ttggccttgg tagtttgggt gggcgagagg cggcttcgtg cgcgcccaga tcggtgcgcg   1380 ggagggggcgg gatctcgcgg ctggggctct cgccggcgtg gatccggccc ggatctcgcg   1440
gggaatgggg ctctcggatg tagatctgcg atccgccgtt gttggggggag atgatggggg   1500 gtttaaaatt tccgccatgc taaacaagat caggaagagg ggaaaaggggc actatggttt   1560 atattttttat atatttctgc tgcttcgtca ggcttagatg tgctagatct ttctttcttc   1620
```

```
tttttgtggg tagaatttga atccctcagc attgttcatc ggtagttttt cttttcatga    1680
tttgtgacaa atgcagcctc gtgcggagct tttttgtagg tagaccatgg cttctccgga    1740
gaggagacca gttgagatta ggccagctac agcagctgat atggccgcgg tttgtgatat    1800
cgttaaccat tacattgaga cgtctacagt gaacttuagg acagagccac aaacaccaca    1860
agagtggatt gatgatctag agaggttgca agatagatac ccttggttgg ttgctgaggt    1920
tgagggtgtt gtggctggta ttgcttacgc tgggccctgg aaggctagga acgcttacga    1980
ttggacagtt gagagtactg tttacgtgtc acataggcat caaaggttgg gcctaggatc    2040
cacattgtac acacatttgc ttaagtctat ggaggcgcaa ggttttaagt ctgtggttgc    2100
tgttataggc cttccaaacg atccatctgt taggttgcat gaggctttgg gatacacagc    2160
ccggggtaca ttgcgcgcag ctggatacaa gcatggtgga tggcatgatg ttggtttttg    2220
gcaaagggat tttgagttgc cagctcctcc aaggccagtt aggccagtta cccagatctg    2280
aggtaccctg agctcggtcg cagcgtgtgc gtgtccgtcg tacgttctgg ccggccgggc    2340
cttgggcgcg cgatcagaag cgttgcgttg gcgtgtgtgt gcttctggtt tgctttaatt    2400
ttaccaagtt tgtttcaagg tggatcgcgt ggtcaaggcc cgtgtgcttt aaagacccac    2460
cggcactggc agtgagtgtt gctgcttgtg taggcttlggg tacgtatggg ctttatttgc    2520
ttctggatgt tgtgtactac ttgggttlgt tgaattatta tgagcagttg cgtattgtaa    2580
ttcagctggg ctacctggac attgttatgt attaataaat gctttgcttt cttctaaaga    2640
tctttaagtg ctgaattcac tggccgtcgt tttacaacgt cgtgactggg aaaaccctgg    2700
cgttacccaa cttaatcgcc ttgcagcaca tccccctttc gccagctggc gtaatagcga    2760
agaggcccgc accgatcgcc cttcccaaca gttgcgcagc ctgaatggcg aatggcgcct    2820
gatgcggtat tttctcctta cgcatctgtg cggtatttca caccgcatat ggtgcactct    2880
cagtacaatc tgctctgatg ccgcatagtt aagccagccc cgacacccgc caacacccgc    2940
tgacgcgccc tgacgggctt gtctgctccc ggcatccgct tacagacaag ctgtgaccgt    3000
ctccgggagc tgcatgtgtc agaggttttc accgtcatca ccgaaacgcg cgagacgaaa    3060
gggcctcgtg atacgcctat ttttataggt taatgtcatg ataataatgg tttcttagac    3120
gtcaggtggc acttttcggg gaaatgtgcg cggaaccccl atttgtttat ttttctaaat    3180
acattcaaat atgtatccgc tcatgagaca ataaccctga taaatgcttc aataatattg    3240
aaaaaggaag agtatgagta ttcaacattt ccgtgtcgcc cttattccct ttttgcggc    3300 attttgcctt cctgtttttg ctcacccaga aacgctggtg aaagtaaaag atgctgaaga    3360
tcagttgggt gcacgagtgg gttacatcga actggatctc aacagcggta agatccttga    3420
gagttttcgc cccgaagaac gttttccaat gatgagcact tttaaagttc tgctatgtgg    3480
cgcggtatta tcccgtattg acgccgggca agagcaactc ggtcgccgca tacactattc    3540
tcagaatgac ttggttgagt actcaccagt cacagaaaag catcttacgg atggcatgac    3600
agtaagagaa ttatgcagtg ctgccataac catgagtgat aacactgcgg ccaacttact    3660
tctgacaacg atcggaggac cgaaggagct aaccgctttt ttgcacaaca tgggggatca    3720
tgtaactcgc cttgatcgtt gggaaccgga gctgaatgaa gccataccaa acgacgagcg    3780
tgacaccacg atgcctgtag caatggcaac aacgttgcgc aaactattaa ctggcgaact    3840
acttactcta gcttcccggc aacaattaat agactggatg gaggcggata agttgcagg    3900 accacttctg cgctcggccc ttccggctgg ctggtttatt gctgataaat ctggagccgg    3960
tgagcgtggg tctcgcggta tcattgcagc actggggcca gatggtaagc cctcccgtat    4020
```

```
cgtagttatc tacacgacgg ggagtcaggc aactatggat gaacgaaata gacagatcgc    4080
tgagataggt gcctcactga ttaagcattg gtaactgtca gaccaagttt actcatatat    4140
actttagatt gatttaaaac ttcatttta atttaaaagg atctaggtga agatcctttt     4200
tgataatctc atgaccaaaa tcccttaacg tgagttttcg ttccactgag cgtcagaccc    4260
cgtagaaaag atcaaaggat cttcttgaga tcctttttt ctgcgcgtaa tctgctgctt     4320
gcaaacaaaa aaaccaccgc taccagcggt ggtttgtttg ccggatcaag agctaccaac    4380 tcttttccg aaggtaactg gcttcagcag agcgcagata ccaaatactg ttcttctagt     4440
gtagccgtag ttaggccacc acttcaagaa ctctgtagca ccgcctacat acctcgctct    4500
gctaatcctg ttaccagtgg ctgctgccag tggcgataag tcgtgtctta ccgggttgga    4560
ctcaagacga tagttaccgg ataaggcgca gcggtcgggc tgaacggggg gttcgtgcac    4620
acagcccagc ttggagcgaa cgacctacac cgaactgaga tacctacagc gtgagctatg    4680
agaaagcgcc acgcttcccg aagggagaaa ggcggacagg tatccggtaa gcggcagggt    4740
cggaacagga gagcgcacga gggagcttcc agggggaaac gcctggtatc tttatagtcc    4800
tgtcgggttt cgccacctct gacttgagcg tcgatttttg tgatgctcgt caggggggcg    4860
gagcctatgg aaaaacgcca gcaacgcggc ctttttacgg ttcctggcct tttgctggcc     4920
ttttgctcac atgttctttc ctgcgttatc ccctgattct gtggataacc gtattaccgc    4980
ctttgagtga gctgataccg ctcgccgcag ccgaacgacc gagcgcagcg agtcagtgag    5040
cgaggaagcg tgcgcagcgg aagagcgccc aatacgcaaa ccgcctctcc ccgcgcgttg    5100
gccgattcat taatgcag                                                  5118

<210> SEQ ID NO 85
<211> LENGTH: 13680
<212> TYPE: DNA
<213> ORGANISM: Artificial sequence
<220> FEATURE:
<223> OTHER INFORMATION: pDAB8505 sequence
<220> FEATURE:
<221> NAME/KEY: misc_feature
<222> LOCATION: (1)..(13680)
<223> OTHER INFORMATION: n = a or c or g or t

<400> SEQUENCE: 85
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt acaccggtgt gatcatgggc     420
cgcgattaaa atcccaatt atatttggtc taatttagtt tggtattgag taaaacaaat      480
tcgaaccaaa ccaaaatata aatatatagt ttttatatat atgccttaa gactttttat      540 agaattttct ttaaaaaata tctagaaata tttgcgactc ttctggcatg taatatttcg     600
ttaaatatga agtgctccat ttttattaac tttaaataat tggttgtacg atcactttct    660
tatcaagtgt tactaaaatg cgtcaatctc tttgttcttc catattcata tgtcaaaatc    720
tatcaaaatt cttatatatc tttttcgaat ttgaagtgaa atttcgataa tttaaaatta    780
aatagaacat atcattattt aggtatcata ttgattttta tacttaatta ctaaatttgg    840
```

```
ttaactttga aagtgtacat caacgaaaaa ttagtcaaac gactaaaata aataaatatc    900
atgtgttatt aagaaaattc tcctataaga atattttaat agatcatatg tttgtaaaaa    960
aaattaattt ttactaacac atatatttac ttatcaaaaa tttgacaaag taagattaaa   1020
ataatattca tctaacaaaa aaaaaaccag aaaatgctga aaacccggca aaaccgaacc   1080
aatccaaacc gatatagttg gtttggtttg attttgatat aaaccgaacc aactcggtcc   1140
atttgcaccc ctaatcataa tagctttaat atttcaagat attattaagt taacgttgtc   1200
aatatcctgg aaattttgca aaatgaatca agcctatatg gctgtaatat gaatttaaaa   1260
gcagctcgat gtggtggtaa tatgtaattt acttgattct aaaaaaatat cccaagtatt   1320
aataatttct gctaggaaga aggttagcta cgatttacag caaagccaga atacaaagaa   1380
ccataaagtg attgaagctc gaaatatacg aaggaacaaa tatttttaaa aaaatacgca   1440
atgacttgga acaaaagaaa gtgatatatt ttttgttctt aaacaagcat cccctctaaa   1500
gaatggcagt tttcctttgc atgtaactat tatgctccct tcgttacaaa aattttggac   1560
tactattggg aacttcttct gaaaatagtg gccaccgctt aattaaggcg cgccatgccc   1620
ggccgcattc ccgggaagct aggccaccgt ggcccgcctg caggggaagc ttagctgaaa   1680
caacccggcc ctaaagcact atcgtatcac ctatctgaaa taagtcacgg gtttcgaacg   1740
tccacttgcg tcgcacggaa ttgcatgttt cttgttggaa gcatattcac gcaatctcca   1800
cacataaagg tttatgtata aacttacatt tagctcagtt taattacagt cttatttgga   1860
tgcatatgta tggttctcaa tccatataag ttagagtaaa aaataagttt aaattttatc   1920
ttaattcact ccaacatata tggattgagt acaatactca tgtgcatcca aacaaactac   1980
ttatattgag gtgaatttgg atagaaatta aactaactta cacactaagc caatctttac   2040
tatattaaag caccagtttc aacgatcgtc ccgcgtcaat attattaaaa aactcctaca   2100
tttctttata atcaacccgc actcttataa tctcttctct actactataa taagagagtt   2160
tatgtacaaa ataaggtgaa attatgtata agtgttctgg atattggttg ttggctccat   2220
attcacacaa cctaatcaat agaaaacata tgttttatta aaacaaaatt tatcatatat   2280
catatatata tatatacata tatatatata tatatataaa ccgtagcaat gcacgggcat   2340
ataactagtg caacttaata catgtgtgta ttaagatgaa taagagggta tccaaataaa   2400
aaacttgttc gcttacgtct ggatcgaaag gggttggaaa cgattaaatc tcttcctagt   2460
caaaattgaa tagaaggaga tttaatctct cccaatcccc ttcgatcatc caggtgcaac   2520
cgtataagtc ctaaagtggt gaggaacacg aaacaaccat gcattggcat gtaaagctcc   2580
aagaatttgt tgtatcctta acaactcaca gaacatcaac caaaattgca cgtcaagggt   2640
attgggtaag aaacaatcaa acaaatcctc tctgtgtgca aagaaacacg gtgagtcatg   2700
ccgagatcat actcatctga tatacatgct tacagctcac aagacattac aaacaactca   2760
tattgcatta caaagatcgt ttcatgaaaa ataaaatagg ccggacagga caaaaatcct   2820
tgacgtgtaa agtaaattta caacaaaaaa aaagccatat gtcaagctaa atctaattcg   2880
ttttacgtag atcaacaacc tgtagaaggc aacaaaactg agccacgcag aagtacagaa   2940
tgattccaga tgaaccatcg acgtgctacg taaagagagt gacgagtcat atacatttgg   3000
caagaaacca tgaagctgcc tacagccgtc tcggtggcat agaacacaag aaattgtgtt   3060
aattaatcaa agctataaat aacgctcgca tgcctgtgca cttctccatc accaccactg   3120
ggtcttcaga ccattagctt tatctactcc agagcgcaga agaacccgat cgacaccatg   3180
ggatggagct ggatctttct cttcctcctg tcaggagctg caggtgtcca ttgccaggtt   3240
```

```
cagctcgtgc agtcaggtgc tgaggtgaag aagcctggct cctcggtgaa ggtctcctgc    3300
aaggcttctg gaggttcctt cagctcctat gctatcaact gggtgaggca agctcctgga    3360
caagggcttg agtggatggg agggctcatg cctatctttg gacaacaaa ctacgcgcag     3420 aagttccagg acaggctcac gattaccgcg gacgtatcca cgagtacagc ctacatgcaa    3480
ctgagcggcc tgacatatga agacacggcc atgtattact gtgcgagagt tgcctacatg    3540
cttgaaccta ccgtcactgc aggtggtttg gacgtctggg gccaagggac cttggtcacc    3600
gtctcctccg catccccgac cagcccgaag gtcttcccgc tgagcctctg tagcacccag    3660
ccagatggga acgtggtcat cgcctgcctg gtccagggct tcttccctca ggagccactc    3720
agtgtgacct ggagcgaaag cggacagggc gtgaccgcca ggaacttccc acccagccag    3780
gatgcctccg gagacctgta caccacgtcc agccagctga cccttccggc cacacagtgc    3840
ctagcgggca agtccgtgac atgccacgtg aagcactaca cgaatcccag ccaggatgtg    3900
actgtgccct gcccagttcc ctcaactcca cctaccccat ctccctcgac tccacctacc    3960
ccatctccct catgctgcca ccccaggctg tcactgcaca ggcctgccct cgaggacctg    4020
ctcttaggtt cggaagcgaa cctcacgtgc acactcaccg gcctgagaga tgcgtcaggt    4080
gtcaccttca cctggacgcc ctcaagtggt aagagcgctg ttcaaggccc acctgagcgt    4140
gacctctgtg gctgctacag cgtgtccagt gtccttccgg gctgtgccga gccttggaat    4200
catgggaaga ccttcacttg cactgctgcc taccccgaga gcaagacccc gctaaccgcc    4260
accctctcga aatccggcaa cacattccgg cccgaggtcc acctgctgcc gccgccgtcg    4320
gaggagctgg ccctgaacga gctggtgacg ctgacgtgcc tggcgcgcgg cttcagcccc    4380
aaggacgtgc tggttcgctg gctgcagggg tcacaggagc tgcctaggga gaagtacctg    4440
acttgggcat cccggcagga gcccagccaa ggcaccacca ccttcgctgt gacctcgata    4500
ctgcgcgtgg cagccgagga ctggaagaag ggtgacacct ctcctgcat ggtgggccac     4560 gaggcccttc cgctggcctt cacacagaag accatcgacc gcttggcggg taaacccacc    4620
catgtcaatg tgtctgttgt catggcggag gtggacggca cctgctactg agagctcgct    4680
gagggcactg aagtcgcttg atgtgctgaa ttgtttgtga tgttggtggc gtattttgtt    4740
taaataagta agcatggctg tgattttatc atatgatcga tctttggggt tttatttaac    4800
acattgtaaa atgtgtatct attaataact caatgtataa gatgtgttca ttcttcggtt    4860
gccatagatc tgcttatttg acctgtgatg ttttgactcc aaaaaccaaa atcacaactc    4920
aataaactca tggaatatgt ccacctgttt cttgaagagt tcatctacca ttccagttgg    4980
catttatcag tgttgcagcg gcgctgtgct ttgtaacata acaattgtta cggcatatat    5040 ccaacgccg gcctagctag gccacggtgg ccagatccac tagttctaga gcggccgggc    5100
aagcggccgc attcccggga agctaggcca ccgtggcccg cctgcagggg aagcttagct    5160
gaaacaaccc ggccctaaag cactatcgta tcacctatct gaaataagtc acgggtttcg    5220
aacgtccact tgcgtcgcac ggaattgcat gtttcttgtt ggaagcatat tcacgcaatc    5280
tccacacata aaggtttatg tataaactta catttagctc agtttaattaa cagtcttatt    5340 tggatgcata tgtatggttc tcaatccata taagttagag taaaaaataa gtttaaattt    5400
tatcttaatt cactccaaca tatatggatt gagtacaata ctcatgtgca tccaaacaaa    5460
ctacttatat tgaggtgaat ttggatagaa attaaactaa cttacacact aagccaatct    5520
ttactatatt aaagcaccag tttcaacgat cgtcccgcgt caatattatt aaaaaactcc    5580
tacatttctt tataatcaac ccgcactctt ataatctctt ctctactact ataataagag    5640
```

| | |
|---|---|
| agtttatgta caaaataagg tgaaattatg tataagtgtt ctggatattg gttgttggct | 5700 |
| ccatattcac acaacctaat caatagaaaa catatgtttt attaaaacaa aatttatcat | 5760 |
| atatcatata tatatatata catatatata tatatatata taaaccgtag caatgcacgg | 5820 |
| gcatataact agtgcaactt aatacatgtg tgtattaaga tgaataagag ggtatccaaa | 5880 |
| taaaaaactt gttcgcttac gtctggatcg aaagggggttg gaaacgatta aatctcttcc | 5940 |
| tagtcaaaat tgaatagaag gagatttaat ctctcccaat cccttcgat catccaggtg | 6000 |
| caaccgtata agtcctaaag tggtgaggaa cacgaaacaa ccatgcattg gcatgtaaag | 6060 |
| ctccaagaat ttgttgtatc cttaacaact cacagaacat caaccaaaat tgcacgtcaa | 6120 |
| gggtattggg taagaaacaa tcaaacaaat cctctctgtg tgcaaagaaa cacggtgagt | 6180 |
| catgccgaga tcatactcat ctgatataca tgcttacagc tcacaagaca ttacaaacaa | 6240 |
| ctcatattgc attacaaaga tcgtttcatg aaaaataaaa taggccggac aggacaaaaa | 6300 |
| tccttgacgt gtaaagtaaa tttacaacaa aaaaaaagcc atatgtcaag ctaaatctaa | 6360 |
| ttcgttttac gtagatcaac aacctgtaga aggcaacaaa actgagccac gcagaagtac | 6420 |
| agaatgattc cagatgaacc atcgacgtgc tacgtaaaga gagtgacgag tcatatacat | 6480 |
| ttggcaagaa accatgaagc tgcctacagc cgtctcggtg gcatagaaca caagaaattg | 6540 |
| tgttaattaa tcaaagctat aaataacgct cgcatgcctg tgcacttctc catcaccacc | 6600 |
| actgggtctt cagaccatta gctttatcta ctccagagcg cagaagaacc cgatcgacac | 6660 |
| catgggatgg tcctggatct ttctcttcct tctgtcagga gctgcaggtg tccactgcga | 6720 |
| gatcgtgctc acgcagtctc caggcaccct gtctttgtcg ccaggggaac gtgccaccct | 6780 |
| ctcctgccgg gccagtcagt ccgttttccag cgcgtacctt gcctggtacc agcagaagcc | 6840 |
| tggccaagct cccaggctcc tcatctatgg tgcgtccagc agggctactg gcattccaga | 6900 |
| ccgcttctca ggcagtgggt ctgggacaga cttcacgctc accattagca ggctggaacc | 6960 |
| tgaggatttt gcagtgtact actgtcagca gtatggtcgc tcacccacgt tcggccaggg | 7020 |
| gaccaaggtg gagatcaagc gcactgtggc tgcaccgtcg gtcttcatat tcccgccatc | 7080 |
| cgatgagcag ctgaagtctg gcactgcctc tgttgtgtgc ctgctgaata acttctatcc | 7140 |
| gagagaggcg aaggtacagt ggaaggtgga taacgccctc caatcgggta actcccaaga | 7200 |
| gtccgttaca gagcaggaca gcaaggacag cacctacagc ctcagcaaca ccttgacgct | 7260 |
| gagcaaagcg gactacgaga aacacaaggt ctacgcctgc gaagtcaccc atcaaggcct | 7320 |
| gcgctcgccc gtcacaaaga gcttcaaccg gggagagtgt tgagagctcg ctgagggcac | 7380 |
| tgaagtcgct tgatgtgctg aattgtttgt gatgttggtg gcgtattttg tttaaataag | 7440 |
| taagcatggc tgtgattttta tcatatgatc gatctttggg gttttattta acacattgta | 7500 |
| aaatgtgtat ctattaataa ctcaatgtat aagatgtgtt cattcttcgg ttgccataga | 7560 |
| tctgcttatt tgacctgtga tgttttgact ccaaaaacca aaatcacaac tcaataaact | 7620 |
| catggaatat gtccacctgt ttcttgaaga gttcatctac cattccagtt ggcatttatc | 7680 |
| agtgttgcag cggcgctgtg ctttgtaaca taacaattgt tacggcatat atccaacggc | 7740 |
| cggcctagct aggccacggt ggccagatcc actagttcta gagcggccgc ttaattaaat | 7800 |
| ttaaatgttt aaactaggaa atccaagctt gggctgcagg tcaatcccat tgcttttgaa | 7860 |
| gcagctcaac attgatctct ttctcgaggt cattcatatg cttgagaaga gagtcgggat | 7920 |
| agtccaaaat aaaacaaagg taagattacc tggtcaaaag tgaaacatc agttaaaagg | 7980 |
| tggtataagt aaaatatcgg taataaaagg tggcccaaag tgaaatttac tcttttctac | 8040 |

```
tattataaaa attgaggatg ttttgtcggt actttgatac gtcattttg tatgaattgg    8100 tttttaagtt tattcgcgat tttggaaatg catatctgta tttgagtcgg gttttaagtt    8160
cgtttgcttt tgtaaataca gagggatttg tataagaaat atcttaaaa aaaccatatg     8220 ctaatttgac ataattttg agaaaaatat atattcaggc gaattctcac aatgaacaat     8280
aataagatta aaatagcttg ccccgttgc agcgatgggt atttttcta gtaaaataaa      8340 agataaactt agactcaaaa catttacaaa aacaaccct aaagtcctaa agcccaaagt     8400
gctatgcacg atccatagca agcccagccc aacccaaccc aacccaaccc accccagtgc    8460
agccaactgg caaatagtct ccacaccccg gcactatcac cgtgagttgt ccgcaccacc    8520
gcacgtctcg cagccaaaaa aaaaaaaga agaaaaaaa agaaaagaa aaaacagcag       8580 gtgggtccgg gtcgtggggg ccggaaaagc gaggaggatc gcgagcagcg acgaggccgg    8640
ccctccctcc gcttccaaag aaacgccccc catcgccact atatacatac ccccccctct    8700
cctcccatcc ccccaaccct accaccacca ccaccaccac ctcctccccc ctcgctgccg    8760
gacgacgcct cccccctccc cctccgccgc cgccggtaac caccccgccc ctctcctctt    8820
tctttctccg tttttttttt cgtctccggtc tcgatccttg gccttggtag tttgggtggg   8880
cgagagcggc ttcgtcgccc agatcggtgc gcgggagggg cgggatctcg cggctggcgt    8940
ctccgggcgt gagtcggccc ggatcctcgc ggggaatggg gctctcggat gtagatctgc    9000
gatccgccgt tgttggggga gatgatgggg ggtttaaaat ttccgccatg ctaaacaaga    9060
tcaggaagag gggaaaaggg cactatggtt tatattttta tatttctg ctgcttcgtc      9120 aggcttagat gtgctagatc ttctttcttt cttctttttg tgggtagaat ttgaatccct    9180
cagcattgtt catcggtagt ttttcttttc atgatttgtg acaaatgcag cctcgtgcgg    9240 agctttttg taggtagacc atggcttctc cggagaggag accagttgag attaggccag     9300
ctacagcagc tgatatggcc gcggtttgtg atatcgttaa ccattacatt gagacgtcta    9360
cagtgaactt taggacagag ccacaaacac cacaagagtg gattgatgat ctagagaggt    9420
tgcaagatag atacccttgg ttggttgctg aggttgaggg tgttgtggct ggtattgctt    9480
acgctgggcc ctggaaggct aggaacgctt acgattggac agttgagagt actgtttacg    9540
tgtcacatag gcatcaaagg ttgggcctag gatccacatt gtacacacat ttgcttaagt    9600
ctatggaggc gcaaggtttt aagtctgtgg ttgctgttat aggccttcca aacgatccat    9660
ctgttaggtt gcatgaggct ttgggataca cagcccgggg tacattgcgc gcagctggat    9720
acaagcatgg tggatggcat gatgttggtt tttggcaaag ggattttgag ttgccagctc    9780
ctccaaggcc agttaggcca gttacccaga tctgaggtac caatgagctc ggtcgcagcg    9840
tgtgcgtgtc cgtcgtacgt tctggccggc cgggccttgg gcgcgcgatc agaancgttg    9900
cgttggcgtg tgtgtgcttc tggtttgctt taatttttacc aagtttgttt caaggtggat    9960
cgcgtggtca aggcccgtgt gctttaaana cccaccggca ctggcagtga gtgttgctgc    10020
ttgtgtaggc tttggtacgt atgggcttta tttgcttctg gatgttgtgt actacttggg    10080
tttgttgaat tattatganc agttgcgtat tgtaattcag ctgggctacc tggacattgt    10140
tatgtattaa taaatgcttt gctttcttct aaagatcttt aagtgctgaa ttcatatttc    10200
ctcctgcagg gtttaaactt gccgtggcct attttcagaa gaagttccca atagtagtcc    10260
aaaatttttg taacgaaggg agcataatag ttacatgcaa aggaaaactg ccattcttta    10320
gaggggatgc ttgtttaaga acaaaaaata tatcactttc ttttgttcca agtcattgcg    10380 tatttttta aaaatatttg ttccttcgta tatttcgagc ttcaatcact ttatggttct     10440
```

```
ttgtattctg gctttgctgt aaatcgtagc taaccttctt cctagcagaa attattaata   10500
cttgggatat tttttagaa tcaagtaaat tacatattac caccacatcg agctgctttt   10560
aaattcatat tacagccata taggcttgat tcattttgca aaatttccag gatattgaca   10620
acgttaactt aataatatct tgaaatatta aagctattat gattaggggt gcaaatggac   10680
cgagttggtt cggtttatat caaaatcaaa ccaaaccaac tatatcggtt tggattggtt   10740
cggttttgcc gggttttcag cattttctgg tttttttttt gttagatgaa tattattta   10800 atcttacttt gtcaaatttt tgataagtaa atatatgtgt tagtaaaaat taattttttt   10860
tacaaacata tgatctatta aaatattctt ataggagaat tttcttaata acacatgata   10920
tttatttatt ttagtcgttt gactaatttt tcgttgatgt acactttcaa agttaaccaa   10980
atttagtaat taagtataaa aatcaatatg atacctaaat aatgatatgt tctatttaat   11040
tttaaattat cgaaatttca cttcaaattc gaaaagata tataagaatt ttgatagatt   11100
ttgacatatg aatatggaag aacaaagaga ttgacgcatt ttagtaacac ttgataagaa   11160
agtgatcgta caaccaatta tttaaagtta ataaaaatgg agcacttcat atttaacgaa   11220
atattacatg ccagaagagt cgcaaatatt tctagatatt ttttaaagaa aattctataa   11280
aaagtcttaa aggcatatat ataaaaacta tatatttata ttttggtttg gttcgaatt   11340 gttttactca ataccaaact aaattagacc aaatataatt gggattttta atcgcggccc   11400
actagtcacc ggtgtgcttg gcgtaatcat ggtcatagct gtttcctgtg tgaaattgtt   11460
atccgctcac aattccacac aacatacgag ccggaagcat aaagtgtaaa gcctgggtg   11520 cctaatgagt gagctaactc acattaattg cgttgcgctc actgcccgct ttccagtcgg   11580
gaaacctgtc gtgccagctg cattaatgaa tcggccaacg cgcggggaga ggcggtttgc   11640
gtattgggcg ctcttccgct cgcacgctg cgcacgctgc gcacgcttcc tcgctcactg   11700
actcgctgcg ctcggtcgtt cggctgcggc gagcggtatc agctcactca aaggcggtaa   11760
tacggttatc cacagaatca ggggataacg caggaaagaa catgtgagca aaaggccagc   11820
aaaaggccag gaaccgtaaa aaggccgcgt tgctggcgtt tttccatagg ctccgccccc   11880
ctgacgagca tcacaaaaat cgacgctcaa gtcagaggtg gcgaaacccg acaggactat   11940
aaagatacca ggcgtttccc cctggaagct ccctcgtgcg ctctcctgtt ccgaccctgc   12000
cgcttaccgg atacctgtcc gcctttctcc cttcgggaag cgtggcgctt tctcatagct   12060
cacgctgtag gtatctcagt tcggtgtagg tcgttcgctc caagctgggc tgtgtgcacg   12120
aaccccccgt tcagcccgac cgctgcgcct tatccggtaa ctatcgtctt gagtccaacc   12180
cggtaagaca cgacttatcg ccactggcag cagccactgg taacaggatt agcagagcga   12240
ggtatgtagg cggtgctaca gagttcttga agtggtggcc taactacggc tacactagaa   12300
ggacagtatt tggtatctgc gctctgctga gccagttac cttcggaaaa agagttggta   12360
gctcttgatc cggcaaacaa accaccgctg gtagcggtgg tttttttgtt tgcaagcagc   12420
agattacgcg cagaaaaaaa ggatctcaag aagatccttt gatcttttct acgggtctg   12480 acgctcagtg gaacgaaaac tcacgttaag ggattttggt catgagatta tcaaaaagga   12540
tcttcaccta gatccttta aattaaaaat gaagttttaa atcaatctaa agtatatatg   12600
agtaaacttg gtctgacagt taccaatgct taatcagtga ggcacctatc tcagcgatct   12660
gtctatttcg ttcatccata gttgcctgac tccccgtcgt gtagataact acgatacggg   12720
agggcttacc atctggcccc agtgctgcaa tgataccgcg agacccacgc tcaccggctc   12780
cagatttatc agcaataaac cagccagccg gaagggccga gcgcagaagt ggtcctgcaa   12840
```

```
ctttatccgc ctccatccag tctattaatt gttgccggga agctagagta agtagttcgc    12900
cagttaatag tttgcgcaac gttgttgcca ttgctacagg catcgtggtg tcacgctcgt    12960
cgtttggtat ggcttcattc agctccggtt cccaacgatc aaggcgagtt acatgatccc    13020
ccatgttgtg caaaaaagcg gttagctcct tcggtcctcc gatcgttgtc agaagtaagt    13080
tggccgcagt gttatcactc atggttatgg cagcactgca taattctctt actgtcatgc    13140
catccgtaag atgcttttct gtgactggtg agtactcaac caagtcattc tgagaatagt    13200
gtatgcggcg accgagttgc tcttgcccgg cgtcaatacg ggataatacc gcgccacata    13260
gcagaacttt aaaagtgctc atcattgaa aacgttcttc ggggcgaaaa ctctcaagga     13320
tcttaccgct gttgagatcc agttcgatgt aacccactcg tgcacccaac tgatcttcag    13380
catcttttac tttcaccagc gtttctgggt gagcaaaaac aggaaggcaa aatgccgcaa    13440
aaaagggaat aagggcgaca cggaaatgtt gaatactcat actcttcctt tttcaatatt    13500
attgaagcat ttatcagggt tattgtctca tgagcggata catatttgaa tgtatttaga    13560
aaaataaaca aatagggggtt ccgcgcacat ttccccgaaa agtgccacct gacgtctaag   13620
aaaccattat tatcatgaca ttaacctata aaaataggcg tatcacgagg ccctttcgtc    13680
```